US012582722B2

(12) United States Patent
Kato et al.

(10) Patent No.: US 12,582,722 B2
(45) Date of Patent: Mar. 24, 2026

(54) BIFUNCTIONAL COMPOUNDS FOR DEGRADING BTK VIA UBIQUITIN PROTEOSOME PATHWAY

(71) Applicant: NURIX THERAPEUTICS, INC., San Francisco, CA (US)

(72) Inventors: Daisuke Kato, San Francisco, CA (US); Zef Konst, San Francisco, CA (US); Jeffrey Mihalic, San Francisco, CA (US); Daniel W. Robbins, San Francisco, CA (US); Arthur T. Sands, San Francisco, CA (US)

(73) Assignee: NURIX THERAPEUTICS, INC., San Francisco, CA (US)

( * ) Notice: Subject to any disclaimer, the term of this patent is extended or adjusted under 35 U.S.C. 154(b) by 1018 days.

(21) Appl. No.: 17/430,721

(22) PCT Filed: Feb. 4, 2020

(86) PCT No.: PCT/US2020/016489

§ 371 (c)(1),
(2) Date: Aug. 12, 2021

(87) PCT Pub. No.: WO2020/167518

PCT Pub. Date: Aug. 20, 2020

(65) Prior Publication Data

US 2022/0143195 A1 May 12, 2022

Related U.S. Application Data

(60) Provisional application No. 62/804,822, filed on Feb. 13, 2019.

(51) Int. Cl.
*A61K 47/55* (2017.01)
*A61K 47/54* (2017.01)
*A61P 35/00* (2006.01)

(52) U.S. Cl.
CPC .............. *A61K 47/55* (2017.08); *A61K 47/54* (2017.08); *A61K 47/545* (2017.08); *A61P 35/00* (2018.01)

(58) Field of Classification Search
CPC ...... A61K 47/55; A61K 47/545; A61K 47/54; A61P 35/00
See application file for complete search history.

(56) References Cited

U.S. PATENT DOCUMENTS

| | | | |
|---|---|---|---|
| 8,586,751 | B2 | 11/2013 | De Lucca et al. |
| 10,130,659 | B2 | 11/2018 | Wardell et al. |
| 10,166,257 | B2 | 1/2019 | Wardell et al. |
| 10,272,113 | B2 | 4/2019 | Wardell et al. |
| 10,336,744 | B2 | 7/2019 | Harling et al. |
| 10,363,273 | B2 | 7/2019 | Wardell et al. |
| 10,398,734 | B2 | 9/2019 | Wardell et al. |
| 10,415,015 | B2 | 9/2019 | Veerapathran et al. |
| 10,420,799 | B2 | 9/2019 | Wardell et al. |
| 10,463,697 | B2 | 11/2019 | Wardell et al. |
| 10,517,894 | B2 | 12/2019 | Frank et al. |
| 10,537,595 | B2 | 1/2020 | Wardell et al. |
| 10,639,330 | B2 | 5/2020 | Wardell et al. |
| 10,646,517 | B2 | 5/2020 | Wardell et al. |
| 10,653,723 | B1 | 5/2020 | Wardell et al. |
| 10,695,372 | B2 | 6/2020 | Wardell et al. |
| 10,894,063 | B2 | 1/2021 | Wardell et al. |
| 10,918,666 | B2 | 2/2021 | Wardell et al. |
| 10,933,094 | B2 | 3/2021 | Wardell et al. |
| 10,946,044 | B2 | 3/2021 | Wardell et al. |
| 10,946,045 | B2 | 3/2021 | Wardell et al. |
| 10,953,046 | B2 | 3/2021 | Wardell et al. |
| 10,953,047 | B2 | 3/2021 | Wardell et al. |
| 11,007,226 | B2 | 5/2021 | Wardell et al. |
| 11,013,770 | B1 | 5/2021 | Wardell et al. |
| 11,026,974 | B2 | 6/2021 | Wardell et al. |
| 11,040,070 | B2 | 6/2021 | Wardell et al. |
| 11,052,115 | B2 | 7/2021 | Wardell et al. |
| 11,052,116 | B2 | 7/2021 | Wardell et al. |
| 11,058,728 | B1 | 7/2021 | Frank et al. |
| 11,083,752 | B2 | 8/2021 | Wardell et al. |
| 11,123,371 | B2 | 9/2021 | Wardell et al. |
| 11,479,556 | B1 | 10/2022 | Robbins et al. |
| 11,541,051 | B2 | 1/2023 | Jin et al. |
| 11,820,781 | B2 | 11/2023 | Kelly et al. |
| 11,866,442 | B2 | 1/2024 | Robbins et al. |
| 2007/0054355 | A1 | 3/2007 | Reiss et al. |

(Continued)

FOREIGN PATENT DOCUMENTS

| | | | |
|---|---|---|---|
| CN | 112 812 109 | A | 5/2021 |
| JP | 2016-539152 | A | 12/2016 |

(Continued)

OTHER PUBLICATIONS

Narula et al. Pediatr Blood Cancer. 2008; 51(6):826-8). (Year: 2008).*
International Search Report and Written Opinion for International Patent Application PCT/US2019/060584, 13 pages, Dec. 6, 2019.
International Search Report and Written Opinion for International Patent Application PCT/US2022/037029, 11 pages, Oct. 10, 2022.
International Search Report and Written Opinion for International Patent Application PCT/US2022/038084, 10 pages, Oct. 11, 2022.
International Search Report and Written Opinion for International Patent Application PCT/US2022/047767, 10 pages, Feb. 6, 2023.
International Search Report and Written Opinion for International Patent Application PCT/US2019/015250, 10 pages, Jun. 11, 2019.
International Search Report and Written Opinion for International Patent Application PCT/US2019/056112, 8 pages, Dec. 6, 2019.

(Continued)

*Primary Examiner* — Clinton A Brooks
*Assistant Examiner* — Jerica Katlynn Wilson
(74) *Attorney, Agent, or Firm* — Squire Patton Boggs (US) LLP

(57) ABSTRACT

The present invention relates to compounds useful for degrading BTK via a ubiquitin proteolytic pathway. The invention also provides pharmaceutically acceptable compositions comprising said compounds and methods of using the compositions in the treatment of various disease, conditions, or disorders.

21 Claims, No Drawings

(56) References Cited

U.S. PATENT DOCUMENTS

| | | | |
|---|---|---|---|
| 2017/0015655 | A1 | 1/2017 | Kaieda et al. |
| 2020/0323904 | A1 | 10/2020 | Sands et al. |
| 2021/0053961 | A1 | 2/2021 | Sands et al. |
| 2021/0053986 | A1 | 2/2021 | Sands et al. |
| 2021/0085717 | A1 | 3/2021 | Gosling et al. |
| 2021/0087259 | A1 | 3/2021 | Gosling et al. |
| 2021/0198280 | A1 | 7/2021 | Kelly et al. |
| 2023/0024442 | A1 | 1/2023 | Robbins et al. |
| 2023/0029378 | A1 | 1/2023 | Robbins et al. |
| 2023/0149416 | A1 | 5/2023 | Brown et al. |
| 2023/0227471 | A1 | 7/2023 | Kelly et al. |
| 2025/0017922 | A1 | 1/2025 | Guiducci et al. |
| 2025/0136579 | A1 | 5/2025 | Phiasivongsa et al. |

FOREIGN PATENT DOCUMENTS

| | | | | |
|---|---|---|---|---|
| WO | WO 2007/072225 | A2 | 6/2007 | |
| WO | WO 2008/033403 | A2 | 3/2008 | |
| WO | WO 2009/073905 | A2 | 6/2009 | |
| WO | WO 2009/098144 | A1 | 8/2009 | |
| WO | WO 2010/144647 | A1 | 12/2010 | |
| WO | WO 2011/140488 | A1 | 11/2011 | |
| WO | WO 2012/020008 | A1 | 2/2012 | |
| WO | WO 2012/089736 | A1 | 7/2012 | |
| WO | WO 2013/067264 | A1 | 5/2013 | |
| WO | WO 2013/067274 | A1 | 5/2013 | |
| WO | WO 2013/106643 | A2 | 7/2013 | |
| WO | WO 2014/040965 | A1 | 3/2014 | |
| WO | WO 2016/169989 | | 10/2016 | |
| WO | WO 2015/084998 | A1 | 12/2016 | |
| WO | WO-2016196776 | A2 * | 12/2016 | ........... A61K 31/497 |
| WO | WO 2018/098275 | A1 | 5/2018 | |
| WO | WO 2018/106870 | | 6/2018 | |
| WO | WO 2019/148005 | A1 | 8/2019 | |
| WO | WO 2019/148150 | A1 | 8/2019 | |
| WO | WO 2019/246315 | A1 | 12/2019 | |
| WO | WO 2020/081450 | A1 | 4/2020 | |
| WO | WO 2020/167518 | A1 | 8/2020 | |
| WO | WO 2020/210508 | A1 | 10/2020 | |
| WO | WO 2020/236654 | A1 | 11/2020 | |
| WO | WO 2020/264398 | A1 | 12/2020 | |
| WO | WO 2021/021761 | A1 | 2/2021 | |
| WO | WO 2021/061853 | A1 | 4/2021 | |
| WO | WO 2021/061870 | A1 | 4/2021 | |
| WO | WO 2021/091575 | A1 | 5/2021 | |
| WO | WO 2021/113557 | A1 | 6/2021 | |
| WO | WO 2022/093742 | | 5/2022 | |
| WO | WO 2023/004163 | A1 | 1/2023 | |
| WO | WO 2023/287928 | A1 | 1/2023 | |
| WO | WO 2023/076303 | A1 | 5/2023 | |
| WO | WO 2024/227104 | A1 | 10/2024 | |
| WO | WO 2025/090535 | A1 | 5/2025 | |

OTHER PUBLICATIONS

International Search Report and Written Opinion for International Patent Application PCT/US2020/016489, 8 pages, May 27, 2020.

International Search Report and Written Opinion for International Patent Application PCT/US2020/033274, 19 pages, Oct. 23, 2020.

International Search Report and Written Opinion for International Patent Application PCT/US2020/027492, 21 pages, Aug. 11, 2020.

International Search Report and Written Opinion for International Patent Application PCT/US2020/039957, 16 pages, Oct. 5, 2020.

International Search Report and Written Opinion for International Patent Application PCT/US2020/043788, 16 pages, Oct. 23, 2020.

International Search Report and Written Opinion for International Patent Application PCT/US2020/063176, 12 pages, Mar. 5, 2021.

International Search Report and Written Opinion for International Patent Application PCT/US2020/052317, 12 pages, Apr. 1, 2021.

International Search Report and Written Opinion for International Patent Application PCT/US2020/052335, 12 pages, Apr. 1, 2021.

Gosling et al.: "Abstract 2696: Genetic and pharmacologic evaluation of the ubiquitin ligase CBL-B as a small-molecule, tumor immunotherapy target I Cancer Research," Apr. 3, 2019 (Apr. 3, 2019), XP055701108, Retrieved from the Internet:U RL:https:// cancerres.aacrjournals.org/content/79/13_Supplement/2696 [retrieved on Jun. 4, 2020].

Marshall et al., "Superior Activity of the Type C Class of ISS In Vitro and In Vivo Across Multiple Species," DNA and Cell Biology, vol. 24, No. 2, 2005, pp. 63-72.

Riling et al.: "Abstract A206: Small-molecule Cbl-b inhibitors as novel intracellular checkpoint inhibitors for cancer immunotherapy I Molecular Cancer Therapeutics," Jan. 1, 2018 (Jan. 1, 2018), XP055700949, Retrieved from the Internet: URL:https:// mct. aacrjournals.org/content/17/1_Supplement/A206 [retrieved on Jun. 4, 2020].

Yang et al., "Exploiting Synthetic Lethality for the Therapy of ABC Diffuse Large B Cell Lymphoma," Cancer Cell, 21, 2012, pp. 723-737, DOI 10.1016/j.ccr.2012.05.024.

Bondeson et al., "Catalytic in vivo protein knockdown by small-molecule PROTACs," Nature Chemical Biology, published online Jun. 10, 2015; DOI: 10.1038/NCHEMBIO.1858.

Good et al., Proliferative tracing with single-cell mass cytometry optimizes generation of stem cell memory-like T cells, Nature Biotechnology Mar. 2019; 37(3): 259-266. DOI:10.1038/s41587-019-0033-2.

Howe et al, " Models of Energy in the Human Jurkat T Cell Line," Assay and Drug Development Technologies, vol. 1, No. 4, 2003, pp. 537-544.

Stewart et al., "Efforts toward elucidating Thalidomide's molecular target: an expedient synthesis of the first Thalidomide biotin analogue," Org. Biomol. Chem., 2010, 8:4059-4062.

Tigno-Aranjuez et al., "Inhibition of RIP2's tyrosine kinase activity limits NOD2-driven cytokine responses," Genes & Development, 2010, 24:2666-2677; http://www.genesdev.org/cgi/doi/10.1101/gad.964410.

Hines et al., "Posttranslational protein knockdown coupled to receptor tyrosine kinase activation with phophoPROTACs," 2013, PNAS, 110(22):8942-8947.

International Search Report and Written Opinion for International Patent Application PCT/US2024/026679, 8 pages, Sep. 18, 2024.

Advani et al., "Bruton tyrosine kinase inhibitor ibrutinib (PCI-32765) has significant activity in patients with relapsed/refractory B-cell malignancies", . J Clin Oncol. Jan. 1, 2013;31(1):88-94. doi: 10.1200/JCO.2012.42.7906. Epub Oct. 8, 2012. PMID: 23045577; PMCID: PMC5505166.

Caira Ed, Montchamp Jean-Luc, "Crystalline Polymorphism of Organic Compounds", Topics in Current Chemistry, Springer, Berlin DE, vol. 198, Jan. 1, 1998, pp. 163-208, XP008166276, ISSN: 0340-1022.

Cancer.Net, "What to Expect When Having Chemotherapy", Cancer. Net, Asco | Knowledge Conquers Center pp. 1-5, 2024.

Gerritse et al., "High-dose administration of tyrosine kinase inhibitors to improve clinical benefit: A systematic review", Cancer Treatment Reviews, 97(2021) 102171.

Golub et a., "Moleucuar classification of cancer: class discovery classs prediction by gene expression monitoring", Science, Oct. 15, 1999: 286(5439):531-537; doi10.1126/science.286.5439.531.

Hilfiker R (Editor) Ed, "Polymorphism in the Pharmaceutical Industry", Jan. 1, 2006, pp. 1-19, XP002528052, ISBN: 978-3-527-31146-0.

Kim et al., "A novel cereblon modulator for targeted protein degradation". Eur J Med Chem. Mar. 15, 2019;166:65-74. doi: 10.1016/j.ejmech.2019.01.023. Epub Jan. 17, 2019. PMID: 30684871.

Liang et al., "The development of Bruton's tyrosine kinase (BTK) inhibitors from 2012 to 2017: A mini-review", Eur J Med Chem. May 10, 2018;151:315-326. doi: 10.1016/j.ejmech.2018.03.062. Epub Mar. 23, 2018. PMID: 29631132.

Marini et al. "Investigation into the Use of Encorafenib to Develop Potential PROTACs Directed Against BRAFV600E Protein", Molecules, vol. 27, No. 23, Dec. 2022. DOI:10.3390/molecules27238513.

Montoya et al., "Kinase-impaired BTK Mutations are susceptible to clinical-stage BTK and IKZF1/3 degrader NX-2127", Science, 383, 496 (2024) 1-13. Https://doi.org/10.1126/science.adi5798.

(56) References Cited

OTHER PUBLICATIONS

Rothman et al., "The Use of Common Genetic Polymorphisms to enhance the epidemiologic study of environmental carcinogens", Biochimica et Biophysica Acta 1471 C1-C10 (2001).
Srushti Tambe, "Recent Advances in Amorphous Solid Dispersions: Preformulation, Formulation Strategies, Technological Advancements and Characterization", Pharmaceutics, vol. 14, No. 10, Oct. 16, 2022 (Oct. 16, 2022), CH , pp. 1-33, XP093156308, ISSN: 1999-4923, DOI: 10.3390/pharmaceutics14102203.
Steinbach et al. "A Medchem toolbox for cereblon-directed PROTRACs" Medchemcom, vol. 10, No. Julne 19, 20219 pp. 1037-1041. DOI:10.1039/C9MD00185A.
Ye et al., "Engineered Artificial Antigen Presenting Cells Facilitate Direct and Efficient Expansion of Tumor Infiltrating Lymphocytes", Journal of Translation Medicine 2011, 9:131, 13 pages.

* cited by examiner

BIFUNCTIONAL COMPOUNDS FOR DEGRADING BTK VIA UBIQUITIN PROTEOSOME PATHWAY

CROSS REFERENCE TO RELATED APPLICATION

The present application is a 35 USC 371 national phase filing of PCT/US2020/016489 filed on Feb. 4, 2020, which claims the benefit and priority of U.S. provisional application No. 62/804,822, filed on Feb. 13, 2019, all of which applications are herein incorporated by reference in their entireties.

FIELD OF THE INVENTION

The present invention provides novel bifunctional compounds for proteolytically degrading targeted Bruton's tyrosine kinases (BTK) and methods for treating diseases modulated by BTK.

BACKGROUND

B cell receptor (BCR) signaling controls B cell development, as well as mature B cell activation, signaling and survival. Mis-regulation of the BCR signaling pathway is associated with numerous disease indications involving B cell function, and targeting B cells and BCR signaling has clear therapeutic potential (Woyach, et al.; *Blood.* 120(6); 1175-1184. 2012.). For example, depletion of B cells with monoclonal antibodies targeting CD20 has significant effects in treatment of B cell malignancies and auto-immune and inflammatory diseases (Cang, et al.; *J Hematolo Oncol.* 5; 64, 2012.).

BTK is a member of the TEC family of kinases and is a crucial signaling hub in the BCR pathway. Mutations in BTK result in X-linked agammaglobulinemia (XLA), in which B cell maturation is impaired, resulting in reduced immunoglobulin production (Hendriks, et al.; *Expert Opin Ther Targets* 15; 1002-1021, 2011.). The central role of BTK in B cell signaling and function makes BTK an attractive therapeutic target for B cell malignancies as well as autoimmune and inflammatory diseases. Ibrutinib, a covalent inhibitor of BTK, has been approved to treat chronic lymphocytic leukemia (CLL), mantle cell lymphoma (MCL) and other B cell malignancies, as well as graft-versus-host disease (GvHD) (Miklos, et al.; *Blood.* 120(21); 2243-2250. 2017). Currently, ibrutinib and second-generation BTK inhibitors are being investigated for oncology and immune-related indications such as rheumatoid arthritis (Akinleye, et al.; *J of Hematolo Oncol.* 6: 59, 2013; Liu, et al.; *J Pharm and Exper Ther.* 338(1): 154-163. 2011; Di Paolo, et al.; *Nat Chem Biol.* 7(1): 41-50. 2011).

As an alternative to stoichiometric inhibition, proteolytic degradation of BTK could have dramatic consequences for B cell function by effectively blocking BCR signaling. Removal of BTK protein would eliminate BTK kinase activity as well as any protein interaction or scaffolding function of BTK. Specific degradation of BTK could be accomplished using heterobifunctional small molecules to recruit BTK to a ubiquitin ligase and thus promoting ubiquitylation and proteasomal degradation of BTK. Thalidomide derivatives, such as lenalidomide or pomalidomide, can be used to recruit potential substrates to cereblon (CRBN), a component of a ubiquitin ligase complex. This unique therapeutic approach could present a mechanism of action for interfering with BTK activity and BCR signaling that is distinct from the mechanism of stoichiometric BTK inhibition. Furthermore, this degradative approach could effectively target the C481S mutated form of BTK, which mutation has been clinically observed and confers resistance to inhibition by ibrutinib (Woyach, et al.; *Blood.* 120(6): 1175-1184. 2012.).

Presently, there remains a need for bifunctional molecules that can induce the proteolytic degradation of BTK via a ubiquitin proteolytic pathway.

SUMMARY OF THE INVENTION

The present invention provides bifunctional compounds that induce the proteolytic degradation of BTK via a ubiquitin proteolysis pathway. The present invention also provides a compound of Formula (I)

(I)

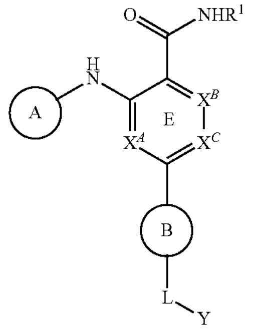

or a pharmaceutically acceptable salt thereof, wherein $R^1$ is —H or —$C_{1-4}$ alkyl; each of $X^A$, $X^B$, and $X^C$ is independently N or $CR^2$; each $R^2$ is independently —H or —$C_{1-4}$ alkyl, or $R^1$ and $R^2$ taken together with the atoms to which they are attached form a monocyclic heterocycle fused to ring E; ring A is phenyl, a 4-6 membered monocyclic heteroaryl group having 1-3 heteroatoms independently selected from N, O, and S, or a 9-10 membered bicyclic heteroaryl having 1-3 heteroatoms independently selected from N, O, and S, wherein ring A is optionally substituted with —$Z^A$—$R^A$, $Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, —$CO_2$—, —OCO—, —O—, —S—, —S(O)—, —$S(O)_2$—, —$S(O)_2N(R)$—, or —$N(R)S(O)_2$—, and $R^A$ is hydrogen, halo, —OH, —$NH_2$, —$NO_2$, —CN, —$CF_3$, —$CH_3$, or —$OCH_3$, or ring A, $X^A$, and the atoms to which they are attached form a ring fused to ring E selected from

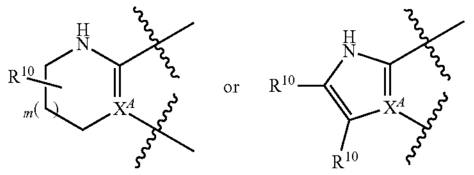

wherein $X^A$ is C, $X^B$ of ring E is N, each $R^{10}$ is independently —H or —$C_{1-4}$ alkyl, and m is 0, 1, or 2; ring B is an unsaturated 4-8 membered monocyclic heterocycle having one nitrogen atom and up to 1 additional heteroatom selected from N, O, or S; L is —$X^1$—$X^2$—$X^3$—$X^4$—; $X^1$ is —N(R)—C(O)—O—, —N(R)—C(O)—, —C(O)—N(R)—, or 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo; $X^2$ is a bond, —$(CH_2)_n$—O—, —O—$(CH_2)_n$—, —$C_{1-8}$ alkyl-, a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, a 6-10 membered fused bicyclic heterocycloalkyl having 1-3 heteroatoms independently selected from N, O, or S, or a 6-9 membered bridged bicyclic heterocycloalkyl having 1-3 heteroatoms independently selected from N, O, or S, wherein the spiro bicyclic heterocycloalkyl ring system is optionally substituted with —OH or oxo; $X^3$ is a bond, —O—, —$(CH_2)_n$—O—, —$C_{1-4}$ alkyl-, or a 4-6 membered heterocycloalkyl ring having 1-2 heteroatoms independently selected from N, O, or S; $X^4$ is a bond, —$C_{1-4}$ alkyl-, or a 4-6 membered heterocycloalkyl ring having 1-2 heteroatoms independently selected from N, O, or S; each R is independently —H or —$C_{1-3}$ alkyl; each n is independently 1, 2, or 3;

Y is

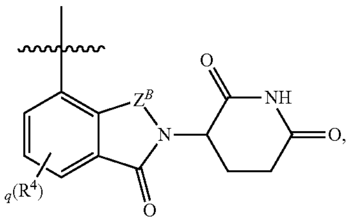

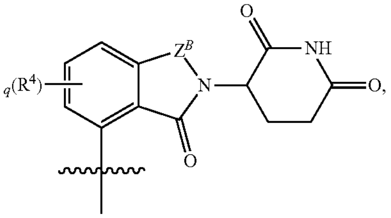

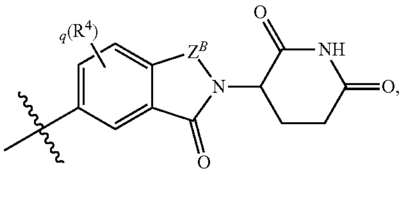

or

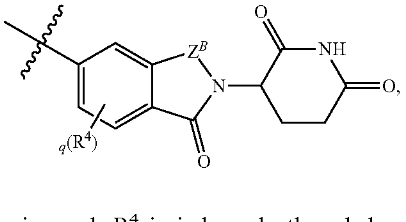

wherein; each $R^4$ is independently a halo or a $C_{1-4}$ alkyl; each $Z^B$ is —$C(R^B)_2$— or —C(O)—; each $R^B$ is —H or —$C_{1-4}$ alkyl; and q is 0, 1, or 2.

In some embodiments, the compound of Formula (I) is (I)

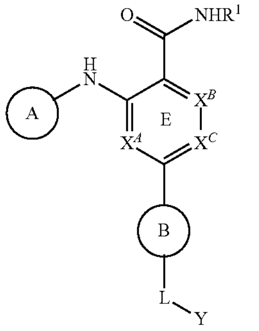

or a pharmaceutically acceptable salt thereof, wherein $R^1$ is —H or —$C_{1-4}$ alkyl; each of $X^A$, $X^B$, and $X^C$ is independently N or $CR^2$; each $R^2$ is independently —H or —$C_{1-4}$ alkyl, or $R^1$ and $R^2$ taken together with the atoms to which they are attached form a monocyclic heterocycle fused to ring E; ring A is phenyl, a 4-6 membered monocyclic heteroaryl group having 1-3 heteroatoms independently selected from N, O, and S, or a 9-10 membered bicyclic heteroaryl having 1-3 heteroatoms independently selected from N, O, and S, wherein ring A is optionally substituted with —$Z^A$—$R^A$, $Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, —$CO_2$—, —OCO—, —O—, —S—, —S(O)—, —$S(O)_2$—, —$S(O)_2N(R)$—, or —$N(R)S(O)_2$—, and $R^A$ is hydrogen, halo, —OH, —$NH_2$, —$NO_2$, —CN, —$CF_3$, —$CH_3$, or —$OCH_3$; ring B is an unsaturated 4-8 membered monocyclic heterocycle having one nitrogen atom and up to 1 additional heteroatom selected from N, O, or S; L is —$X^1$—$X^2$—$X^3$—$X^4$—; $X^1$ is —N(R)—C(O)—O—, —N(R)—C(O)—, —C(O)—N(R)—, or 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo; $X^2$ is a bond, —$(CH_2)_n$—O—, —O—$(CH_2)_n$—, —$C_{1-8}$ alkyl-, a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, a 6-10 membered fused bicyclic heterocycloalkyl having 1-3 heteroatoms independently selected from N, O, or S, or a 6-9 membered bridged bicyclic heterocycloalkyl having 1-3 heteroatoms independently selected from N, O, or S, wherein the spiro bicyclic heterocycloalkyl ring system is optionally substituted with —OH or oxo; $X^3$ is a bond, —O—, —$(CH_2)_n$—O—, —$C_{1-4}$ alkyl-, or a 4-6 membered heterocycloalkyl ring having 1-2 heteroatoms independently selected from N, O, or S; $X^4$ is a bond, —$C_{1-4}$ alkyl-, or a 4-6 membered heterocycloalkyl ring having 1-2 heteroatoms independently selected from N, O, or S; each R is independently —H or —$C_{1-3}$ alkyl; each n is independently 1, 2, or 3; Y is

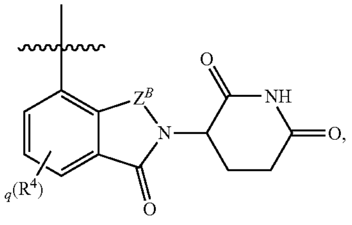

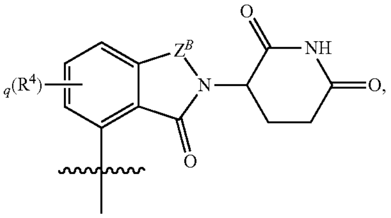

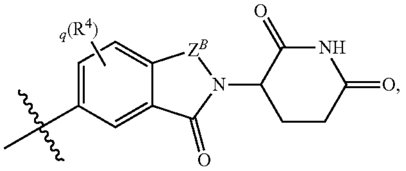

or

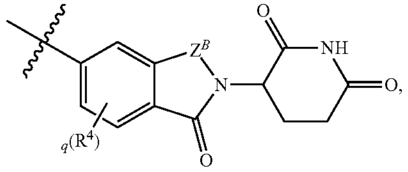

wherein; each $R^4$ is independently a halo or a $C_{1-4}$ alkyl; each $Z^B$ is $—C(R^B)_2—$ or —C(O)—; each $R^B$ is —H or $—C_{1-4}$ alkyl; and q is 0, 1, or 2.

In some embodiments, q is 0. In other embodiments, q is 1.

In some embodiments, Y is

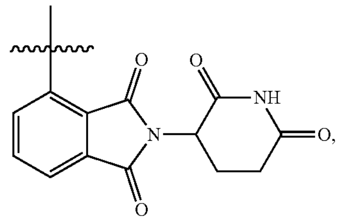

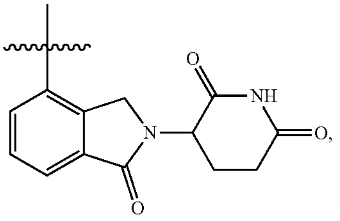

or

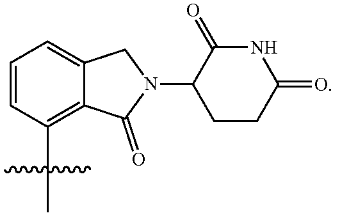

In other embodiments, Y is

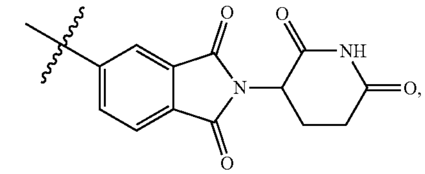

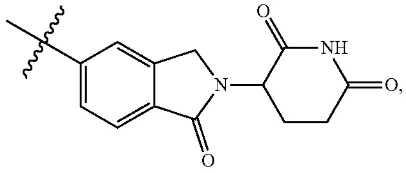

or

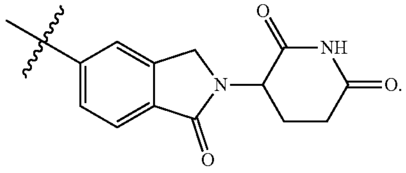

For example, Y is

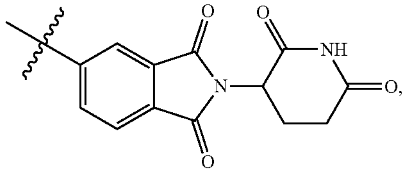 [SMILES: *c1ccc2c(c1)C(=O)N(C1CCC(=O)NC1=O)C2=O]

In some embodiments, ring A is phenyl optionally substituted with $—Z^A—R^A$, wherein $Z^A$ is a bond, —C(O)—, $—CO_2—$, —OCO—, —S—, —O—, —S(O)—, or $—S(O)_2—$, and $R^A$ is hydrogen, halo, —OH, $—CF_3$, or $—CH_3$. In some examples, ring A is

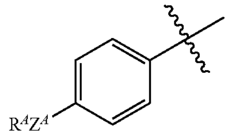

or

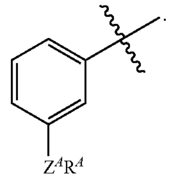

In other examples, ring A is

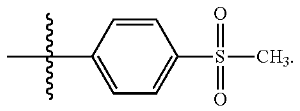 [SMILES: *c1ccc(S(C)(=O)=O)cc1]

In some embodiments, ring A is a 5-6 membered monocyclic heteroaryl group having 1-3 heteroatoms independently selected from N, O, and S optionally substituted with $—Z^A—R^A$, wherein $Z^A$ is an optionally substituted branched or straight $C_{1-3}$ aliphatic chain, and $R^A$ is hydrogen, halo, —OH, $—NH_2$, $—NO_2$, —CN, $—CF_3$, or $—OCH_3$. In some examples, ring A is

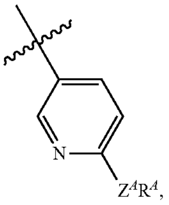

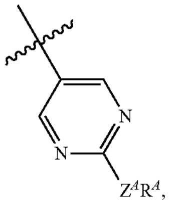

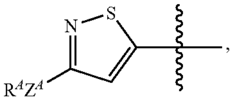

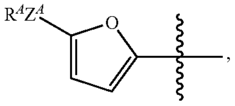

or

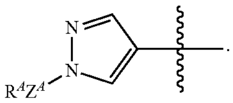

In other examples, ring A is

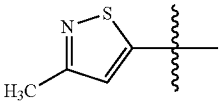

or

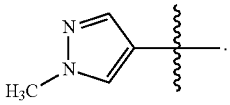

In some embodiments, $X^1$ is —N(H)—C(O)—, —C(O)—N(H)—, —N(CH$_3$)—C(O)—, or —C(O)—N(CH$_3$)—. In some examples, $X^1$ is —NH—C(O)— or —N(CH$_3$)—C(O)—.

In some embodiments, $X^2$ is —CH$_2$—O—, —(CH$_2$)$_2$—O—, —(CH$_2$)$_3$—O—, —CH$_2$—, -n-butyl-, or -n-hexyl-.

In some embodiments, $X^2$ is an 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo. In some examples, $X^2$ is

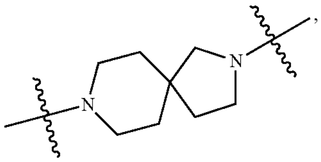

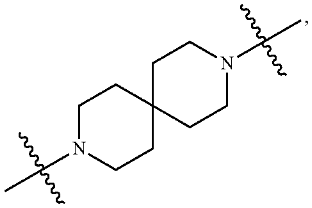

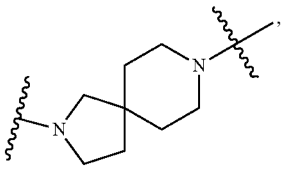

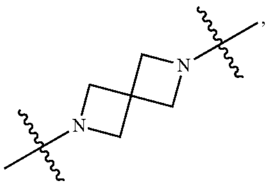

-continued

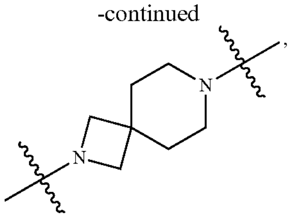

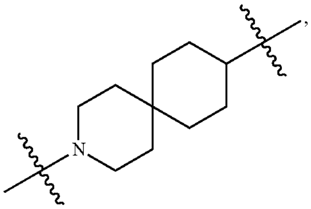

or

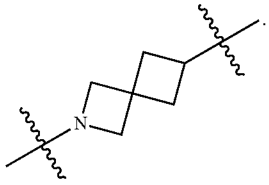

In some embodiments, $X^2$ is a 4-6 membered monocyclic heterocycloalkyl having 1-2 heteroatoms independently selected from N, O, or S. In some examples, $X^2$ is

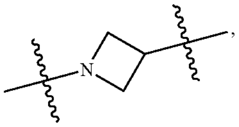

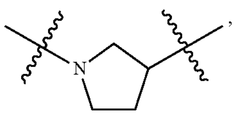

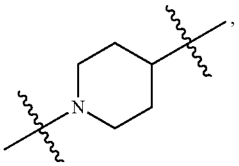

or

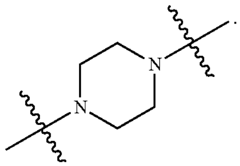

In some embodiments, $X^2$ is a 6-10 membered fused bicyclic heterocycloalkyl having 1-3 heteroatoms independently selected from N, O, or S. In some examples, $X^2$ is

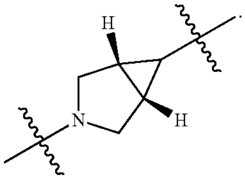 [SMILES: *C1[C@H]2CN(*)C[C@@H]12]

In some embodiments, $X^2$ is a 6-9 membered bridged bicyclic heterocycloalkyl having 1-3 heteroatoms independently selected from N, O, or S. In some examples, $X^2$ is

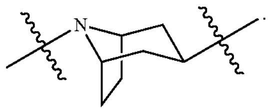

In some embodiments, $X^3$ is a bond, —$CH_2$—O—, —$C_{1-4}$ alkyl-,
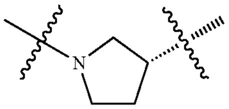,
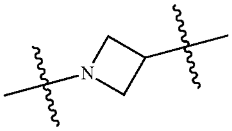,
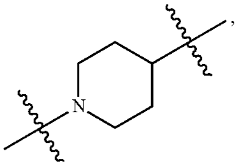, or
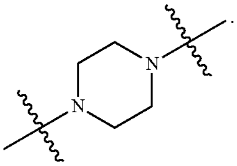.
In some embodiments, $X^4$ is a bond, —$C_{1-4}$ alkyl-,
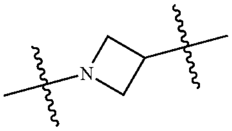, or
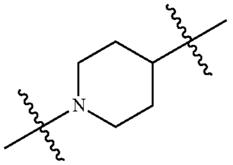.
In some embodiments, L is selected from
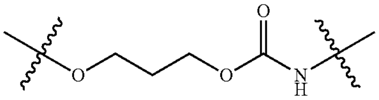,
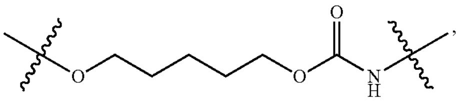,
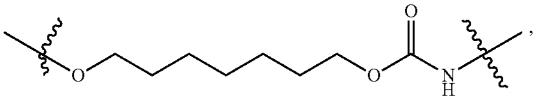,
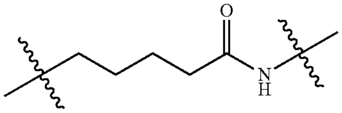,
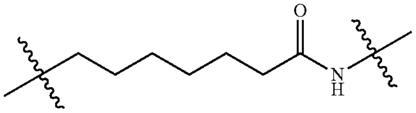,
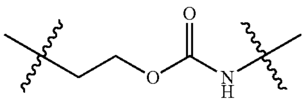,
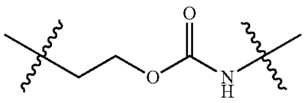,
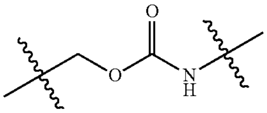,
-continued
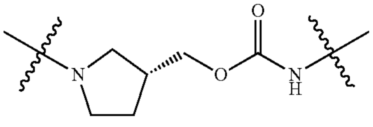,
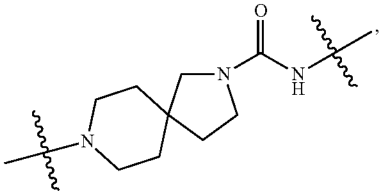,
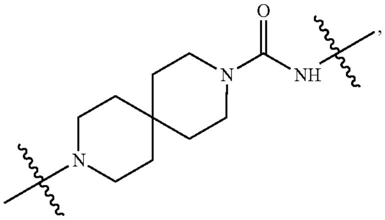,
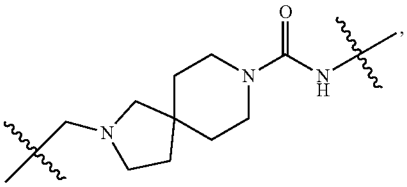,
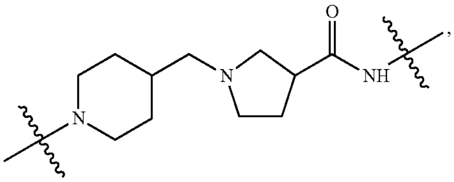,
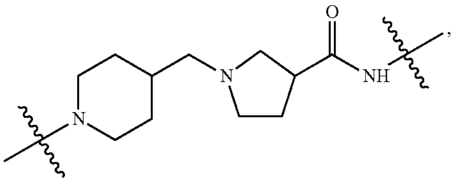,
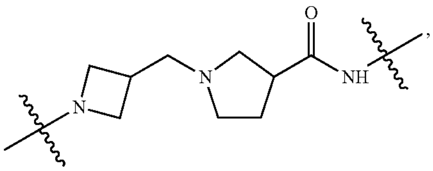,
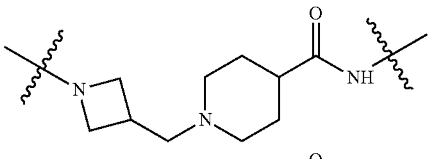,
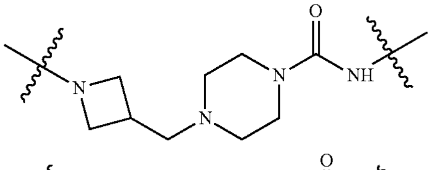,
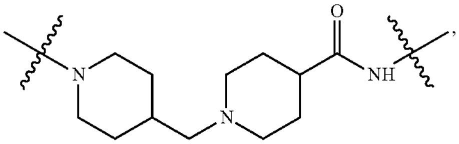, -continued
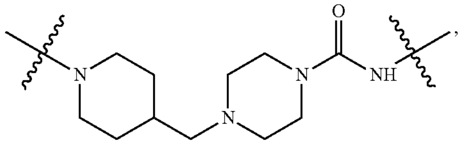
,
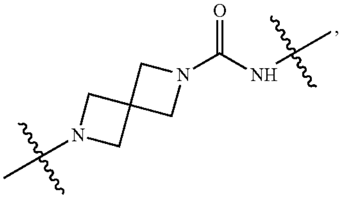
,
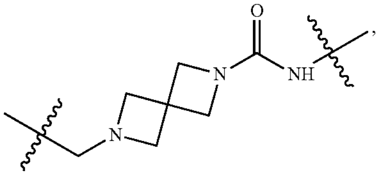
,
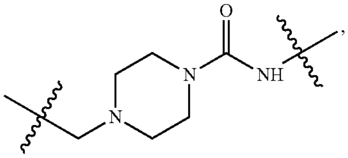
,
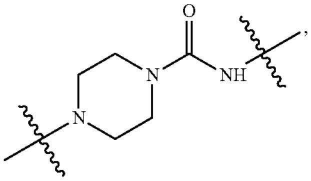
,
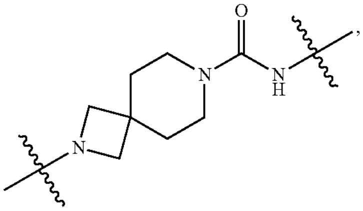
,
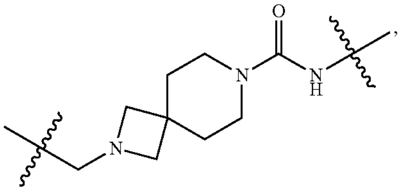
,
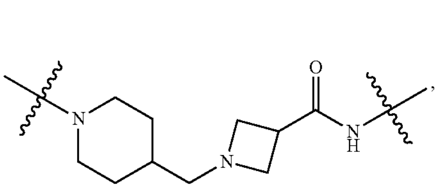
,
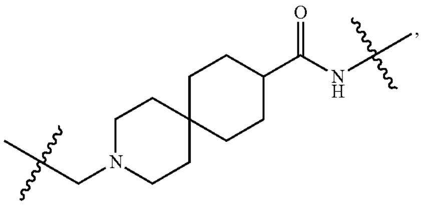
,
-continued
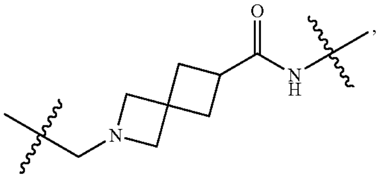
,
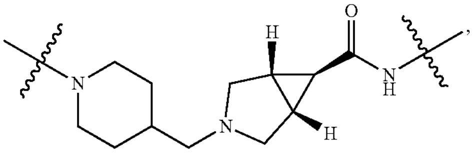
,
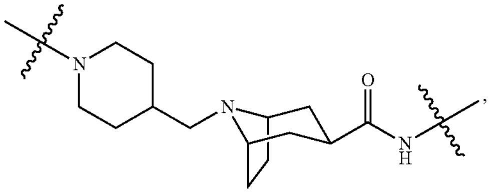
,
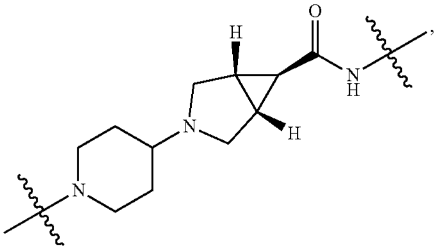
,
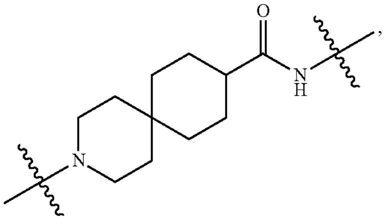
,
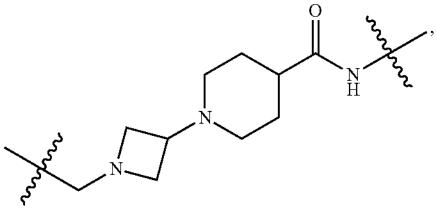
,
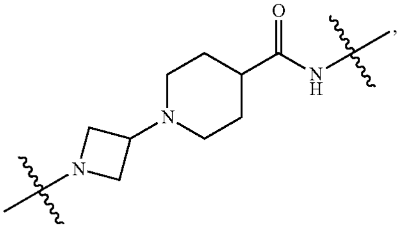
,
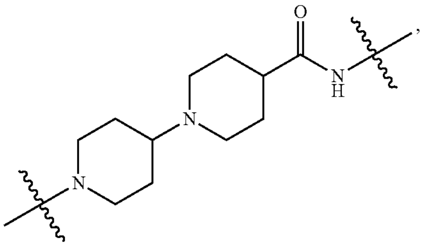
, -continued

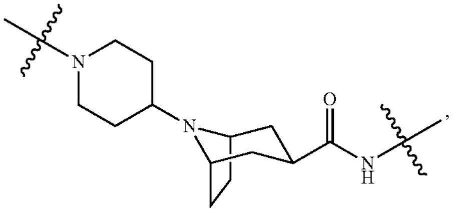

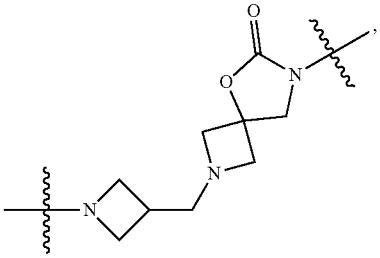

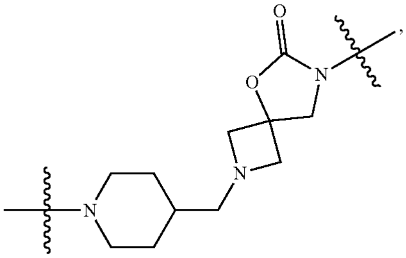

or

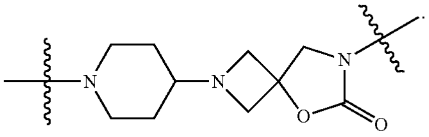

In some embodiments for the compound of Formula (I), (i) ring A is

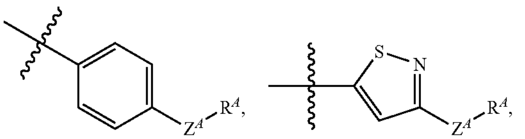

or

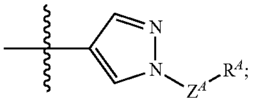

(ii) L is —$X^1$—$X^2$—$X^3$—$X^4$—;

(iii) $X^1$ is —NH—C(O)—;

(iv) $X^2$ is a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, or a 6-10 membered fused bicyclic heterocycloalkyl having 1-3 heteroatoms independently selected from N, O, or S, wherein the spiro bicyclic heterocycloalkyl ring system is optionally substituted with —OH or oxo;

(v) $X^3$ is a bond, a 4-6 membered monocyclic heterocycloalkyl having 1-2 heteroatoms independently selected from N, O, or S, or a —$C_{1-4}$ alkyl-;

(vi) $X^4$ is a bond, a 4-6 membered heterocycloalkyl having 1-2 heteroatoms independently selected from N, O, or S, or a —$C_{1-4}$ alkyl-; and (vii) Y is

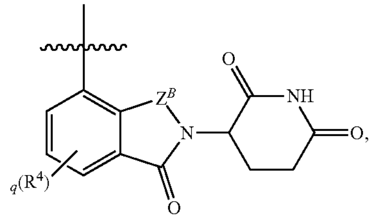

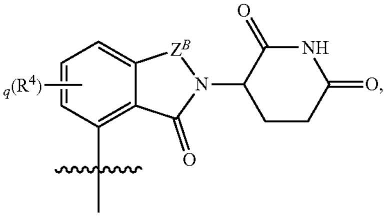

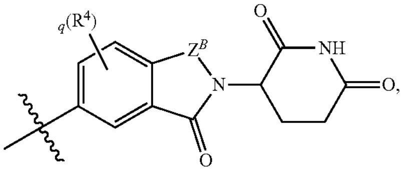

or

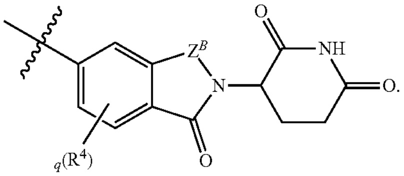

In some embodiments, q is 0.

In some embodiments, Y is

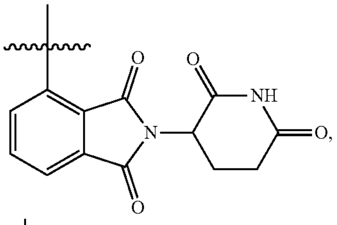

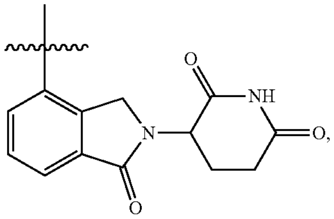

or

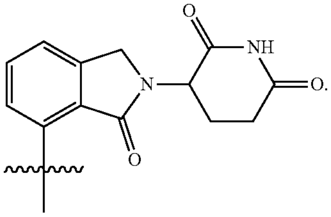

In other embodiments, Y is
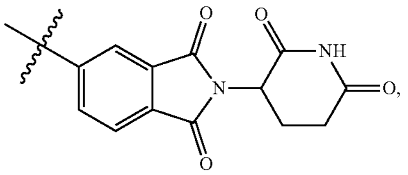
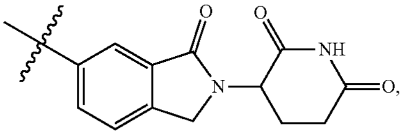
or
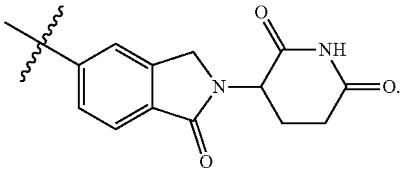
For example, Y is
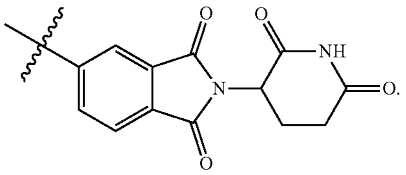 [SMILES: *c1ccc2c(c1)C(=O)N(C1CCC(=O)NC1=O)C2=O]
In some embodiments, ring A is
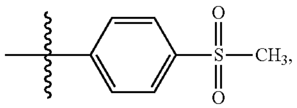
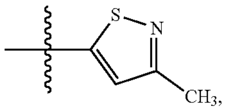
or
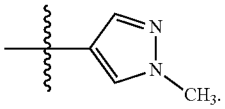
In some embodiments, $X^2$ is
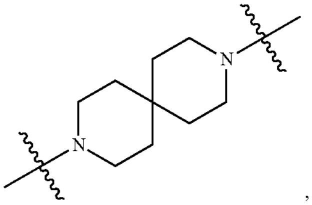
,
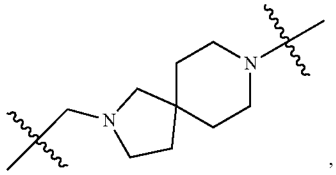
,
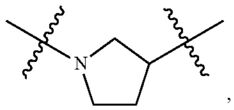
,
-continued
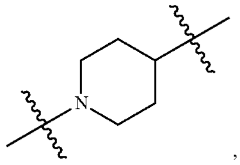
,
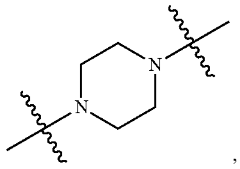
,
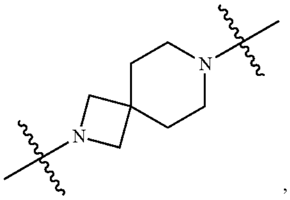
,
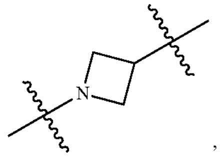
,
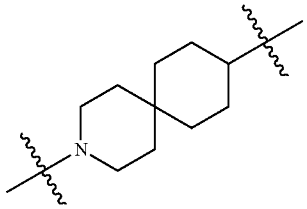
, or
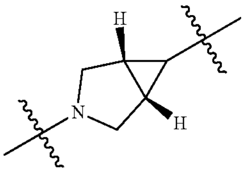
.
In some embodiments, $X^3$ is bond, —$C_{1-4}$ alkyl-, or
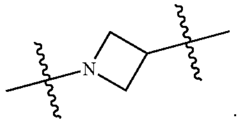 [SMILES: *C1CN(*)C1]
.
In some embodiments, $X^4$ is bond, —$C_{1-4}$ alkyl-,
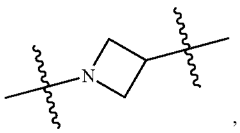
, or
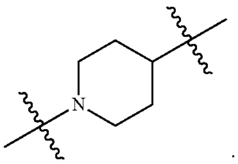
.
In some embodiments, L is selected from
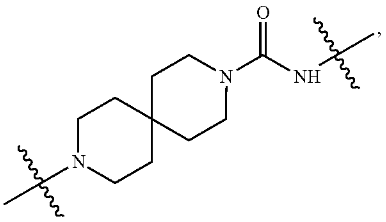

-continued
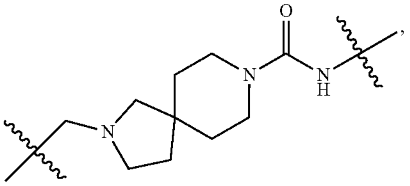
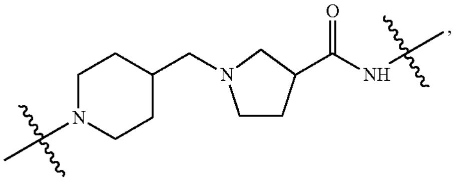
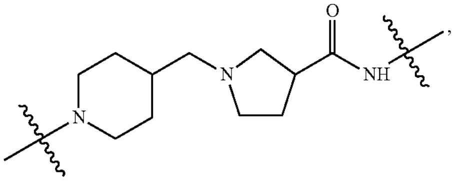
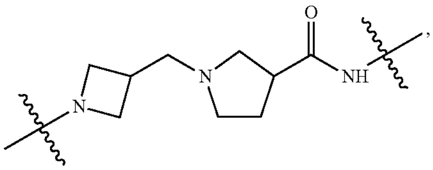
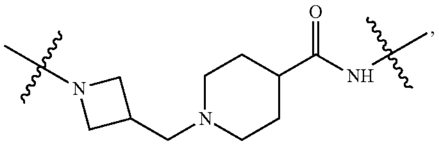
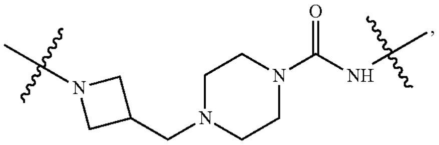
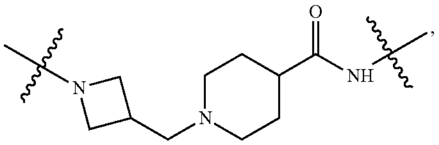
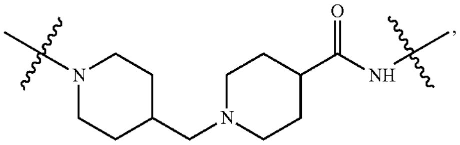
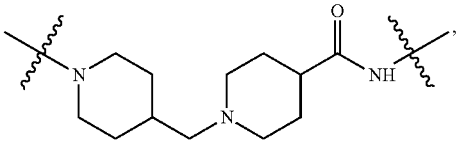
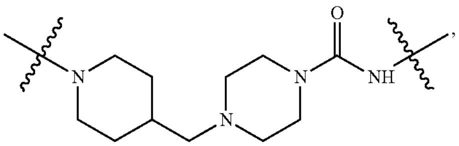
-continued
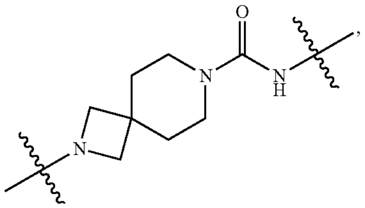
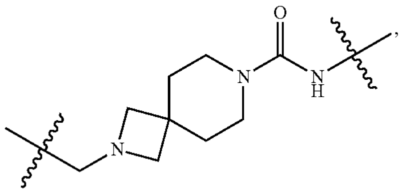
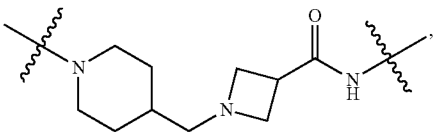
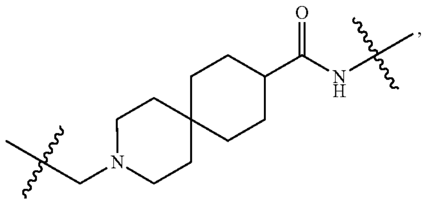
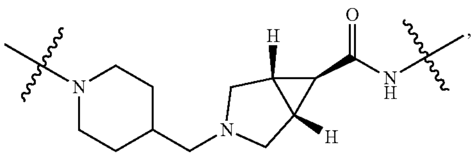
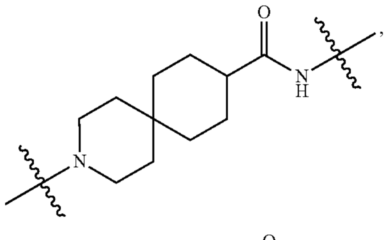
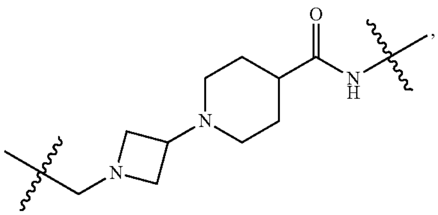
and
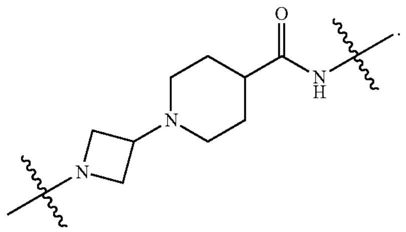

In some embodiments, the compound of Formula (I) is a compound of Formula (IA) or a compound of Formula (IB)

(IA)

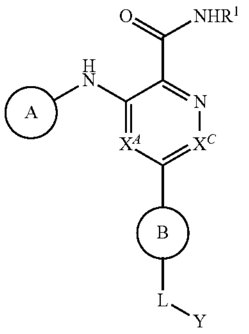

(IB)

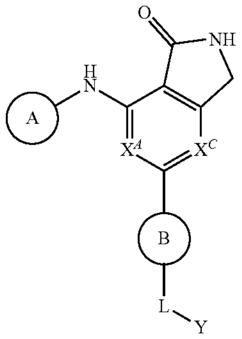

or a pharmaceutically acceptable salt thereof, wherein $R^1$, $X^A$, $X^C$, ring A, ring B, L and Y are as defined for any embodiment of the compound of Formula (I).

In some embodiments, the compound of Formula (IA) is a compound of Formula (IA-1)

(IA-1)

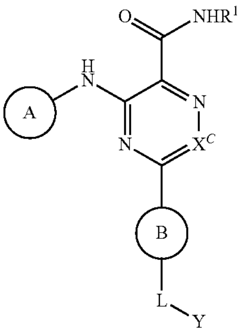

or a pharmaceutically acceptable salt thereof, wherein $R^1$, $X^C$, ring A, ring B, L and Y are as defined for any embodiment of the compound of Formula (I).

In some embodiments, the compound of Formula (IA-1) is a compound of Formula (IA-1A), (IA-1B), or (IA-1C)

(IA-1A)

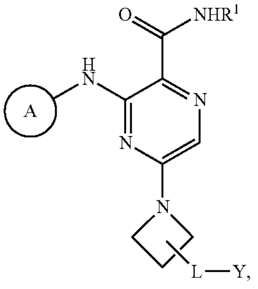

(IA-1B)

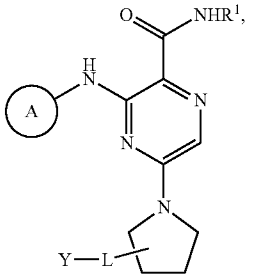

(IA-1C)

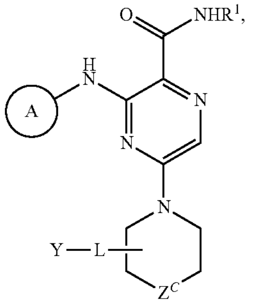

or a pharmaceutically acceptable salt thereof, wherein $Z^C$ is —$NR^3$—, —O—, —$CHR^3$—, or —$S(O)_2$—; and each $R^3$ is independently selected from —H and $C_{1-4}$ alkyl. $R^1$, $X^C$, ring A, L, and Y are as defined for any embodiment of the compound of Formula (I).

In some embodiments, the compound of Formula (IA-1C) is a compound of Formula (IA-2A)

(IA-2A)

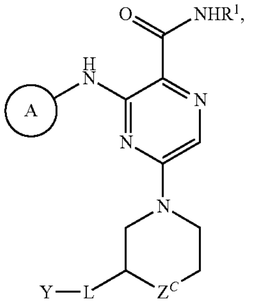

or a pharmaceutically acceptable salt thereof, wherein $R^1$, $R^3$, $Z^C$, ring A, L, and Y are as defined for the compound of Formula (1A-1C).

In some embodiments, the compound of Formula (IA-1B) is a compound of Formula (IA-2B) or (IA-2C)

(IA-2B)

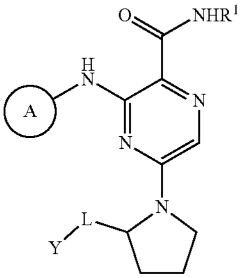

(IA-2C)

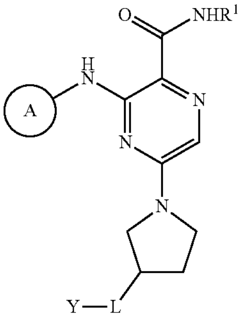

or a pharmaceutically acceptable salt thereof, wherein $R^1$, ring A, L, and Y are as defined for the compound of Formula (IA-1B).

In some embodiments, the compound of Formula (IA-1A) is a compound of Formula (IA-2D) or (IA-2E)

(IA-2D)

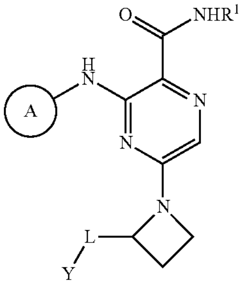

(IA-2E)

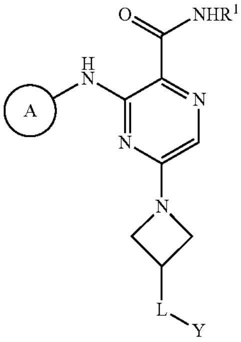

or a pharmaceutically acceptable salt thereof, wherein $R^1$, ring A, L, and Y are as defined for the compound of Formula (IA-1A).

In some embodiments, the compound of Formula (IB) is a compound of Formula (IB-1)

(IB-1)

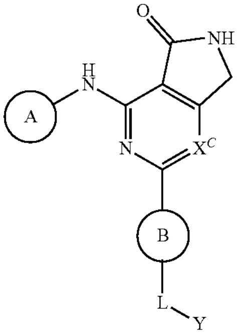

or a pharmaceutically acceptable salt thereof, wherein $X^C$, ring A, ring B, L, and Y are as defined for the compound of Formula (IB).

In some embodiments, the compound of Formula (IB-1) is a compound of Formula (IB-1A), (IB-1B), or (TB-1C)

(IB-1A)

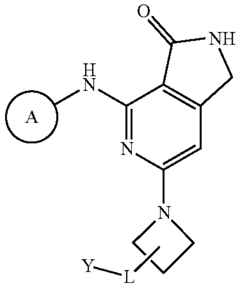

(IB-1B)

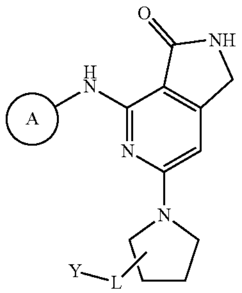

(IB-1C)

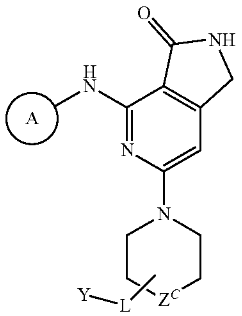

or a pharmaceutically acceptable salt thereof, wherein $Z^C$ is $—NR^3—$, —O—, $—CHR^3—$, or $—S(O)_2—$; and each $R^3$ is independently selected from —H and $C_{1-4}$ alkyl. Ring A, L, and Y are as defined for the compound of Formula (IB-1).

In some embodiments, the compound of Formula (IB-1C) is a compound of Formula (IB-2A)

(IB-2A)

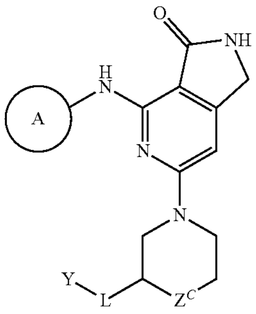

or a pharmaceutically acceptable salt thereof, wherein ring A, $Z^C$, L, and Y are as defined for the compound of Formula (IB-1C).

In some embodiments, the compound of Formula (IB-1B) is a compound of Formula (IB-2B) or (IB-2C)

(IB-2B)

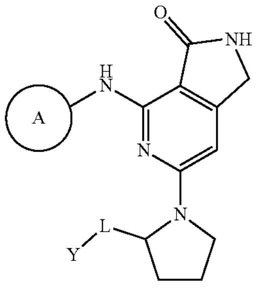

(IB-2C)

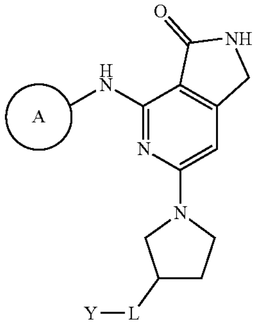

or a pharmaceutically acceptable salt thereof, wherein ring A, L, and Y are as defined for the compound of Formula (IB-1B).

In some embodiments, the compound of Formula (IB-1A) is a compound of Formula (IB-2D) or (IB-2E)

(IB-2D)

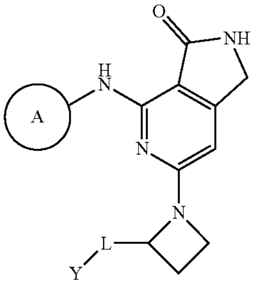

(IB-2E)

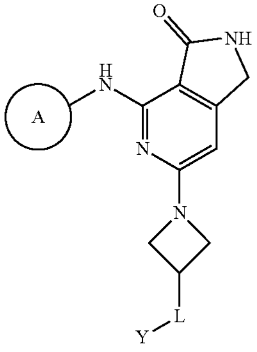

or a pharmaceutically acceptable salt thereof, wherein ring A, L, and Y are as defined for the compound of Formula (IB-1A).

Another aspect of the present invention provides a compound of Formula (II)

(II)

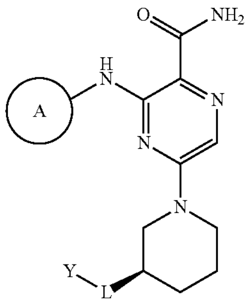

or a pharmaceutically acceptable salt thereof, wherein ring A, L and Y are as defined for any embodiment of the compound of Formula (I).

In some embodiments, ring A is a 9-10 membered bicyclic heteroaryl having 1-3 heteroatoms independently selected from N, O, and S, wherein ring A is optionally substituted with $—Z^A—R^A$, $Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, $—CO_2—$, —OCO—, —O—, —S—, —S(O)—, $—S(O)_2—$, $—S(O)_2N(R)—$, or $—N(R)S(O)_2—$, and $R^A$ is hydrogen, halo, —OH, $—NH_2$, $—NO_2$, —CN, $—CF_3$, $—CH_3$, or $—OCH_3$.

In some embodiments, the compound of Formula (II) is a compound of Formula (II-A)

(II-A)

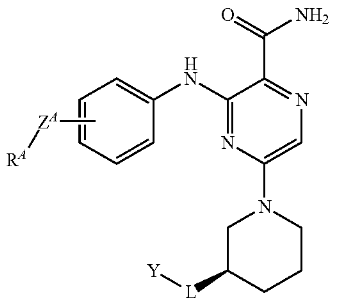

or a pharmaceutically acceptable salt thereof, wherein $Z^A$, $R^A$, L and Y are as defined for the compound of Formula (I) or (II).

In some embodiments, the compound of Formula (II) is a compound of Formula (II-B) or (II-C)

(II-B)

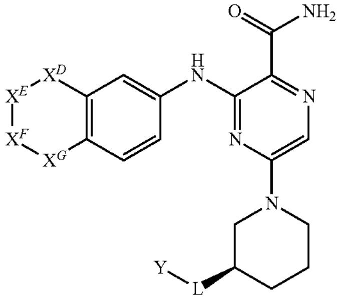

(II-C)

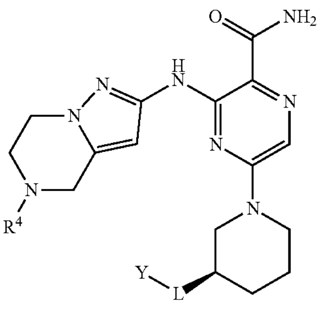

or a pharmaceutically acceptable salt thereof, wherein one of $X^D$, $X^E$, $X^F$, and $X^G$ is optionally a bond, one of $X^D$, $X^E$, $X^F$, and $X^G$ is —$CH_2$— or —$CH_2$—$CH_2$—, one of $X^D$, $X^E$, $X^F$, and $X^G$ is —$NR^5$—, and the remainder are —$CH_2$—; and each $R^5$ is independently —H or —$C_{1-4}$ alkyl optionally substituted with halo. L and Y are as defined for the compound of Formula (I) or (II).

In some embodiments, the compound of (II-B) is a compound of Formula (II-B1), (II-B2), (II-B3), or (II-B4)

(II-B1)

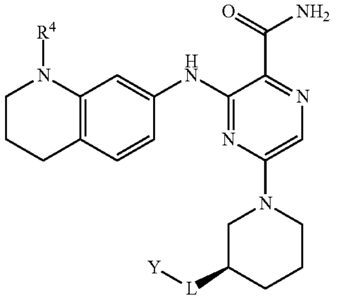

(II-B2)

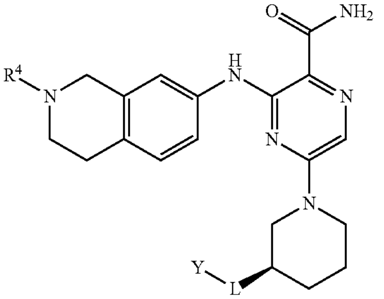

(II-B3)

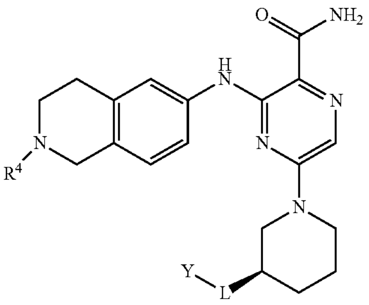

(II-B4)

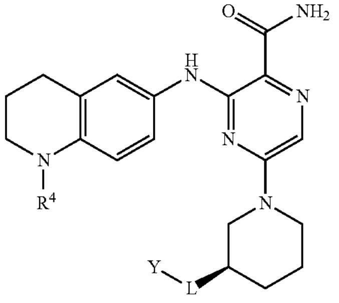

or a pharmaceutically acceptable salt thereof, wherein $R^4$, L, and Y are each as defined for the compound of Formula (I) or (II-B).

The present invention also provides a method of synthesizing a compound of Formula (I) or a pharmaceutically acceptable salt thereof.

DETAILED DESCRIPTION

The present invention provides bifunctional compounds that induce the proteolytic degradation of BTK via a ubiquitin proteolysis pathway. The present invention also provides a compound of Formula (I).

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis," 4th Ed, Wuts, P. G. M. and Greene, T. W., Wiley-Interscience, New York: 2006.

As described herein, compounds of the invention optionally may be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, and alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino." These terms when used alone or in connection with another group refer to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ can be aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic) aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—, where $R^X$ has the same meaning as defined above.

As used herein, an "aryl" group used alone or as part of a larger moiety as in "aralkyl," "aralkoxy," or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl) aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo [2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, bicyclo[2.2.2]octenyl, or bicyclo [3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, that would be categorized as heteroaryls.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic) carbonylamino, (aryl)carbonylamino, (araliphatic)carbonylamino, (heterocycloaliphatic)carbonylamino, ((heterocycloaliphatic) aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; or (haloalkyl)heteroaryl [e.g., trihaloalkylheteroaryl].

As used herein, a "heteroaraliphatic" (such as a heteroaralkyl group) refers to an aliphatic group (e.g., a $C_{1-4}$ alkyl group) that is substituted with a heteroaryl group. "Aliphatic," "alkyl," and "heteroaryl" have been defined above.

As used herein, a "heteroaralkyl" group refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicaliphatic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—$NR^XR^Y$ or —$NR^X$—CO—O—$R^Z$, wherein $R^X$ and $R^Y$ have been defined above and $R^Z$ can be aliphatic, aryl, araliphatic, heterocycloaliphatic, heteroaryl, or heteroaraliphatic.

As used herein, a "carboxy" group refers to —COOH, —$COOR^X$, —OC(O)H, —OC(O)$R^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfamoyl" group refers to the structure —O—$S(O)_2$—$NR^YR^Z$ wherein $R^Y$ and $R^Z$ have been defined above.

As used herein, a "sulfonamide" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)— when used internally, wherein $R^X$ has been defined above. Examples of sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —$S(O)_2$—$R^X$ when used terminally and —$S(O)_2$— when used internally, wherein $R^X$ has been defined above. Examples of sulfonyl groups include aliphatic-$S(O)_2$—, aryl-$S(O)_2$—, (cycloaliphatic(aliphatic))-$S(O)_2$—, cycloaliphatic-$S(O)_2$—, heterocycloaliphatic-$S(O)_2$—, heteroaryl-$S(O)_2$—, (cycloaliphatic(amido(aliphatic)))-$S(O)_2$— or the like.

As used herein, a "sulfoxy" group refers to —O—S(O)—$R^X$ or —S(O)—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refers to —C(O)—.

As used herein, an "oxo" refers to =O.

As used herein, the term "phospho" refers to phosphinates and phosphonates. Examples of phosphinates and phosphonates include —P(O)$(R^P)_2$, wherein $R^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure $(R^X)_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and R have been defined above.

As used herein, the term "vicinal" generally refers to the placement of substituents on a group that includes two or more carbon atoms, wherein the substituents are attached to adjacent carbon atoms.

As used herein, the term "geminal" generally refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)C$-alkyl, is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure $—[CH_2]_v—$, where v is 1-12. A branched aliphatic chain is a straight aliphatic chain that is substituted with one or more aliphatic groups. A branched aliphatic chain has the structure $—[CQQ]_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used herein interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables ring A, ring B, $Z^A$, $Z^B$, $Z^C$, L, Y, R, $R^A$, $R^B$, $R^1$, $R^2$, $R^3$, $R^4$, $R^5$, $X^1$, $X^2$, $X^3$, $X^4$, $X^D$, $X^E$, $X^F$, $X^G$, and other variables contained in Formula (I), (IA), (IB), (IA-1), (IA-1A), (IA-1B), (IA-1C), (1A-2A), (IA-2B), (IA-2C), (IA-2D), (IA-2E), (IB-1), (TB-1A), (IB-1B), (IB-1C), (IB-2A), (IB-2B), (IB-2C), (IB-2D), (IB-2E), (II), (II-A), (II-B), (IT-C), (II-B1), (II-B2), (II-B3), and (II-B4) described herein encompass specific groups, such as alkyl and aryl. Unless otherwise noted, each of the specific groups for the variables ring A, ring B, $Z^A$, $Z^B$, $Z^C$, L, Y, R, $R^A$, $R^B$, $R^1$, $R^2$, $R^3$, $R^4$, $R^5$, $R^{10}$, $X^1$, $X^2$, $X^3$, $X^4$, $X^D$, $X^E$, $X^F$, $X^G$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

As used herein, the term "substituted," whether preceded by the term "optionally" or not, refers generally to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

As used herein, the phrase "stable or chemically feasible" refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein also are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein also are meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays, or as therapeutic agents.

Chemical structures and nomenclature are derived from ChemDraw, version 11.0.1, Cambridge, MA.

It is noted that the use of the descriptors "first," "second," "third," or the like is used to differentiate separate elements (e.g., solvents, reaction steps, processes, reagents, or the like) and may or may not refer to the relative order or relative chronology of the elements described.

II. Bifunctional Compounds of the Present Invention

The present invention provides bifunctional compounds that induce the proteolytic degradation of targeted BTK via a ubiquitin proteasome pathway.

A. Bifunctional Compounds

The present invention provides a compound of Formula (I)

(I)

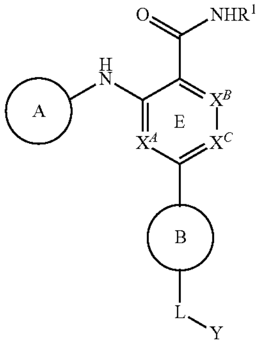

or a pharmaceutically acceptable salt thereof, wherein $R^1$ is —H or —$C_{1-4}$ alkyl; each of $X^A$, $X^B$, and $X^C$ is independently N or $CR^2$; each $R^2$ is independently —H or —$C_{1-4}$ alkyl, or $R^1$ and $R^2$ taken together with the atoms to which they are attached form a ring (i.e., a monocyclic heterocycle fused to ring E); ring A is phenyl, a 4-6 membered monocyclic heteroaryl group having 1-3 heteroatoms independently selected from N, O, and S, or a 9-10 membered bicyclic heteroaryl having 1-3 heteroatoms independently selected from N, O, and S, wherein ring A is optionally substituted with —$Z^A$—$R^A$, $Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, —$CO_2$—, —OCO—, —O—, —S—, —S(O)—, —$S(O)_2$—, —$S(O)_2N(R)$—, or —N(R)$S(O)_2$—, and $R^A$ is hydrogen, halo, —OH, —$NH_2$, —$NO_2$, —CN, —$CF_3$, —$CH_3$, or —$OCH_3$, or ring A, $X^A$, and the atoms to which they are attached form a ring fused to ring E selected from

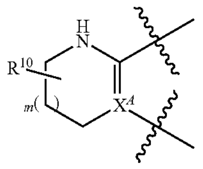

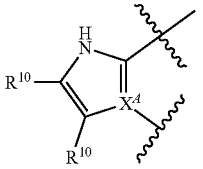

wherein $X^A$ is C, $X^B$ of ring E is N, each $R^{10}$ is independently —H or —$C_{1-4}$ alkyl, and m is 0, 1, or 2; ring B is an unsaturated 4-8 membered monocyclic heterocycle having one nitrogen atom and up to 1 additional heteroatom selected from N, O, or S; L is —$X^1$—$X^2$—$X^3$—$X^4$—; $X^1$ is —N(R)—C(O)—O—, —N(R)—C(O)—, —C(O)—N(R)—, or 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo; $X^2$ is a bond, —$(CH_2)_n$—O—, —O—$(CH_2)_1$—, —$C_{1-8}$ alkyl-, a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, a 6-10 membered fused bicyclic heterocycloalkyl having 1-3 heteroatoms independently selected from N, O, or S, or a 6-9 membered bridged bicyclic heterocycloalkyl having 1-3 heteroatoms independently selected from N, O, or S, wherein the spiro bicyclic heterocycloalkyl ring system is optionally substituted with —OH or oxo; $X^3$ is a bond, —O—, —$(CH_2)_n$—O—, —$C_{1-4}$ alkyl-, or a 4-6 membered heterocycloalkyl ring having 1-2 heteroatoms independently selected from N, O, or S; $X^4$ is a bond, —$C_{1-4}$ alkyl-, or a 4-6 membered heterocycloalkyl ring having 1-2 heteroatoms independently selected from N, O, or S; each R is independently —H or —$C_{1-3}$ alkyl; each n is independently 1, 2, or 3;

Y is

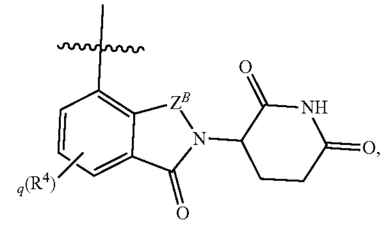

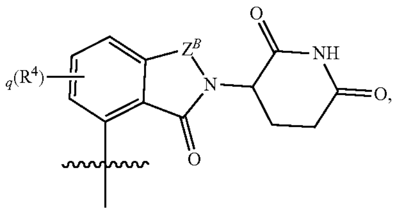

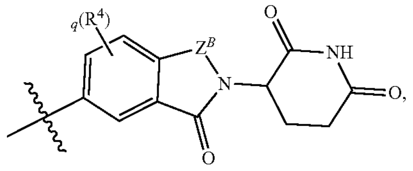

or

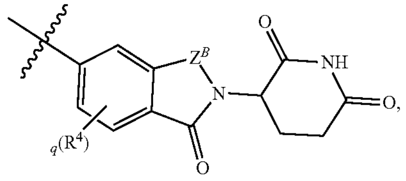

wherein; each $R^4$ is independently a halo or a $C_{1-4}$ alkyl; each $Z^B$ is —$C(R^B)_2$— or —C(O)—; each $R^B$ is —H or —$C_{1-4}$ alkyl; and q is 0, 1, or 2.

With the exception of the moieties of group R, all moieties of the linking group L as defined in the compound of Formula (I) are bivalent moieties unless otherwise specified. For example any alkyl (e.g., n-propyl, n-butyl, n-hexyl, and the like), aryl (e.g., phenyl), cycloalkyl (e.g., cyclopropyl, cyclohexyl, and the like), heteroaryl, heterocycloalkyl (e.g., piperidine, piperazine, and the like) that is present in L is bivalent unless otherwise specified.

In some embodiments, the compound of Formula (I) is (I)

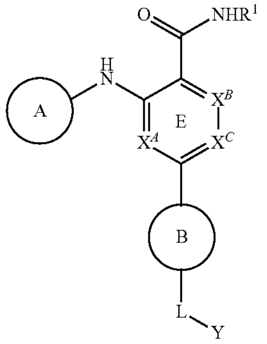

or a pharmaceutically acceptable salt thereof, wherein $R^1$ is —H or —$C_{1-4}$ alkyl; each of $X^A$, $X^B$, and $X^C$ is independently N or $CR^2$; each $R^2$ is independently —H or —$C_{1-4}$ alkyl, or $R^1$ and $R^2$ taken together with the atoms to which they are attached form a ring; ring A is phenyl, a 4-6 membered monocyclic heteroaryl group having 1-3 heteroatoms independently selected from N, O, and S, or a 9-10 membered bicyclic heteroaryl having 1-3 heteroatoms independently selected from N, O, and S, wherein ring A is optionally substituted with —$Z^A$—$R^A$, $Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, —$CO_2$—, —OCO—, —O—, —S—, —S(O)—, —$S(O)_2$—, —S$(O)_2$N(R)—, or —N(R)$S(O)_2$—, and $R^A$ is hydrogen, halo, —OH, —$NH_2$, —$NO_2$, —CN, —$CF_3$, —$CH_3$, or —$OCH_3$; ring B is an unsaturated 4-8 membered monocyclic heterocycle having one nitrogen atom and up to 1 additional heteroatom selected from N, O, or S; L is —$X^1$—$X^2$—$X^3$—$X^4$—; $X^1$ is —N(R)—C(O)—O—, —N(R)—C(O)—, —C(O)—N(R)—, or 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo; $X^2$ is a bond, —$(CH_2)_n$—O—, —O—$(CH_2)_n$—, —$C_{1-8}$ alkyl-, a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, a 6-10 membered fused bicyclic heterocycloalkyl having 1-3 heteroatoms independently selected from N, O, or S, or a 6-9 membered bridged bicyclic heterocycloalkyl having 1-3 heteroatoms independently selected from N, O, or S, wherein the spiro bicyclic heterocycloalkyl ring system is optionally substituted with —OH or oxo; $X^3$ is a bond, —O—, —$(CH_2)_n$—O—, —$C_{1-4}$ alkyl-, or a 4-6 membered heterocycloalkyl ring having 1-2 heteroatoms independently selected from N, O, or S; $X^4$ is a bond, —$C_{1-4}$ alkyl-, or a 4-6 membered heterocycloalkyl ring having 1-2 heteroatoms independently selected from N, O, or S; each R is independently —H or —$C_{1-3}$ alkyl; each n is independently 1, 2, or 3; Y is

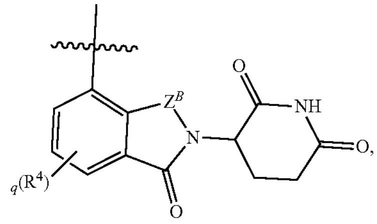

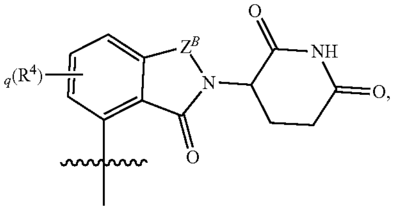

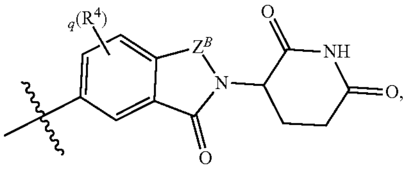

or

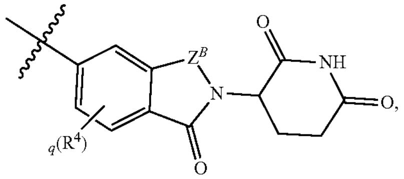

wherein; each $R^4$ is independently a halo or a $C_{1-4}$ alkyl; each $Z^B$ is —$C(R^B)_2$— or —C(O)—; each $R^B$ is —H or —$C_{1-4}$ alkyl; and q is 0, 1, or 2.

In some embodiments, two of $X^A$, $X^B$, and $X^C$ are N. For example, $X^A$ and $X^B$ are N. In other examples, $X^B$ and $X^C$ are N and $X^A$ is $CR^2$.

In some embodiments, q is 0 or 1. In other embodiments, q is 1. And, in some embodiments, q is 2. In other embodiments, q is 0.

In some embodiments, Y is

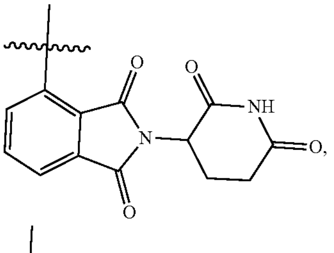

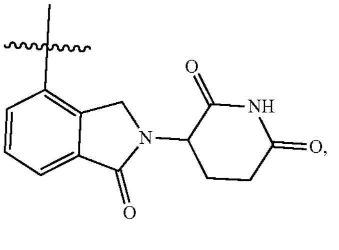

or

-continued

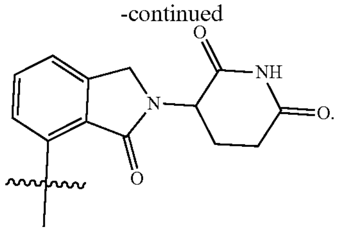

In other embodiments, Y is

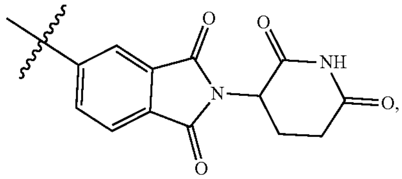 [SMILES: *c1ccc2c(c1)C(=O)N(C1CCC(=O)NC1=O)C2=O]

,

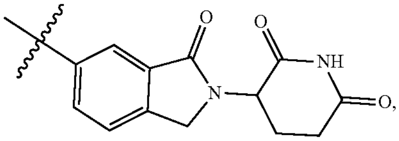

, or

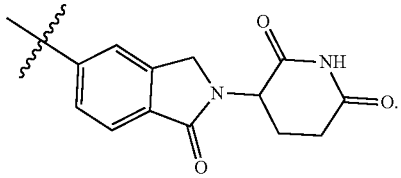

.

For example, Y is

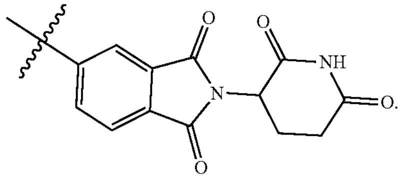

.

In some embodiments, ring A is phenyl optionally substituted with —$Z^A$—$R^A$, wherein $Z^A$ is a bond, —C(O)—, —$CO_2$—, —OCO—, —S—, —O—, —S(O)—, or —S$(O)_2$—, and $R^A$ is hydrogen, halo, —OH, —$CF_3$, or —$CH_3$. In some examples, ring A is phenyl substituted with —$Z^A$—$R^A$ at its ortho position. In some examples, ring A is phenyl substituted with —$Z^A$—$R^A$ at its meta position. And, in some examples, ring A is phenyl substituted with —$Z^A$—$R^A$ at its para position. In some examples, ring A is

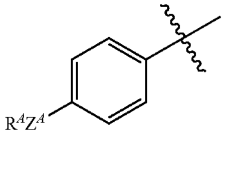

or

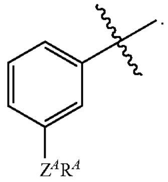

.

In some embodiments, ring A is phenyl substituted with —$Z^A$—$R^A$ at its meta position, wherein —$Z^A$—$R^A$ is —$CH_3$ or —$S(O)_2$—$CH_3$.

In some embodiments, ring A is phenyl substituted with —$Z^A$—$R^A$ at its para position, wherein —$Z^A$—$R^A$ is —$CH_3$ or —$S(O)_2$—$CH_3$.

In some embodiments, ring A is unsubstituted phenyl.

In other examples, ring A is

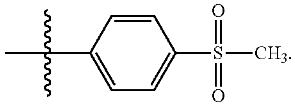 [SMILES: *c1ccc(S(C)(=O)=O)cc1]

In some embodiments, ring A is a 5-6 membered monocyclic heteroaryl group having 1-3 heteroatoms independently selected from N, O, and S optionally substituted with —$Z^A$—$R^A$, wherein $Z^A$ is a bond or an optionally substituted branched or straight $C_{1-3}$ aliphatic chain, and $R^A$ is hydrogen, halo, —OH, —$NH_2$, —$NO_2$, —CN, —$CF_3$, or —$OCH_3$. In some examples, ring A is is

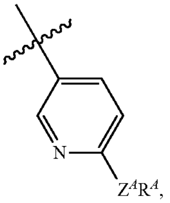

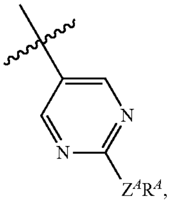

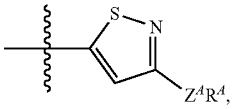

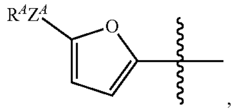

, or

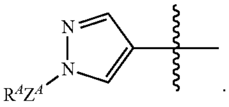

.

In other examples, ring A is

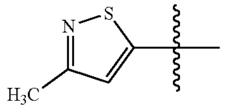

or

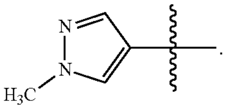

.

In some embodiments, $X^1$ is —NH—C(O)—, —C(O)—N(H)—, —N($CH_3$)—C(O)—, or —C(O)—N($CH_3$)—. For example, $X^1$ is —NH—C(O)— or —N($CH_3$)—C(O)—. In other examples, $X^1$ is —NH—C(O)—. And, in some examples, $X^1$ is —C(O)—N(H)— or —C(O)—N($CH_3$)—.

In some embodiments, $X^2$ is —$CH_2$—O—, —O—$CH_2$—, —$(CH_2)_2$—O—, —O—$(CH_2)_2$—, —$(CH_2)_3$—O—, —O—$(CH_2)_3$—, —$CH_2$—, -n-butyl-, or -n-hexyl-. For example, $X^2$ is —$CH_2$—O—, —O—$CH_2$—, —$(CH_2)_2$—O—, —O—$(CH_2)_2$—, —$(CH_2)_3$—O—, —O—$(CH_2)_3$—, or —$CH_2$—.

In some embodiments, $X^2$ is an 7-12 membered spiro bicyclic heterocycloalkyl ring system having 1-3 heteroatoms independently selected from N, O, or S, wherein the spiro heterocycloalkyl ring system is optionally substituted with —OH or oxo. In some instances, $X^2$ is

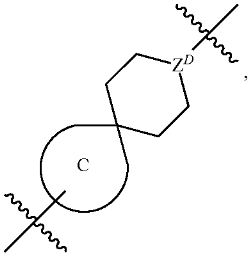
,
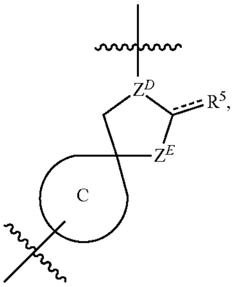
or
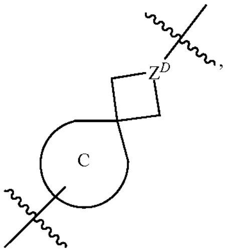

wherein each ring C is independently a 4-6 membered (e.g., 5-6 membered) partially saturated or fully saturated (e.g., fully saturated) ring having 0-2 nitrogen atoms; each $Z^D$ is independently N or CH; $Z^E$ is —$CH_2$—, —O—, or N; $R^5$ is —H, or —OH when - - - is absent, or $R^5$ is oxo when - - - is a bond. In some examples, $X^2$ is

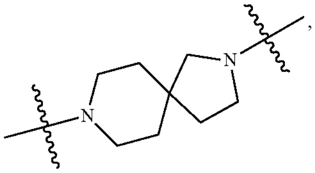
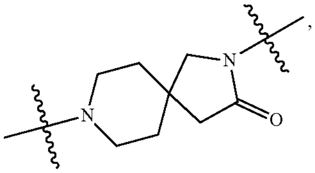
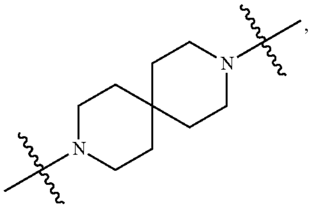
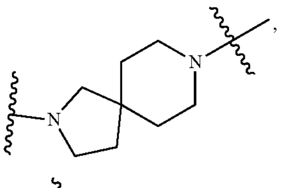
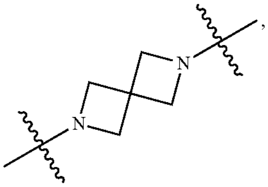
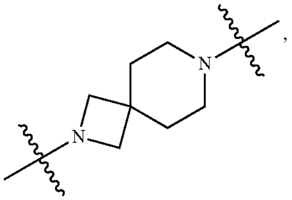

-continued

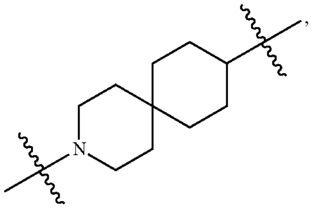
or
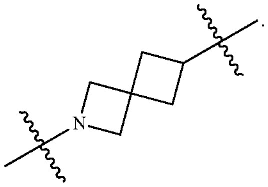

In some embodiments, $X^2$ is a 4-6 membered monocyclic heterocycloalkyl having 1-2 heteroatoms independently selected from N, O, or S. For example, $X^2$ is a 4-6 membered monocyclic heterocycloalkyl having 1-2 N atoms. In other examples, $X^2$ is

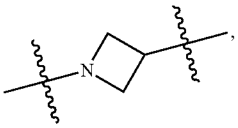
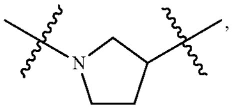
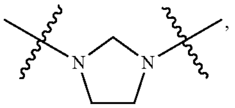
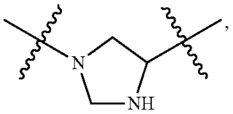
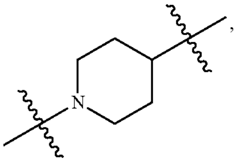
or
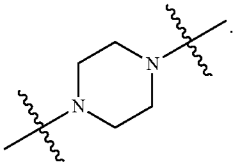

In some embodiments, $X^2$ is a 6-10 membered fused bicyclic heterocycloalkyl having 1-3 heteroatoms independently selected from N, O, or S. For example, $X^2$ is a 6-9 membered (e.g., 6-8 membered) fused bicyclic heterocycloalkyl having 1-2 N atoms. In other examples, $X^2$ is

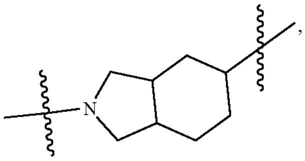
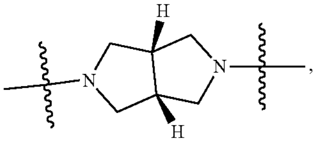

-continued

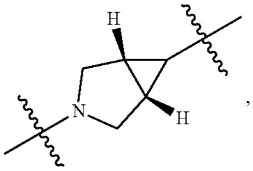,

In some embodiments, $X^2$ is a 6-9 membered bridged bicyclic heterocycloalkyl having 1-3 heteroatoms independently selected from N, O, or S. For example, $X^2$ is a 6-9 membered bridged bicyclic heterocycloalkyl having 1-2 N atoms. In other examples, $X^2$ is

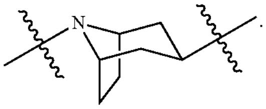 [SMILES: *C1CC2CCC(C1)N2*].

In some embodiments, $X^3$ is a bond, $—CH_2—O—$, $—C_{1-4}$ alkyl-,

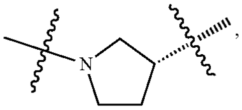, 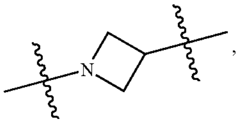,

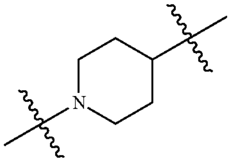, or 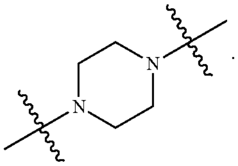.

In some embodiments, $X^4$ is a bond, $—C_{1-4}$ alkyl-,

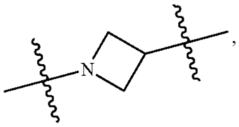, or 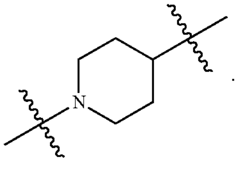.

For example, $X^4$ is a bond, $—CH_2—$, $—CH_2CH_2—$, $—CH_2CH_2CH_2—$, or $—CH_2CH_2CH_2CH_2—$.

In some embodiments, L is selected from

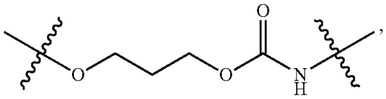,

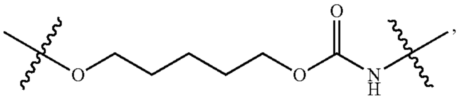,

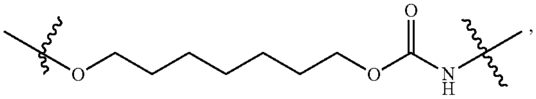,

-continued

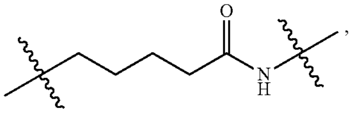,

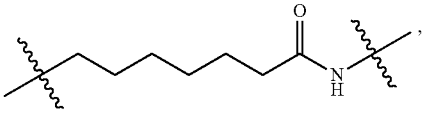,

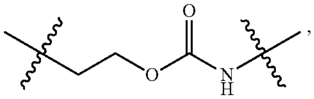,

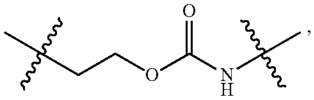,

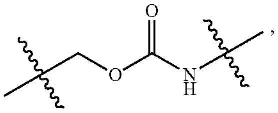,

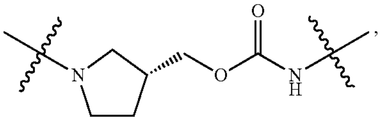,

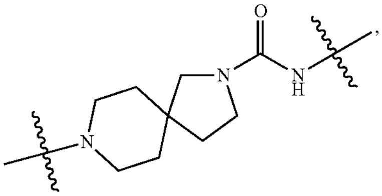,

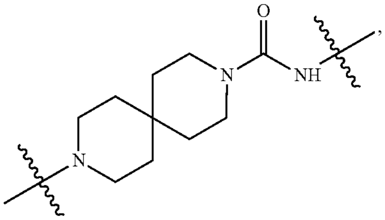,

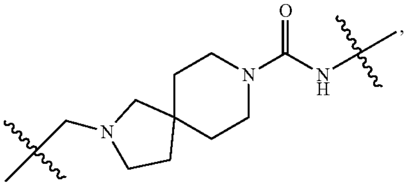,

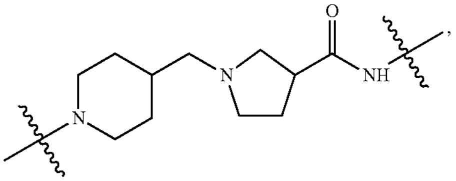,

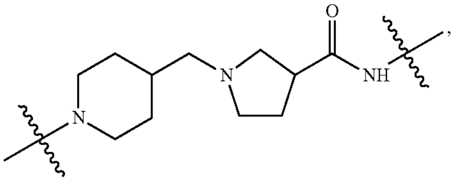,

-continued
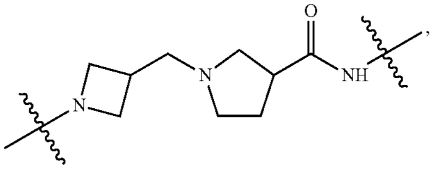,
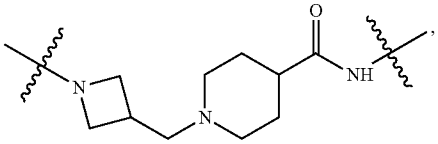,
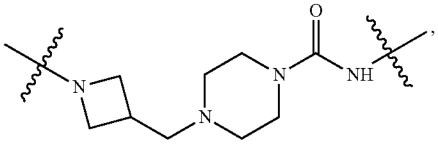,
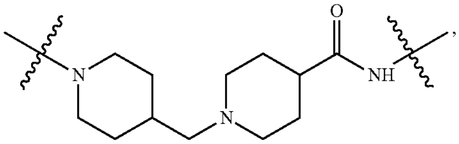,
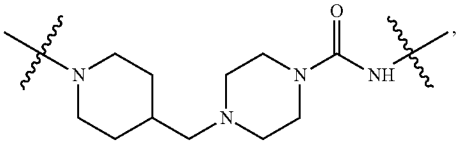,
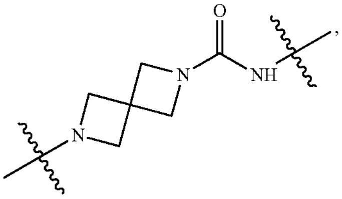,
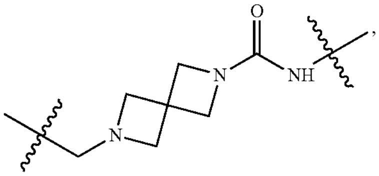,
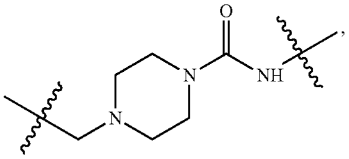,
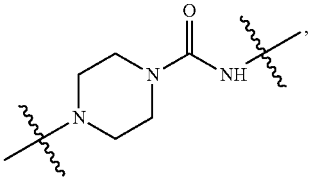,
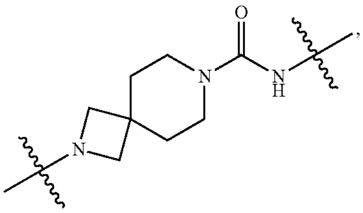,
-continued
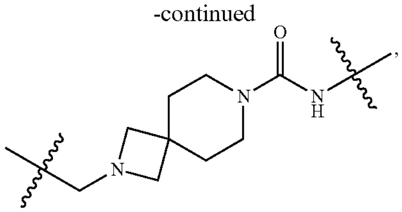,
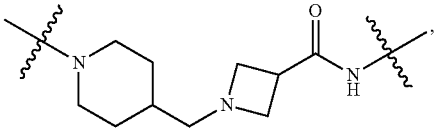,
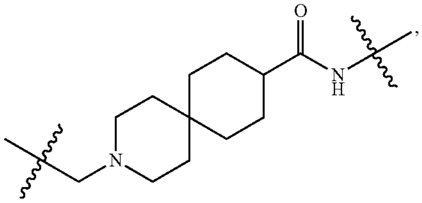,
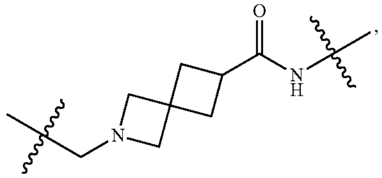,
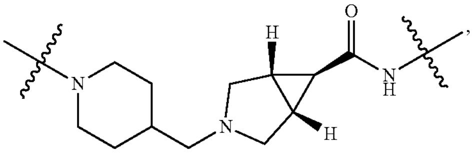,
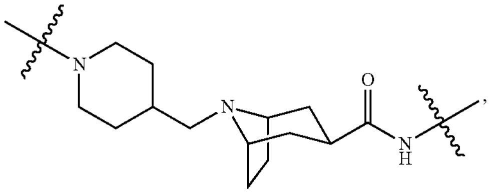,
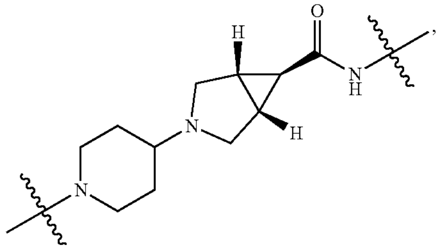,
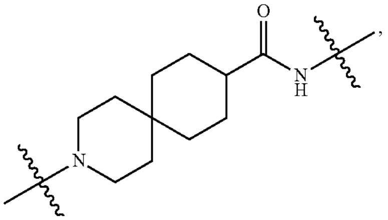,
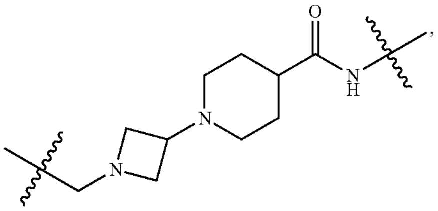, -continued

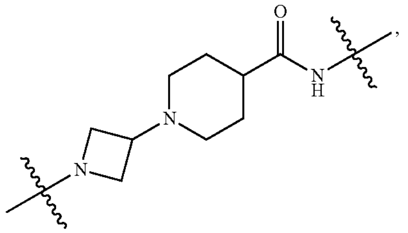

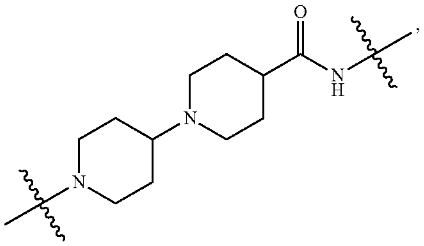

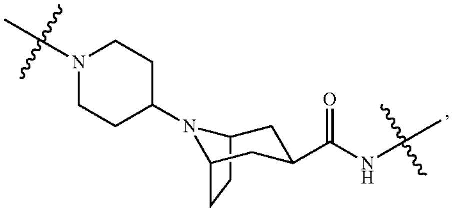

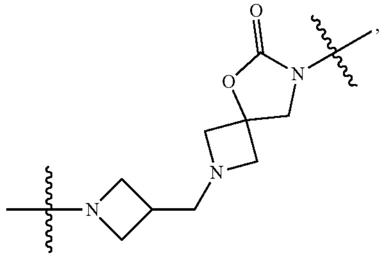

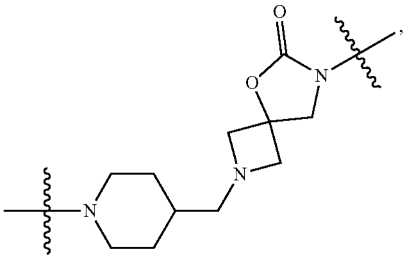

or

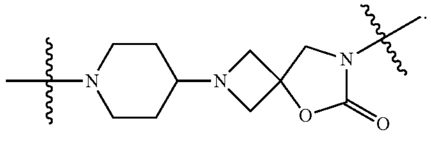

In some embodiments, the compound is a compound of Formula (I), as described herein, or a pharmaceutically acceptable salt thereof, wherein (i) ring A is

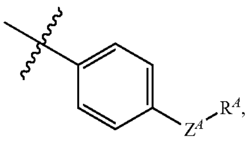

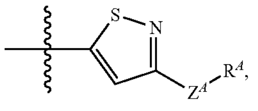

or

-continued

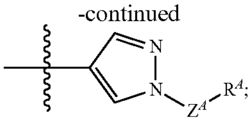

(ii) L is —$X^1$—$X^2$—$X^3$—$X^4$—;

(iii) $X^1$ is —NH—C(O)—;

(iv) $X^2$ is a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, or a 6-10 membered fused bicyclic heterocycloalkyl having 1-3 heteroatoms independently selected from N, O, or S, wherein the spiro heterocycloalkyl ring system is optionally substituted with —OH or oxo;

(v) $X^3$ is a bond, a 4-6 membered monocyclic heterocycloalkyl having 1-2 heteroatoms independently selected from N, O, or S, or a —$C_{1-4}$ alkyl-;

(vi) $X^4$ is a bond, a 4-6 membered heterocycloalkyl having 1-2 heteroatoms independently selected from N, O, or S, or a —$C_{1-4}$ alkyl-; and (vii) Y is

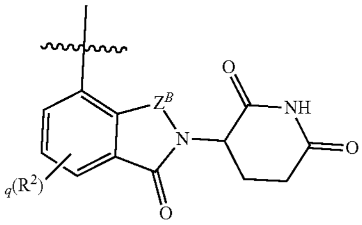

or

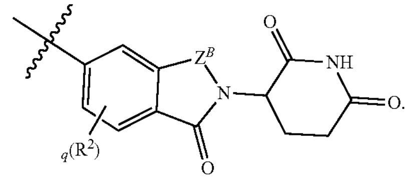

In some embodiments, q is 0.

In some embodiments, Y is

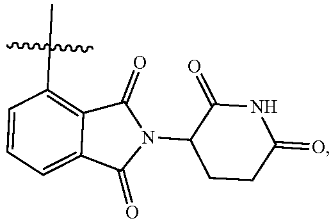

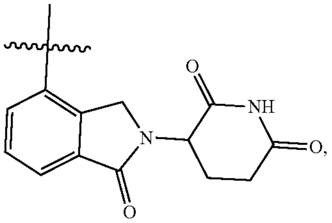

or

-continued
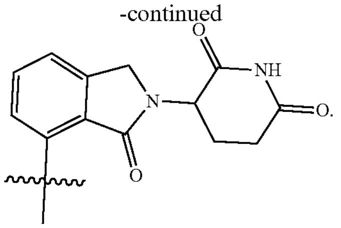
In some embodiments, Y is
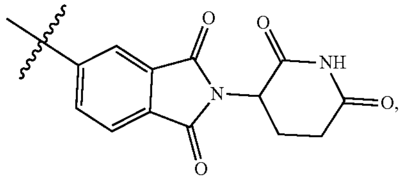
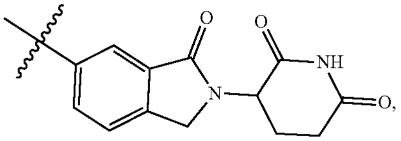
or
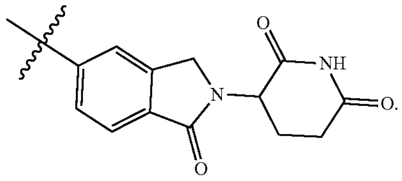
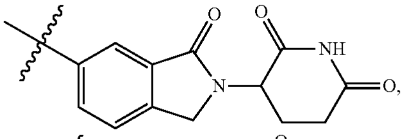
or
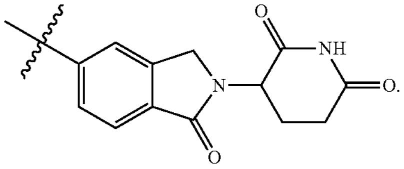
For example, Y is
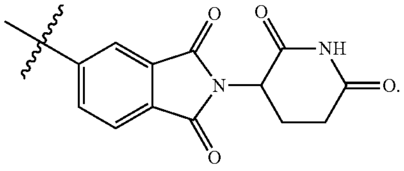 [SMILES: *c1ccc2c(c1)C(=O)N(C1CCC(=O)NC1=O)C2=O]
In some embodiments, ring A is
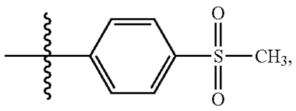
-continued
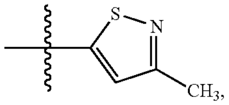
or
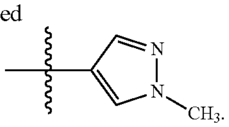
In some embodiments, $X^2$ is
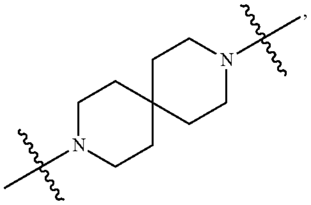
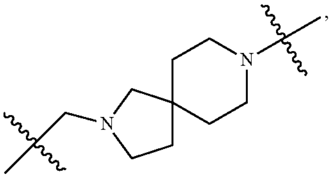
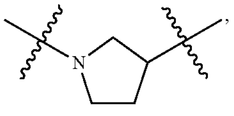
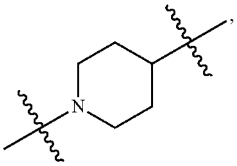
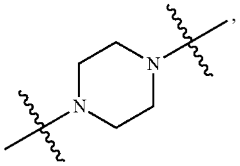
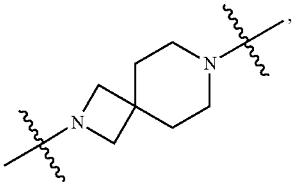
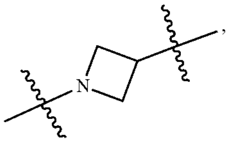
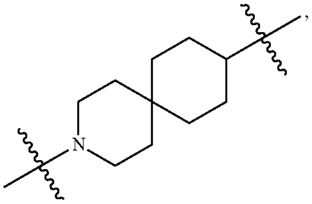
or
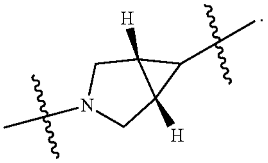

In some embodiments, $X^3$ is bond, —$C_{1-4}$ alkyl-, or
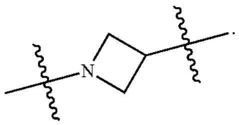 [SMILES: *C1CN(*)C1]
In some embodiments, $X^4$ is bond, —$C_{1-4}$ alkyl-, or
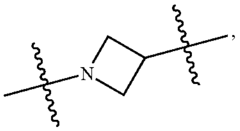
or
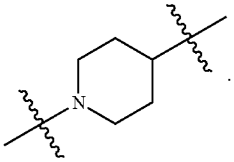
In some embodiments, L is selected from
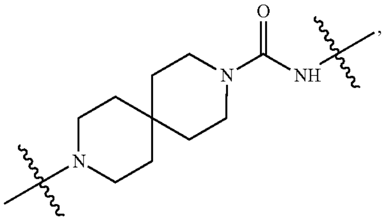
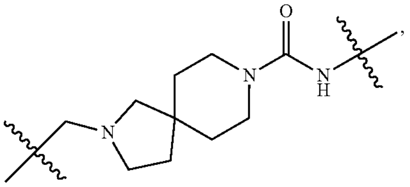
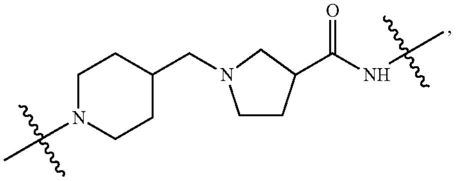
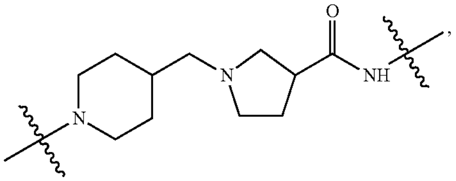
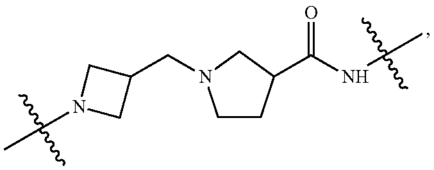
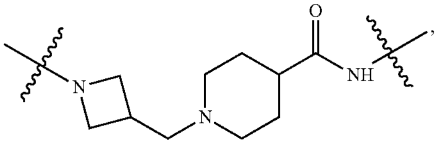
-continued
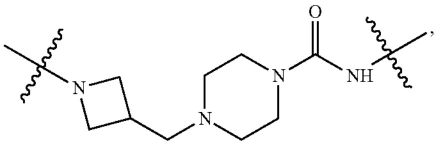
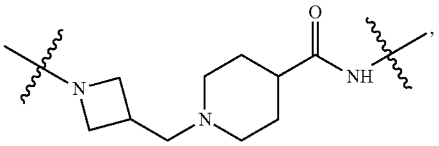
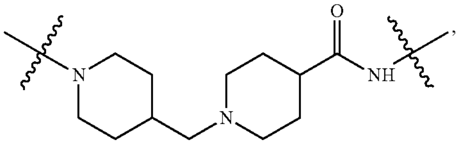
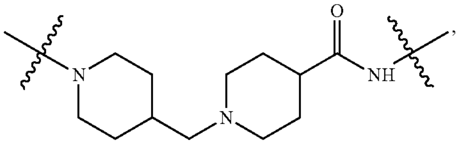
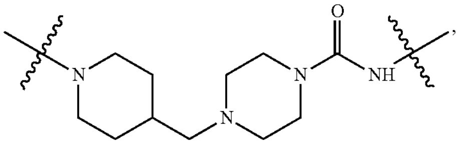
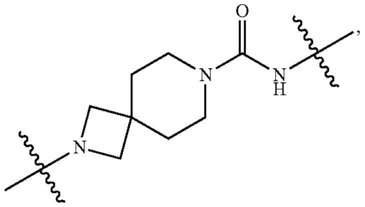
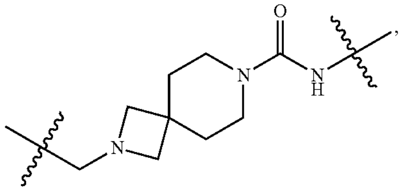
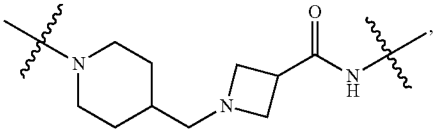
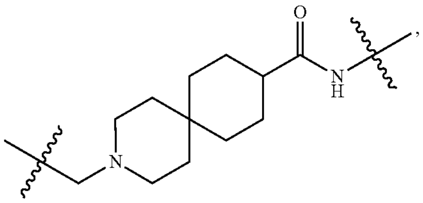
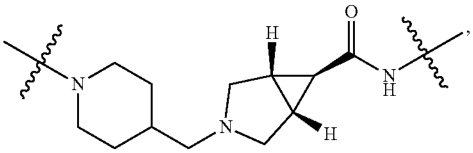

-continued

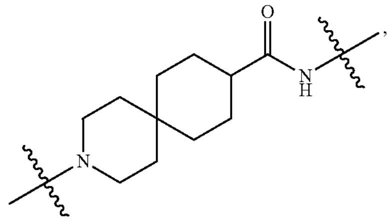

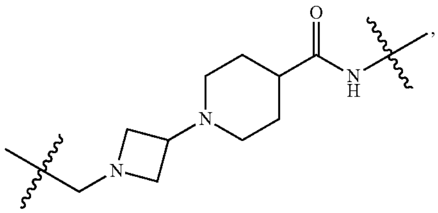

and

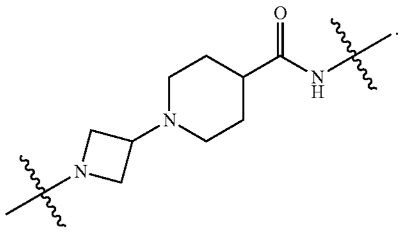

Another aspect of the present invention provides a compound of Formula (IA)

(IA)

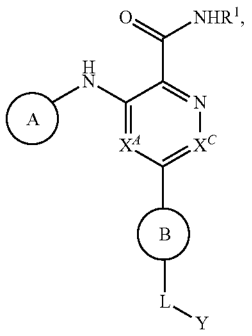

or a pharmaceutically acceptable salt thereof, wherein ring A, ring B, $R^1$, $X^A$, $X^C$, L and Y are as defined for any embodiment of the compound of Formula (I).

In some embodiments, the compound of Formula (IA) is a compound of Formula (IA-1)

(IA-1)

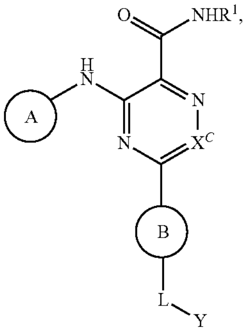

or a pharmaceutically acceptable salt thereof, wherein ring A, ring B, $R^1$, $X^C$, L and Y are as defined for any embodiment of the compound of Formula (I) or (IA).

In some embodiments, $X^C$ is CH.

In some embodiments, the compound of Formula (IA-1) is a compound of Formula (IA-1A), (IA-1B), or (IA-1C)

(IA-1A)

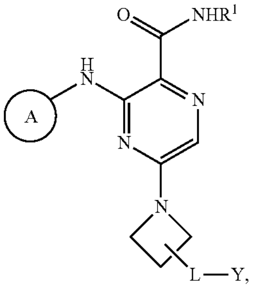

(IA-1B)

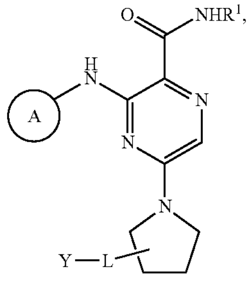

(IA-1C)

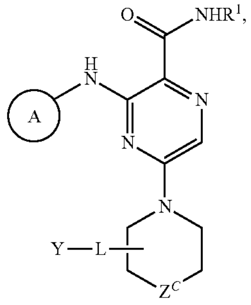

or a pharmaceutically acceptable salt thereof, wherein $Z^C$ is —$NR^3$—, —O—, —$CHR^3$—, or —$S(O)_2$—; and each $R^3$ is independently selected from —H and $C_{1-4}$ alkyl. Ring A, $R^1$, L and Y are as defined for any embodiment of the compound of Formula (I) or (IA).

In some embodiments, the compound of Formula (IA-1A) is a compound of Formula (IA-2D) or (IA-2E)

(IA-2D)

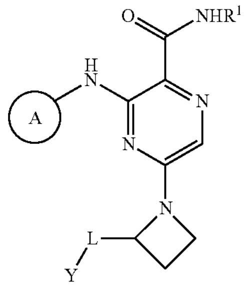

(IA-2E)

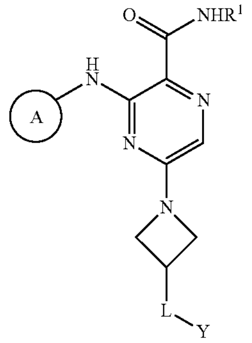

or a pharmaceutically acceptable salt thereof, wherein ring A, $R^1$, L and Y are as defined for any embodiment of the compound of Formula (I) or (IA).

In some embodiments, the compound of Formula (IA-1B) is a compound of Formula (IA-2B) or (IA-2C)

(IA-2B)

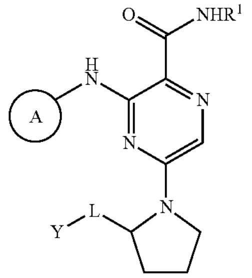

(IA-2C)

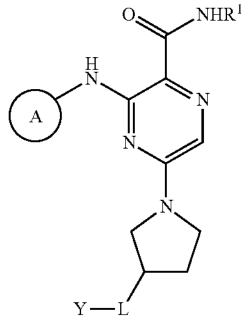

or a pharmaceutically acceptable salt thereof, wherein ring A, $R^1$, L and Y are as defined for any embodiment of the compound of Formula (I) or (IA).

In some embodiments, the compound of Formula (1A-1C) is a compound of Formula (1A-2A)

(IA-2A)

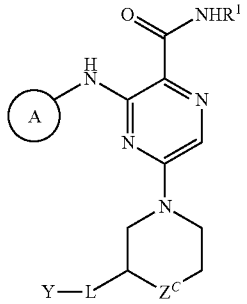

or a pharmaceutically acceptable salt thereof, wherein $Z^C$ is —$NR^3$—, —O—, —$CHR^3$—, or —$S(O)_2$—; and each $R^3$ is independently selected from —H and $C_{1-4}$ alkyl. Ring A, $R^1$, L and Y are as defined for any embodiment of the compound of Formula (I).

Another aspect of the present invention provides a compound of Formula (IB)

(IB)

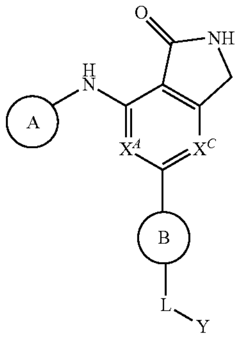

or a pharmaceutically acceptable salt thereof, wherein ring A, ring B, $X^A$, $X^C$, L and Y are as defined for any embodiment of the compound of Formula (I) or (IA).

In some embodiments, the compound of Formula (IB) is a compound of Formula (IB-1)

(IB-1)

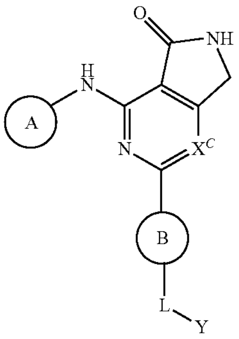

or a pharmaceutically acceptable salt thereof, wherein ring A, ring B, $X^C$, L and Y are as defined for any embodiment of the compound of Formula (I) or (IB).

In some embodiments, $X^C$ is N. In other embodiments, $X^C$ is CH.

In some embodiments, the compound of Formula (IB-1) is a compound of Formula (TB-1A), (TB-1B), or TB-1C (IB-1A)

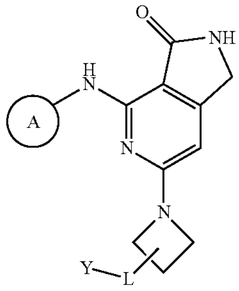

(IB-1B)

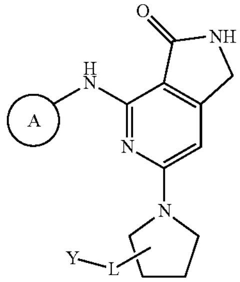

(IB-1C)

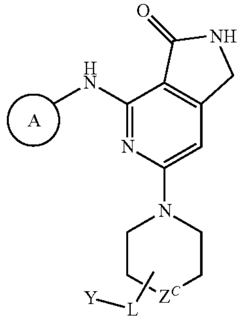

or a pharmaceutically acceptable salt thereof, wherein $Z^C$ is —$NR^3$—, —O—, —$CHR^3$—, or —$S(O)_2$—; and each $R^3$ is independently selected from —H and $C_{1-4}$ alkyl. Ring A, L, and Y are as defined for any embodiment of the compound of Formula (T) or (IB).

In some embodiments, the compound of Formula (IB-1A) is a compound of Formula (IB-2D) or (IB-2E)

(IB-2D)

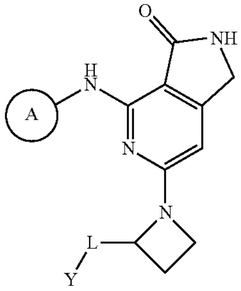

-continued (IB-2E)

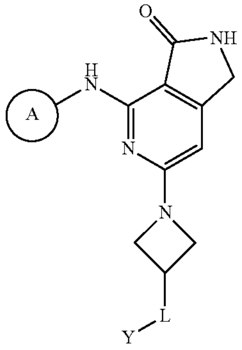

or a pharmaceutically acceptable salt thereof, wherein ring A, L, and Y are as defined for any embodiment of the compound of Formula (T) or (IB).

In some embodiments, the compound of Formula (IB-1B) is a compound of Formula (IB-2B) or (IB-2C)

(IB-2B)

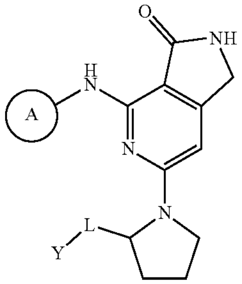

(IB-2C)

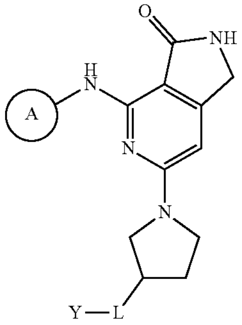

or a pharmaceutically acceptable salt thereof, wherein ring A, L, and Y are as defined for any embodiment of the compound of Formula (I) or (IB).

In some embodiments, the compound of Formula (IB-1C) is a compound of Formula (IB-2A)

(IB-2A)

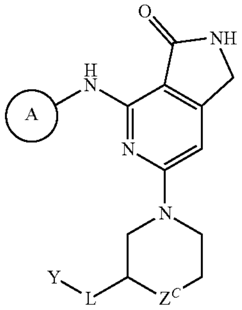

or a pharmaceutically acceptable salt thereof, wherein $Z^C$ is $—NR^3—$, $—O—$, $—CHR^3—$, or $—S(O)_2—$; and each $R^3$ is independently selected from —H and $C_{1-4}$ alkyl. Ring A, L, and Y are as defined for any embodiment of the compound of Formula (I) or (IB).

Another aspect of the present invention provides a compound of Formula (II)

(II)

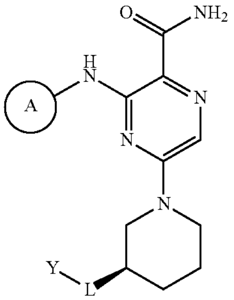

or a pharmaceutically acceptable salt thereof, wherein ring A is phenyl, a 4-6 membered monocyclic heteroaryl group having 1-3 heteroatoms independently selected from N, O, and S, or a 9-10 membered bicyclic heteroaryl having 1-3 heteroatoms independently selected from N, O, and S, wherein ring A is optionally substituted with $—Z^A—R^A$, $Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, $—CO_2—$, —OCO—, —O—, —S—, —S(O)—, $—S(O)_2—$, $—S(O)_2N(R)—$, or $—N(R)S(O)_2—$, and $R^A$ is hydrogen, halo, —OH, $—NH_2$, $—NO_2$, —CN, $—CF_3$, $—CH_3$, or $—OCH_3$; ring B is an unsaturated 4-8 membered monocyclic heterocycle having one nitrogen atom and up to 1 additional heteroatom selected from N, O, or S; L is $—X^1—X^2—X^3—X^4—$; $X^1$ is —N(R)—C(O)—O—, —N(R)—C(O)—, —C(O)—N(R)—, or 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo; $X^2$ is a bond, $—(CH_2)_n—O—$, $—O—(CH_2)_n—$, $—C_{1-8}$ alkyl-, a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, a 6-10 membered fused bicyclic heterocycloalkyl having 1-3 heteroatoms independently selected from N, O, or S, or a 6-9 membered bridged bicyclic heterocycloalkyl having 1-3 heteroatoms independently selected from N, O, or S, wherein the spiro bicyclic heterocycloalkyl ring system is optionally substituted with —OH or oxo; $X^3$ is a bond, —O—, $—(CH_2)_n—O—$, $—C_{1-4}$ alkyl-, or a 4-6 membered heterocycloalkyl ring having 1-2 heteroatoms independently selected from N, O, or S; $X^4$ is a bond, $—C_{1-4}$ alkyl-, or a 4-6 membered heterocycloalkyl ring having 1-2 heteroatoms independently selected from N, O, or S; each R is independently —H or $—C_{1-3}$ alkyl; n is 1, 2, or 3;

Y is

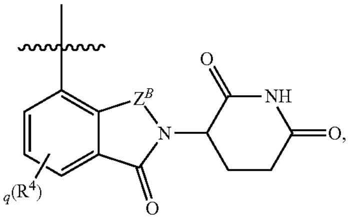

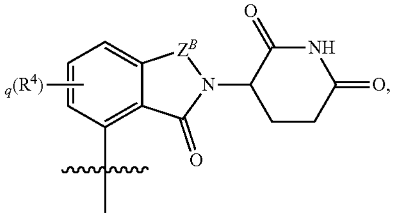

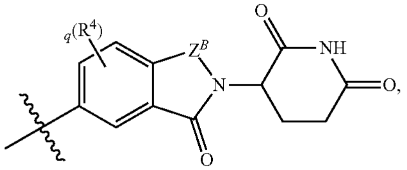

or

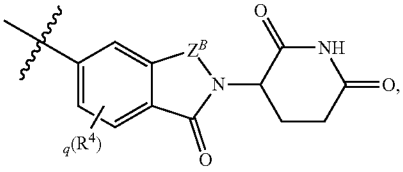

wherein; each $R^4$ is independently a halo or a $C_{1-4}$ alkyl; each $Z^B$ is $—C(R^B)_2—$ or —C(O)—; each $R^B$ is —H or $—C_{1-4}$ alkyl; and q is 0, 1, or 2.

In some embodiments, q is 0 or 1. In other embodiments, q is 1. And, in some embodiments, q is 2. In other embodiments, q is 0.

In some embodiments, Y is

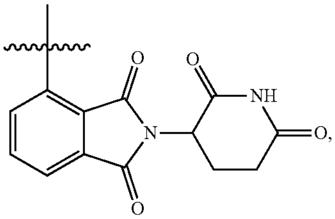

-continued

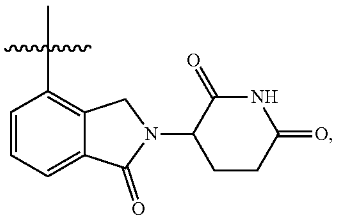

or

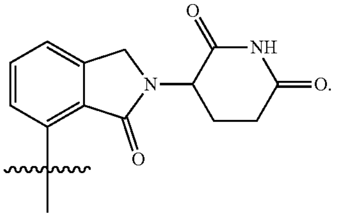

In other embodiments, Y is

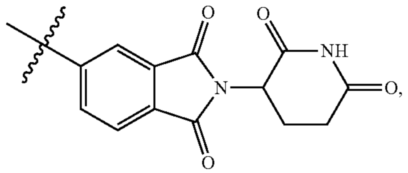

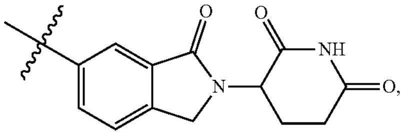

or

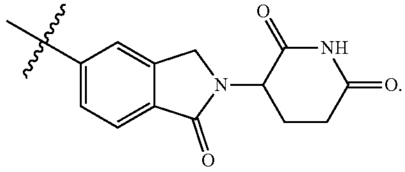

For example, Y is

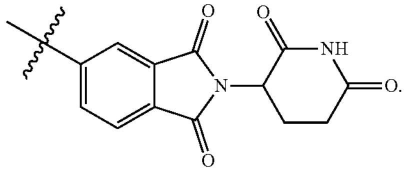 [SMILES: *c1ccc2c(c1)C(=O)N(C1CCC(=O)NC1=O)C2=O]

In some embodiments, ring A is phenyl optionally substituted with —$Z^A$—$R^A$, wherein $Z^A$ is a bond, —C(O)—, —$CO_2$—, —OCO—, —S—, —O—, —S(O)—, or —S$(O)_2$—, and $R^A$ is hydrogen, halo, —OH, —$CF_3$, or —$CH_3$. In some examples, ring A is phenyl substituted with —$Z^A$—$R^A$ at its ortho position. In some examples, ring A is phenyl substituted with —$Z^A$—$R^A$ at its meta position. And, in some examples, ring A is phenyl substituted with —$Z^A$—$R^A$ at its para position. In some examples, ring A is

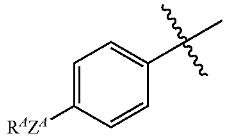

or

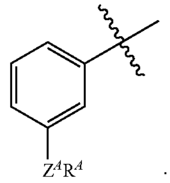

.

In some embodiments, ring A is phenyl substituted with —$Z^A$—$R^A$ at its meta position, wherein —$Z^A$—$R^A$ is —$CH_3$ or —$S(O)_2$—$CH_3$.

In some embodiments, ring A is phenyl substituted with —$Z^A$—$R^A$ at its para position, wherein —$Z^A$—$R^A$ is —$CH_3$ or —$S(O)_2$—$CH_3$.

In some embodiments, ring A is unsubstituted phenyl.

In other examples, ring A is

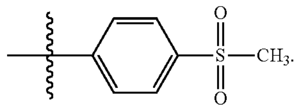 [SMILES: *c1ccc(S(C)(=O)=O)cc1]

In some embodiments, ring A is a 5-6 membered monocyclic heteroaryl group having 1-3 heteroatoms independently selected from N, O, and S optionally substituted with —$Z^A$—$R^A$, wherein $Z^A$ is a bond or an optionally substituted branched or straight $C_{1-3}$ aliphatic chain, and $R^A$ is hydrogen, halo, —OH, —$NH_2$, —$NO_2$, —CN, —$CF_3$, or —$OCH_3$. In some examples, ring A is is

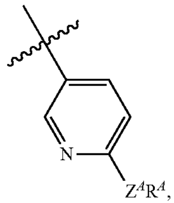

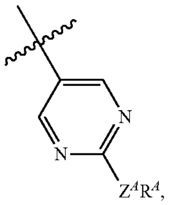

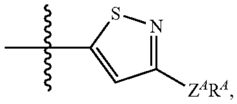

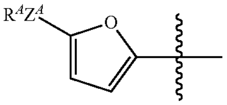

, or

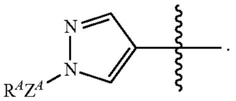

In other examples, ring A is

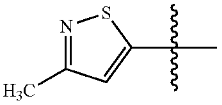

or

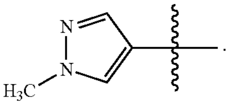

In some embodiments, $X^1$ is —NH—C(O)—, —C(O)—N(H)—, —N($CH_3$)—C(O)—, or —C(O)—N($CH_3$)—. For example, $X^1$ is —NH—C(O)— or —N($CH_3$)—C(O)—. In other examples, $X^1$ is —NH—C(O)—. And, in some examples, $X^1$ is —C(O)—N(H)— or —C(O)—N($CH_3$)—. In some embodiments, $X^2$ is —$CH_2$—O—, —O—$CH_2$—, —$(CH_2)_2$—O—, —O—$(CH_2)_2$—, —$(CH_2)_3$—O—, —O—$(CH_2)_3$—, —$CH_2$—, -n-butyl-, or -n-hexyl-.

For example, $X^2$ is —$CH_2$—O—, —O—$CH_2$—, —$(CH_2)_2$—O—, —O—$(CH_2)_2$—, —$(CH_2)_3$—O—, —O—$(CH_2)_3$—, or —$CH_2$—.

In some embodiments, $X^2$ is an 7-12 membered spiro bicyclic heterocycloalkyl ring system having 1-3 heteroatoms independently selected from N, O, or S, wherein the spiro heterocycloalkyl ring system is optionally substituted with —OH or oxo. In some instances, $X^2$ is

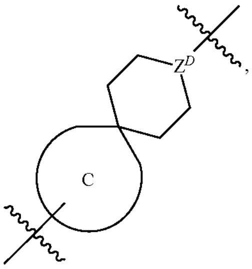,
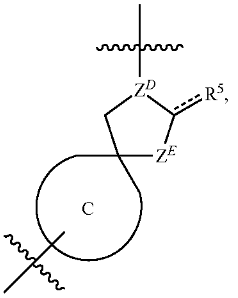, or
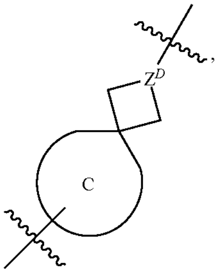, wherein each ring C is independently a 4-6 membered (e.g., 5-6 membered) partially saturated or fully saturated (e.g., fully saturated) ring having 0-2 nitrogen atoms; each $Z^D$ is independently N or CH; $Z^E$ is —$CH_2$—, —O—, or N; $R^5$ is —H, or —OH when - - - is absent, or $R^5$ is oxo when - - - is a bond. In some examples, $X^2$ is

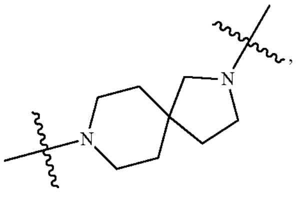,
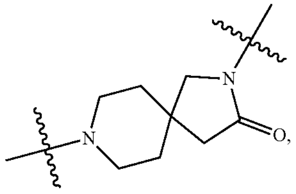,
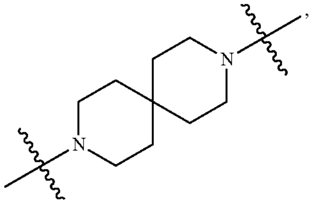,

-continued

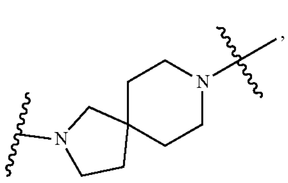,
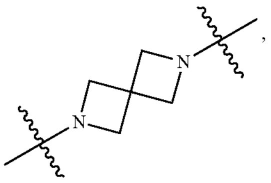,
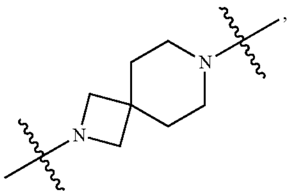,
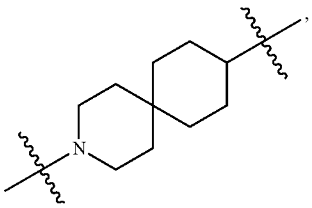, or
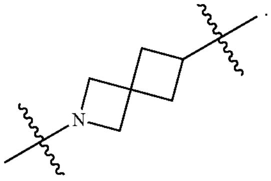.

In some embodiments, $X^2$ is a 4-6 membered monocyclic heterocycloalkyl having 1-2 heteroatoms independently selected from N, O, or S. For example, $X^2$ is a 4-6 membered monocyclic heterocycloalkyl having 1-2 N atoms. In other examples, $X^2$ is

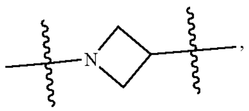,
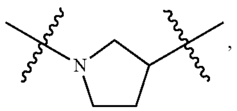,
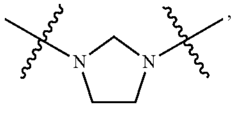,
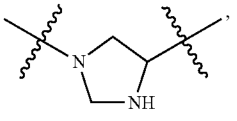,
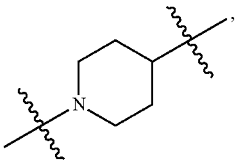, or
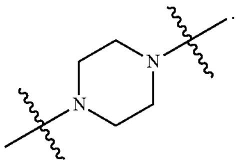.

In some embodiments, $X^2$ is a 6-10 membered fused bicyclic heterocycloalkyl having 1-3 heteroatoms independently selected from N, O, or S. For example, $X^2$ is a 6-9 membered (e.g., 6-8 membered) fused bicyclic heterocycloalkyl having 1-2 N atoms. In other examples, $X^2$ is

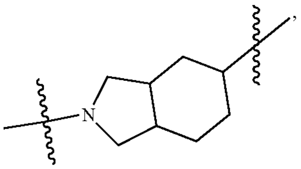

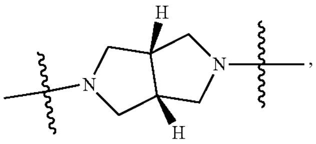

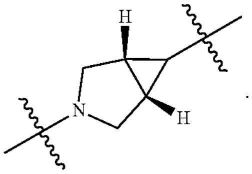

In some embodiments, $X^2$ is a 6-9 membered bridged bicyclic heterocycloalkyl having 1-3 heteroatoms independently selected from N, O, or S. For example, $X^2$ is a 6-9 membered bridged bicyclic heterocycloalkyl having 1-2 N atoms. In other examples, $X^2$ is

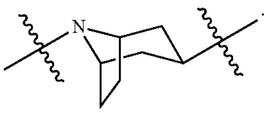 [SMILES: *C1CC2CCC(C1)N2*]

In some embodiments, $X^3$ is a bond, $—CH_2—O—$, $—C_{1-4}$ alkyl-,

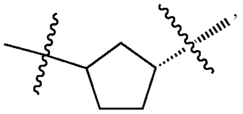

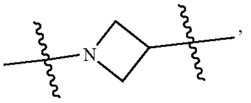

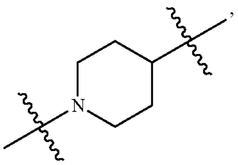

or

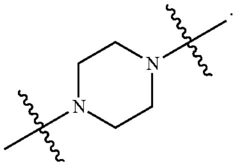

In some embodiments, $X^4$ is a bond, $—C_{1-4}$ alkyl-,

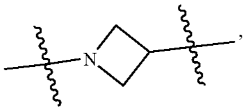

or

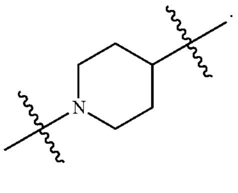

For example, $X^4$ is a bond, $—CH_2—$, $—CH_2CH_2—$, $—CH_2CH_2CH_2—$, or $—CH_2CH_2CH_2CH_2—$.

In some embodiments, L is selected from

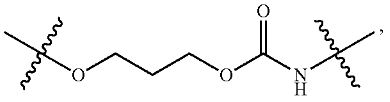

-continued

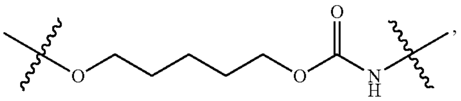

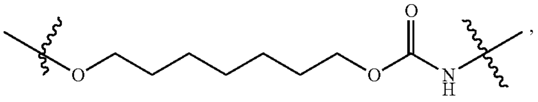

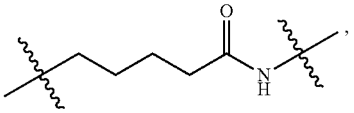

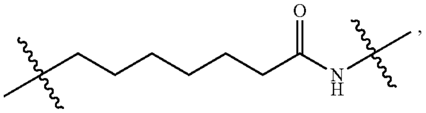

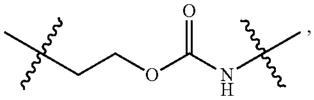

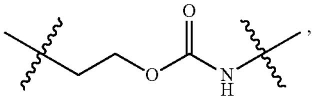

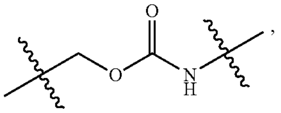

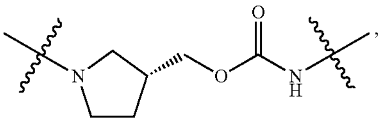

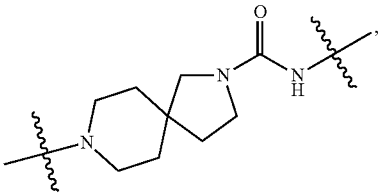

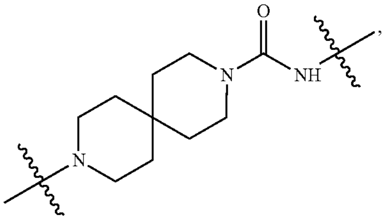

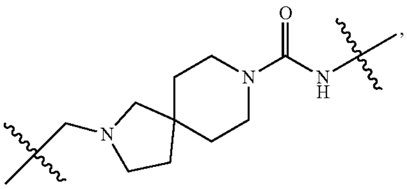

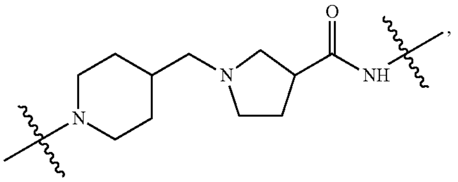

-continued
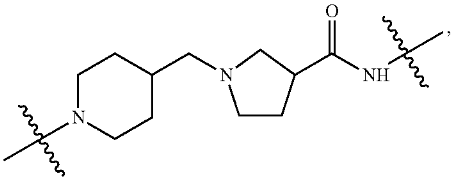
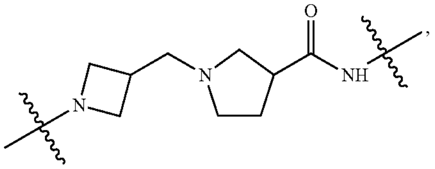
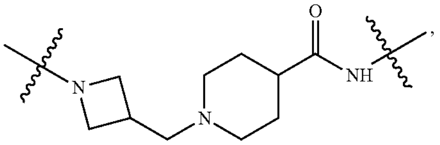
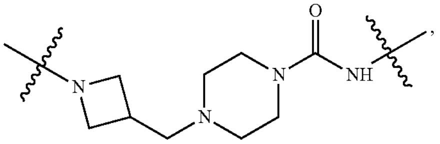
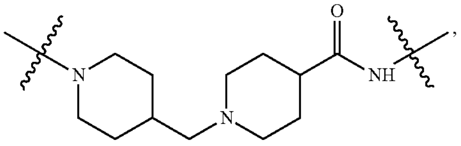
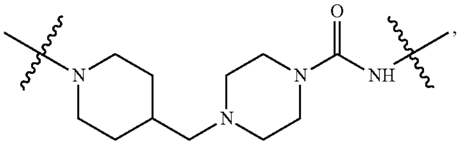
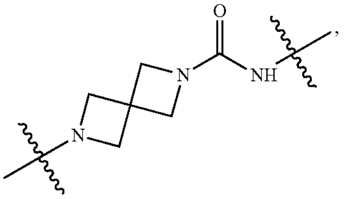
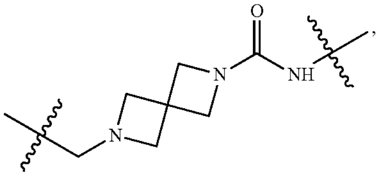
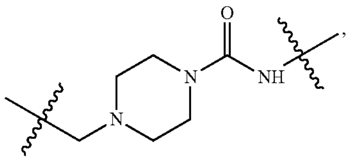
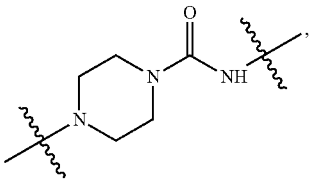
-continued
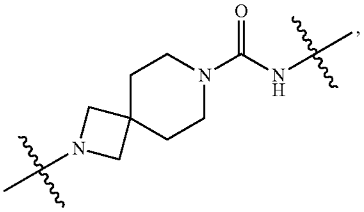
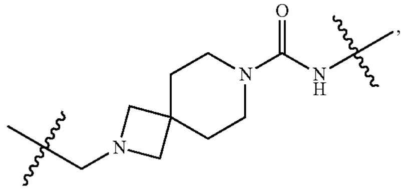
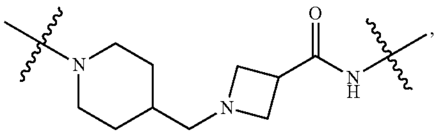
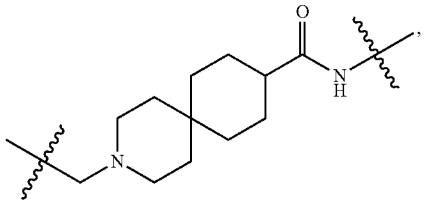
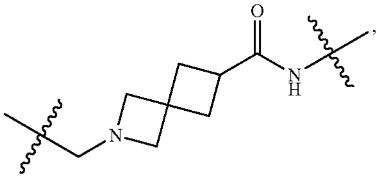
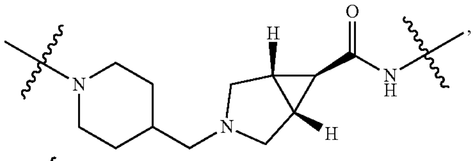
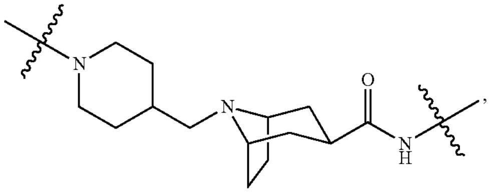
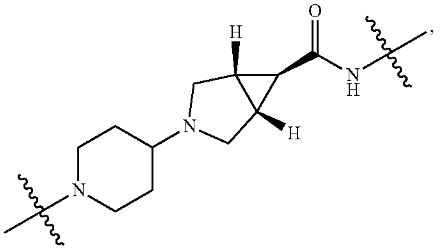
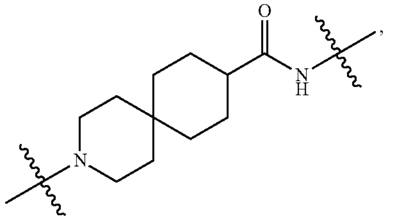

-continued

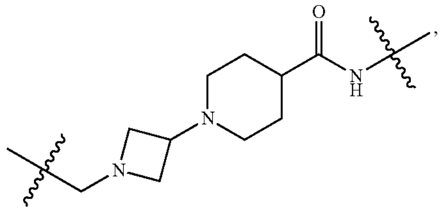

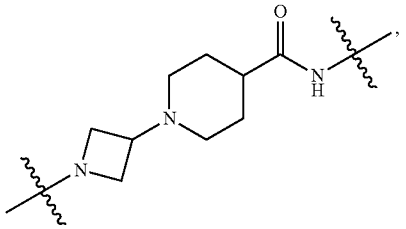

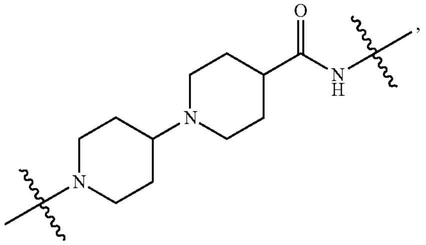

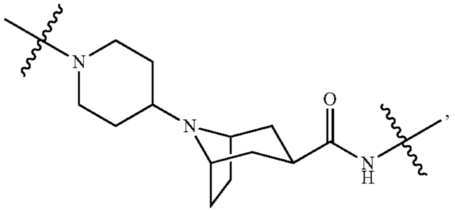

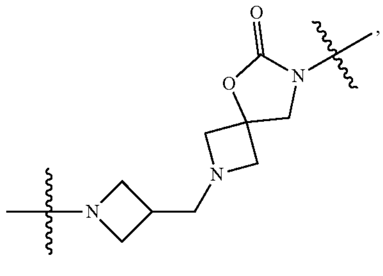

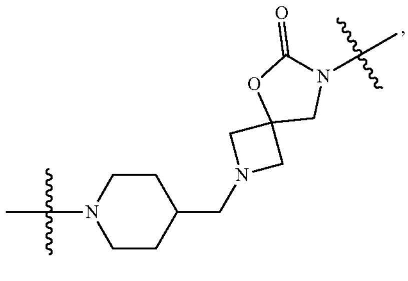

or

-continued

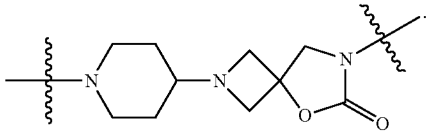

In some embodiments, the compound is a compound of Formula (II), as described herein, or a pharmaceutically acceptable salt thereof, wherein (i) ring A is

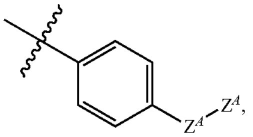

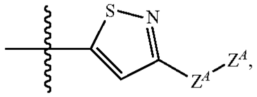

or

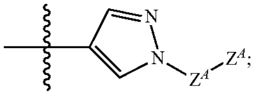

(ii) L is —$X^1$—$X^2$—$X^3$—$X^4$—;

(iii) $X^1$ is —NH—C(O)—;

(iv) $X^2$ is a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, or a 6-10 membered fused bicyclic heterocycloalkyl having 1-3 heteroatoms independently selected from N, O, or S, wherein the spiro heterocycloalkyl ring system is optionally substituted with —OH or oxo;

(v) $X^3$ is a bond, a 4-6 membered monocyclic heterocycloalkyl having 1-2 heteroatoms independently selected from N, O, or S, or a —$C_{1-4}$ alkyl-;

(vi) $X^4$ is a bond, a 4-6 membered heterocycloalkyl having 1-2 heteroatoms independently selected from N, O, or S, or a —$C_{1-4}$ alkyl-; and (vii) Y is

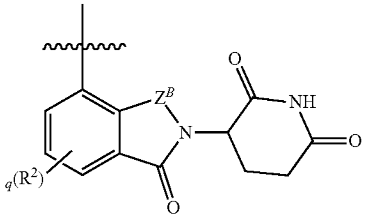

or

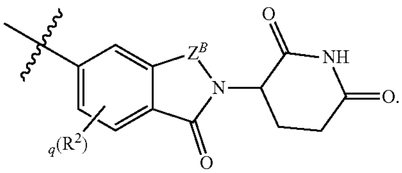

B. General Synthetic Schemes

Compounds of the present invention can be synthesized according to the following general synthetic schemes: General Procedure 1: Pyrazine Moiety Synthesis.

Scheme 1: Synthesis of amine-containing intermediates useful for synthesizing compounds of Formula (I).

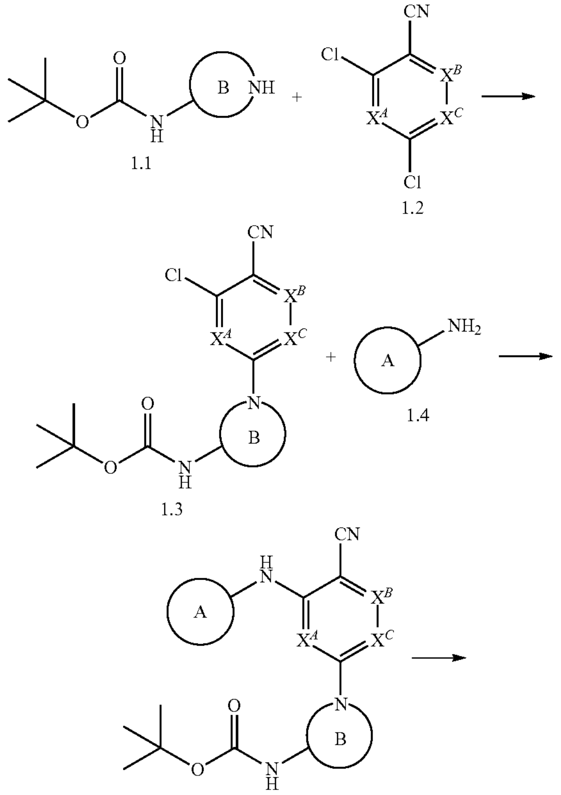
1.1
1.2
1.3
1.4
1.5

-continued

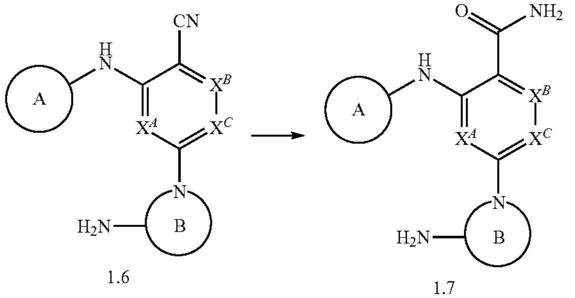
1.6
1.7 where 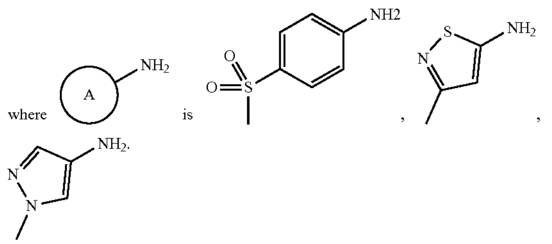 is , , or

Boc-protected ring B intermediate (1.1) is reacted with the dichloro carbonitrile intermediate (1.2) under nucleophilic substitution conditions to generate intermediate (1.3). Intermediate (1.3) can be coupled to an amine-substituted ring A intermediate (1.4) to form intermediate (1.5). Intermediate (1.5) can undergo Boc-deprotection to form intermediate (1.6), which can then be oxidized to form carbamoyl intermediate (1.7).

General Procedure 2: Carbamate Coupling.

Intermediate (2.1) is reacted with 4-nitrophenyl chloroformate under nucleophilic substitution conditions to generate intermediate (2.2). Intermediate (2.2) is reacted with intermediate (1.7) (from Scheme 1 above) under coupling conditions for afford carbamate compound (2.3).

Scheme 2: Synthesis of carbamate-containing compound of Formula (I).

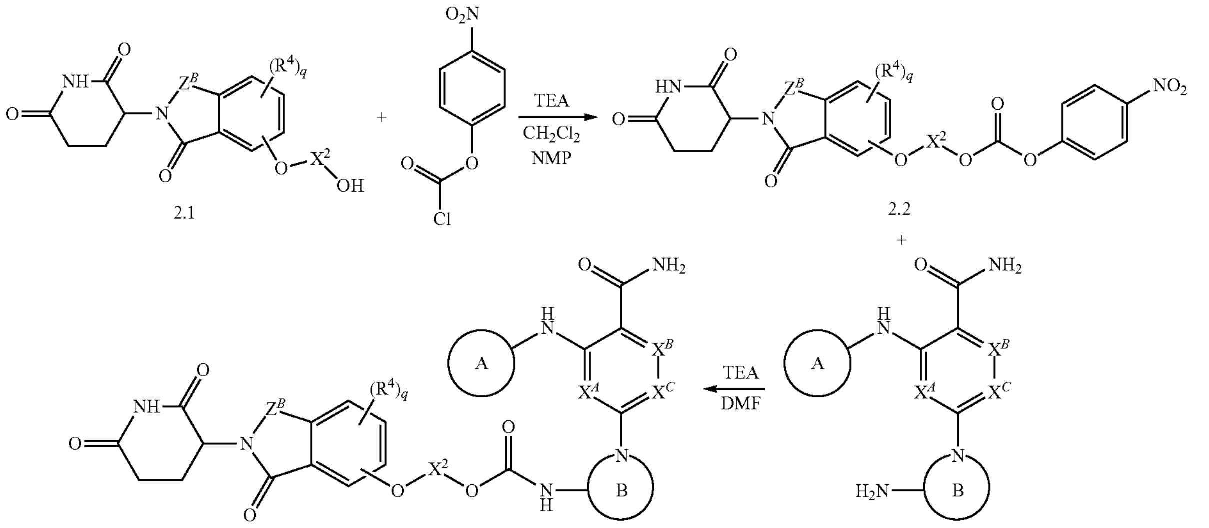

2.1
2.2
2.3
1.7

Examples of carbamate compounds of Formula (I) synthesized according to general procedure 2 include Compounds 1-3 and 6-12.

General Procedure 3: Reductive Amination.

Aldehyde intermediate (3.1) is reacted with amine intermediate (3.2) under reductive conditions to generate the amine containing compound (3.3) of Formula (I). As used in Schemes 3 and 4 herein, ring D is a fully saturated monocyclic ring or a fully saturated bicyclic (e.g., bridged bicyclic or spiro bicyclic) ring system containing a nitrogen atom.

Scheme 3: Synthesis of amine containing compound of Formula (I).

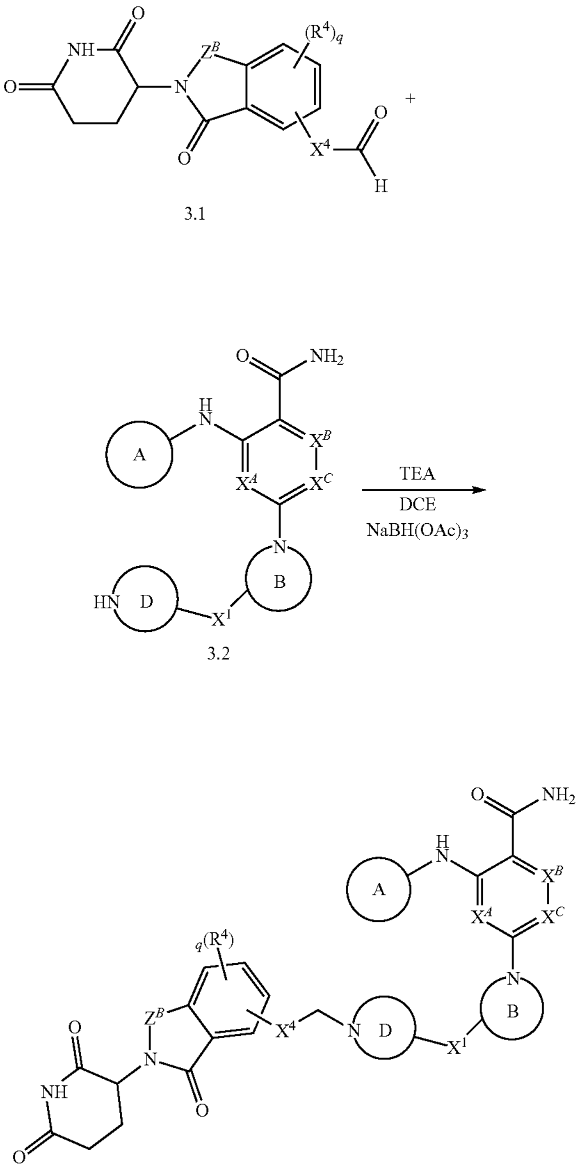

3.1

3.2

3.3

Other amine containing compounds of Formula (I) synthesized according to general procedure 3 include Compounds 13-23, 25-26, 29-35, 37, and 39-47.

General Procedure 4: Aryl Fluoride Displacement.

Fluoro intermediate (4.1) is reacted with amine intermediate (3.2) (from Scheme 3 above) under elimination or displacement reaction conditions (e.g., basic conditions) to afford the aryl amine containing compound (4.2) of Formula (I).

Scheme 4: Synthesis of aryl amine containing compounds of Formula (I) via aryl fluoride displacement.

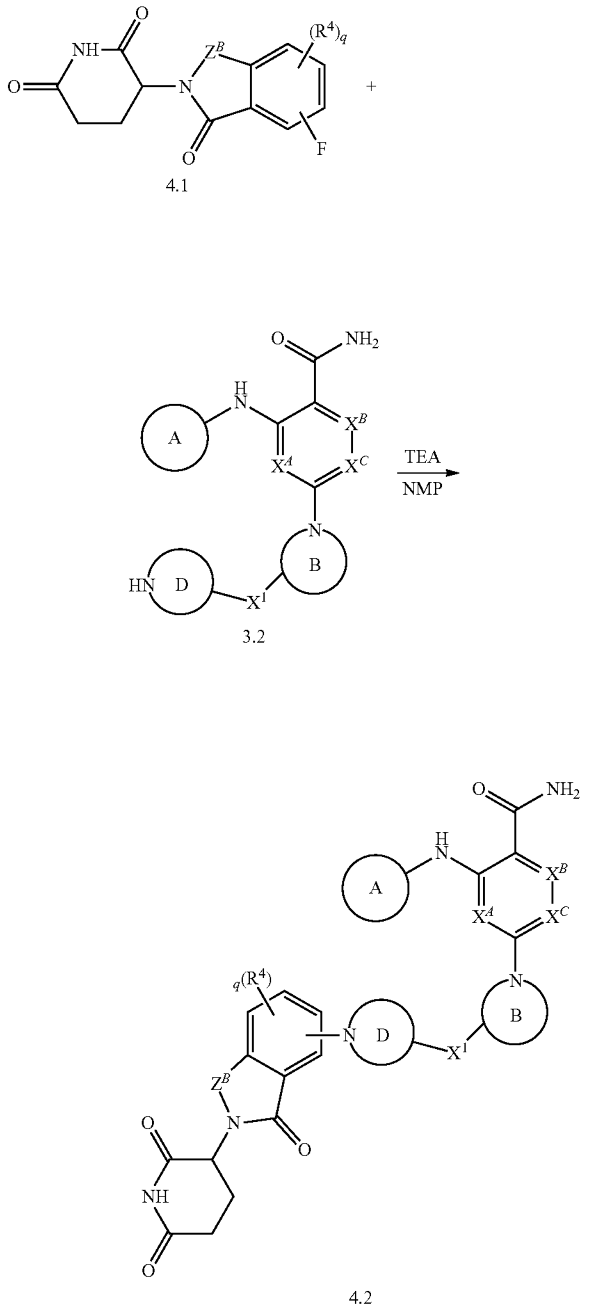

4.1

3.2

4.2

Other aryl amine containing compounds of Formula (I) synthesized according to general procedure 4 include Compounds 24, 27-28, 36, and 38.

The abovementioned synthetic schemes were used to synthesize the compounds in Table 1.

TABLE 1
| Representative compounds of Formula (I). | |
|---|---|
| 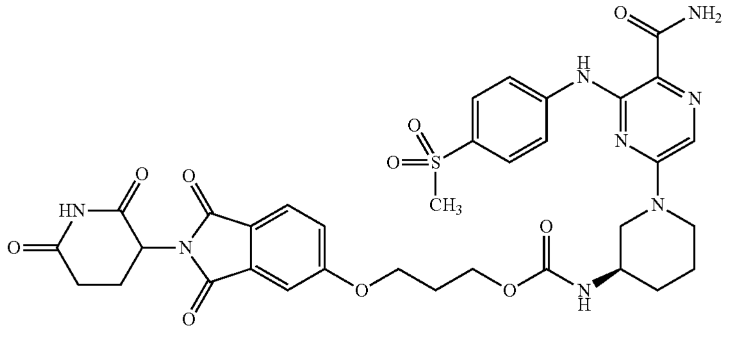 [SMILES: CS(=O)(=O)c1ccc(Nc2nc(N3CCC[C@@H](NC(=O)OCCCOc4ccc5c(c4)C(=O)N(C4CCC(=O)NC4=O)C5=O)C3)cnc2C(N)=O)cc1] | 1 |
| 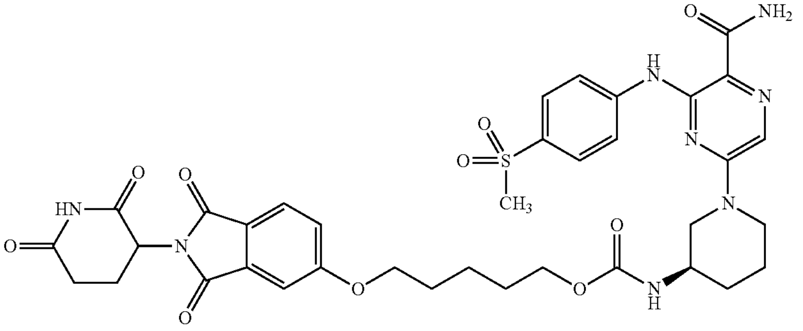 [SMILES: CS(=O)(=O)c1ccc(Nc2nc(N3CCC[C@@H](NC(=O)OCCCCCOc4ccc5c(c4)C(=O)N(C4CCC(=O)NC4=O)C5=O)C3)cnc2C(N)=O)cc1] | 2 |
| 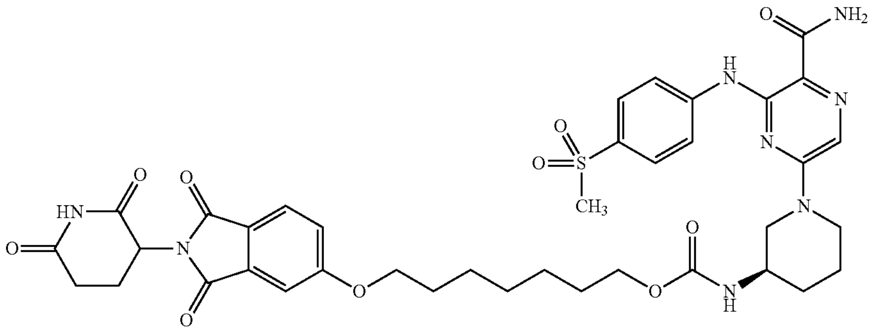 [SMILES: CS(=O)(=O)c1ccc(Nc2nc(N3CCC[C@@H](NC(=O)OCCCCCCCOc4ccc5c(c4)C(=O)N(C4CCC(=O)NC4=O)C5=O)C3)cnc2C(N)=O)cc1] | 3 |
| 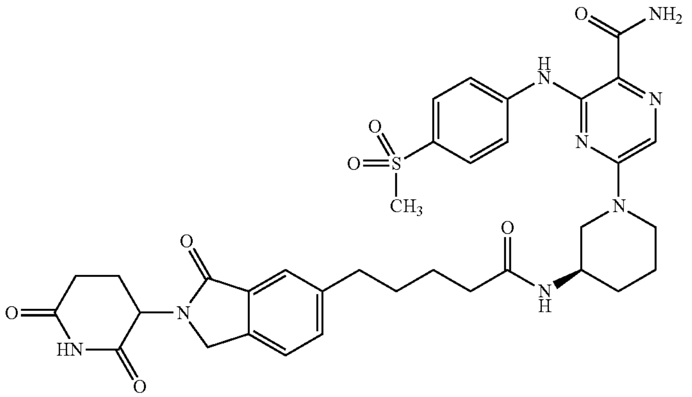 [SMILES: CS(=O)(=O)c1ccc(Nc2nc(N3CCC[C@@H](NC(=O)CCCCc4ccc5c(c4)C(=O)N(C4CCC(=O)NC4=O)C5)C3)cnc2C(N)=O)cc1] | 4 |

TABLE 1-continued
| Representative compounds of Formula (I). | |
| --- | --- |
| 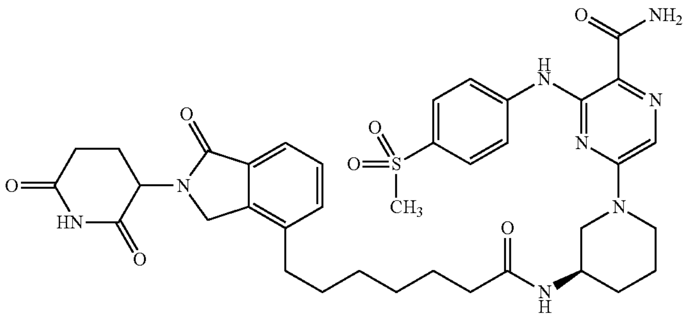 [SMILES: CS(=O)(=O)c1ccc(Nc2nc(N3CCC[C@@H](NC(=O)CCCCCCc4cccc5c4CN(C4CCC(=O)NC4=O)C5=O)C3)cnc2C(N)=O)cc1] | 5 |
| 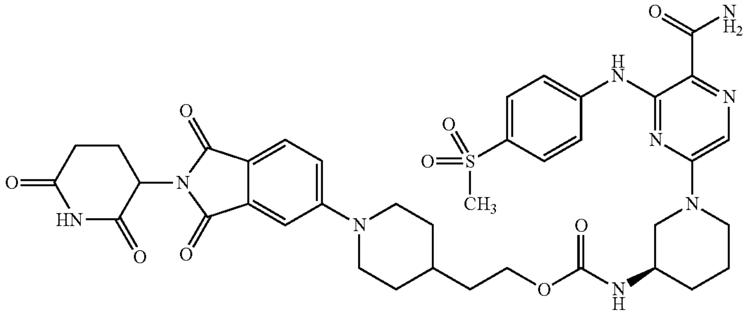 [SMILES: CS(=O)(=O)c1ccc(Nc2nc(N3CCC[C@@H](NC(=O)OCCC4CCN(c5ccc6c(c5)C(=O)N(C5CCC(=O)NC5=O)C6=O)CC4)C3)cnc2C(N)=O)cc1] | 6 |
| 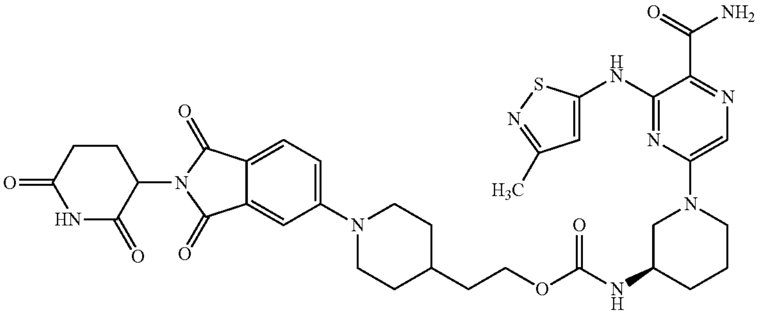 [SMILES: Cc1cc(Nc2nc(N3CCC[C@@H](NC(=O)OCCC4CCN(c5ccc6c(c5)C(=O)N(C5CCC(=O)NC5=O)C6=O)CC4)C3)cnc2C(N)=O)sn1] | 7 |
| 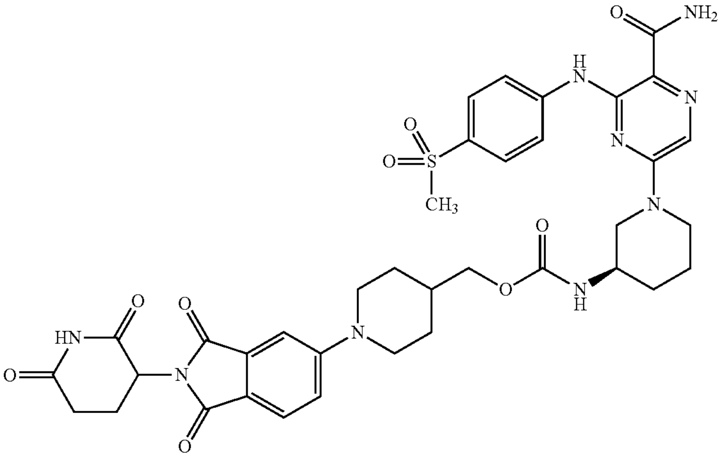 [SMILES: CS(=O)(=O)c1ccc(Nc2nc(N3CCC[C@@H](NC(=O)OCC4CCN(c5ccc6c(c5)C(=O)N(C5CCC(=O)NC5=O)C6=O)CC4)C3)cnc2C(N)=O)cc1] | 8 |

TABLE 1-continued
Representative compounds of Formula (I).
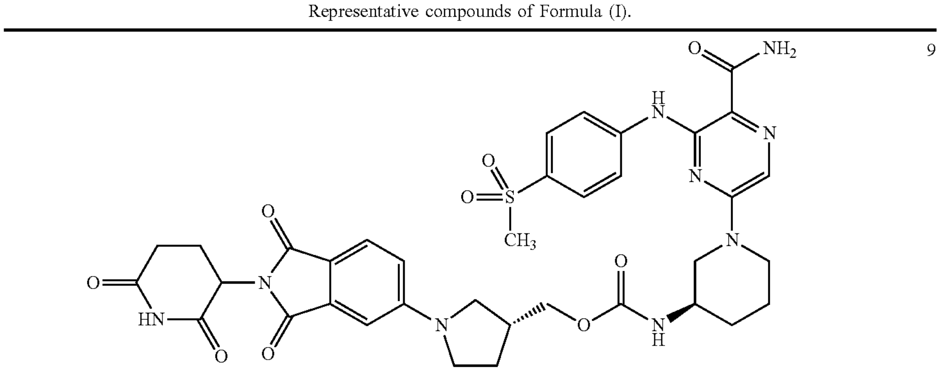
9
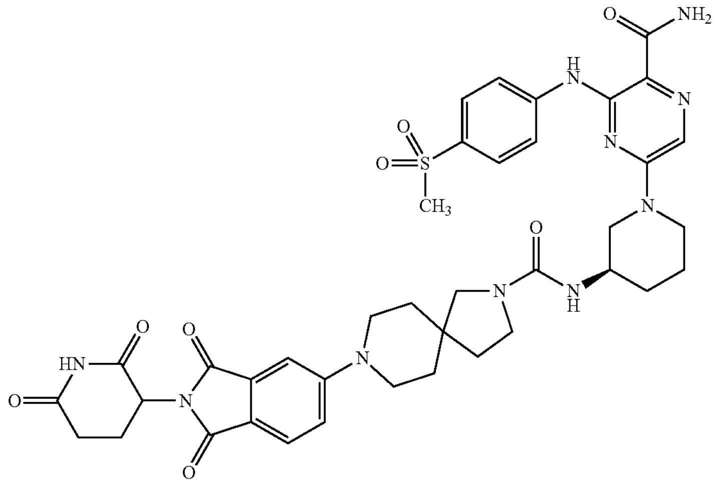 [SMILES: CS(=O)(=O)c1ccc(Nc2nc(N3CCC[C@@H](NC(=O)N4CCC5(CCN(c6ccc7c(c6)C(=O)N(C6CCC(=O)NC6=O)C7=O)CC5)C4)C3)cnc2C(N)=O)cc1]
10
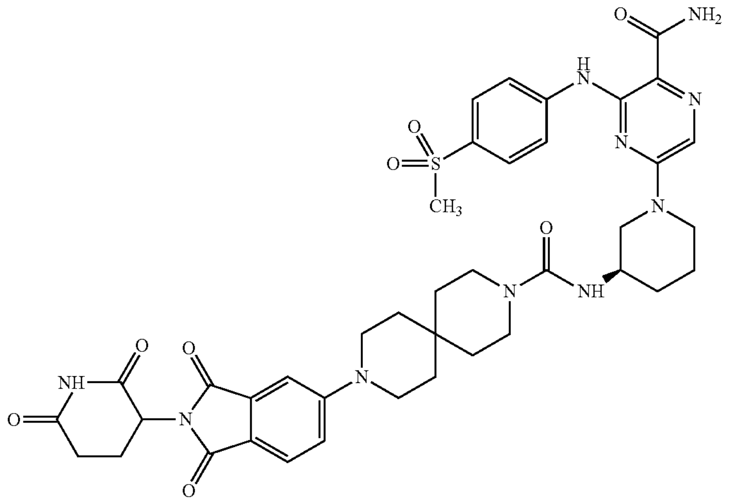 [SMILES: CS(=O)(=O)c1ccc(Nc2nc(N3CCC[C@@H](NC(=O)N4CCC5(CC4)CCN(c4ccc6c(c4)C(=O)N(C4CCC(=O)NC4=O)C6=O)CC5)C3)cnc2C(N)=O)cc1]
11

TABLE 1-continued
| Representative compounds of Formula (I). |  |
|---|---|
| 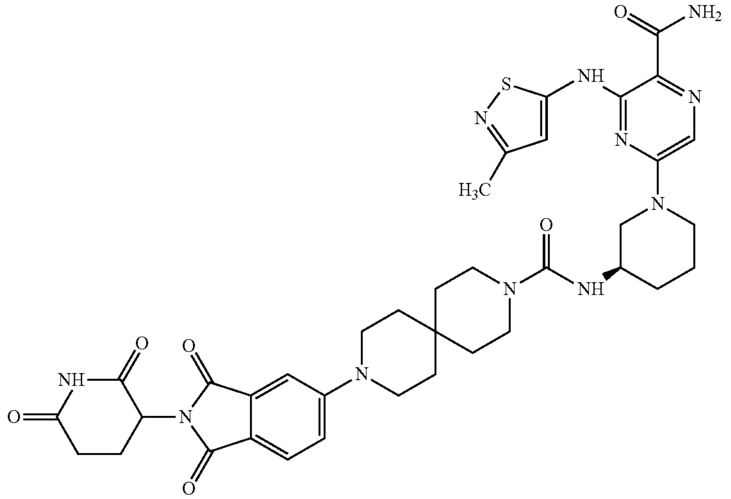 [SMILES: Cc1cc(Nc2nc(N3CCC[C@@H](NC(=O)N4CCC5(CC4)CCN(c4ccc6c(c4)C(=O)N(C4CCC(=O)NC4=O)C6=O)CC5)C3)cnc2C(N)=O)sn1] | 12 |
| 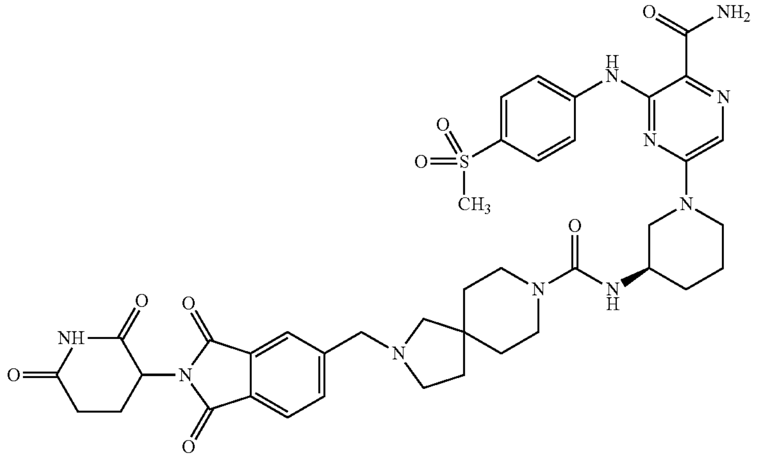 [SMILES: CS(=O)(=O)c1ccc(Nc2nc(N3CCC[C@@H](NC(=O)N4CCC5(CCN(Cc6ccc7c(c6)C(=O)N(C6CCC(=O)NC6=O)C7=O)C5)CC4)C3)cnc2C(N)=O)cc1] | 13 |
| 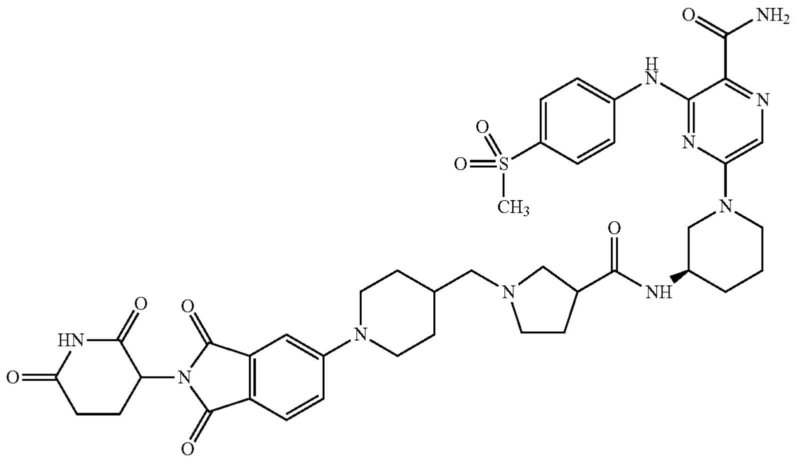 [SMILES: CS(=O)(=O)c1ccc(Nc2nc(N3CCC[C@@H](NC(=O)C4CCN(CC5CCN(c6ccc7c(c6)C(=O)N(C6CCC(=O)NC6=O)C7=O)CC5)C4)C3)cnc2C(N)=O)cc1] | 14 |

TABLE 1-continued
| Representative compounds of Formula (I). |
|---|
| 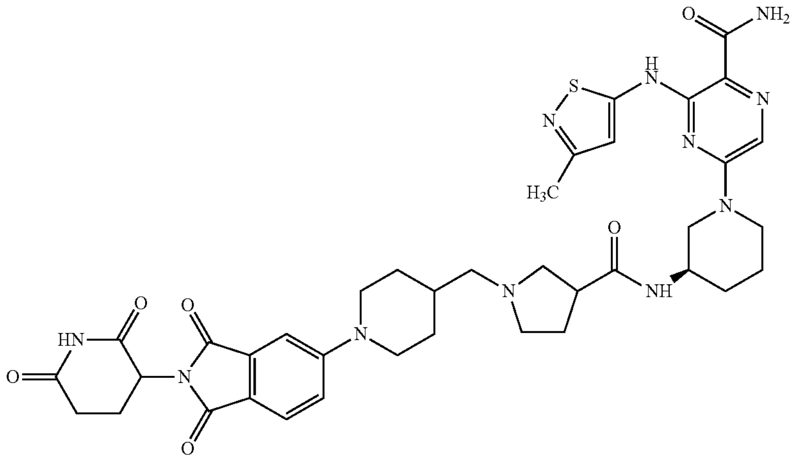 [SMILES: Cc1cc(Nc2nc(N3CCC[C@@H](NC(=O)C4CCN(CC5CCN(c6ccc7c(c6)C(=O)N(C6CCC(=O)NC6=O)C7=O)CC5)C4)C3)cnc2C(N)=O)sn1] 15 |
| 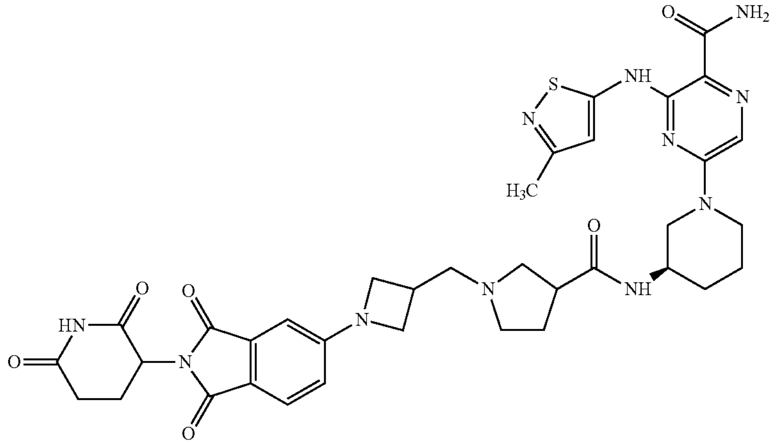 [SMILES: Cc1cc(Nc2nc(N3CCC[C@@H](NC(=O)C4CCN(CC5CN(c6ccc7c(c6)C(=O)N(C6CCC(=O)NC6=O)C7=O)C5)C4)C3)cnc2C(N)=O)sn1] 16 |
| 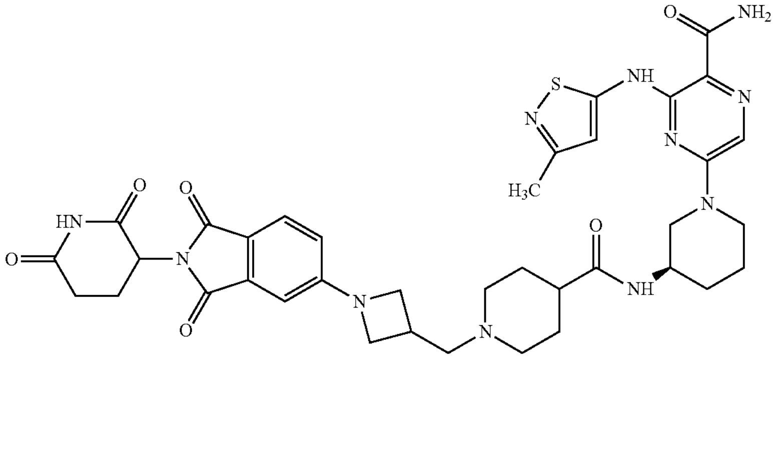 17 |

TABLE 1-continued
| Representative compounds of Formula (I). | |
|---|---|
| 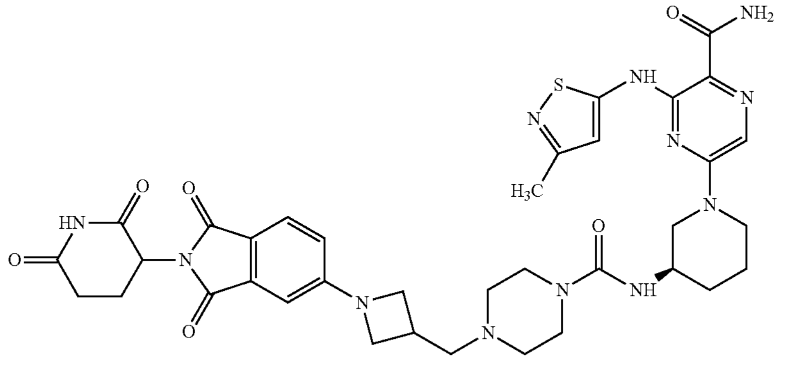 [SMILES: Cc1cc(Nc2nc(N3CCC[C@@H](NC(=O)N4CCN(CC5CN(c6ccc7c(c6)C(=O)N(C6CCC(=O)NC6=O)C7=O)C5)CC4)C3)cnc2C(N)=O)sn1] | 18 |
| 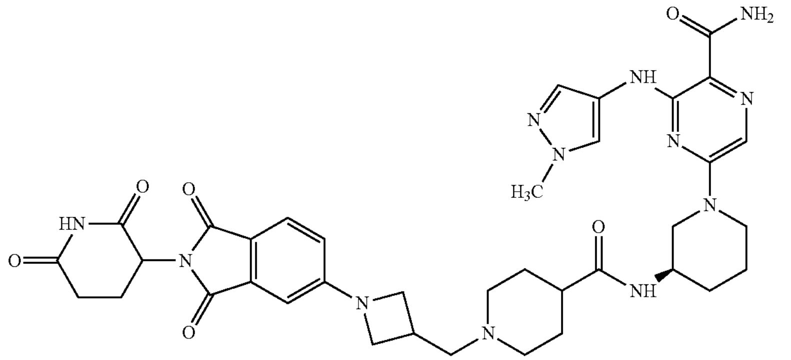 [SMILES: Cn1cc(Nc2nc(N3CCC[C@@H](NC(=O)C4CCN(CC5CN(c6ccc7c(c6)C(=O)N(C6CCC(=O)NC6=O)C7=O)C5)CC4)C3)cnc2C(N)=O)cn1] | 19 |
| 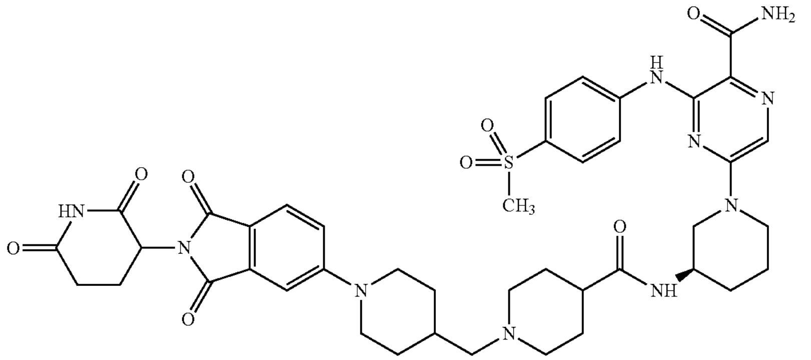 [SMILES: CS(=O)(=O)c1ccc(Nc2nc(N3CCC[C@@H](NC(=O)C4CCN(CC5CCN(c6ccc7c(c6)C(=O)N(C6CCC(=O)NC6=O)C7=O)CC5)CC4)C3)cnc2C(N)=O)cc1] | 20 |
| 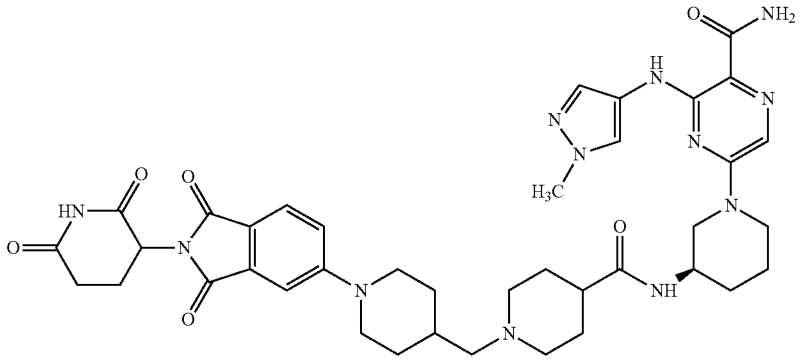 [SMILES: Cn1cc(Nc2nc(N3CCC[C@@H](NC(=O)C4CCN(CC5CCN(c6ccc7c(c6)C(=O)N(C6CCC(=O)NC6=O)C7=O)CC5)CC4)C3)cnc2C(N)=O)cn1] | 21 |

TABLE 1-continued
Representative compounds of Formula (I).
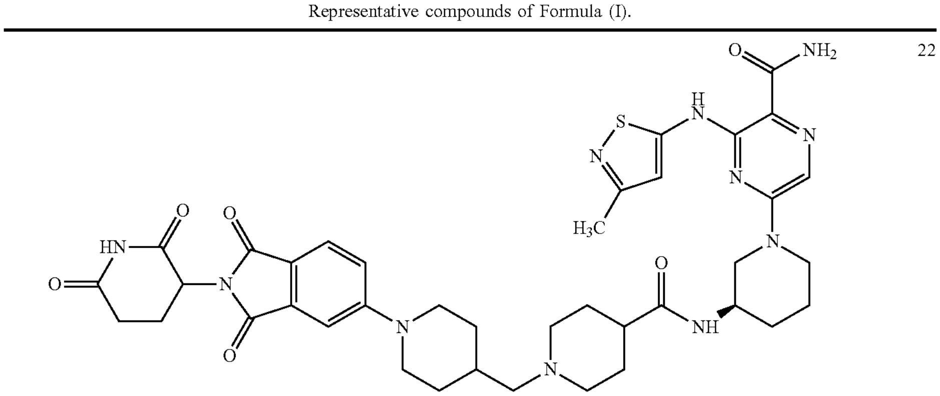
22
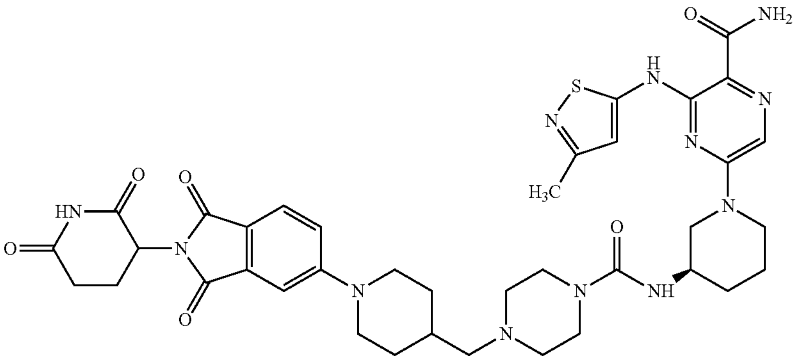 [SMILES: Cc1cc(Nc2nc(N3CCC[C@@H](NC(=O)C4CCN(CC5CCN(c6ccc7c(c6)C(=O)N(C6CCC(=O)NC6=O)C7=O)CC5)CC4)C3)cnc2C(N)=O)sn1]
23
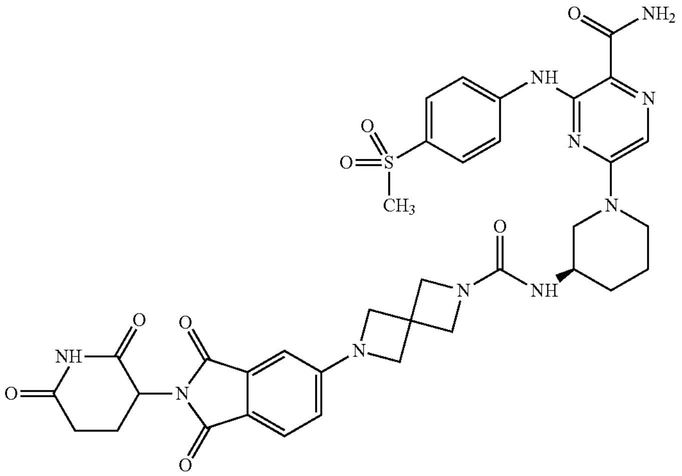 [SMILES: CS(=O)(=O)c1ccc(Nc2nc(N3CCC[C@@H](NC(=O)N4CC5(C4)CN(c4ccc6c(c4)C(=O)N(C4CCC(=O)NC4=O)C6=O)C5)C3)cnc2C(N)=O)cc1]
24
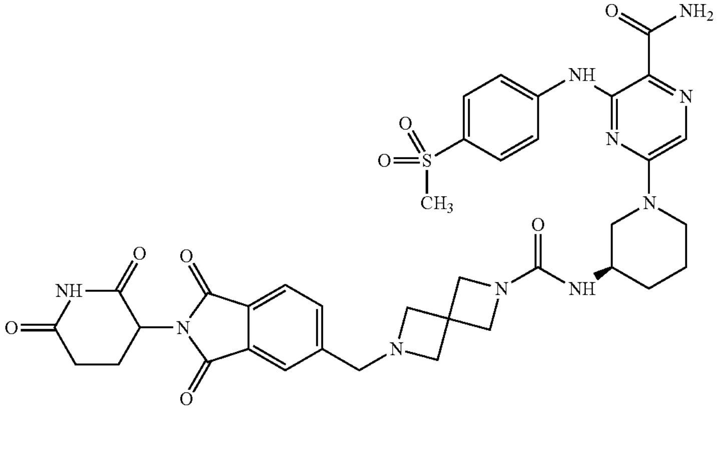 [SMILES: CS(=O)(=O)c1ccc(Nc2nc(N3CCC[C@@H](NC(=O)N4CC5(CN(Cc6ccc7c(c6)C(=O)N(C6CCC(=O)NC6=O)C7=O)C5)C4)C3)cnc2C(N)=O)cc1]
25

TABLE 1-continued
Representative compounds of Formula (I).
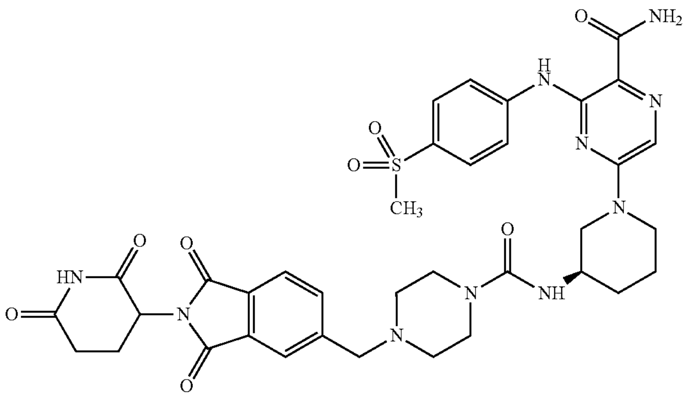 [SMILES: CS(=O)(=O)c1ccc(Nc2nc(N3CCC[C@@H](NC(=O)N4CCN(Cc5ccc6c(c5)C(=O)N(C5CCC(=O)NC5=O)C6=O)CC4)C3)cnc2C(N)=O)cc1]
26
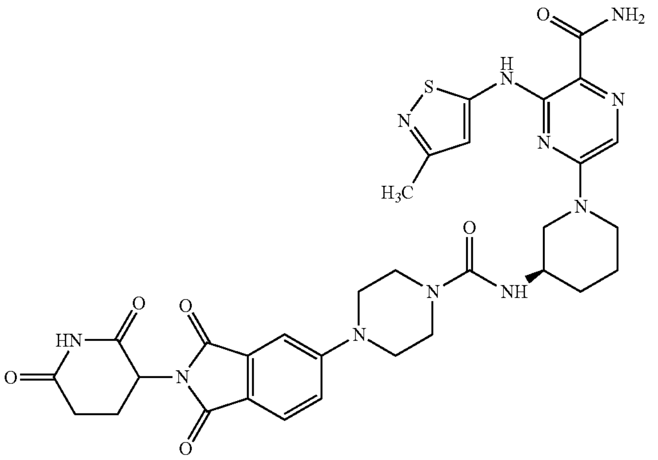 [SMILES: Cc1cc(Nc2nc(N3CCC[C@@H](NC(=O)N4CCN(c5ccc6c(c5)C(=O)N(C5CCC(=O)NC5=O)C6=O)CC4)C3)cnc2C(N)=O)sn1]
27
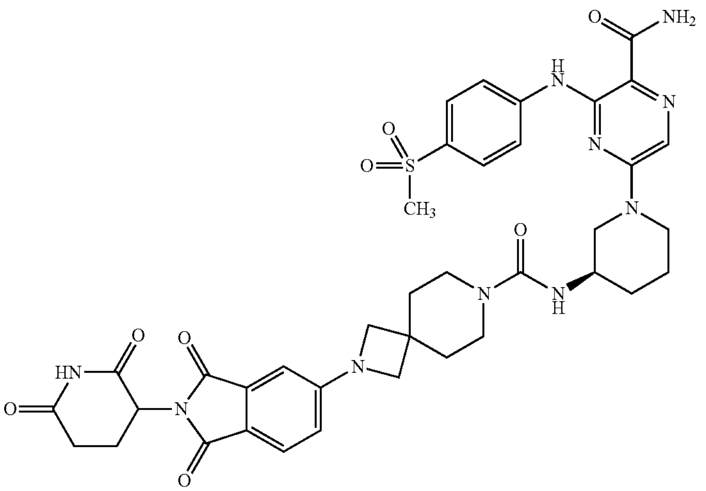 [SMILES: CS(=O)(=O)c1ccc(Nc2nc(N3CCC[C@@H](NC(=O)N4CCC5(CC4)CN(c4ccc6c(c4)C(=O)N(C4CCC(=O)NC4=O)C6=O)C5)C3)cnc2C(N)=O)cc1]
28

TABLE 1-continued
Representative compounds of Formula (I).
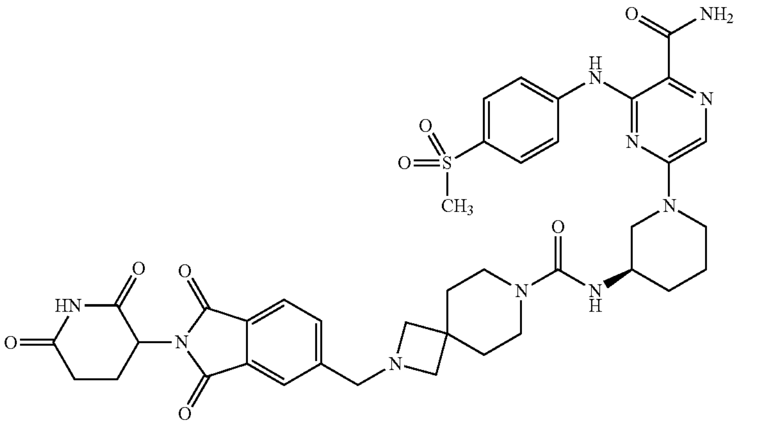 [SMILES: CS(=O)(=O)c1ccc(Nc2nc(N3CCC[C@@H](NC(=O)N4CCC5(CC4)CN(Cc4ccc6c(c4)C(=O)N(C4CCC(=O)NC4=O)C6=O)C5)C3)cnc2C(N)=O)cc1]
29
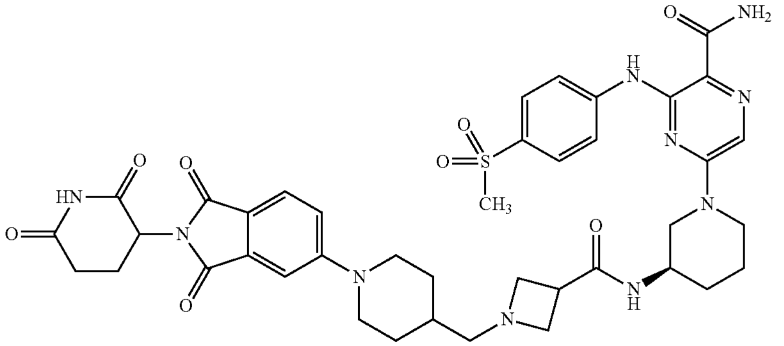 [SMILES: CS(=O)(=O)c1ccc(Nc2nc(N3CCC[C@@H](NC(=O)C4CN(CC5CCN(c6ccc7c(c6)C(=O)N(C6CCC(=O)NC6=O)C7=O)CC5)C4)C3)cnc2C(N)=O)cc1]
30
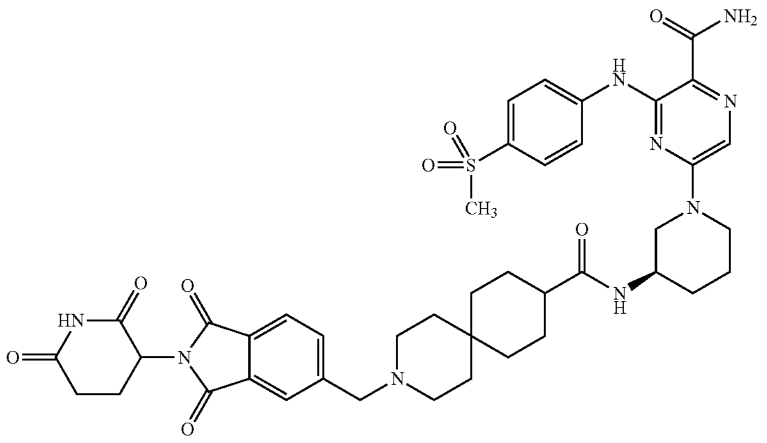 [SMILES: CS(=O)(=O)c1ccc(Nc2nc(N3CCC[C@@H](NC(=O)C4CCC5(CC4)CCN(Cc4ccc6c(c4)C(=O)N(C4CCC(=O)NC4=O)C6=O)CC5)C3)cnc2C(N)=O)cc1]
31

TABLE 1-continued
| Representative compounds of Formula (I). |
| --- |
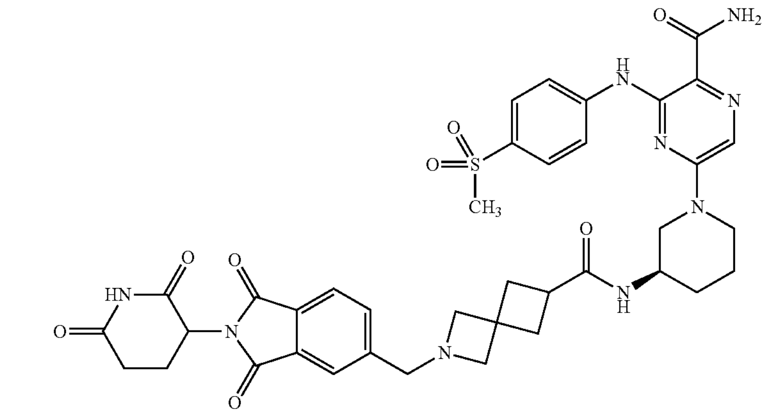 [SMILES: CS(=O)(=O)c1ccc(Nc2nc(N3CCC[C@@H](NC(=O)C4CC5(C4)CN(Cc4ccc6c(c4)C(=O)N(C4CCC(=O)NC4=O)C6=O)C5)C3)cnc2C(N)=O)cc1]
32
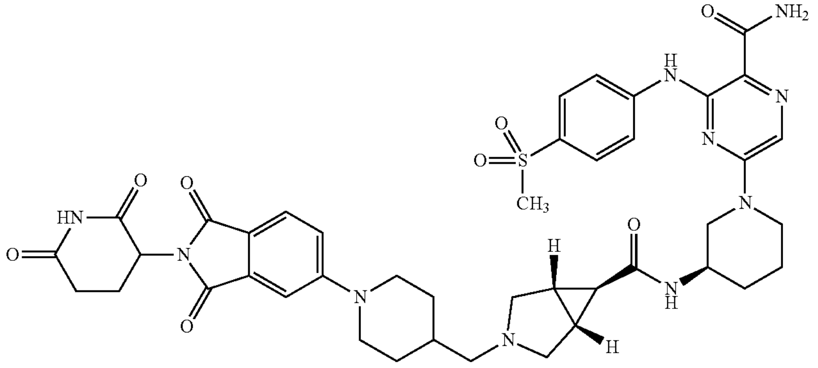 [SMILES: CS(=O)(=O)c1ccc(Nc2nc(N3CCC[C@@H](NC(=O)[C@H]4[C@@H]5CN(CC6CCN(c7ccc8c(c7)C(=O)N(C7CCC(=O)NC7=O)C8=O)CC6)C[C@@H]54)C3)cnc2C(N)=O)cc1]
33
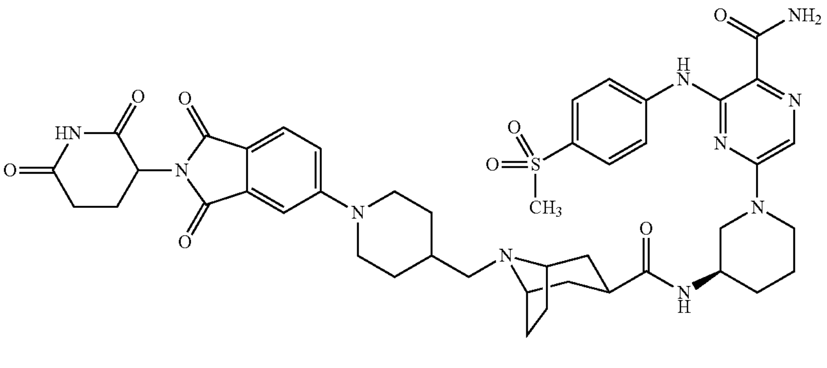 [SMILES: CS(=O)(=O)c1ccc(Nc2nc(N3CCC[C@@H](NC(=O)C4CC5CCC(C4)N5CC4CCN(c5ccc6c(c5)C(=O)N(C5CCC(=O)NC5=O)C6=O)CC4)C3)cnc2C(N)=O)cc1]
34

TABLE 1-continued
| Representative compounds of Formula (I). |
| --- |
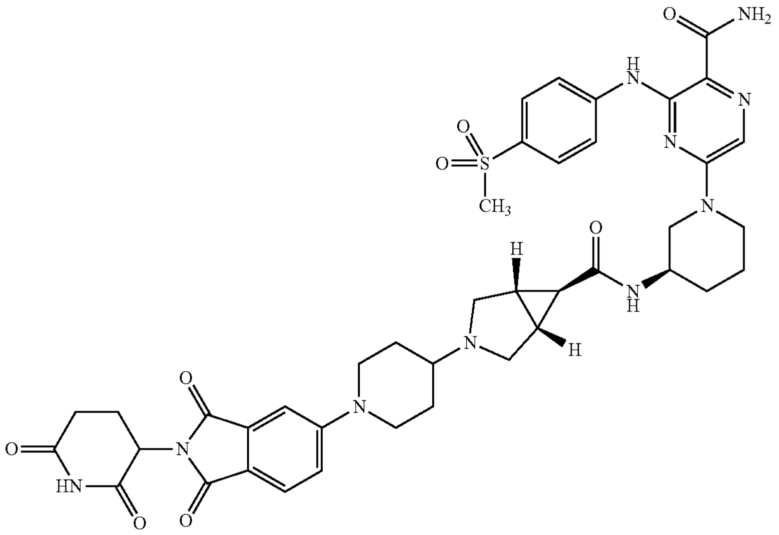 [SMILES: CS(=O)(=O)c1ccc(Nc2nc(N3CCC[C@@H](NC(=O)[C@H]4[C@@H]5CN(C6CCN(c7ccc8c(c7)C(=O)N(C7CCC(=O)NC7=O)C8=O)CC6)C[C@@H]54)C3)cnc2C(N)=O)cc1]
35
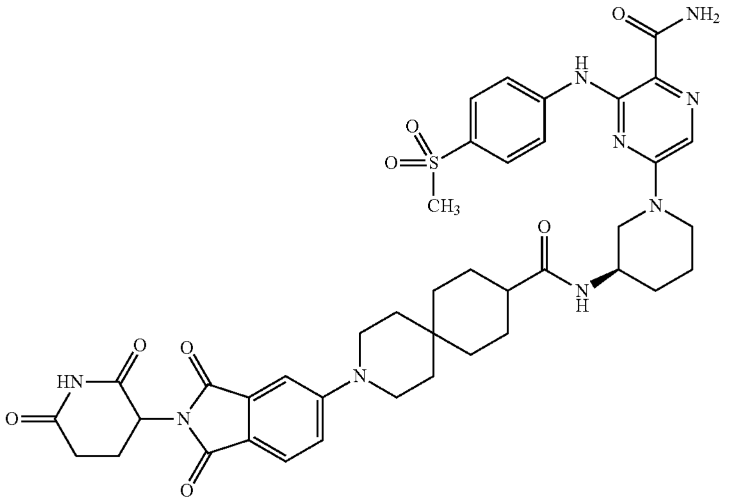 [SMILES: CS(=O)(=O)c1ccc(Nc2nc(N3CCC[C@@H](NC(=O)C4CCC5(CC4)CCN(c4ccc6c(c4)C(=O)N(C4CCC(=O)NC4=O)C6=O)CC5)C3)cnc2C(N)=O)cc1]
36
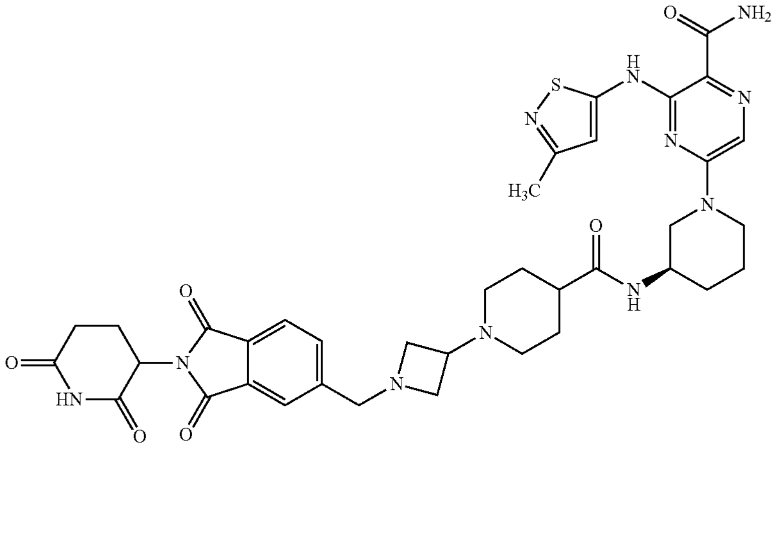 [SMILES: Cc1cc(Nc2nc(N3CCC[C@@H](NC(=O)C4CCN(C5CN(Cc6ccc7c(c6)C(=O)N(C6CCC(=O)NC6=O)C7=O)C5)CC4)C3)cnc2C(N)=O)sn1]
37

TABLE 1-continued
Representative compounds of Formula (I).
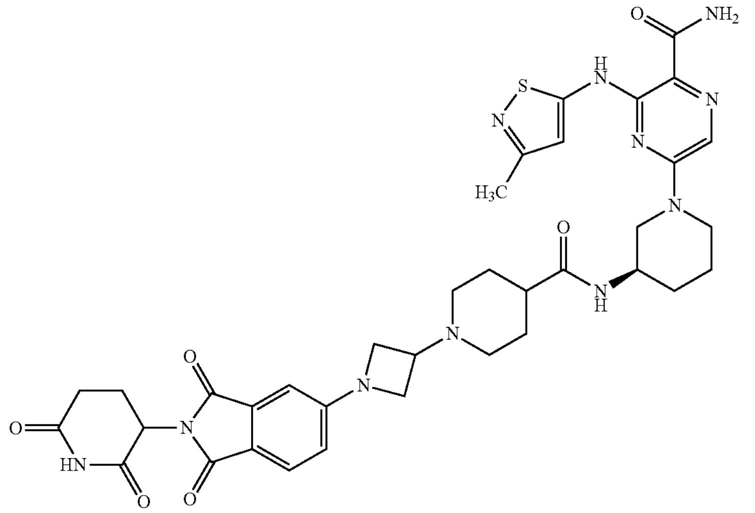 [SMILES: Cc1cc(Nc2nc(N3CCC[C@@H](NC(=O)C4CCN(C5CN(c6ccc7c(c6)C(=O)N(C6CCC(=O)NC6=O)C7=O)C5)CC4)C3)cnc2C(N)=O)sn1]
38
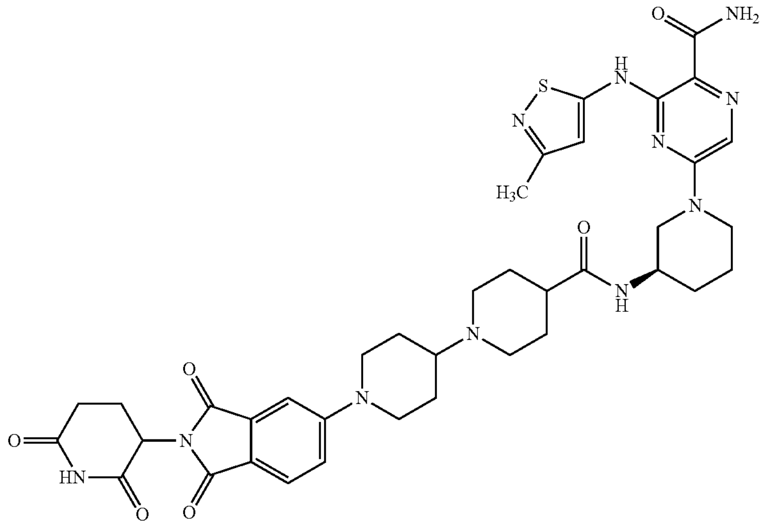 [SMILES: Cc1cc(Nc2nc(N3CCC[C@@H](NC(=O)C4CCN(C5CCN(c6ccc7c(c6)C(=O)N(C6CCC(=O)NC6=O)C7=O)CC5)CC4)C3)cnc2C(N)=O)sn1]
39
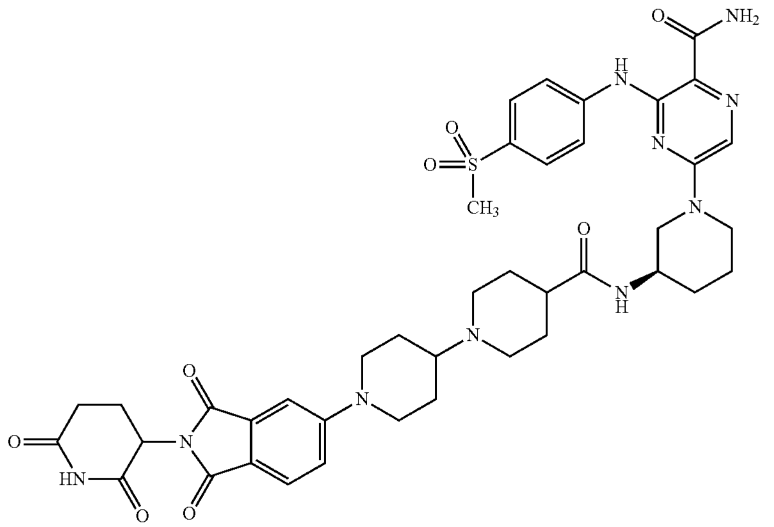 [SMILES: CS(=O)(=O)c1ccc(Nc2nc(N3CCC[C@@H](NC(=O)C4CCN(C5CCN(c6ccc7c(c6)C(=O)N(C6CCC(=O)NC6=O)C7=O)CC5)CC4)C3)cnc2C(N)=O)cc1]
40

TABLE 1-continued
| Representative compounds of Formula (I). | |
|---|---|
| 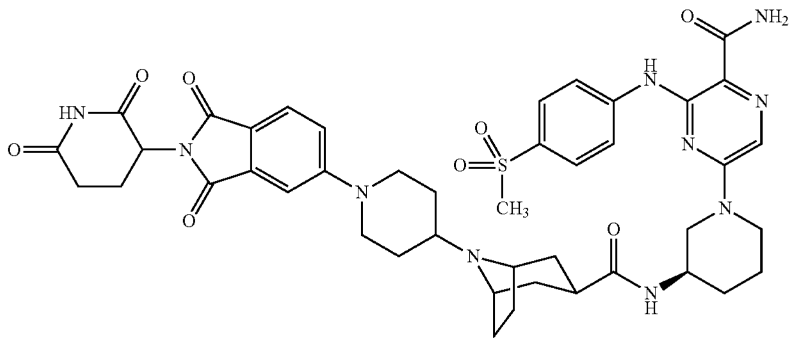 [SMILES: CS(=O)(=O)c1ccc(Nc2nc(N3CCC[C@@H](NC(=O)C4CC5CCC(C4)N5C4CCN(c5ccc6c(c5)C(=O)N(C5CCC(=O)NC5=O)C6=O)CC4)C3)cnc2C(N)=O)cc1] | 41 |
| 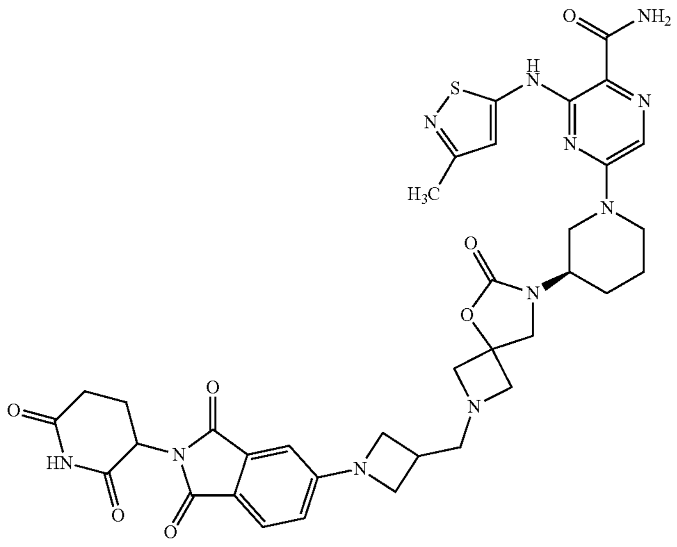 [SMILES: Cc1cc(Nc2nc(N3CCC[C@@H](N4CC5(CN(CC6CN(c7ccc8c(c7)C(=O)N(C7CCC(=O)NC7=O)C8=O)C6)C5)OC4=O)C3)cnc2C(N)=O)sn1] | 42 |
| 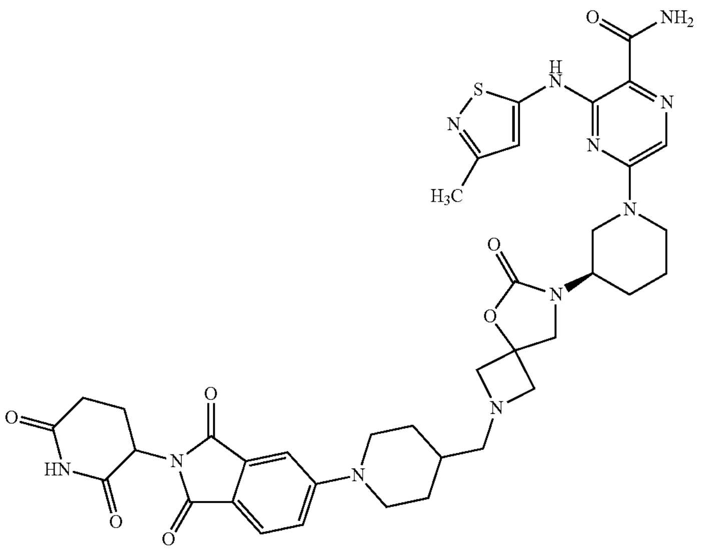 [SMILES: Cc1cc(Nc2nc(N3CCC[C@@H](N4CC5(CN(CC6CCN(c7ccc8c(c7)C(=O)N(C7CCC(=O)NC7=O)C8=O)CC6)C5)OC4=O)C3)cnc2C(N)=O)sn1] | 43 |

TABLE 1-continued
| Representative compounds of Formula (I). |
| --- |
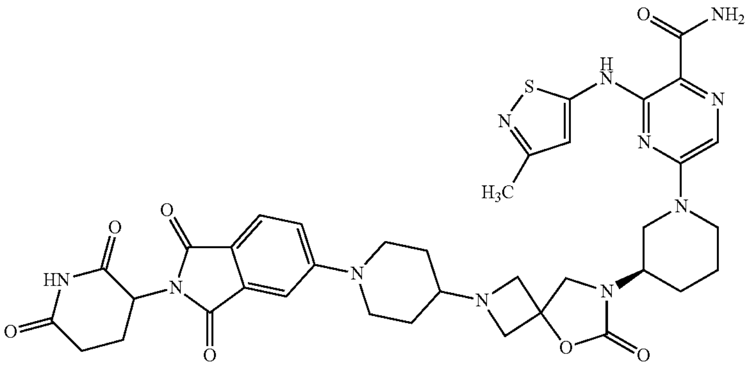 [SMILES: Cc1cc(Nc2nc(N3CCC[C@@H](N4CC5(CN(C6CCN(c7ccc8c(c7)C(=O)N(C7CCC(=O)NC7=O)C8=O)CC6)C5)OC4=O)C3)cnc2C(N)=O)sn1]
44
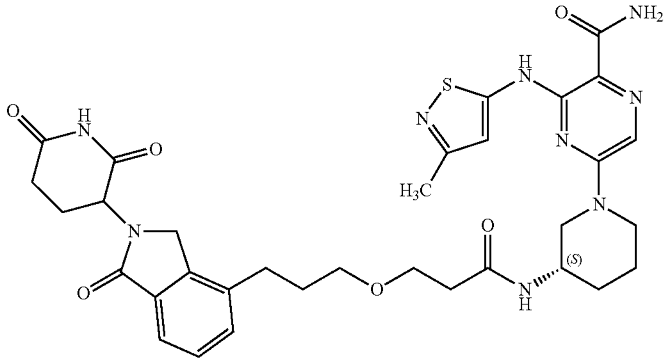
45
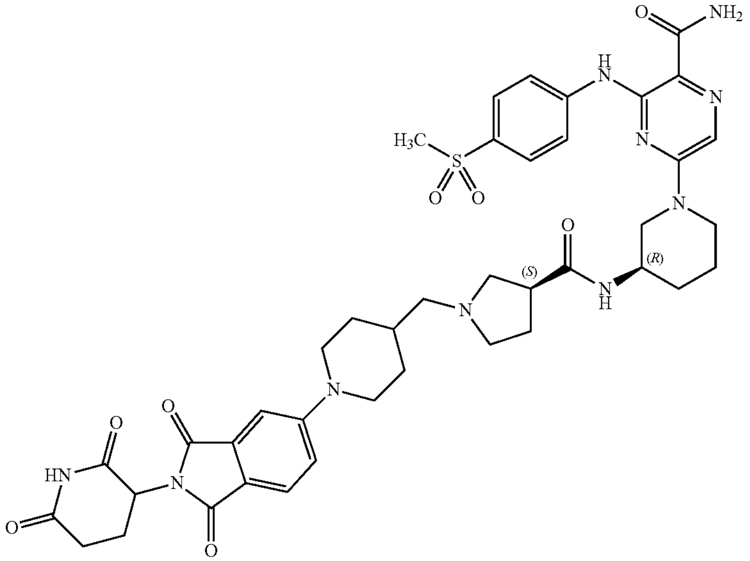
46

TABLE 1-continued
| Representative compounds of Formula (I). | |
|---|---|
| 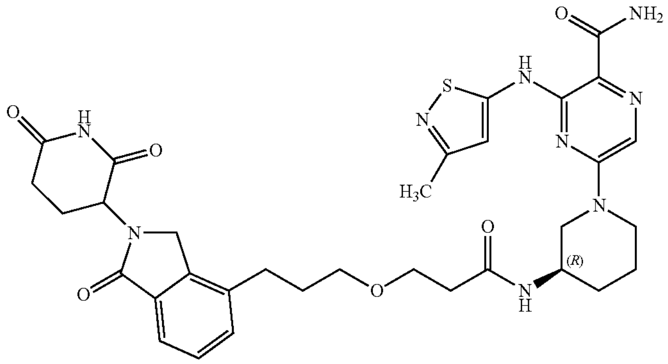 | 47 |
| 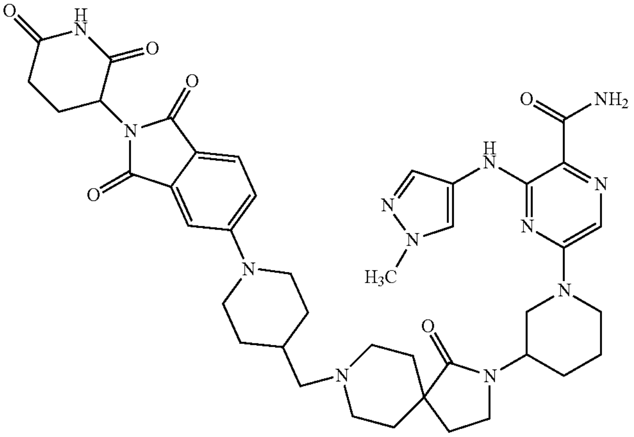 [SMILES: Cn1cc(Nc2nc(N3CCCC(N4CCC5(CCN(CC6CCN(c7ccc8c(c7)C(=O)N(C7CCC(=O)NC7=O)C8=O)CC6)CC5)C4=O)C3)cnc2C(N)=O)cn1] | 48 |
| 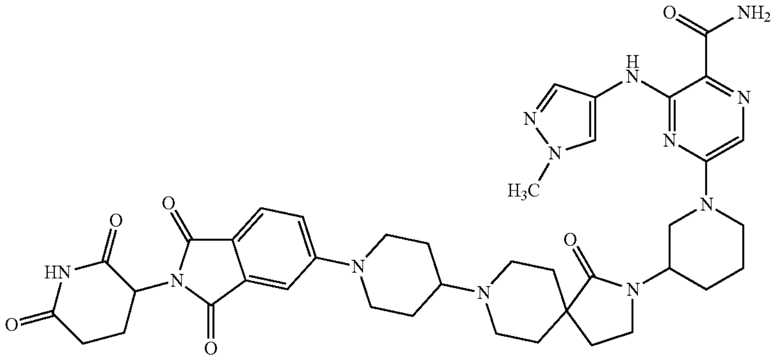 [SMILES: Cn1cc(Nc2nc(N3CCCC(N4CCC5(CCN(C6CCN(c7ccc8c(c7)C(=O)N(C7CCC(=O)NC7=O)C8=O)CC6)CC5)C4=O)C3)cnc2C(N)=O)cn1] | 49 |

TABLE 1-continued

Representative compounds of Formula (I).

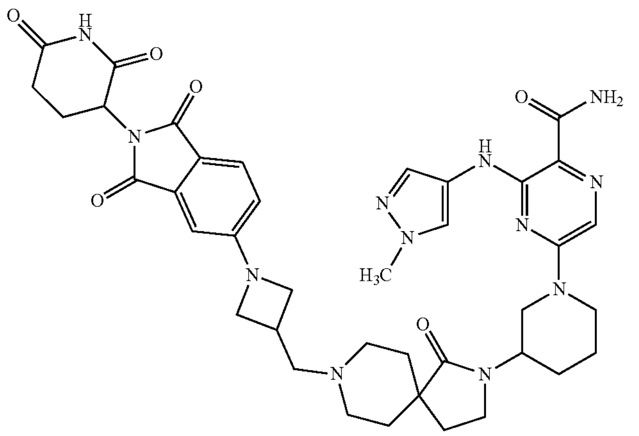 [SMILES: Cn1cc(Nc2nc(N3CCCC(N4CCC5(CCN(CC6CN(c7ccc8c(c7)C(=O)N(C7CCC(=O)NC7=O)C8=O)C6)CC5)C4=O)C3)cnc2C(N)=O)cn1]

III. Uses, Formulations, and Administration

A. Pharmaceutical Compositions

The compounds described herein can be formulated into pharmaceutical compositions that further comprise a pharmaceutically acceptable carrier, diluent, adjuvant or vehicle. In one embodiment, the present invention provides a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

According to another embodiment, the invention provides a composition comprising a compound of this invention or a pharmaceutically acceptable salt thereof and a pharmaceutically acceptable carrier, adjuvant, or vehicle. Pharmaceutical compositions of this invention comprise a therapeutically effective amount of a compound of Formula (I) and (II), wherein a "therapeutically effective amount" is an amount that is (a) effective to measurably degrade BTK (or reduce the amount of BTK) in a biological sample or in a patient, or (b) effective in treating and/or ameliorating a disease or disorder that is mediated by BTK.

The term "patient," as used herein, means an animal, preferably a mammal, and most preferably a human.

It also will be appreciated that certain of the compounds of the present invention can exist in free form for treatment, or where appropriate, as a pharmaceutically acceptable derivative (e.g., a salt) thereof. According to the present invention, a pharmaceutically acceptable derivative includes, but is not limited to, pharmaceutically acceptable prodrugs, salts, esters, salts of such esters, or any other adduct or derivative that upon administration to a patient in need is capable of providing, directly or indirectly, a compound as otherwise described herein, or a metabolite or residue thereof.

As used herein, the term "pharmaceutically acceptable salt" refers to those salts that are, within the scope of sound medical judgement, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

A pharmaceutically acceptable carrier may contain inert ingredients that do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, the use of such conventional carrier medium is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful, uncomfortable, or risky. Side effects include, but are not limited to, fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials that can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents. Preservatives and antioxidants can also be present in the composition, according to the judgment of the formulator.

As used herein, the term "measurably degrade," means a measurable reduction in (a) BTK activity, between a sample comprising a compound of this invention and a BTK and an equivalent sample comprising a BTK in the absence of said compound, or (b) the concentration of the BTK in a sample over time.

The compositions of the present invention may be administered orally, parenterally, by inhalation spray, topically, rectally, nasally, buccally, vaginally or via an implanted reservoir. As used herein, the term "parenteral" includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation also may be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions also may contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers that are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents also may be added.

Alternatively, the pharmaceutically acceptable compositions of this invention may be administered in the form of suppositories for rectal or vaginal administration. These can be prepared by mixing the agent with a suitable non-irritating excipient that is solid at room temperature but liquid at rectal temperature and therefore will melt in the rectum or vaginal cavity to release the drug. Such materials include cocoa butter, polyethylene glycol or a suppository wax that is solid at ambient temperature but liquid at body temperature and therefore melt in the rectum or vaginal cavity and release the active compound.

The pharmaceutically acceptable compositions of this invention also may be administered topically, especially when the target of treatment includes areas or organs readily accessible by topical application, including diseases of the eye, skin, or lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches also may be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention also may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions also can include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation also may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations also are prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also may comprise buffering agents.

Solid compositions of a similar type also may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Solid dosage forms optionally may contain opacifying agents. These solid dosage forms also can be of a composition such that they release the active ingredient(s) only, or preferentially, in a certain part of the intestinal tract, optionally, in a delayed manner. Examples of embedding compositions that can be used include polymeric substances and waxes. Solid compositions of a similar type also may be employed as fillers in soft and hard-filled gelatin capsules using such excipients as lactose or milk sugar as well as high molecular weight polyethylene glycols and the like.

The active compounds also can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also may comprise, as is normal practice, additional substances other than inert diluents, e.g., tableting lubricants and other tableting aids such a magnesium stearate and microcrystalline cellulose. In the case of capsules, tablets and pills, the dosage forms also may comprise buffering agents. They may optionally contain opacifying agents and also can be of a composition such that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops also are contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers also can be used to increase the flux of the compound across the skin. The rate can be controlled by either providing a rate controlling membrane or by dispersing the compound in a polymer matrix or gel.

The compounds of the invention preferably are formulated in dosage unit form for ease of administration and uniformity of dosage. As used herein, the phrase "dosage unit form" refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration, and other factors. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, also may be present in the compositions of this invention. As used herein, additional therapeutic agents that are normally administered to treat or prevent a particular disease, or condition, are known as "appropriate for the disease, or condition, being treated."

For example, chemotherapeutic agents or other anti-proliferative agents may be combined with the compounds of this invention to treat proliferative diseases and cancer. Examples of known chemotherapeutic agents include, but are not limited to, PI3K inhibitors (e.g., idelalisib and copanlisib), BCL-2 inhibitors (e.g., venetoclax), BTK inhibitors (e.g., ibrutinib and acalabrutinib), etoposide, CD20 antibodies (e.g., rituximab, ocrelizumab, obinutuzumab, ofatumumab, ibritumomab tiuxetan, tositumomab, and ublituximab), alemtuzumab, bendamustine, cladribine, doxorubicin, chlorambucil, prednisone, midostaurin, lenalidomide, pomalidomide, checkpoint inhibitors (e.g., ipilimumab, nivolumab, pembrolizumab, atezolizumab, avelumab, durvalumab), engineered cell therapy (e.g., CAR-T therapy—Kymriah®, Yescarta®), Gleevec™, adriamycin, dexamethasone, vincristine, cyclophosphamide, fluorouracil, topotecan, taxol, interferons, and platinum derivatives.

And, in some instances, radiation therapy is administered during the treatment course wherein a compound of the present invention (or a pharmaceutically acceptable salt thereof) is administered to a patient in need thereof.

Other examples of agents with which the inhibitors of this invention also may be combined include, without limitation: treatments for Alzheimer's Disease such as Aricept® and Excelon®; treatments for Parkinson's Disease such as L-DOPA/carbidopa, entacapone, ropinirole, pramipexole, bromocriptine, pergolide, trihexyphenidyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

B. Uses of the Compounds and Compositions

The bifunctional compounds of the present invention are useful for degrading BTK in biological samples or in patients via a ubiquitin proteolytic pathway. Thus, an embodiment of the present invention provides a method of treating a BTK-mediated disease or disorder. As used herein, the term "BTK-mediated disease or disorder" means any disease, disorder, or other deleterious condition in which a BTK is known to play a role. In some instances, a BTK-mediated disease or disorder is a proliferative disorder or an autoimmune disorder. Examples of proliferative disorders include cancer.

The term "cancer" includes, but is not limited to, the following cancers, grouped anatomically: Epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders (e.g., mantle cell lymphoma, Waldenstrom's macroglubulinemia, Marginal zone lymphoma, and Follicular lymphoma); Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma.

Examples of autoimmune disorders include urticarial, graft-versus-host disease, pemphigus vulgaris, achalasia, Addison's disease, Adult Still's disease, agammaglobulinemia, alopecia areata, amyloidosis, ankylosing spondylitis, anti-GBM/anti-TBM nephritis, antiphospholipid syndrome, atopic dermatitis, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, axonal and neuronal neuropathy (AMAN), Baló disease, Behcet's disease, benign mucosal pemphigoid, bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss Syndrome (CSS) or Eosinophilic Granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, evans syndrome, fibromyalgia, fibrosing alveolitis, giant cell arteritis (temporal arteritis), giant cell myocarditis, glomerulonephritis, goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (Acne Inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, Multifocal Motor Neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive Arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjögren's syndrome, sperm and testicular autoimmunity, stiff person syndrome (SPS), subacute bacterial endocarditis (SBE), Susac's syndrome, sympathetic ophthalmia (SO), Takayasu's arteritis, temporal arteritis (giant cell arteritis), thrombocytopenic purpura (TTP), Tolosa-Hunt syndrome (THS), transverse myelitis, Type 1 diabetes, ulcerative colitis (UC), undifferentiated connective tissue disease (UCTD), uveitis, vasculitis, vitiligo, Vogt-Koyanagi-Harada Disease, and Wegener's granulomatosis (or Granulomatosis with Polyangiitis (GPA)).

IV. Examples

Additional embodiments are disclosed in further detail in the following examples, which are not in any way intended to limit the scope of the claims.

Example 1: Synthesis of (R)-5-(3-aminopiperidin-1-yl)-3-((4-(methylsulfonyl)phenyl)amino)pyrazine-2-carboxamide

Step 1: tert-butyl (R)-(1-(6-chloro-5-cyanopyrazin-2-yl)piperidin-3-yl)carbamate

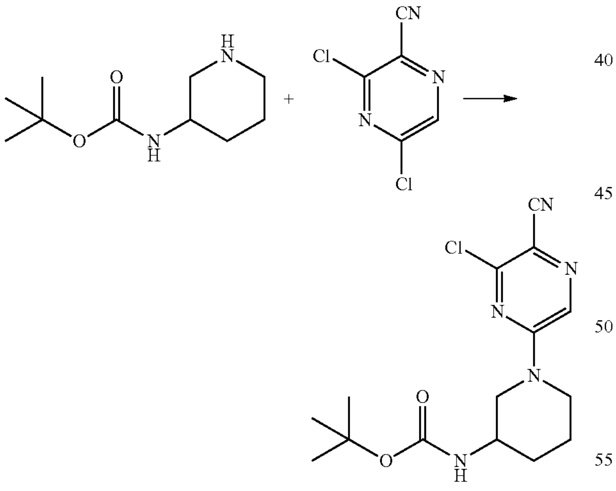

A mixture of 3,5-dichloropyrazine-2-carbonitrile (1.5 g, 8.62 mmol), t-butyl (R)—N-piperidinylcarbamate (2.07 g, 10.4 mmol), and i-$Pr_2NEt$ (3 mL, 17.2 mmol) was dissolved in DMF (10 mL) and stirred for 1.5 h at rt. The reaction mixture was diluted with EtOAc (20 mL) and washed with $H_2O$ (2×30 mL) before being concentrated to a yellow oil. Flash chromatography ($SiO_2$, 10→15% $CH_2Cl_2$/EtOAc) afforded tert-butyl (R)-(1-(6-chloro-5-cyanopyrazin-2-yl)piperidin-3-yl)carbamate (2.5 g) as a white solid. LCMS: $C_{15}H_{20}ClN_5O_2$ requires: 338, found: m/z=339 $[M+H]^+$.

Step 2: tert-butyl (R)-(1-(5-cyano-6-((4-(methylsulfonyl)phenyl)amino)pyrazin-2-yl)piperidin-3-yl)carbamate

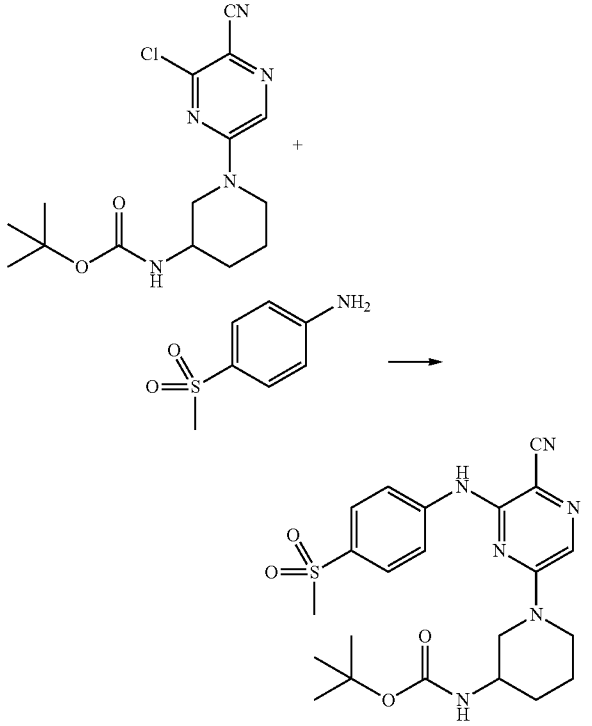

A mixture of tert-butyl (R)-(1-(6-chloro-5-cyanopyrazin-2-yl)piperidin-3-yl)carbamate (800 mg, 2.37 mmol), 4-methylsulfonylaniline (405 mg, 2.37 mmol), (acetyloxy)palladio acetate (106 mg, 0.47 mmol), BINAP (295 mg, 0.47 mmol), and $Cs_2CO_3$ (3.09 g, 9.47 mmol) were suspended in DCE (35 mL) and the mixture was degassed under a stream of $N_2$ for 5 min. The reaction mixture was heated to 110° C. for 2.5 h before being cooled and diluted with EtOAc (50 mL), filtered over celite, and concentrated. Purification ($SiO_2$, 10→65% EtOAc/$CH_2Cl_2$) afforded tert-butyl (R)-(1-(5-cyano-6-((4-(methylsulfonyl)phenyl)amino)pyrazin-2-yl)piperidin-3-yl)carbamate (760 mg). LCMS: $C_{22}H_{28}N_6O_4S$ requires: 472, found: m/z=473 $[M+H]^+$.

Step 3: tert-butyl (R)-(1-(5-carbamoyl-6-((4-(methylsulfonyl)phenyl)amino)pyrazin-2-yl)piperidin-3-yl)carbamate

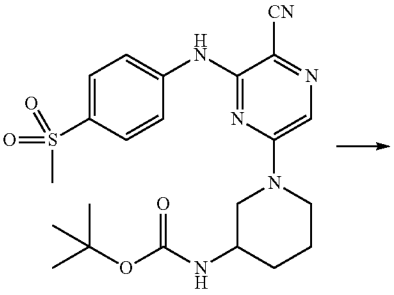

-continued

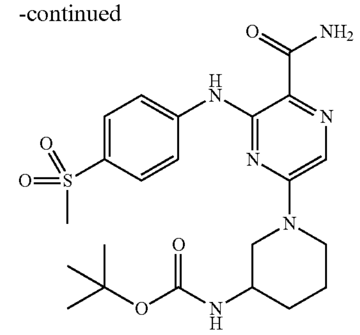

Tert-butyl N-[(3R)-1-{5-cyano-6-[(4-methanesulfonylphenyl)amino]pyrazin-2-yl}piperidin-3-yl]carbamate (760 mg, 1.61 mmol) was dissolved in MeOH (5 mL) and NaOH (100 mg) and $H_2O_2$ (33% aq, 1 mL) were added. The reaction mixture was stirred for 20 min before being diluted with ACN (2 mL) and being stirred for an additional 10 min. An exotherm was observed upon ACN addition. The mixture was concentrated before being diluted with 50 mL EtOAc and the organic phase was washed with $H_2O$ (2×15 mL). The combined organic extracts were dried ($MgSO_4$), filtered, and concentrated to afford tert-butyl (R)-(1-(5-carbamoyl-6-((4-(methylsulfonyl)phenyl)amino)pyrazin-2-yl)piperidin-3-yl)carbamate after purification ($SiO_2$, 0→10% MeOH/$CH_2Cl_2$). LCMS: $C_{22}H_{30}N_6O_5S$ requires: 490, found: m/z=491 $[M+H]^+$.

Step 4: (R)-5-(3-aminopiperidin-1-yl)-3-((4-(methylsulfonyl)phenyl)amino)pyrazine-2-carboxamide

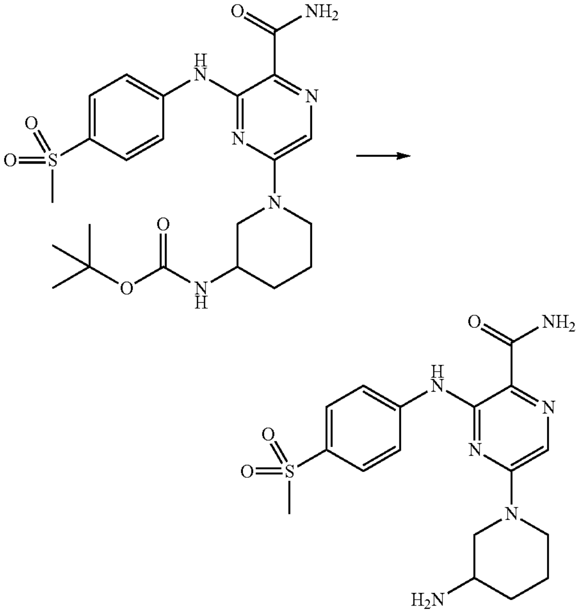

Tert-butyl N-[(3R)-1-{5-carbamoyl-6-[(4-methanesulfonylphenyl)amino]pyrazin-2-yl}piperidin-3-yl]carbamate was dissolved in $CH_2Cl_2$ (5 mL) and TFA (2 mL) was added at rt. After 1 h the reaction mixture was concentrated to a thick oil before being dissolved in ACN/$H_2O$ and lyophilized to afford (R)-5-(3-aminopiperidin-1-yl)-3-((4-(methylsulfonyl)phenyl)amino)pyrazine-2-carboxamide (402 mg, 3 steps) as a TFA salt. LCMS: $C_{17}H_{22}N_6O_3S$ requires: 390, found: m/z=391 $[M+H]^+$.

Example 2: Synthesis of Synthesis of (R)-5-(3-aminopiperidin-1-yl)-3-((3-methylisothiazol-5-yl)amino)pyrazine-2-carboxamide

Step 1: tert-butyl (R)-(1-(5-cyano-6-((3-methylisothiazol-5-yl)amino)pyrazin-2-yl)piperidin-3-yl)carbamate

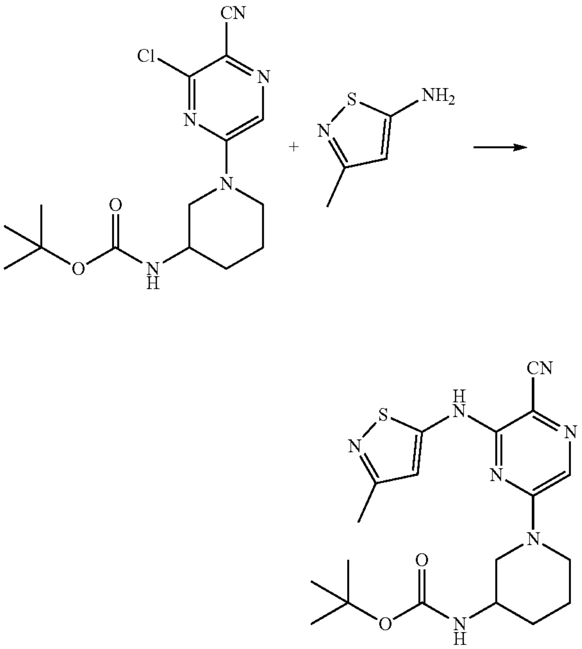

The procedure from Step 2 of Example 1 was followed to afford tert-butyl (R)-(1-(5-cyano-6-((3-methylisothiazol-5-yl)amino)pyrazin-2-yl)piperidin-3-yl)carbamate (5.6 g). LCMS: C19H25N7O2S requires: 415, found: m/z=416 $[M+H]^+$.

Step 2: tert-butyl (R)-(1-(5-carbamoyl-6-((3-methylisothiazol-5-yl)amino)pyrazin-2-yl)piperidin-3-yl)carbamate

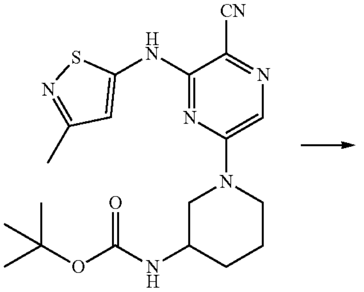

-continued

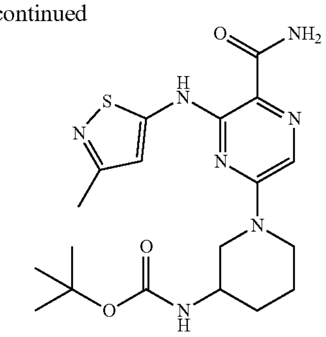

The procedure from Step 3 of Example 1 was followed to afford tert-butyl (R)-(1-(5-carbamoyl-6-((3-methylisothiazol-5-yl)amino)pyrazin-2-yl)piperidin-3-yl)carbamate (850 mg). LCMS: C19H27N7O3S requires: 433, found: m/z=434 [M+H]+.

Step 3: (R)-5-(3-aminopiperidin-1-yl)-3-((3-methylisothiazol-5-yl)amino)pyrazine-2-carboxamide

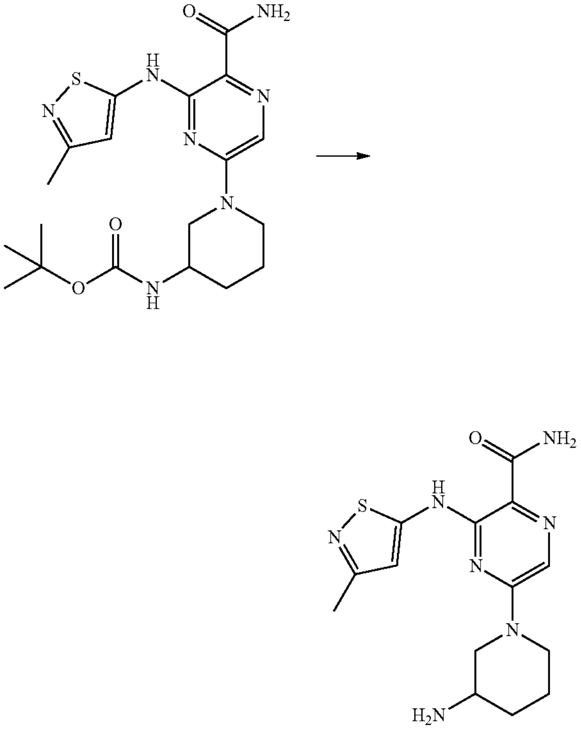 [SMILES: Cc1cc(Nc2nc(N3CCCC(NC(=O)OC(C)(C)C)C3)cnc2C(N)=O)sn1 ; Cc1cc(Nc2nc(N3CCCC(N)C3)cnc2C(N)=O)sn1]

The procedure from Step 4 of Example 1 afforded (R)-5-(3-aminopiperidin-1-yl)-3-((3-methylisothiazol-5-yl)amino)pyrazine-2-carboxamide (600 mg). LCMS: C14H19N70S requires: 333, found: m/z=334 [M+H]+.

Example 3: Synthesis of (R)-5-(3-aminopiperidin-1-yl)-3-((1-methyl-1H-pyrazol-4-yl)amino)pyrazine-2-carboxamide Step 1: tert-butyl (R)-(1-(5-cyano-6-((1-methyl-1H-pyrazol-4-yl)amino)pyrazin-2-yl)piperidin-3-yl)carbamate

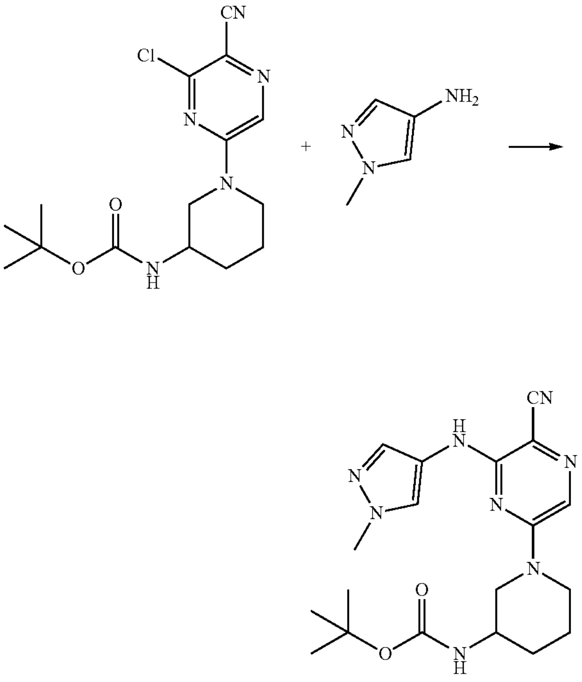

The procedure from Step 2 of Example 1 was followed to afford tert-butyl (R)-(1-(5-cyano-6-((1-methyl-1H-pyrazol-4-yl)amino)pyrazin-2-yl)piperidin-3-yl)carbamate (941 mg). LCMS: $C_{19}H_{26}N_8O_2$ requires: 398, found: m/z=399 [M+H]+.

Step 2: tert-butyl (R)-(1-(5-carbamoyl-6-((1-methyl-1H-pyrazol-4-yl)amino)pyrazin-2-yl)piperidin-3-yl) carbamate

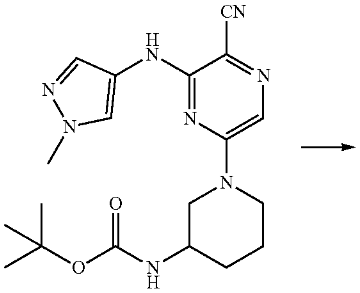

-continued

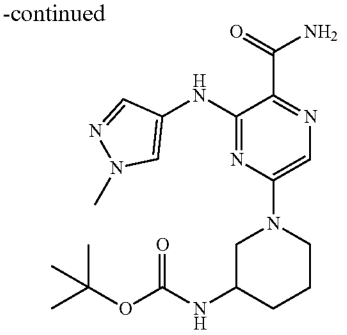

The procedure from Step 3 of Example 1 was followed to afford tert-butyl (R)-(1-(5-carbamoyl-6-((1-methyl-1H-pyrazol-4-yl)amino)pyrazin-2-yl)piperidin-3-yl)carbamate (297 mg). LCMS: $C_{19}H_{28}N_8O_3$ requires: 416, found: m/z=417 $[M+H]^+$.

Step 3: (R)-5-(3-aminopiperidin-1-yl)-3-((1-methyl-1H-pyrazol-4-yl)amino)pyrazine-2-carboxamide

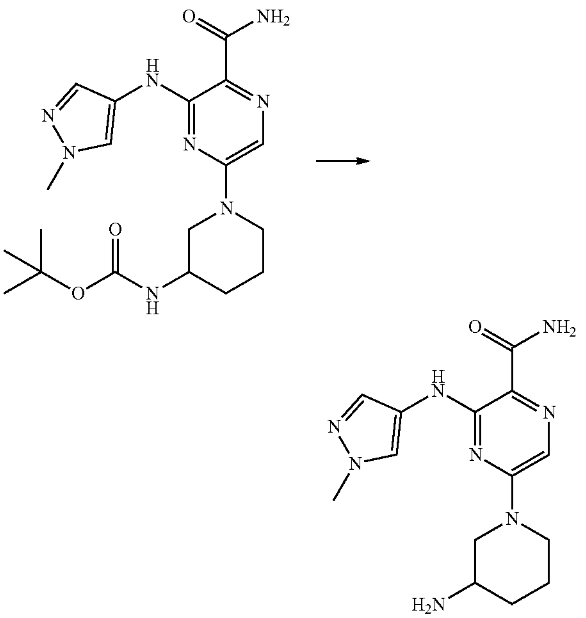

The procedure from Step 4 of Example 1 was followed to afford (R)-5-(3-aminopiperidin-1-yl)-3-((1-methyl-1H-pyrazol-4-yl)amino)pyrazine-2-carboxamide. LCMS: $C_{14}H_{20}N_8O$ requires: 4=316, found: m/z=317 $[M+H]^+$.

Example 4: Synthesis of 2-(2,6-dioxopiperidin-3-yl)-5-(4-oxopiperidin-1-yl)isoindole-1,3-dione

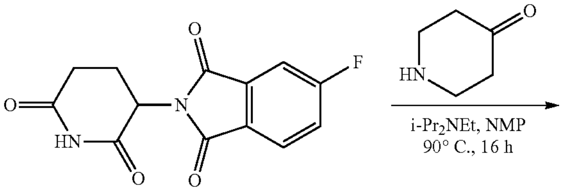

-continued

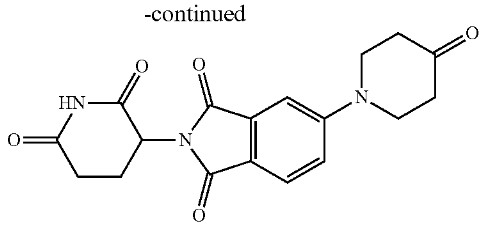

2-(2,6-dioxopiperidin-3-yl)-5-fluoroisoindole-1,3-dione (500 mg, 1.81 mmol) and 4-piperidinone hydrochloride (245 mg, 1.81 mmol) were dissolved in NMP (3 mL) and i-$Pr_2NEt$ (703 mg, 5.43 mmol) was added. The mixture was heated at 90° C. for 16 h before being diluted with EtOAc. The organic phase was washed (2×$H_2O$, sat. aq. NaCl), dried ($Na_2SO_4$), concentrated and purified ($SiO_2$, 10→100% EtOAc/hexanes) to provide 2-(2,6-dioxopiperidin-3-yl)-5-(4-oxopiperidin-1-yl)isoindole-1,3-dione (131 mg). LCMS: $C_{18}H_{17}N_3O_5$ requires 355, found: m/z=356 $[M+H]^+$.

Example 5: Synthesis of 1-[2-(2,6-dioxopiperidin-3-yl)-1,3-dioxoisoindol-5-yl]piperidine-4-carbaldehyde

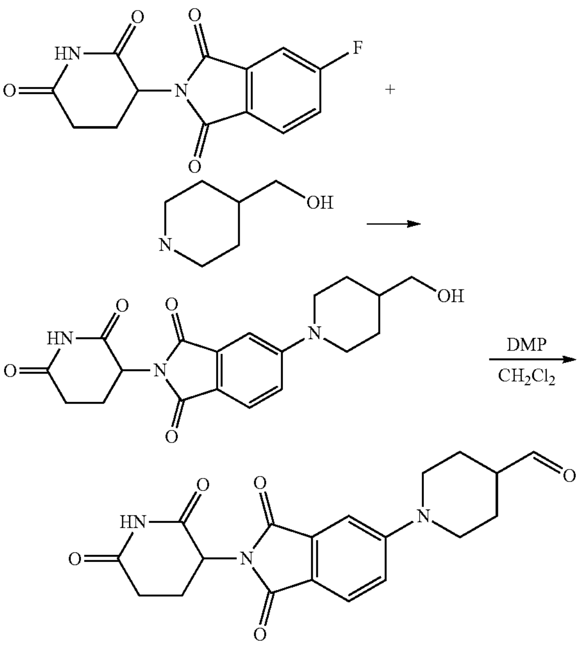

Step 1: 2-(2,6-dioxopiperidin-3-yl)-5-(4-(hydroxymethyl)piperidin-1-yl)isoindoline-1,3-dione The procedure from Example 4 using piperidin-4-yl-methanol was followed to afford 2-(2,6-dioxopiperidin-3-yl)-5-(4-(hydroxymethyl)piperidin-1-yl)isoindoline-1,3-dione (939 mg) as a yellow solid. $^1H$ NMR (300 MHz, DMSO-$d_6$) δ 11.09 (s, 1H), 7.65 (d, J=8.4 Hz, 1H), 7.30 (d, J=2.4 Hz, 1H), 7.23 (dd, J=8.4, 2.4 Hz, 1H), 5.07 (dd, J=12.6, 5.4 Hz, 1H), 4.51 (t, J=5.1 Hz, 1H), 4.07 (d, J=13.2 Hz, 2H), 3.27 (t, J=5.7 Hz, 2H), 2.99-2.80 (m, 3H), 2.62-2.55 (m, 2H), 2.17-1.95 (m, 1H), 1.76-1.67 (m, 3H), 1.24-1.12 (m, 2H). LCMS: $C_{19}H_{21}N_3O_5$ requires: 371, found: m/z=372 $[M+H]^+$.

Step 2: 1-[2-(2,6-dioxopiperidin-3-yl)-1,3-dioxoisoindol-5-yl]piperidine-4-carbaldehyde 2-(2,6-dioxopiperidin-3-yl)-5-[4-(hydroxymethyl)piperidin-1-yl]isoindole-1,3-dione (1.50 g, 4.04 mmol) was dissolved in $CH_2Cl_2$ (15 mL) and 1,1-bis(acetyloxy)-3-oxo-1lambda5,2-benzodioxol-1-yl acetate (1.88 g, 4.44 mmol) was added in one portion at rt. After 5 h the reaction mixture was diluted with $NaHCO_3$ (2 mL sat. aq.) and $Na_2S_2O_3$ (sat. aq.) was added and the mixture was stirred for 30 min. The organic phase was removed. The aqueous layer was extracted (2×20 mL $CH_2Cl_2$) and the combined organic phases were dried ($Na_2SO_4$), filtered, and concentrated. Purification ($SiO_2$, 2→6% $CH_2Cl_2$/MeOH) afforded 1-[2-(2,6-dioxopiperidin-3-yl)-1,3-dioxoisoindol-5-yl]piperidine-4-carbaldehyde (1.20 g). LCMS: $C_{19}H_{19}N_3O_5$ requires: 369, found: m/z=370 $[M+H]^+$.

Example 6: Synthesis of 1-(2-(2,6-dioxopiperidin-3-yl)-1,3-dioxoisoindolin-5-yl)piperidine-4-carbaldehyde Carboxamide

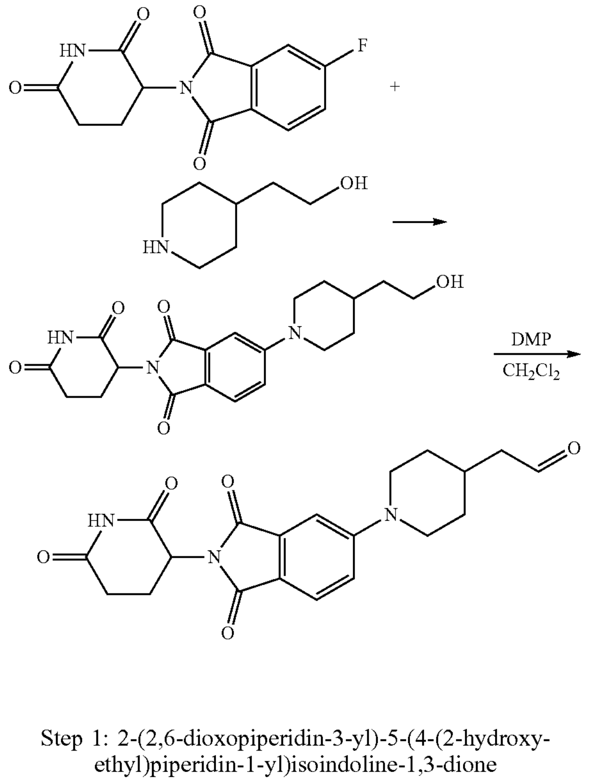

Step 1: 2-(2,6-dioxopiperidin-3-yl)-5-(4-(2-hydroxyethyl)piperidin-1-yl)isoindoline-1,3-dione The procedure from Example 4 was followed to afford 2-(piperidin-4-yl)ethan-1-ol, 2-(2,6-dioxopiperidin-3-yl)-5-(4-(2-hydroxyethyl)piperidin-1-yl)isoindoline-1,3-dione (823 mg) as a yellow solid. $^1$H NMR (300 MHz, DMSO-$d_6$) δ11.09 (s, 1H), 7.65 (d, J=8.4 Hz, 1H), 7.30 (d, J=2.4 Hz, 1H), 7.23 (dd, J=8.4, 2.4 Hz, 1H), 5.07 (dd, J=12.6, 5.4 Hz, 1H), 4.40 (t, J=5.1 Hz, 1H), 4.04 (d, J=13.2 Hz, 2H), 3.64-3.40 (m, 2H), 3.09-2.79 (m, 3H), 2.70-2.51 (m, 2H), 2.07-1.94 (m, 1H), 1.77-1.66 (m, 3H), 1.41-1.34 (m, 2H), 1.24-1.12 (m, 2H). LCMS: $C_{20}H_{23}N_3O_5$ requires: 385, found: m/z=386 $[M+H]^+$.

Step 2: 1-(2-(2,6-dioxopiperidin-3-yl)-1,3-dioxoisoindolin-5-yl)piperidine-4-carbaldehyde carboxamide The procedure from Example 5 was followed to afford 1-(2-(2,6-dioxopiperidin-3-yl)-1,3-dioxoisoindolin-5-yl)piperidine-4-carbaldehyde carboxamide (83 mg). LCMS: $C_{20}H_{21}N_3O_5$ requires: 383, found: m/z=384 $[M+H]^+$.

Example 7: Synthesis of 1-[2-(2,6-dioxopiperidin-3-yl)-1,3-dioxoisoindol-5-yl]azetidine-3-carbaldehyde

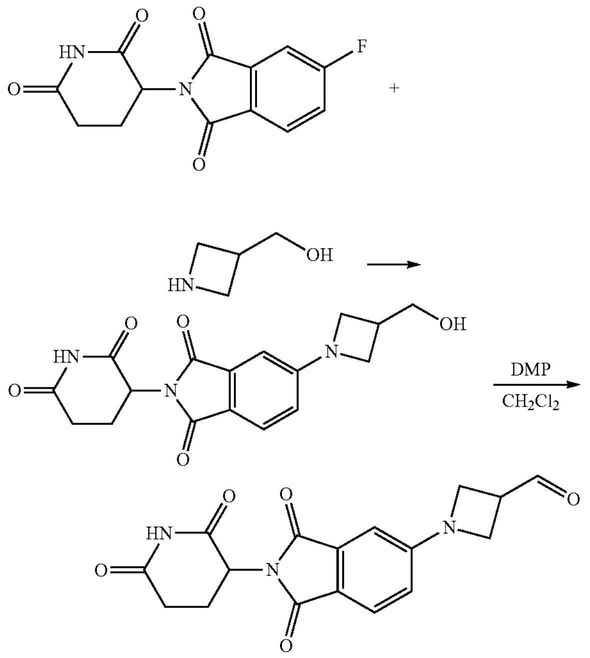

Step 1: 2-(2,6-dioxopiperidin-3-yl)-5-(3-(hydroxymethyl)azetidin-1-yl)isoindoline-1,3-dione The procedure from Example 4 was followed with azetidin-3-ylmethanol hydrochloride to afford 2-(2,6-dioxopiperidin-3-yl)-5-(3-(hydroxymethyl)azetidin-1-yl)isoindoline-1,3-dione (1.85 g) as a yellow solid. $^1$H NMR (400 MHz, DMSO-$d_6$) δ 11.09 (s, 1H), 7.63 (d, J=8.4 Hz, 1H), 6.76 (d, J=2.0 Hz, 1H), 6.62 (dd, J=8.4, 2.0 Hz, 1H), 5.06 (dd, J=12.4, 5.2 Hz, 1H), 4.86 (t, J=5.2 Hz, 1H), 4.05 (t, J=8.4 Hz, 2H), 3.77 (dd, J 8.4, 5.2 Hz, 2H), 3.60 (t, J=5.2 Hz, 2H), 3.00-2.81 (m, 2H), 2.65-2.53 (m, 2H), 2.06-1.96 (m, 1H). LCMS: $C_{17}H_{17}N_3O_5$ requires: 343, found: m/z=344 $[M+H]^+$.

Step 2: 1-[2-(2,6-dioxopiperidin-3-yl)-1,3-dioxoisoindol-5-yl]azetidine-3-carbaldehyde The procedure from Example 5 was followed to afford 1-[2-(2,6-dioxopiperidin-3-yl)-1,3-dioxoisoindol-5-yl]azetidine-3-carbaldehyde (94 mg). LCMS: $C_{17}H_{15}N_3O_5$ requires: 341, found: m/z=342 $[M+H]^+$.

Example 8: Synthesis of (R)-pyrrolidin-3-ylmethanol, 2-(2,6-dioxopiperidin-3-yl)-5-((R)-3-(hydroxymethyl)pyrrolidin-1-yl)isoindoline-1,3-dione

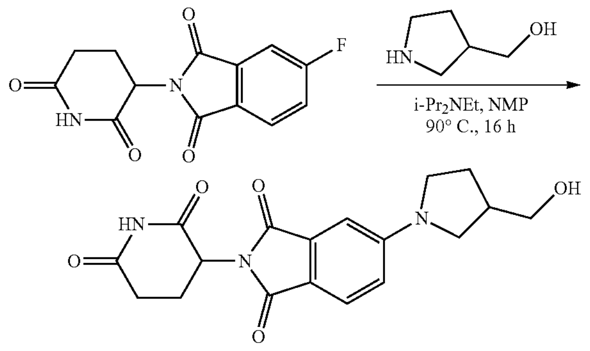

The procedure from Example 4 was followed to afford with (R)-pyrrolidin-3-ylmethanol, 2-(2,6-dioxopiperidin-3-yl)-5-((R)-3-(hydroxymethyl)pyrrolidin-1-yl)isoindoline-1,3-dione (481 mg) as a yellow solid. $^1$H NMR (300 MHz, DMSO-$d_6$) δ 11.08 (s, 1H), 7.64 (d, J=8.4 Hz, 1H), 6.89 (d, J=2.1 Hz, 1H), 6.80 (dd, J=8.4, 2.1 Hz, 1H), 5.06 (dd, J=12.9, 5.4 Hz, 1H), 4.78 (s, 1H), 3.65-3.36 (m, 5H), 3.22-3.17 (m, 1H), 2.95-2.83 (m, 1H), 2.67-2.44 (m, 3H), 2.11-1.89 (m, 2H), 1.87-1.78 (m, 1H). LCMS: $C_{18}H_{19}N_3O_5$ requires: 357, found: m/z=358 $[M+H]^+$.

Example 9: Synthesis of 3-hydroxypropyl, 5-hydroxypentyl, and 7-hydroxyheptyl 1-(4-methylbenzenesulfonate)

Step 1: 5-hydroxypentyl 4-methylbenzenesulfonate

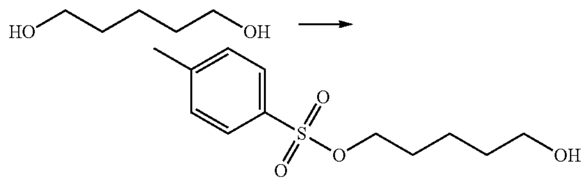

To a solution of pentane-1,5-diol (5.0 g, 48.0 mmol) in $CH_2Cl_2$ (60 mL) were added pTsCl (10.1 g, 52.8 mmol) and pyridine (4.18 g, 52.8 mmol) at 0° C. The mixture was stirred at room temperature for 16 h. The resulting mixture was diluted with $H_2O$ and extracted with $CH_2Cl_2$. The combined organic layers were washed with brine, dried $Na_2SO_4$ and concentrated under vacuum. The residue was purified ($SiO_2$, 0→70% EtOAc/petroleum ether to afford 5-hydroxypentyl 4-methylbenzenesulfonate (5.2 g) as a light yellow oil. LCMS: $C_{12}H_{18}O_4S$ requires: 258, found: m/z=259 $[M+H]^+$.

Step 2: 3-hydroxypropyl 4-methylbenzenesulfonate

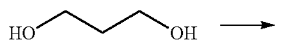

-continued

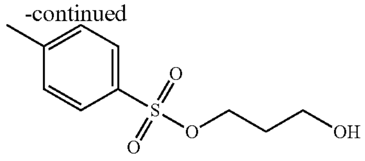

The procedure of Step 1 was followed to afford 3-hydroxypropyl 4-methylbenzenesulfonate as a colorless oil. The 3-hydroxypropyl 4-methylbenzenesulfonate is additionally available commercially.

Step 3: 7-hydroxyheptyl 4-methylbenzenesulfonate

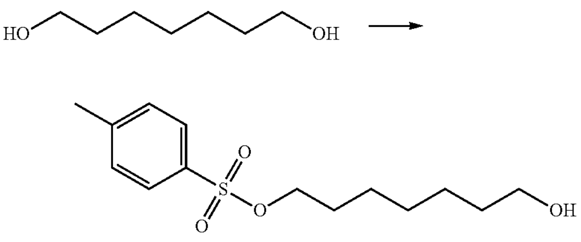

The procedure of Step 1 was followed to afford 7-hydroxyheptyl 4-methylbenzenesulfonate (4.2 g) as a colorless oil. LCMS: $C_{14}H_{22}O_4S$ requires: 286, found: m/z=287 $[M+H]^+$.

Example 10: Synthesis of 2-(2,6-dioxopiperidin-3-yl)-5-(3-hydroxypropoxy)isoindoline-1,3-dione

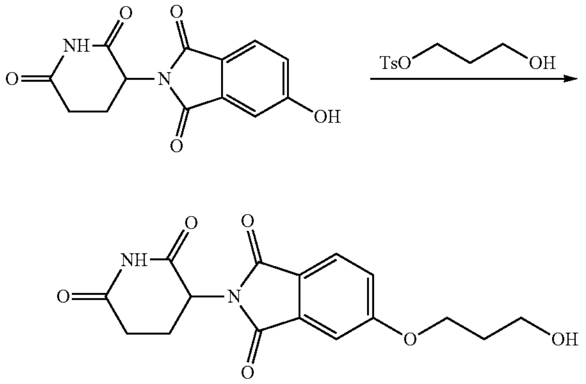

A mixture of 2-(2,6-dioxopiperidin-3-yl)-5-hydroxy-2,3-dihydro-1H-isoindole-1,3-dione (3.0 g, 10.9 mmol), 3-[(4-methylbenzenesulfonyl)oxy]propan-1-ol (5.0 g, 21.9 mmol), i-$Pr_2$NEt (4.2 g, 32.8 mmol) and KI (182 mg, 1.09 mmol) in DMF (40 mL) was stirred at 80° C. for 16 h. The resulting mixture was cooled to rt and diluted with water. The aqueous phase was extracted with $CH_2Cl_2$ and the combined organic layers were washed with brine, dried ($Na_2SO_4$), filtered, and concentrated. The residue was purified (RP-$SiO_2$, 5-50% ACN/$H_2O$) to afford 2-(2,6-dioxopiperidin-3-yl)-5-(3-hydroxypropoxy)isoindoline-1,3-dione (1.8 g) as a white solid.

Example 11: Synthesis of 2-(2,6-dioxopiperidin-3-yl)-5-((5-hydroxypentyl)oxy)isoindoline-1,3-dione

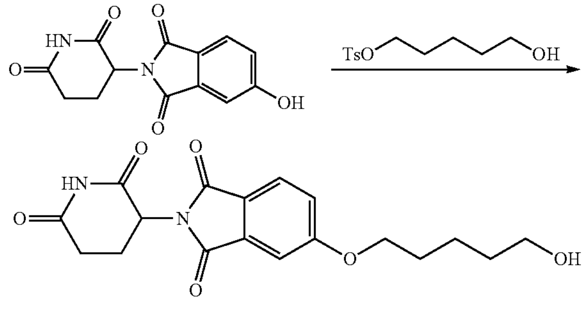

The procedure from Example 10 was followed to afford 2-(2,6-dioxopiperidin-3-yl)-5-((5-hydroxypentyl)oxy)isoindoline-1,3-dione (1.46 g) as a white solid. LCMS: $C_{18}H_{20}N_2O_6$ requires: 360, found: m/z=361 $[M+H]^+$. $^1H$ NMR (300 MHz, DMSO-$d_6$) δ 11.11 (s, 1H), 7.81 (d, J=8.4 Hz, 1H), 7.40 (d, J=2.4 Hz, 1H), 7.33 (dd, J=8.4, 2.4 Hz, 1H), 5.15-5.09 (m, 1H), 4.38 (t, J=5.1 Hz, 1H), 4.15 (t, J=6.6 Hz, 2H), 3.39 (q, J=5.7 Hz, 2H), 2.98-2.76 (m, 1H), 2.63-2.48 (m, 2H), 2.13-1.93 (m, 1H), 1.80-1.66 (m, 2H), 1.51-1.40 (m, 4H).

Example 12: Synthesis of 2-(2,6-dioxopiperidin-3-yl)-5-((7-hydroxyheptyl)oxy)isoindoline-1,3-dione

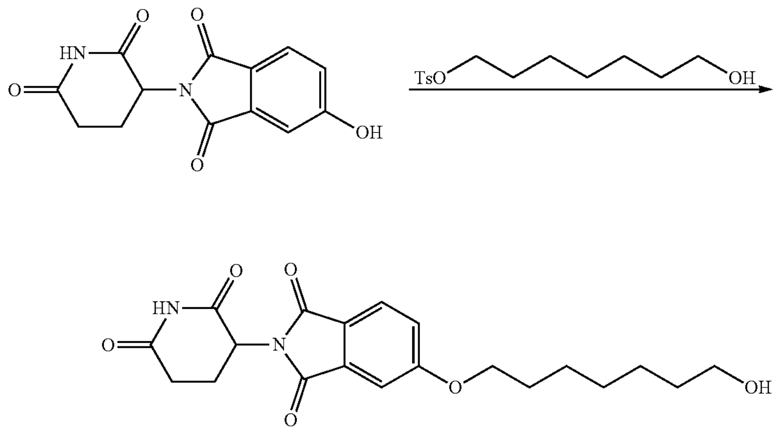

The procedure from Example 10 was followed to afford 2-(2,6-dioxopiperidin-3-yl)-5-((7-hydroxyheptyl)oxy)isoindoline-1,3-dione (1.2 g) as an off-white solid. LCMS: $C_{20}H_{24}N_2O_6$ requires: 388, found: m/z=389 $[M+H]^+$. $^1H$ NMR (300 MHz, DMSO-$d_6$) δ 11.12 (s, 1H), 7.83 (d, J=8.4 Hz, 1H), 7.42 (d, J=2.4 Hz, 1H), 7.36-7.33 (m, 1H), 5.15-5.09 (m, 1H), 4.34 (t, J=5.1 Hz, 1H), 4.17 (t, J=6.6 Hz, 2H), 3.45-3.31 (m, 2H), 2.96-2.84 (m, 1H), 2.66-2.52 (m, 2H), 2.13-1.96 (m, 1H), 1.83-1.68 (m, 2H), 1.43-1.30 (m, 8H).

Example 13: Synthesis of 3-{[2-(2,6-dioxopiperidin-3-yl)-1,3-dioxoisoindol-5-yl]oxy}propyl N-[(1R)-3-{5-carbamoyl-6-[(4-methanesulfonylphenyl)amino]pyrazin-2-yl}cyclohexyl]carbamate (Compound 1)

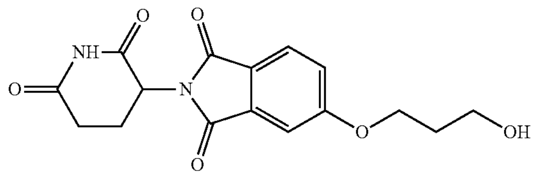

+

-continued

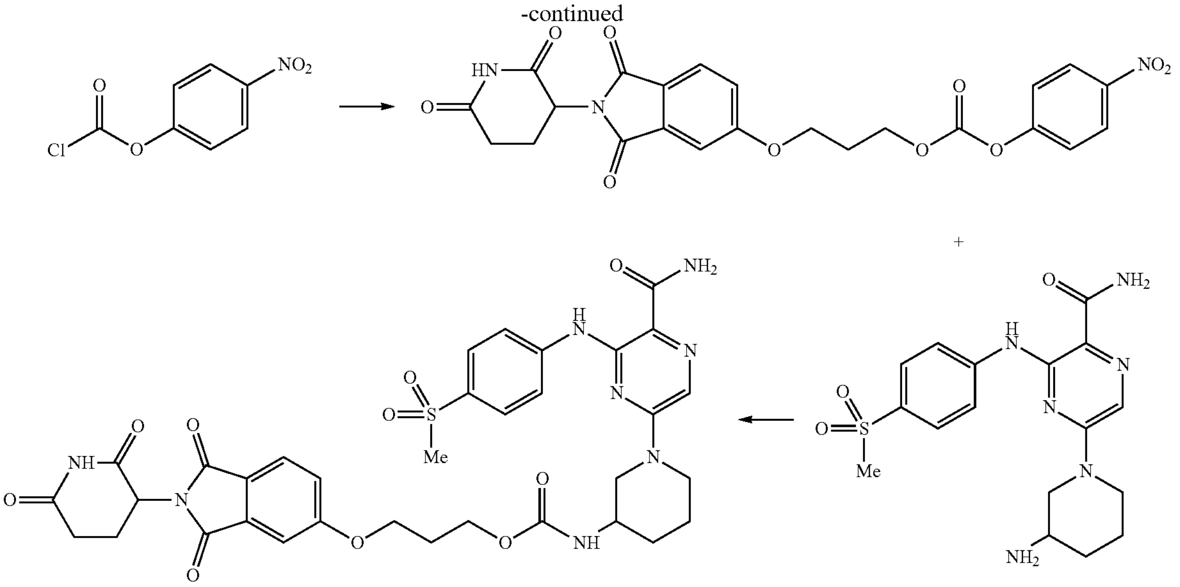

A solution of 2-(2,6-dioxopiperidin-3-yl)-5-(3-hydroxypropoxy)isoindole-1,3-dione (33 mg, 100 μmol) and $Et_3N$ (18.1 μL, 13 mg, 130 μmol) in a mixture of $CH_2Cl_2$ (1 mL) and NMP (0.1 mL) was cooled to 0° C. before a 100 μL solution of 4-nitrophenyl chloroformate (20.2 mg, 0.10 mmol) was added. After 10 min the ice bath was removed and the reaction mixture was stirred for 1 h, diluted with $H_2O$ (1 mL) and extracted (2×3 mL $CH_2Cl_2$). The combined organic extracts were dried ($Na_2SO_4$), filtered, and concentrated. The crude 3-{[2-(2,6-dioxopiperidin-3-yl)-1,3-dioxoisoindol-5-yl]oxy}propyl 4-nitrophenyl carbonate and 5-[(3R)-3-aminocyclohexyl]-3-[(4-methanesulfonylphenyl)amino]pyrazine-2-carboxamide (19.5 mg, 50 μmol) was dissolved in DMF (0.5 mL) and $Et_3N$ (18.1 μL, 13.1 mg, 130 μmol) was added. The mixture was stirred for 1 h at rt before being filtered and purified (RP-HPLC) to afford 3-{[2-(2,6-dioxopiperidin-3-yl)-1,3-dioxoisoindol-5-yl]oxy}propyl N-[(1R)-3-{5-carbamoyl-6-[(4-methanesulfonylphenyl)amino]pyrazin-2-yl}cyclohexyl]carbamate (6.2 mg).

Example 14: Synthesis of 5-((2-(2,6-dioxopiperidin-3-yl)-1,3-dioxoisoindolin-5-yl)oxy)pentyl ((R)-1-(5-carbamoyl-6-((4-(methylsulfonyl)phenyl)amino)pyrazin-2-yl)piperidin-3-yl)carbamate (Compound 2)

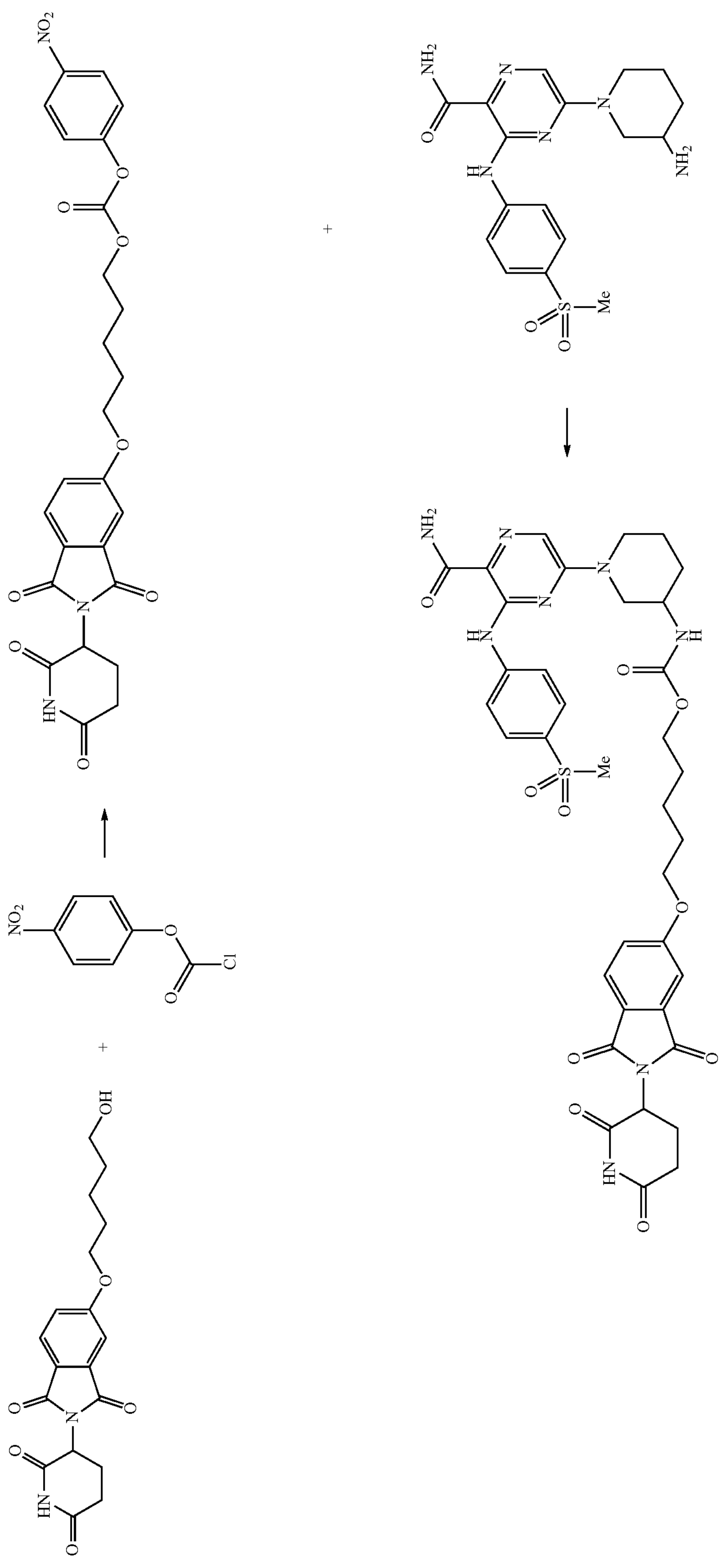

The procedure from Example 13 was followed starting with 2-(2,6-dioxopiperidin-3-yl)-5-((5-hydroxypentyl)oxy) isoindoline-1,3-dione to afford 5-((2-(2,6-dioxopiperidin-3-yl)-1,3-dioxoisoindolin-5-yl)oxy)pentyl ((R)-1-(5-carbamoyl-6-((4-(methylsulfonyl)phenyl)amino)pyrazin-2-yl) piperidin-3-yl)carbamate (5 mg). $^1$H NMR (500 MHz, DMSO-$d_6$) δ 11.97 (s, 1H), 11.10 (s, 1H), 8.09-7.62 (m, 8H), 7.62-7.07 (m, 5H), 5.11 (dd, J=12.8, 5.4 Hz, 1H), 4.43-3.77 (m, 6H), 3.14 (s, 3H), 2.89 (ddd, J=16.8, 13.8, 5.5 Hz, 1H), 2.74-2.55 (m, 3H), 2.16-1.91 (m, 1H), 1.91-0.97 (m, 11H). LCMS: $C_{37}H_{41}N_7O_{10}S$ requires: 775, found: m/z=776 $[M+H]^+$.

Example 15: Synthesis of 7-((2-(2,6-dioxopiperidin-3-yl)-1,3-dioxoisoindolin-5-yl)oxy)heptyl ((R)-1-(5-carbamoyl-6-((4-(methylsulfonyl)phenyl)amino) pyrazin-2-yl)piperidin-3-yl)carbamate (Compound 3)

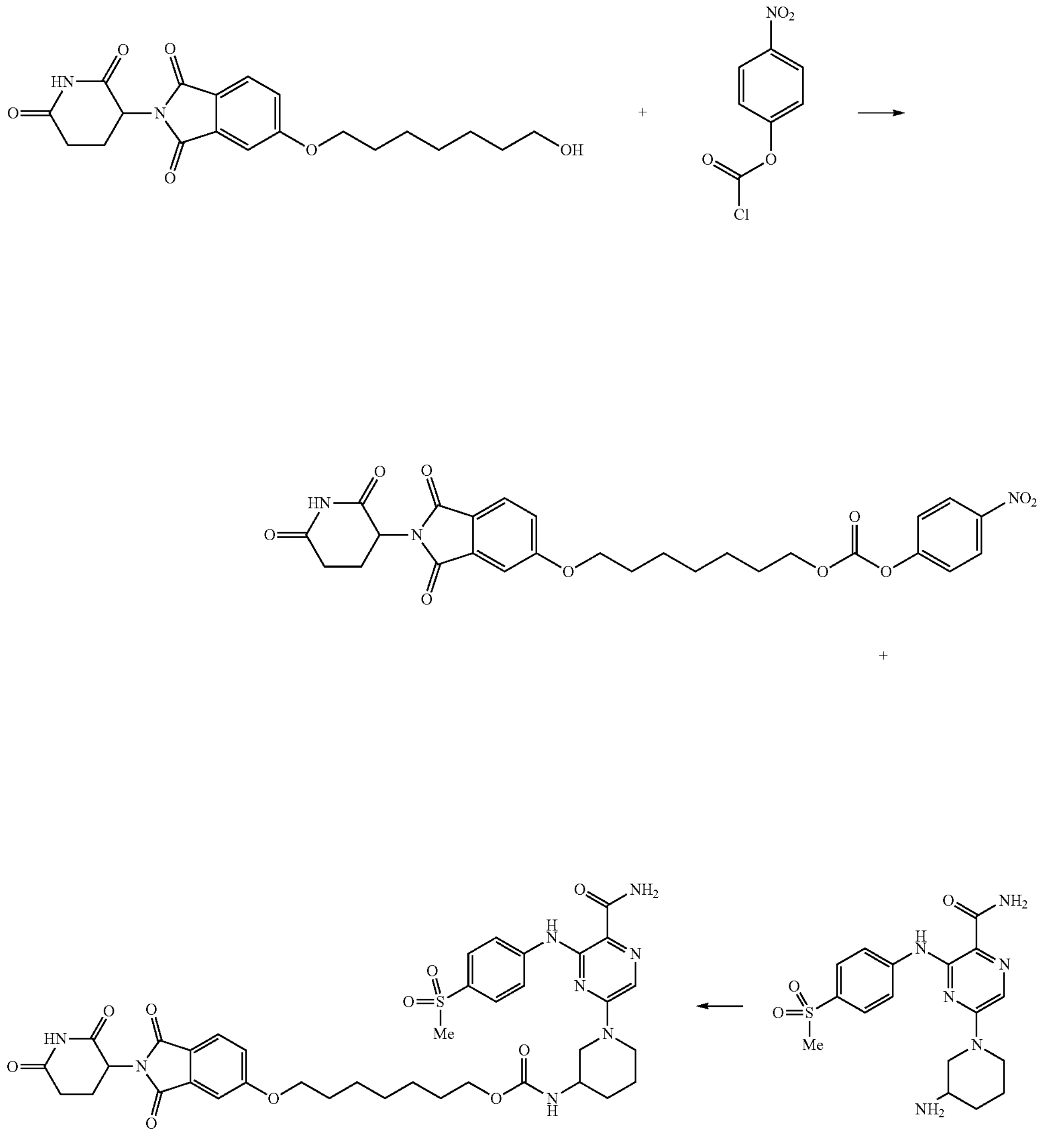

The procedure from Example 13 was followed starting with 2-(2,6-dioxopiperidin-3-yl)-5-((5-hydroxypentyl)oxy) isoindoline-1,3-dione to afford 7-((2-(2,6-dioxopiperidin-3-yl)-1,3-dioxoisoindolin-5-yl)oxy)heptyl ((R)-1-(5-carbamoyl-6-((4-(methylsulfonyl)phenyl)amino)pyrazin-2-yl) piperidin-3-yl)carbamate (6 mg). $^1$H NMR (500 MHz, DMSO-$d_6$) δ 12.01 (s, 1H), 11.12 (s, 1H), 8.02-7.71 (m, 6H), 7.64-7.10 (m, 4H), 5.12 (dd, J=12.8, 5.4 Hz, 1H), 4.08 (s, 7H), 3.15 (s, 3H), 2.90 (ddd, J=16.9, 13.8, 5.4 Hz, 1H), 2.75-2.57 (m, 2H), 2.22-1.92 (m, 2H), 1.92-0.79 (m, 17H). LCMS: $C_{39}H_{45}N_7O_{10}S$ requires: 803, found: m/z=804 $[M+H]^+$.

Example 16: Synthesis of 2-(1-(2-(2,6-dioxopiperidin-3-yl)-1,3-dioxoisoindolin-5-yl)piperidin-4-yl) ethyl ((R)-1-(5-carbamoyl-6-((4-(methylsulfonyl) phenyl)amino)pyrazin-2-yl)piperidin-3-yl)carbamate (4.2 mg, 20%) (Compound 6)

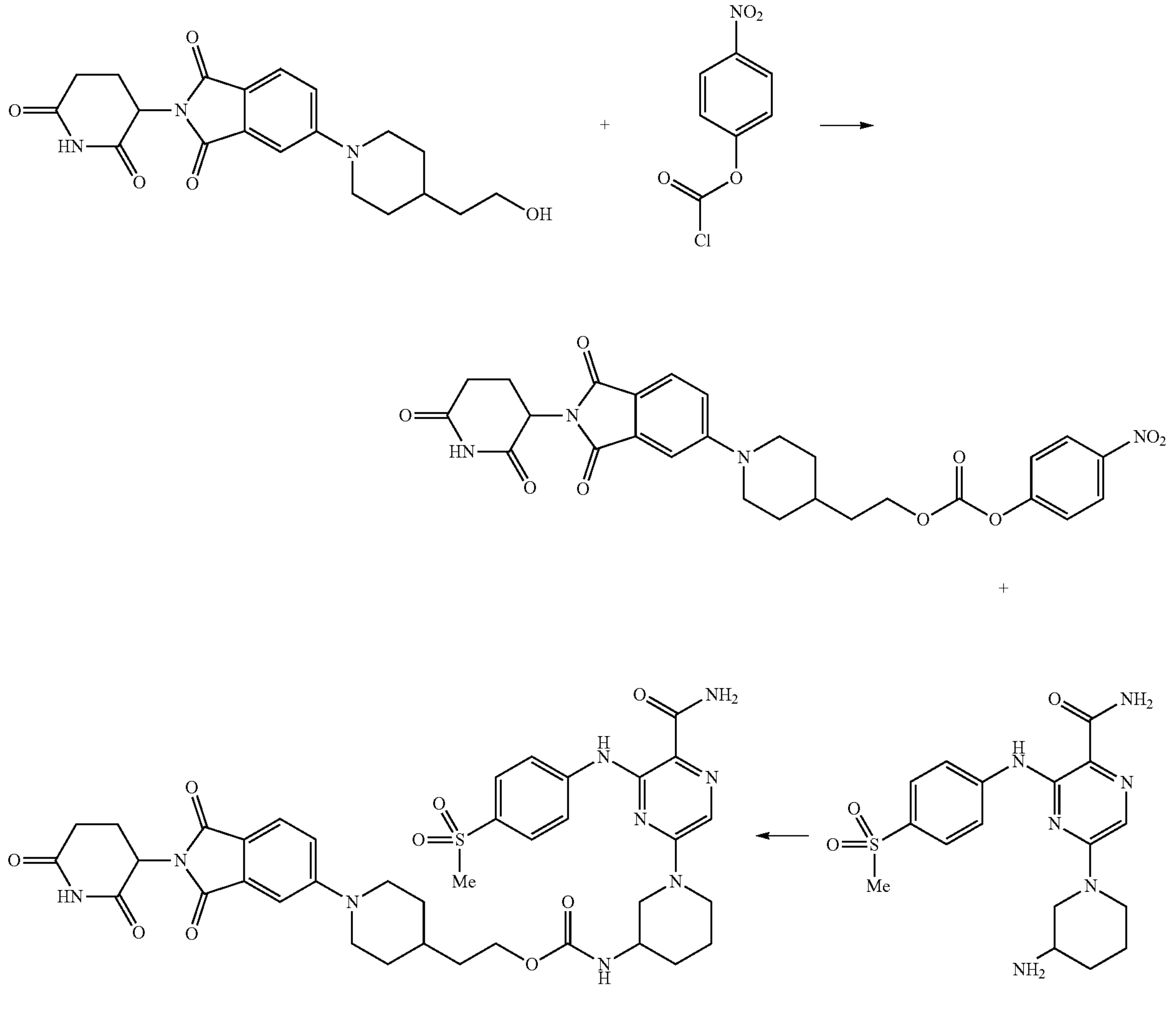

The procedure from Example 13 was followed starting with 2-(2,6-dioxopiperidin-3-yl)-5-(4-(2-hydroxyethyl)piperidin-1-yl)isoindoline-1,3-dione to afford 2-(1-(2-(2,6-dioxopiperidin-3-yl)-1,3-dioxoisoindolin-5-yl)piperidin-4-yl) ethyl ((R)-1-(5-carbamoyl-6-((4-(methylsulfonyl)phenyl) amino)pyrazin-2-yl)piperidin-3-yl)carbamate (4.2 mg). $^1$H NMR (500 MHz, Chloroform-d) δ 11.55 (d, J=8.4 Hz, 1H), 8.23 (s, 1H), 7.92-7.78 (m, 3H), 7.74-7.60 (m, 1H), 7.45 (d, J=12.2 Hz, 1H), 7.32 (d, J=2.0 Hz, 1H), 7.06 (d, J=12.9 Hz, 1H), 5.82-5.25 (m, 1H), 5.15 (s, 1H), 4.95 (dd, J=12.2, 5.3 Hz, 1H), 4.36-3.11 (m, 11H), 2.82 (dddd, J=40.8, 29.1, 16.4, 4.2 Hz, 3H), 2.14 (td, J=7.5, 2.5 Hz, 1H), 2.09-1.96 (m, 1H), 1.95-1.29 (m, 15H). LCMS: $C_{38}H_{43}N_9O_9S$ requires: 801, found: m/z=802 $[M+H]^+$.

Example 17: Synthesis of 2-(1-(2-(2,6-dioxopiperidin-3-yl)-1,3-dioxoisoindolin-5-yl)piperidin-4-yl) ethyl ((R)-1-(5-carbamoyl-6-((3-methylisothiazol-5-yl)amino)pyrazin-2-yl)piperidin-3-yl)carbamate (Compound 7)

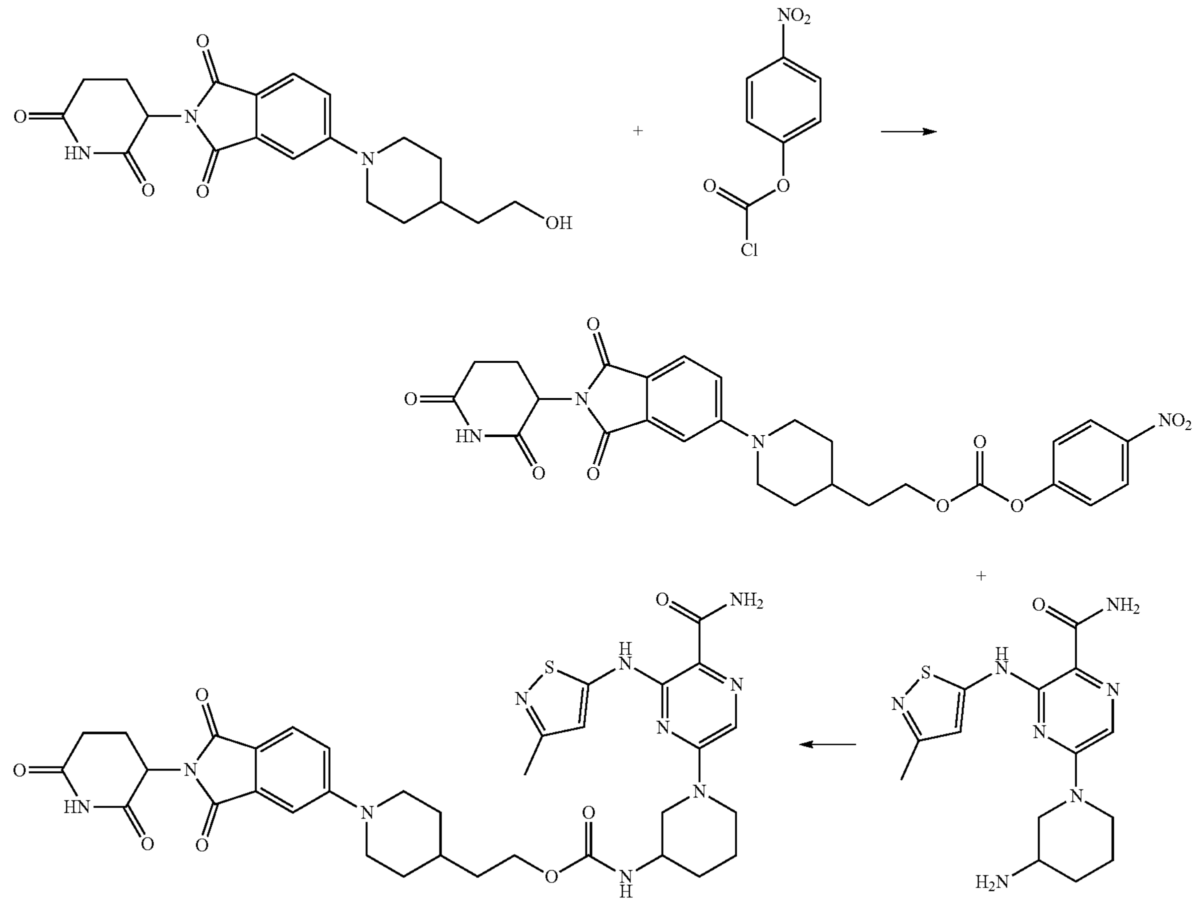

The procedure from Example 13 was followed starting with 2-(2,6-dioxopiperidin-3-yl)-5-(4-(2-hydroxyethyl)piperidin-1-yl)isoindoline-1,3-dione to afford 2-(1-(2-(2,6-dioxopiperidin-3-yl)-1,3-dioxoisoindolin-5-yl)piperidin-4-yl) ethyl ((R)-1-(5-carbamoyl-6-((3-methylisothiazol-5-yl) amino)pyrazin-2-yl)piperidin-3-yl)carbamate (1.9 mg). $^1H$ NMR (500 MHz, Chloroform-d) δ 12.01 (s, 1H), 8.26 (s, 1H), 7.68-7.62 (m, 1H), 7.39 (s, 1H), 7.35 (s, 1H), 7.22 (s, 2H), 7.00 (s, 1H), 6.64 (s, 1H), 5.50 (s, 2H), 4.99-4.91 (m, 1H), 4.40 (d, J=43.4 Hz, 1H), 4.14 (s, 2H), 4.04-3.18 (m, 8H), 2.93-2.69 (m, 3H), 2.46 (s, 3H), 2.17-2.10 (m, 0H), 1.78 (d, J=61.7 Hz, 9H), 1.25 (s, 2H). LCMS: $C_{35}H_{40}N_{10}O_7S$ requires: 744, found: m/z=745 $[M+H]^+$.

Example 18: Synthesis of (1-(2-(2,6-dioxopiperidin-3-yl)-1,3-dioxoisoindolin-5-yl)piperidin-4-yl)methyl ((R)-1-(5-carbamoyl-6-((4-(methylsulfonyl)phenyl) amino)pyrazin-2-yl)piperidin-3-yl)carbamate (Compound 8)

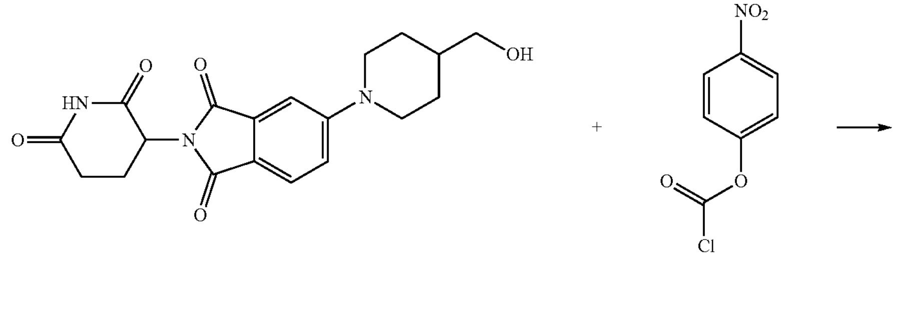

-continued

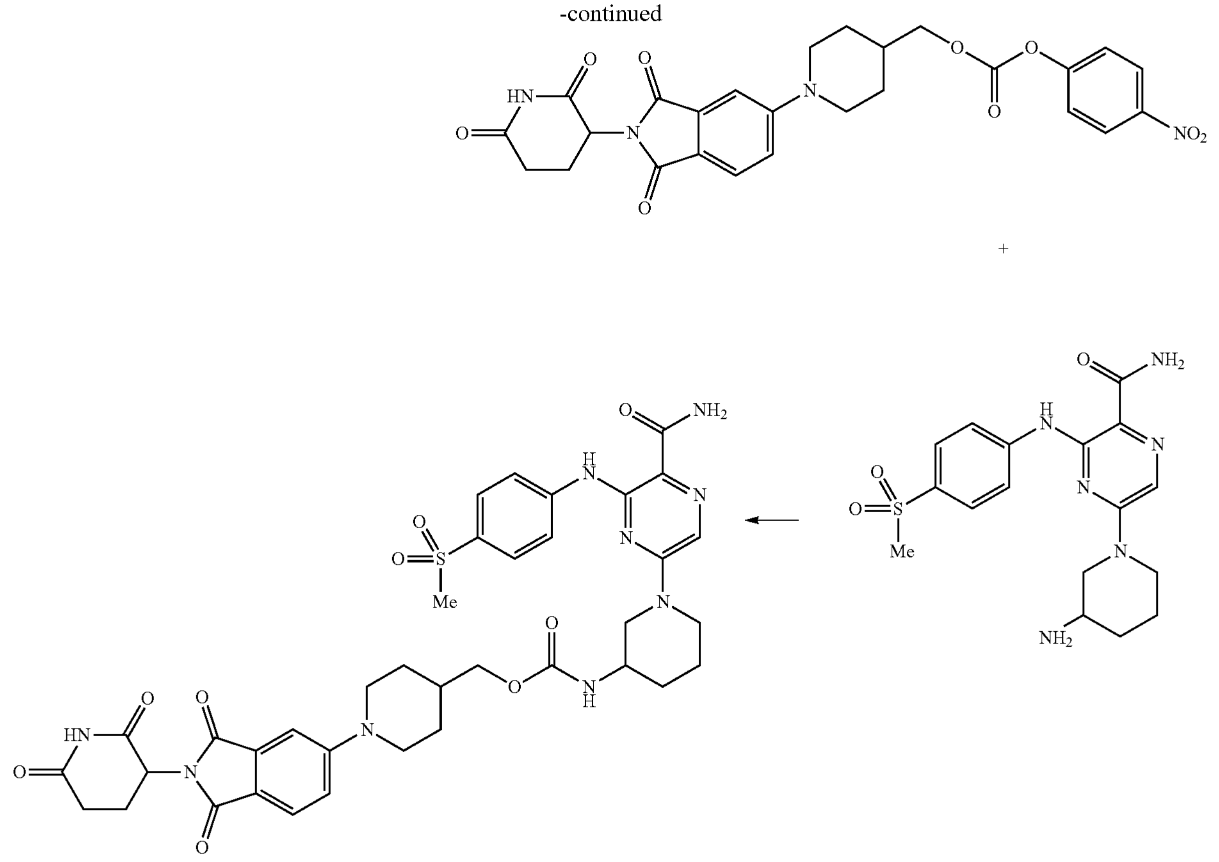

The procedure from Example 13 was followed starting with 2-(2,6-dioxopiperidin-3-yl)-5-(4-(hydroxymethyl)piperidin-1-yl)isoindoline-1,3-dione to afford (1-(2-(2,6-dioxopiperidin-3-yl)-1,3-dioxoisoindolin-5-yl)piperidin-4-yl) methyl ((R)-1-(5-carbamoyl-6-((4-(methylsulfonyl)phenyl) amino)pyrazin-2-yl)piperidin-3-yl)carbamate (17 mg). $^1$H NMR (500 MHz, Chloroform-d) δ 11.60 (s, 1H), 7.99 (d, J=13.7 Hz, 1H), 7.94-7.75 (m, 4H), 7.55 (s, 0H), 5.30 (s, 2H), 4.96 (dd, J=12.2, 5.8 Hz, 1H), 4.39-3.12 (m, 13H), 2.89 (t, J=19.6 Hz, 1H), 2.84-2.65 (m, 1H), 2.20-2.10 (m, 1H), 2.10-1.98 (m, 1H), 1.59 (s, 15H). LCMS: $C_{37}H_{41}N_9O_9S$ requires: 787, found: m/z=788 $[M+H]^+$.

Example 19: Synthesis of ((3R)-1-(2-(2,6-dioxopiperidin-3-yl)-1,3-dioxoisoindolin-5-yl)pyrrolidin-3-yl)methyl ((R)-1-(5-carbamoyl-6-((4-(methylsulfonyl)phenyl)amino)pyrazin-2-yl)piperidin-3-yl) carbamate (Compound 9)

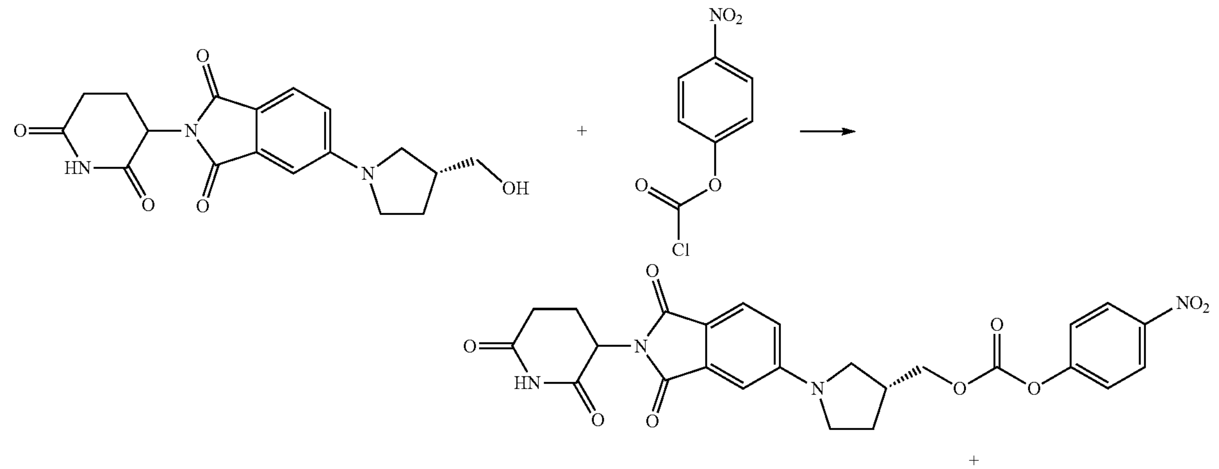

-continued

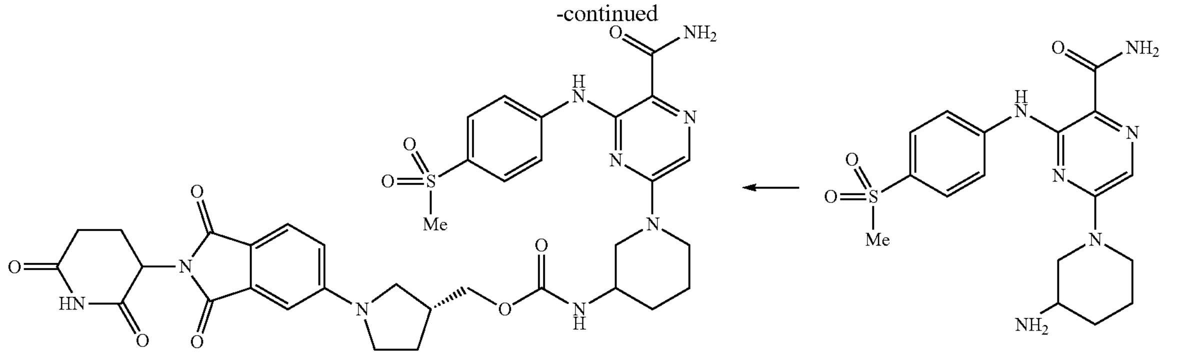

The procedure from Example 13 was followed starting with 2-(2,6-dioxopiperidin-3-yl)-5-((R)-3-(hydroxymethyl)pyrrolidin-1-yl)isoindoline-1,3-dione to afford ((3R)-1-(2-(2,6-dioxopiperidin-3-yl)-1,3-dioxoisoindolin-5-yl)pyrrolidin-3-yl)methyl ((R)-1-(5-carbamoyl-6-((4-(methylsulfonyl)phenyl)amino)pyrazin-2-yl)piperidin-3-yl)carbamate (9.4 mg). $^1$H NMR (500 MHz, Chloroform-d) δ 11.55 (s, 1H), 8.07 (s, 2H), 7.86 (q, J=9.0 Hz, 5H), 7.50 (d, J=32.5 Hz, 1H), 7.34-7.26 (m, 1H), 5.33 (s, 2H), 4.94 (dd, J=11.9, 5.3 Hz, 1H), 4.12 (s, 2H), 4.02 (s, 1H), 3.84 (s, 4H), 3.68 (s, 2H), 3.33 (s, 4H), 3.05 (d, J=12.0 Hz, 4H), 2.88 (s, 1H), 2.79-2.69 (m, 1H), 2.14 (d, J=10.4 Hz, 1H), 2.06 (s, 2H), 1.67 (s, 2H), 1.25 (s, 2H). LCMS: $C_{36}H_{39}N_9O_9S$ requires: 773, found: m/z=774.

Example 20: Synthesis of 5-{3,9-diazaspiro[5.5]undecan-3-yl}-2-(2,6-dioxopiperidin-3-yl)isoindole-1,3-dione

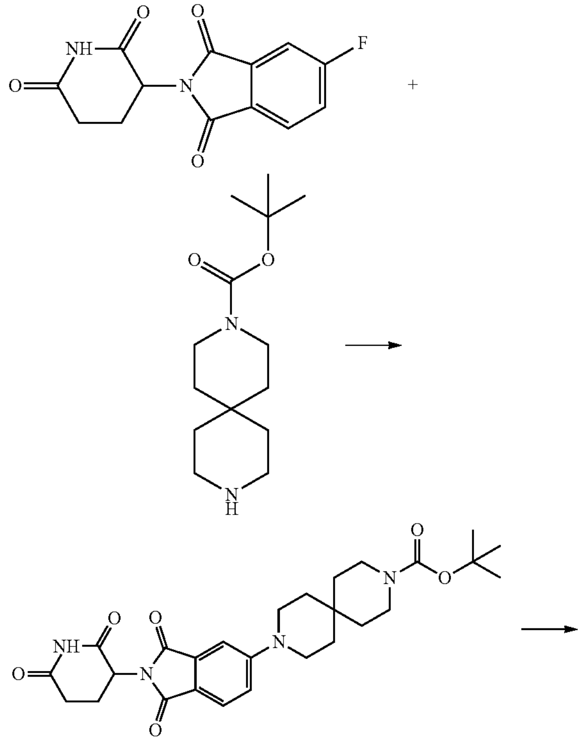

-continued

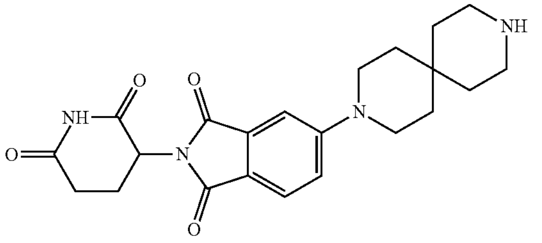

Step 1: tert-butyl 9-[2-(2,6-dioxopiperidin-3-yl)-1,3-dioxoisoindol-5-yl]-3,9-diazaspiro[5.5]undecane-3-carboxylate A mixture of 2-(2,6-dioxopiperidin-3-yl)-5-fluoroisoindole-1,3-dione (218 mg, 0.79 mmol), i-$Pr_2$NEt (412 μL, 2.37 mmol), and tert-butyl 3,9-diazaspiro[5.5]undecane-3-carboxylate (201 mg, 0.79 mmol) was dissolved in N-methylpyrrolidone (1 mL) and heated to 65° C. for 2 h before being cooled and purified ($SiO_2$, 0-100% EtOAc/Hexanes) to afford tert-butyl 9-[2-(2,6-dioxopiperidin-3-yl)-1,3-dioxoisoindol-5-yl]-3,9-diazaspiro[5.5]undecane-3-carboxylate (306 mg). LCMS: $C_{27}H_{34}N_4O_6$ requires: 510, found: m/z=511 $[M+H]^+$.

Step 2: 5-{3,9-diazaspiro[5.5]undecan-3-yl}-2-(2,6-dioxopiperidin-3-yl)isoindole-1,3-dione The tert-butyl 9-[2-(2,6-dioxopiperidin-3-yl)-1,3-dioxoisoindol-5-yl]-3,9-diazaspiro[5.5]undecane-3-carboxylate was dissolved in a mixture of $CH_2Cl_2$/TFA (3:1, 3.0 mL) and stirred at rt for 2 h before being concentrated to afford 5-{3,9-diazaspiro[5.5]undecan-3-yl}-2-(2,6-dioxopiperidin-3-yl)isoindole-1,3-dione (224 mg) as a yellow solid. LCMS: $C_{22}H_{26}N_4O_4$ requires: 410, found: m/z=411 $[M+H]^+$.

Example 21: Synthesis of 4-nitrophenyl N-[(3R)-1-{5-carbamoyl-6-[(4-methanesulfonylphenyl)amino]pyrazin-2-yl}piperidin-3-yl]carbamate

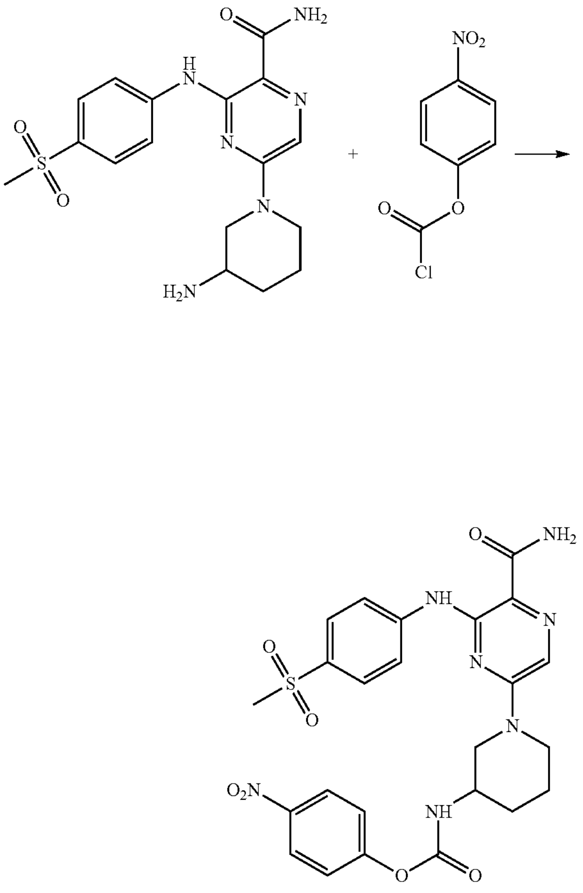

5-[(3R)-3-aminopiperidin-1-yl]-3-[(4-methanesulfonylphenyl)amino]pyrazine-2-carboxamide (40 mg, 80 μmol) and $Et_3N$ (34 μL, 0.24 mmol) were dissolved in $CH_2Cl_2$ and before 4-nitrophenyl carbonochloridate (16.52 mg, 0.08 mmol) (in 100 uL of $CH_2Cl_2$) was added at 0 C. After 10 min the reaction mixture was diluted with $H_2O$ (1 mL) and extracted (2×3 mL $CH_2Cl_2$). The combined organic extracts were dried ($Na_2SO_4$), filtered, and concentrated. The crude residue was purified ($SiO_2$, 0→100% EtOAc/$CH_2Cl_2$) to afford 4-nitrophenyl N-[(3R)-1-{5-carbamoyl-6-[(4-methanesulfonylphenyl)amino]pyrazin-2-yl}piperidin-3-yl]carbamate (40 mg). LCMS $C_{24}H_{25}N_7O_7S$ requires: 555, found: m/z=556 $[M+H]^+$.

Example 22: Synthesis of N-[(3R)-1-{5-carbamoyl-6-[(4-methanesulfonylphenyl)amino]pyrazin-2-yl}piperidin-3-yl]-9-[2-(2,6-dioxopiperidin-3-yl)-1,3-dioxoisoindol-5-yl]-3,9-diazaspiro[5.5]undecane-3-carboxamide (Compound 11)

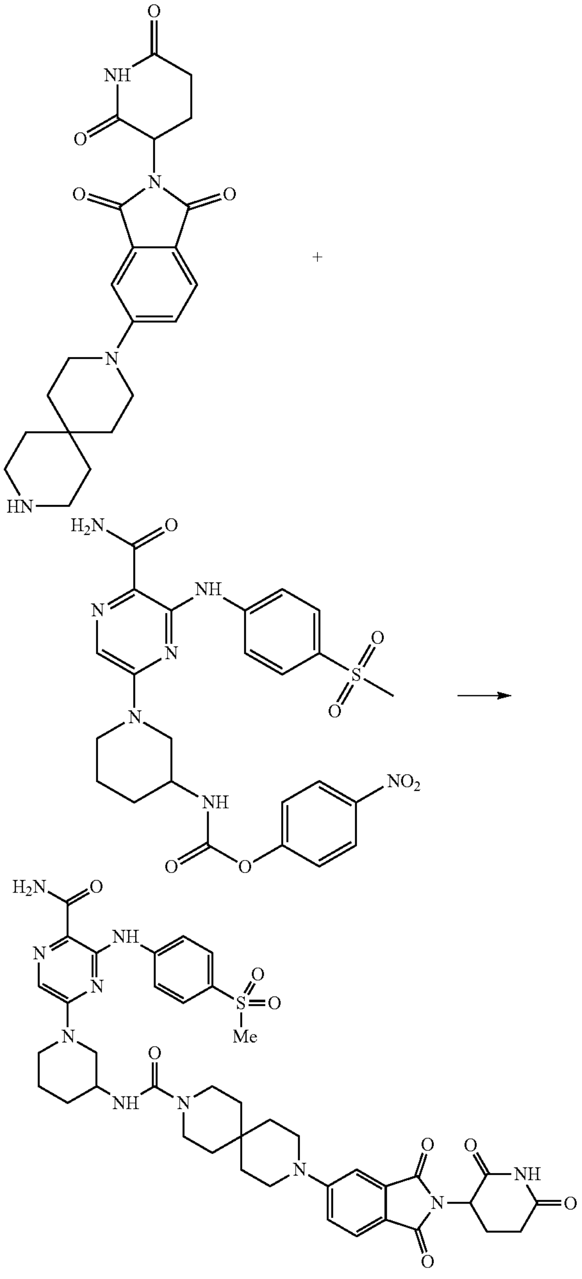

4-nitrophenyl N-[(3R)-1-{5-carbamoyl-6-[(4-methanesulfonylphenyl)amino]pyrazin-2-yl}piperidin-3-yl]carbamate (30 mg, 50 μmol) and 5-{3,9-diazaspiro[5.5]undecan-3-yl}-2-(2,6-dioxopiperidin-3-yl)isoindole-1,3-dione (22 mg, 50 μmol) was dissolved in NMP (0.5 mL) and $Et_3N$ (30 μL, 220 μmol) was added. The reaction mixture was heated to 65° C. for 4 days before being cooled and purified (RP-HPLC) to afford N-[(3R)-1-{5-carbamoyl-6-[(4-methanesulfonylphenyl)amino]pyrazin-2-yl}piperidin-3-yl]-9-[2-(2,6-dioxopiperidin-3-yl)-1,3-dioxoisoindol-5-yl]-3,9- diazaspiro[5.5]undecane-3-carboxamide (7.4 mg) as a yellow solid. $^1$H NMR (500 MHz, Chloroform-d) δ 11.56 (s, 1H), 8.14 (d, J=7.6 Hz, 1H), 7.91 (d, J=8.9 Hz, 2H), 7.83 (d, J=8.9 Hz, 2H), 7.70 (d, J=8.5 Hz, 1H), 7.47 (d, J=7.7 Hz, 1H), 7.39-7.30 (m, 2H), 7.15 (d, J=8.2 Hz, 1H), 5.35 (s, 1H), 4.95 (dd, J=12.3, 5.4 Hz, 1H), 4.06 (s, 1H), 3.63 (s, 1H), 3.50-3.13 (m, 9H), 3.05 (s, 4H), 2.98-2.63 (m, 4H), 2.25-2.05 (m, 3H), 1.95-1.72 (m, 1H), 1.68 (t, J=5.9 Hz, 4H), 1.60-1.41 (m, 5H). LCMS: $C_{40}H_{46}N_{10}O_8S$ requires: 826, found: m/z=827 $[M+H]^+$.

Example 23: Synthesis of N-[(3R)-1-{5-carbamoyl-6-[(3-methyl-1,2-thiazol-5-yl)amino]pyrazin-2-yl}piperidin-3-yl]carbamate

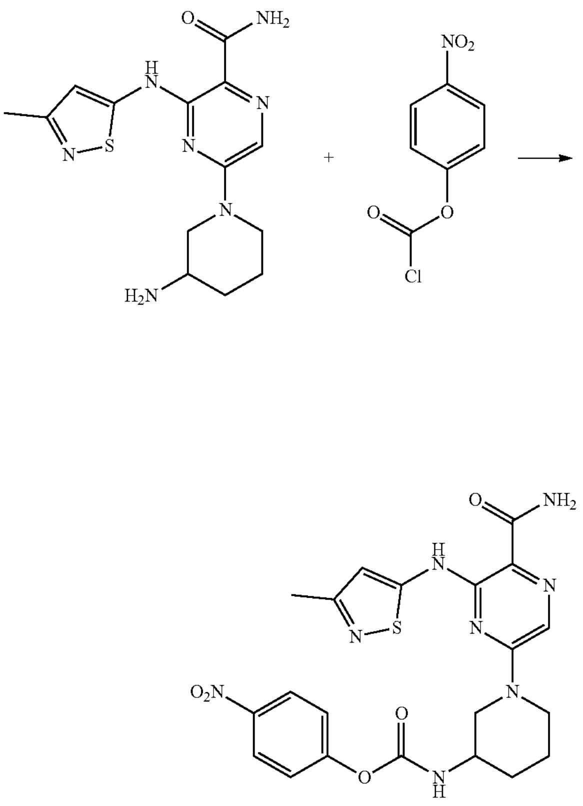

The procedure from Example 21 was followed to afford 4-nitrophenyl N-[(3R)-1-{5-carbamoyl-6-[(3-methyl-1,2-thiazol-5-yl)amino]pyrazin-2-yl}piperidin-3-yl]carbamate (40 mg). LCMS $C_{21}H_{22}N_8O_5S$ requires: 498, found: m/z=499 $[M+H]^+$.

Example 24: Synthesis of N-[(3R)-1-{5-carbamoyl-6-[(3-methyl-1,2-thiazol-5-yl)amino]pyrazin-2-yl}piperidin-3-yl]-9-[2-(2,6-dioxopiperidin-3-yl)-1,3-dioxoisoindol-5-yl]-3,9-diazaspiro[5.5]undecane-3-carboxamide (Compound 12)

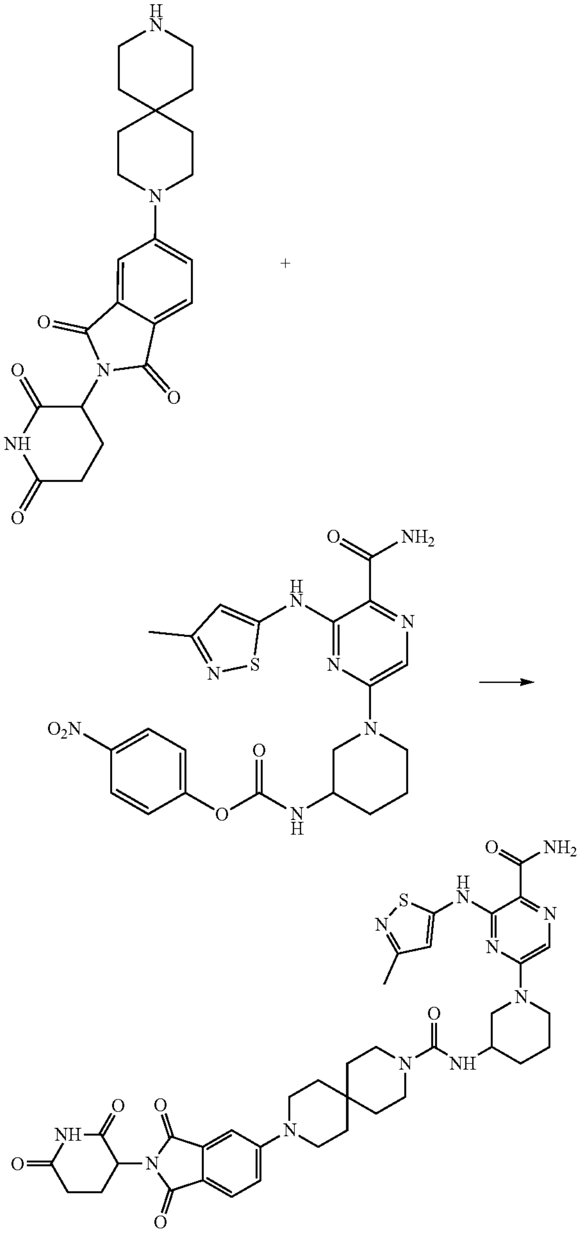

The procedure from Example 22 was followed to afford N-[(3R)-1-{5-carbamoyl-6-[(3-methyl-1,2-thiazol-5-yl)amino]pyrazin-2-yl}piperidin-3-yl]-9-[2-(2,6-dioxopiperidin-3-yl)-1,3-dioxoisoindol-5-yl]-3,9-diazaspiro[5.5]undecane-3-carboxamide (4.4 mg). $^1$H NMR (500 MHz, Chloroform-d) δ 11.88 (s, 1H), 8.18 (d, J=3.5 Hz, 1H), 7.68 (d, J=8.5 Hz, 1H), 7.37 (s, 2H), 7.03 (dd, J=8.6, 2.4 Hz, 1H), 6.63 (s, 1H), 5.38-5.34 (m, 1H), 4.94 (dd, J=12.3, 5.4 Hz, 1H), 4.36 (s, 1H), 3.81 (s, 1H), 3.51-3.38 (m, 5H), 3.37-3.30 (m, 3H), 3.33-3.20 (m, 4H), 3.14 (t, J=12.0 Hz, 1H), 2.93-2.68 (m, 4H), 2.42 (s, 3H), 2.24 (d, J=12.2 Hz, 1H), 2.13 (ddd, J=12.2, 5.5, 2.3 Hz, 1H), 1.94 (t, J=13.0 Hz, 1H), 1.79-1.70 (m, 1H), 1.63 (d, J=11.9 Hz, 2H), 1.50-1.41 (m, 5H), 0.84 (s, 1H). LCMS: $C_{37}H_{43}N_{11}O_6S$ requires: 769, found: m/z=770 $[M+H]^+$.

Example 25: Synthesis of 5-{2,8-diazaspiro[4.5]decan-8-yl}-2-(2,6-dioxopiperidin-3-yl)isoindole-1,3-dione

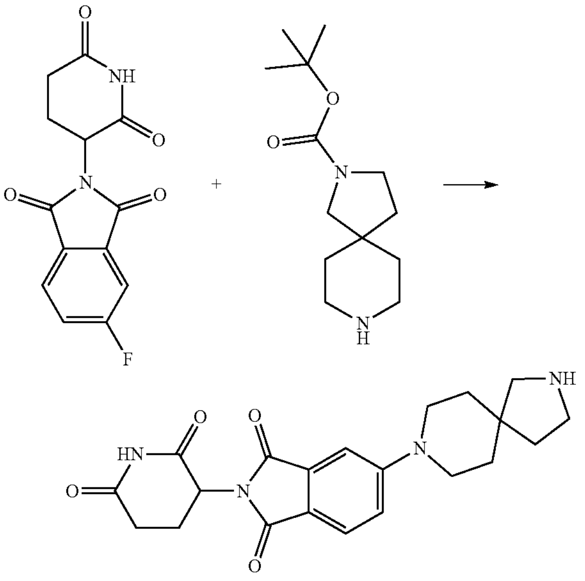

The procedure from Step 1 and Step 2 of Example 20 was followed to afford 5-{2,8-diazaspiro[4.5]decan-8-yl}-2-(2,6-dioxopiperidin-3-yl)isoindole-1,3-dione (170 mg, 2 steps). LCMS: $C_{21}H_{24}N_4O_4$ requires: 396, found: m/z=397 $[M+H]^+$.

Example 26: Synthesis of N—((R)-1-(5-carbamoyl-6-((4-(methylsulfonyl)phenyl) amino)pyrazine-2-yl) piperidin-3-yl)-8-(2-(2,6-dioxopiperidin-3-yl)-1,3-dioxoisoindolin-5-yl)-2,8-diazaspiro[4.5]decane-2-carboxamide (Compound 10)

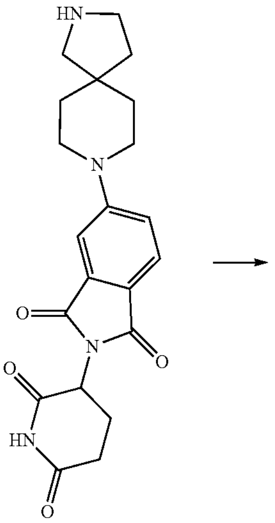

-continued

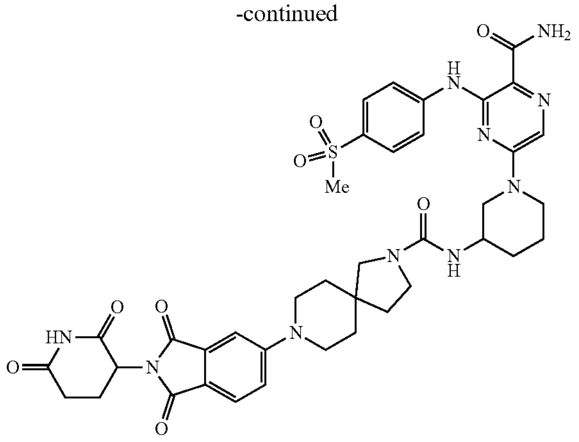

The procedure from Example 22 was followed to afford N—((R)-1-(5-carbamoyl-6-((4-(methylsulfonyl)phenyl) amino)pyrazine-2-yl)piperidin-3-yl)-8-(2-(2,6-dioxopiperidin-3-yl)-1,3-dioxoisoindolin-5-yl)-2,8-diazaspiro[4.5]decane-2-carboxamide (12 mg). $^1H$ NMR (500 MHz, Chloroform-d) δ 11.61 (d, J=2.5 Hz, 1H), 8.37 (d, J=9.0 Hz, 1H), 7.93 (d, J=8.6 Hz, 2H), 7.86 (h, J=3.2, 2.8 Hz, 2H), 7.71 (d, J=8.5 Hz, 1H), 7.50 (s, 1H), 7.39 (s, 1H), 7.33 (d, J=2.3 Hz, 1H), 7.10 (d, J=8.0 Hz, 1H), 6.77 (s, 1H), 5.55-5.50 (m, 1H), 4.97 (dd, J=12.2, 5.4 Hz, 1H), 4.09 (s, 1H), 3.79 (s, 1H), 3.58-3.48 (m, 1H), 3.40 (q, J=6.8 Hz, 1H), 3.35 (s, 4H), 3.29 (d, J=4.6 Hz, 2H), 3.21 (s, 1H), 3.08 (d, J=3.0 Hz, 0H), 3.07 (s, 3H), 2.96-2.71 (m, 3H), 2.20-2.12 (m, 2H), 2.03 (s, 1H), 1.91 (d, J=13.2 Hz, 0H), 1.81 (s, 3H), 1.68 (d, J=11.4 Hz, 2H), 1.66-1.54 (m, 4H), 1.28 (s, 1H). LCMS: $C_{39}H_{44}N_{10}O_8S$ requires: 812, found: m/z=813 $[M+H]^+$.

Example 27: Synthesis of 5-[(3R)-3-{4-[2-(2,6-dioxopiperidin-3-yl)-1,3-dioxoisoindol-5-yl]piperazine-1-carbonylamino}piperidin-1-yl]-3-[(3-methyl-1,2-thiazol-5-yl)amino]pyrazine-2-carboxamide (Compound 27)

Step 1: 1-(tert-butyl) 4-(4-nitrophenyl) piperazine-1,4-dicarboxylate

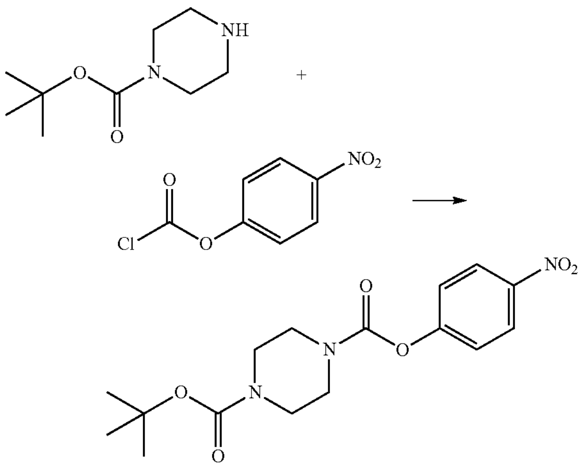

A mixture of tert-butyl piperazine-1-carboxylate (200 mg, 1.07 mmol) and $Et_3N$ (224 μL, 163 mg, 1.61 mmol) in $CH_2Cl_2$ (1 mL) were cooled to 0° C. before 4-nitrophenyl chloroformate (216 mg, 1.07 mmol) was added as a solution in $CH_2Cl_2$ (250 μL) in a dropwise manner. After 10 min the reaction mixture was diluted with $H_2O$ (5 mL) and extracted (3×5 mL $CH_2Cl_2$). The combined organic extracts were dried ($Na_2SO_4$), filtered, and concentrated to afford 1-(tert-butyl) 4-(4-nitrophenyl) piperazine-1,4-dicarboxylate (370 mg). LCMS: $C_{16}H_{21}N_3O_6$ requires: 351, found: m/z=352 $[M+H]^+$.

Step 2: tert-butyl 4-{[(3R)-1-{5-carbamoyl-6-[(3-methyl-1,2-thiazol-5-yl)amino]pyrazine-2-yl}piperidin-3-yl]carbamoyl}piperazine-1-carboxylate

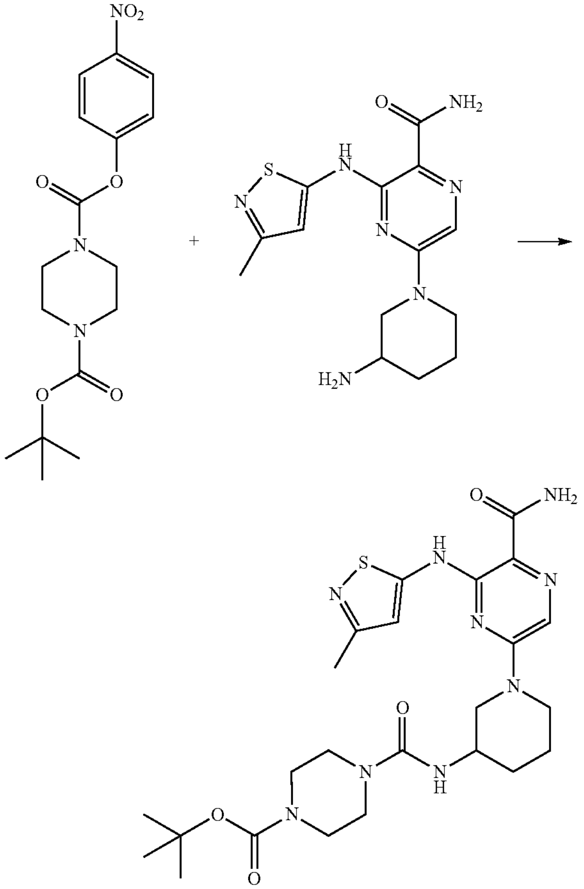

5-[(3R)-3-aminopiperidin-1-yl]-3-[(3-methyl-1,2-thiazol-5-yl)amino]pyrazine-2-carboxamide (50 mg, 0.15 mmol), 1-tert-butyl 4-(4-nitrophenyl) piperazine-1,4-dicarboxylate (105 mg, 0.30 mmol), and $Et_3N$ (63 μL, 0.45 mmol) were dissolved in DMF (0.5 mL) and the mixture was heated to 65° C. for 24 h. The mixture was cooled, diluted with $H_2O$, and extracted (3×5 mL $CH_2Cl_2$). The combined organic extracts were dried ($Na_2SO_4$), filtered, and concentrated. Purification ($SiO_2$, 0→15% MeOH/$CH_2Cl_2$) afforded tert-butyl 4-{[(3R)-1-{5-carbamoyl-6-[(3-methyl-1,2-thiazol-5-yl)amino]pyrazine-2-yl}piperidin-3-yl] carbamoyl}piperazine-1-carboxylate (56 mg). LCMS: $C_{24}H_{35}N_9O_4S$ requires: 545, found: m/z=546 $[M+H]^+$.

Step 3: (R)-3-((3-methylisothiazol-5-yl)amino)-5-(3-(piperazine-1-carboxamido)piperidin-1-yl)pyrazine-2-carboxamide

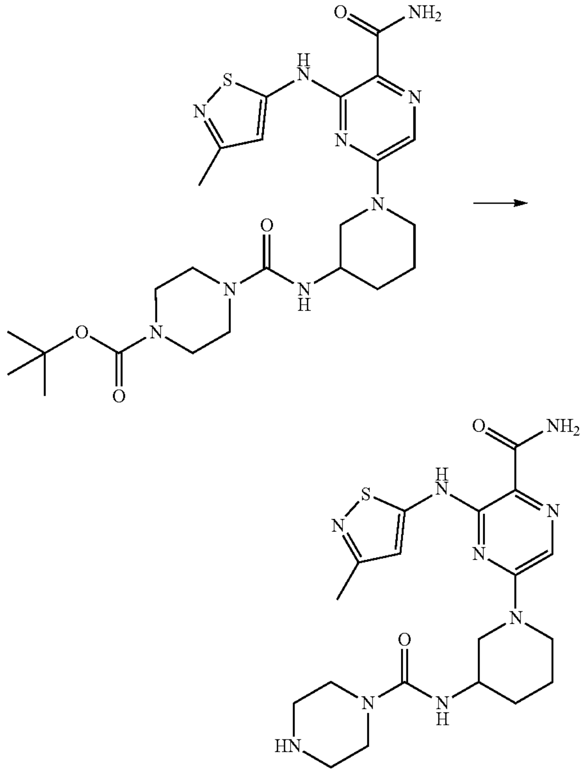

The procedure from Step 2 of Example 20 was followed to afford (R)-3-((3-methylisothiazol-5-yl)amino)-5-(3-(piperazine-1-carboxamido)piperidin-1-yl)pyrazine-2-carboxamide (50 mg) as a TFA salt. LCMS: $C_{24}H_{35}N_9O_4S$ requires: 445, found: m/z=446 $[M+H]^+$.

Step 4: 5-[(3R)-3-{4-[2-(2,6-dioxopiperidin-3-yl)-1,3-dioxoisoindol-5-yl]piperazine-1-carbonylamino}piperidin-1-yl]-3-[(3-methyl-1,2-thiazol-5-yl)amino]pyrazine-2-carboxamide

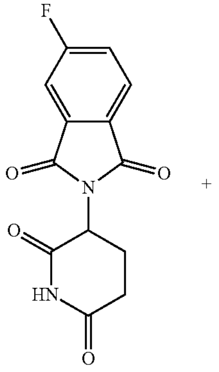

-continued

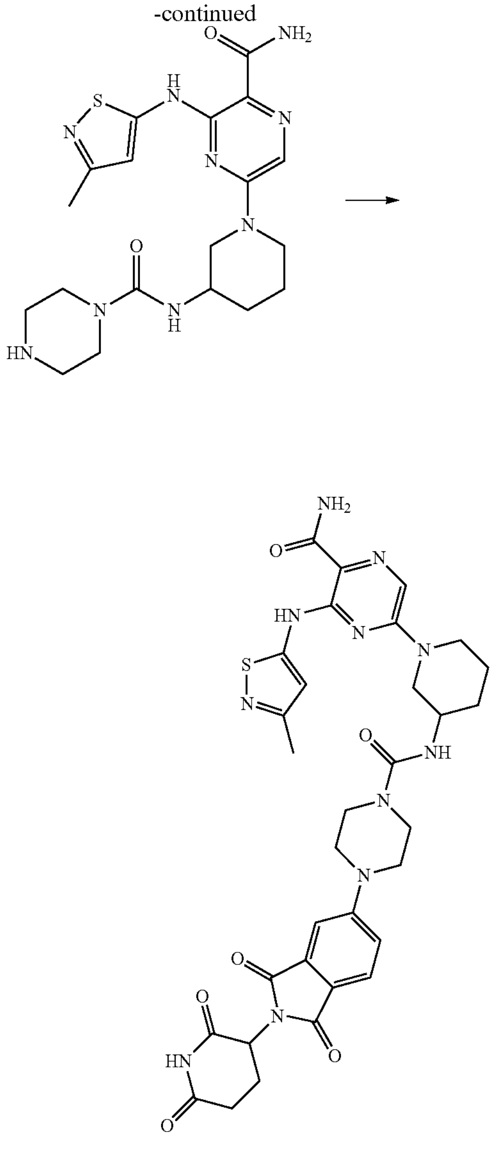

A mixture of 2-(2,6-dioxopiperidin-3-yl)-5-fluoroisoindole-1,3-dione (10 mg, 360 μmol) and 3-[(3-methyl-1,2-thiazol-5-yl)amino]-5-[(3R)-3-(piperazine-1-carbonylamino)piperidin-1-yl]pyrazine-2-carboxamide (16 mg, 36 μmol) were dissolved in NMP before $Et_3N$ (20 μL, 145 μmol) was added. The mixture was heated to 65° C. for 12 h before being cooled, filtered, and purified (RP-HPLC) to afford 5-[(3R)-3-{4-[2-(2,6-dioxopiperidin-3-yl)-1,3-dioxoisoindol-5-yl]piperazine-1-carbonylamino}piperidin-1-yl]-3-[(3-methyl-1,2-thiazol-5-yl)amino]pyrazine-2-carboxamide (1.00 mg). $^1H$ NMR (500 MHz, Acetonitrile-$d_3$) δ 11.97 (d, J=7.3 Hz, 1H), 8.88 (s, 1H), 7.66 (dd, J=8.6, 1.2 Hz, 1H), 7.41 (s, 1H), 7.31 (s, 1H), 7.19 (dd, J=5.0, 2.4 Hz, 1H), 7.07 (t, J=6.7 Hz, 1H), 6.67 (d, J=1.4 Hz, 1H), 6.46 (d, J=6.5 Hz, 1H), 5.88 (s, 1H), 5.06-4.87 (m, 1H), 4.26 (s, 1H), 3.66 (s, 1H), 3.39-3.00 (m, 16H), 2.90-2.56 (m, 4H), 2.16-2.02 (m, 1H), 1.80-1.55 (m, 1H). LCMS: $C_{32}H_{35}N_{11}O_6S$ requires: 701, found: m/z=702 $[M+H]^+$.

Example 28: Synthesis of N-[(3R)-1-{5-carbamoyl-6-[(4-methanesulfonylphenyl)amino]pyrazine-2-yl}piperidin-3-yl]-6-[2-(2,6-dioxopiperidin-3-yl)-1,3-dioxoisoindol-5-yl]-2,6-diazaspiro[3.3]heptane-2-carboxamide (Compound 24)

Step 1: 2-tert-butyl 6-(4-nitrophenyl) 2,6-diazaspiro[3.3]heptane-2,6-dicarboxylate

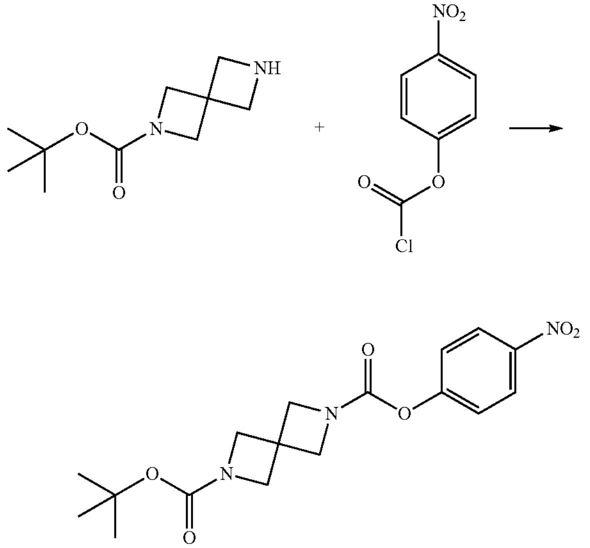

The procedure from Step 1 of Example 27 was followed to afford 2-tert-butyl 6-(4-nitrophenyl) 2,6-diazaspiro[3.3]heptane-2,6-dicarboxylate (168 mg). LCMS: $C_{17}H_{21}N_3O_6$ requires: 363, found: m/z=364.

Step 2: N-[(3R)-1-{5-carbamoyl-6-[(4-methanesulfonylphenyl)aminopyrazine-2-yl}piperidin-3-yl]-2,6-diazaspiro[3.3]heptane-2-carboxamide

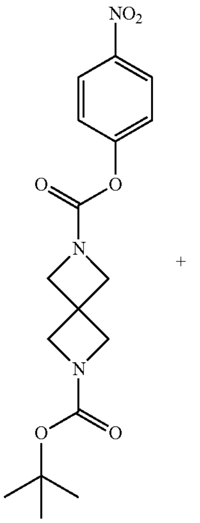

-continued

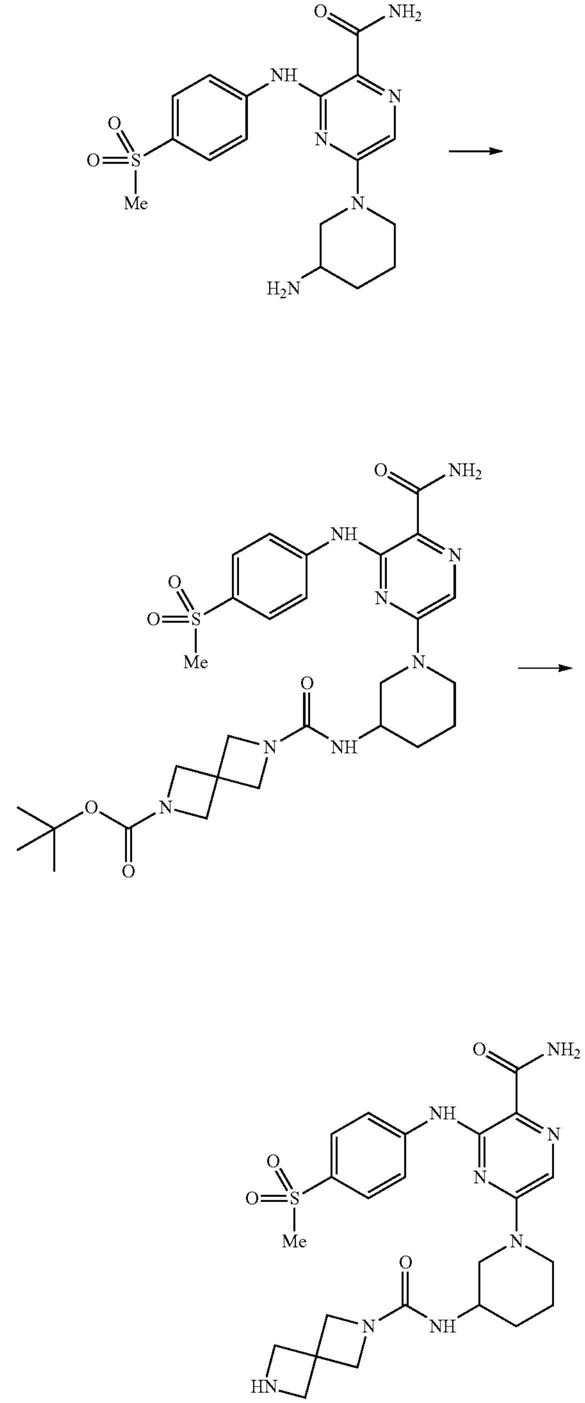

The procedure from Step 2 of Example 27 and the deprotection Step 2 of Example 20 were followed to afford N-[(3R)-1-{5-carbamoyl-6-[(4-methanesulfonylphenyl)amino]pyrazine-2-yl}piperidin-3-yl]-2,6-diazaspiro[3.3]heptane-2-carboxamide (12 mg, 2 steps). LCMS: $C_{23}H_{30}N_8O_4S$ requires 514, found, m/z=515 $[M+H]^+$.

Step 3: N-[(3R)-1-{5-carbamoyl-6-[(4-methanesulfonylphenyl)amino]pyrazine-2-yl}piperidin-3-yl]-6-[2-(2,6-dioxopiperidin-3-yl)-1,3-dioxoisoindol-5-yl]-2,6-diazaspiro[3.3]heptane-2-carboxamide

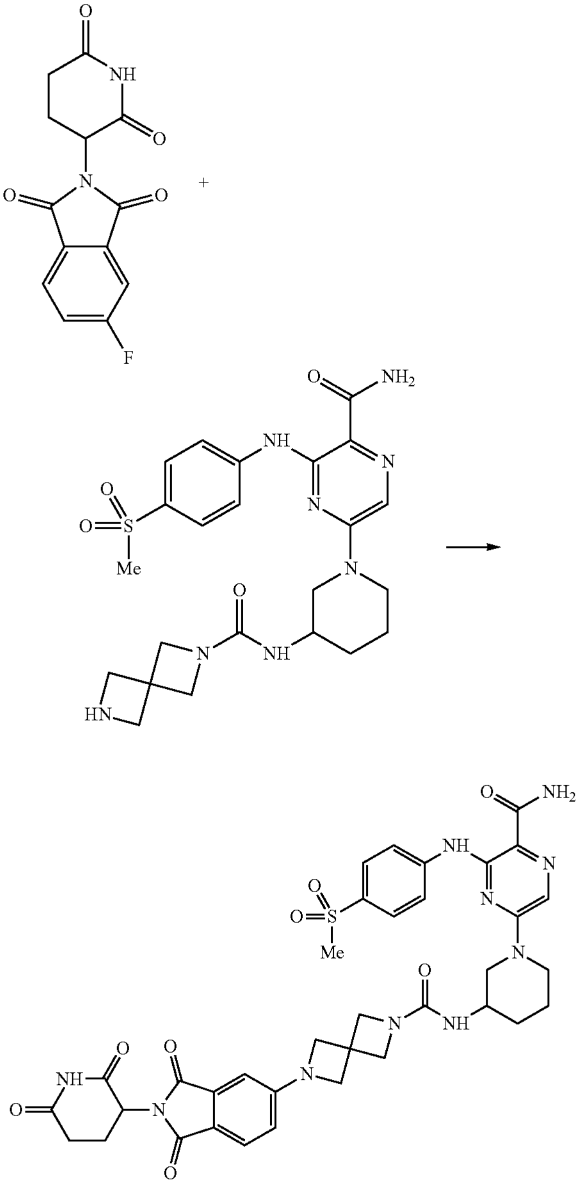

The procedure from Step 4 of Example 27 was followed to afford N-[(3R)-1-{5-carbamoyl-6-[(4-methanesulfonylphenyl)amino]pyrazine-2-yl}piperidin-3-yl]-6-[2-(2,6-dioxopiperidin-3-yl)-1,3-dioxoisoindol-5-yl]-2,6-diazaspiro[3.3]heptane-2-carboxamide (4 mg). $^1$H NMR (500 MHz, Methanol-$d_4$) δ 7.97 (d, J=8.8 Hz, 2H), 7.86 (d, J=8.8 Hz, 2H), 7.63 (d, J=8.3 Hz, 1H), 7.46 (s, 1H), 6.77 (d, J=2.1 Hz, 1H), 6.61 (dd, J=8.2, 2.1 Hz, 1H), 5.05 (dd, J=12.6, 5.5 Hz, 1H), 4.17-4.02 (m, 4H), 4.02-3.93 (m, 4H), 3.77 (d, J=13.3 Hz, 1H), 3.13 (s, 3H), 2.98 (t, J=10.6 Hz, 1H), 2.92-2.81 (m, 2H), 2.79-2.66 (m, 2H), 2.21-2.03 (m, 2H), 1.91-1.81 (m, 2H), 1.74-1.59 (m, 2H). LCMS: $C_{36}H_{38}N_{10}O_8S$ requires: 770, found: m/z=771 $[M+H]^+$.

Example 29: Synthesis of N—((R)-1-(5-carbamoyl-6-((4-(methylsulfonyl)phenyl) amino)pyrazine-2-yl) piperidin-3-yl)-2-(2-(2,6-dioxopiperidin-3-yl)-1,3-dioxoisoindolin-5-yl)-2,7-diazaspiro[3.5]nonane-7-carboxamide (Compound 28)

Step 1: N-[(3R)-1-{5-carbamoyl-6-[(4-methanesulfonylphenyl)amino]pyrazine-2-yl}piperidin-3-yl]-2,7-diazaspiro[3.5]nonane-7-carboxamide

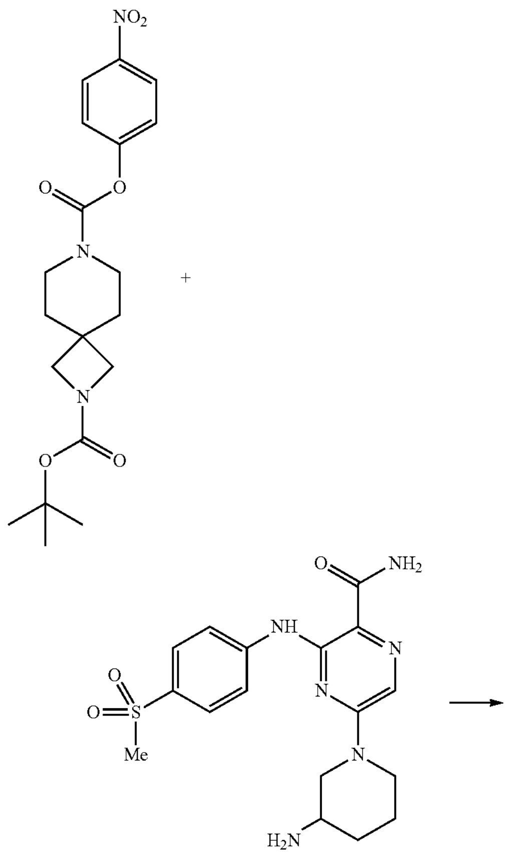

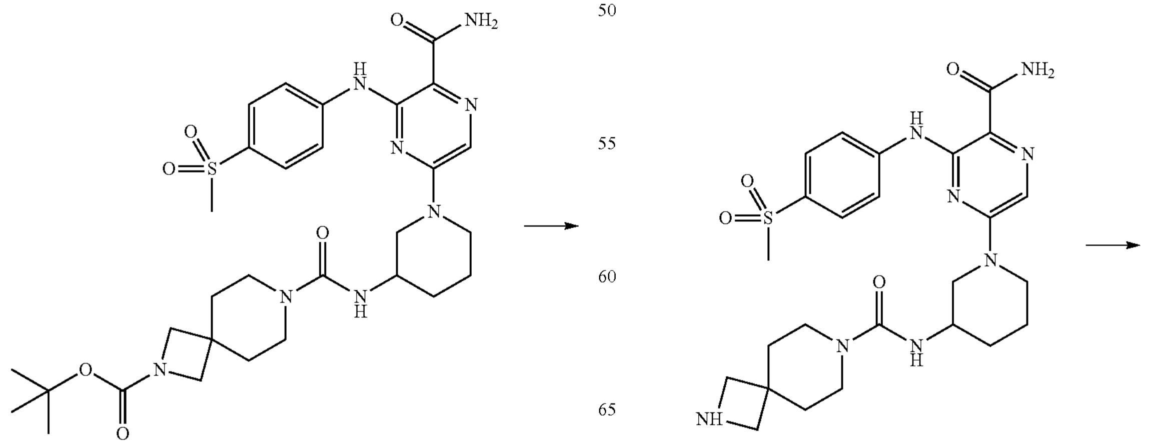

-continued

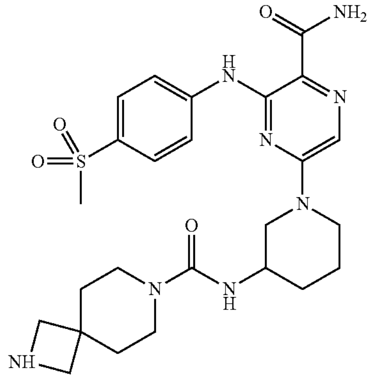

The procedure from Step 2 of Example 27 and the deprotection Step 2 of Example 20 were followed to afford N-[(3R)-1-{5-carbamoyl-6-[(4-methanesulfonylphenyl) aminopyrazine-2-yl}piperidin-3-yl]-2,7-diazaspiro[3.5] nonane-7-carboxamide (25 mg, 2 steps). LCMS: $C_{25}H_{34}N_8O_4S$ requires 542, found, m/z=545 [M+H]$^+$.

Step 2: N—((R)-1-(5-carbamoyl-6-((4-(methylsulfonyl)phenyl)amino)pyrazine-2-yl)piperidin-3-yl)-2-(2-(2,6-dioxopiperidin-3-yl)-1,3-dioxoisoindolin-5-yl)-2,7-diazaspiro[3.5]nonane-7-carboxamide

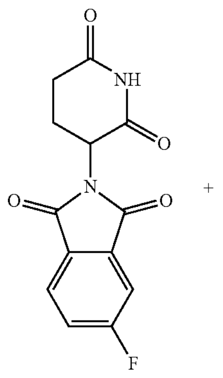

-continued

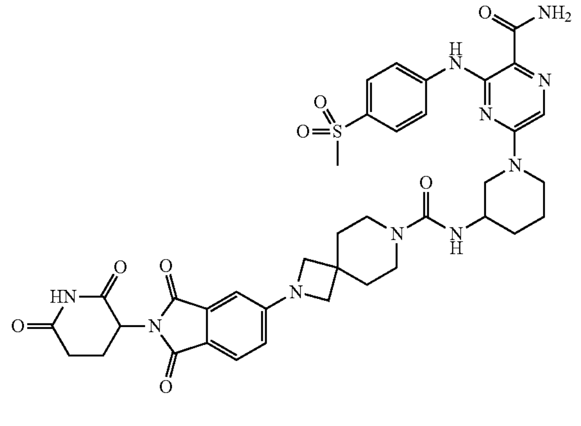

The procedure from Step 4 of Example 27 was followed to afford N—((R)-1-(5-carbamoyl-6-((4-(methylsulfonyl)phenyl)amino)pyrazine-2-yl)piperidin-3-yl)-2-(2-(2,6-dioxopiperidin-3-yl)-1,3-dioxoisoindolin-5-yl)-2,7-diazaspiro[3.5]nonane-7-carboxamide (4 mg). $^1H$ NMR (500 MHz, DMSO-$d_6$) δ 11.97 (s, 1H), 11.06 (s, 1H), 7.91 (d, J=8.6 Hz, 2H), 7.88-7.81 (m, 2H), 7.79 (d, J=8.8 Hz, 2H), 7.64 (d, J=8.2 Hz, 1H), 7.50 (s, 1H), 7.47-7.38 (m, 1H), 6.74 (d, J=2.0 Hz, 1H), 6.62 (dd, J=8.4, 2.1 Hz, 1H), 5.05 (dd, J=12.8, 5.4 Hz, 1H), 3.90 (s, 1H), 3.68 (d, J=10.8 Hz, 5H), 3.16 (s, 3H), 3.04 (d, J=6.7 Hz, 4H), 2.88 (ddd, J=16.5, 13.6, 5.3 Hz, 2H), 2.57 (dd, J=17.5, 12.7 Hz, 4H), 2.00 (d, J=11.5 Hz, 2H), 1.85 (s, 1H), 1.67-1.42 (m, 6H). LCMS: $C_{38}H_{42}N_{10}O_8S$ requires: 799, found: m/z=800 $[M+H]^+$.

Example 30: Synthesis of 5-[(3R)-3-[4-({1-[2-(2,6-dioxopiperidin-3-yl)-1,3-dioxoisoindol-5-yl]azetidin-3-yl]methyl)piperazine-1-carbonylamino}piperidin-1-yl]-3-[(3-methyl-1,2-thiazol-5-yl)amino]pyrazine-2-carboxamide (Compound 18)

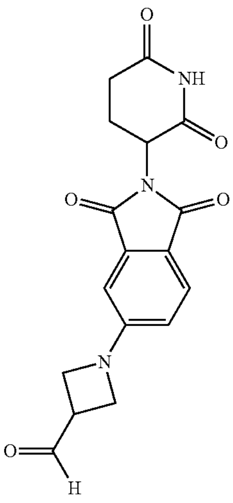

+

-continued

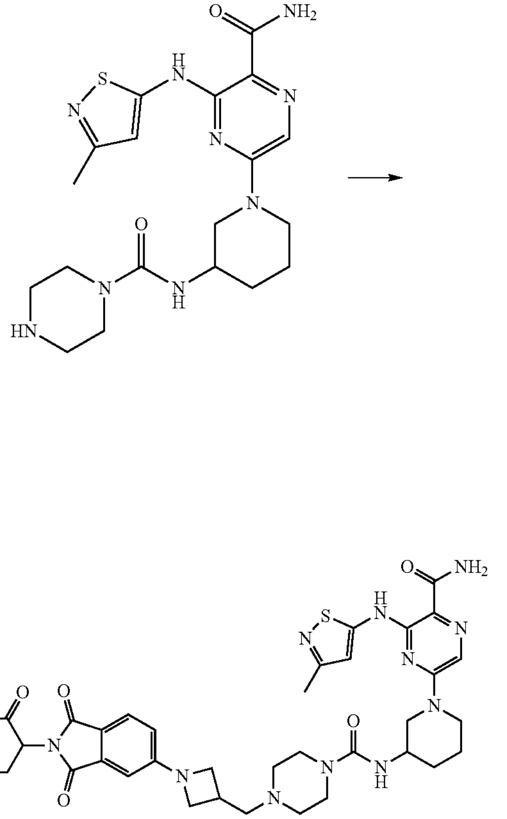

A mixture of 3-[(3-methyl-1,2-thiazol-5-yl)amino]-5-[(3R)-3-(piperazine-1-carbonylamino)piperidin-1-yl]pyrazine-2-carboxamide (10 mg, 20 μmol), 1-[2-(2,6-dioxopiperidin-3-yl)-1,3-dioxoisoindol-5-yl]azetidine-3-carbaldehyde (7.7 mg, 20 μmol), and $Et_3N$ (16 uL, 110 μmol) was dissolved in DCE stirred at rt for 5 min before $NaBH(Oac)_3$ (7.14 mg, 30 μmol) was added in one portion. After 2 h the mixture was diluted with $CH_2Cl_2$ and $NaHCO_3$ (sat. aq.) and the aqueous phase was extracted (3×5 mL $CH_2Cl_2$). The combined organic extracts were dried ($Na_2SO_4$), filtered, and concentrated. The crude residue was purified (RP-HPLC) to afford 5-[(3R)-3-[4-({1-[2-(2,6-dioxopiperidin-3-yl)-1,3-dioxoisoindol-5-yl]azetidin-3-yl}methyl)piperazine-1-carbonylamino]piperidin-1-yl]-3-[(3-methyl-1,2-thiazol-5-yl)amino]pyrazine-2-carboxamide (11 mg) as a yellow solid. $^1H$ NMR (500 MHz, Methanol-$d_4$) δ 7.62 (dd, J=8.3, 1.2 Hz, 1H), 7.48 (s, 1H), 6.78 (dd, J=4.0, 2.1 Hz, 1H), 6.72 (d, J=1.6 Hz, 1H), 6.62 (dd, J=8.3, 2.2 Hz, 1H), 5.06 (dd, J=12.7, 5.5 Hz, 1H), 4.25 (t, J=8.1 Hz, 2H), 4.18 (s, 1H), 4.03 (d, J=12.4, 3.6 Hz, 1H), 3.88-3.78 (m, 3H), 3.68-3.51 (m, 4H), 3.51-3.33 (m, 2H), 3.30-3.15 (m, 2H), 3.10 (ddd, J=13.4, 10.3, 3.1 Hz, 1H), 2.96 (dd, J=12.7, 9.0 Hz, 1H), 2.91-2.78 (m, 1H), 2.77-2.62 (m, 4H), 2.34 (d, J=3.3 Hz, 4H), 2.23-2.14 (m, 1H), 2.09 (dtd, J=13.1, 5.6, 2.8 Hz, 1H), 2.00-1.87 (m, 1H), 1.78 (dt, J=13.8, 10.3 Hz, 1H), 1.72-1.59 (m, 1H). LCMS: $C_{36}H_{42}N_{12}O_6S$ requires: 771, found: m/z=772 $[M+H]^+$.

Example 31: 5-((3R)-3-(4-((2-(2,6-dioxopiperidin-3-yl)-1,3-dioxoisoindolin-5-yl)methyl)piperazine-1-carboxamido)piperidin-1-yl)-3-((4-(methylsulfonyl) phenyl) amino)pyrazine-2-carboxamide (Compound 26)

Step 1: (R)-3-((4-(methylsulfonyl)phenyl)amino)-5-(3-(piperazine-1-carboxamido)piperidin-1-yl)pyrazine-2-carboxamide

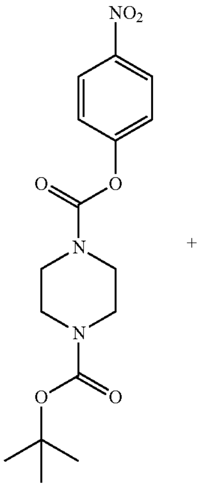

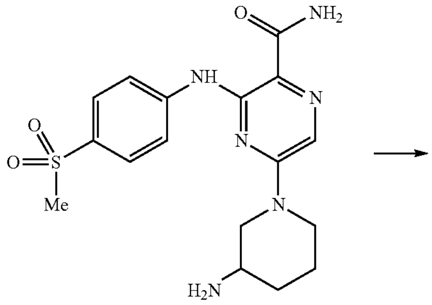

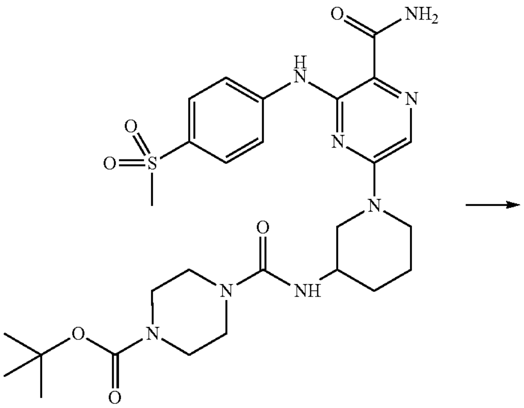

-continued

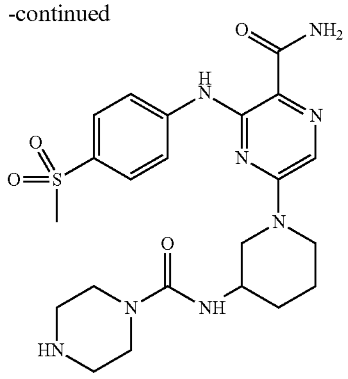

The procedure from Step 2 of Example 27 and the deprotection Step 2 of Example 20 using (R)-5-(3-aminopiperidin-1-yl)-3-((4-(methylsulfonyl)phenyl)amino)pyrazine-2-carboxamide was followed to afford (R)-3-((4-(methylsulfonyl)phenyl)amino)-5-(3-(piperazine-1-carboxamido) piperidin-1-yl)pyrazine-2-carboxamide (50 mg, 2 steps). LCMS: $C_{22}H_{30}N_8O_4S$ requires: 503, found: m/z=504 $[M+H]^+$.

Step 2: 5-((3R)-3-(4-((2-(2,6-dioxopiperidin-3-yl)-1,3-dioxoisoindolin-5-yl)methyl)piperazine-1-carboxamido)piperidin-1-yl)-3-((4-(methylsulfonyl)phenyl) amino)pyrazine-2-carboxamide

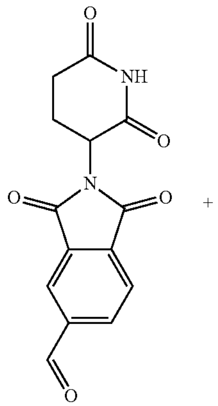

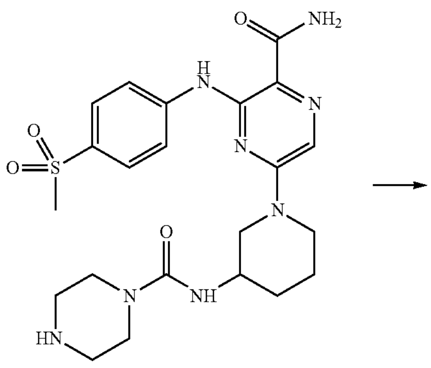

-continued

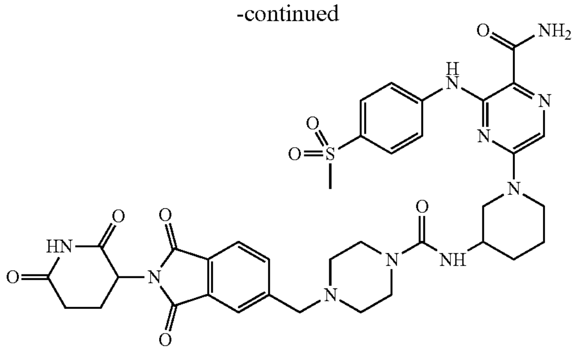

The procedure from Example 30 was followed to afford 5-((3R)-3-(4-((2-(2,6-dioxopiperidin-3-yl)-1,3-dioxoisoindolin-5-yl)methyl)piperazine-1-carboxamido)piperidin-1-yl)-3-((4-(methylsulfonyl)phenyl)amino)pyrazine-2-carboxamide (4 mg). $^1$H NMR (500 MHz, Methanol-$d_4$) δ 8.07-7.98 (m, 2H), 7.95 (d, J=8.8 Hz, 2H), 7.90 (d, J=7.5 Hz, 1H), 7.87-7.81 (m, 2H), 7.46 (s, 1H), 5.20 (dd, J=12.6, 5.4 Hz, 1H), 4.39 (d, J=14.3 Hz, 2H), 4.04 (s, 1H), 3.92 (d, J=12.6 Hz, 1H), 3.59 (d, J=13.9 Hz, 1H), 3.49-3.34 (m, 1H), 3.13 (d, J=1.5 Hz, 3H), 3.07 (d, J=26.5 Hz, 4H), 2.90 (ddd, J=19.1, 14.5, 5.8 Hz, 3H), 2.84-2.68 (m, 3H), 2.16 (t, J=16.0 Hz, 4H), 1.92 (d, J=12.6 Hz, 1H), 1.77-1.58 (m, 2H). LCMS: $C_{36}H_{40}N_{10}O_8S$ requires: 772, found: m/z=773 $[M+H]^+$.

Example 32: Synthesis of N-[(3R)-1-{5-carbamoyl-6-[(4-methanesulfonylphenyl)amino]pyrazin-2-yl}piperidin-3-yl]-2-{[2-(2,6-dioxopiperidin-3-yl)-1,3-dioxoisoindol-5-yl]methyl}-2,8-diazaspiro[4.5]decane-8-carboxamide (Compound 13)

Step 1: 2-tert-butyl 8-(4-nitrophenyl) 2,8-diazaspiro[4.5]decane-2,8-dicarboxylate

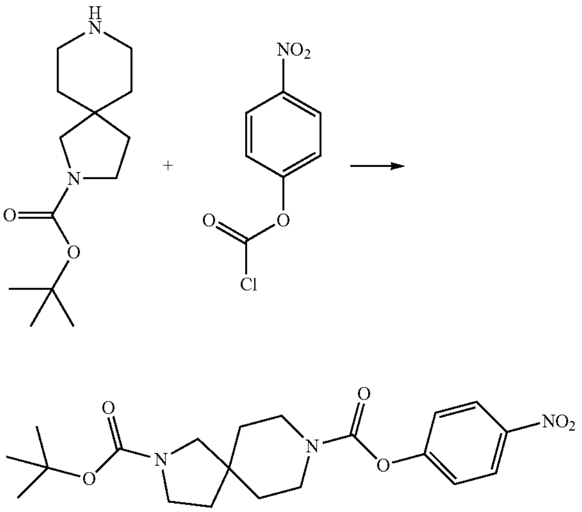

The procedure from Step 1 of Example 27 was followed to afford 2-tert-butyl 8-(4-nitrophenyl) 2,8-diazaspiro[4.5]decane-2,8-dicarboxylate (160 mg). LCMS: $C_{20}H_{27}N_3O_6$ requires: 405, found: m/z=406 $[M+H]^+$.

Step 2: N-[(1R)-3-{5-carbamoyl-6-[(4-methanesulfonylphenyl)amino]pyrazin-2-yl}cyclohexyl]-2,8-diazaspiro[4.5]decane-8-carboxamide

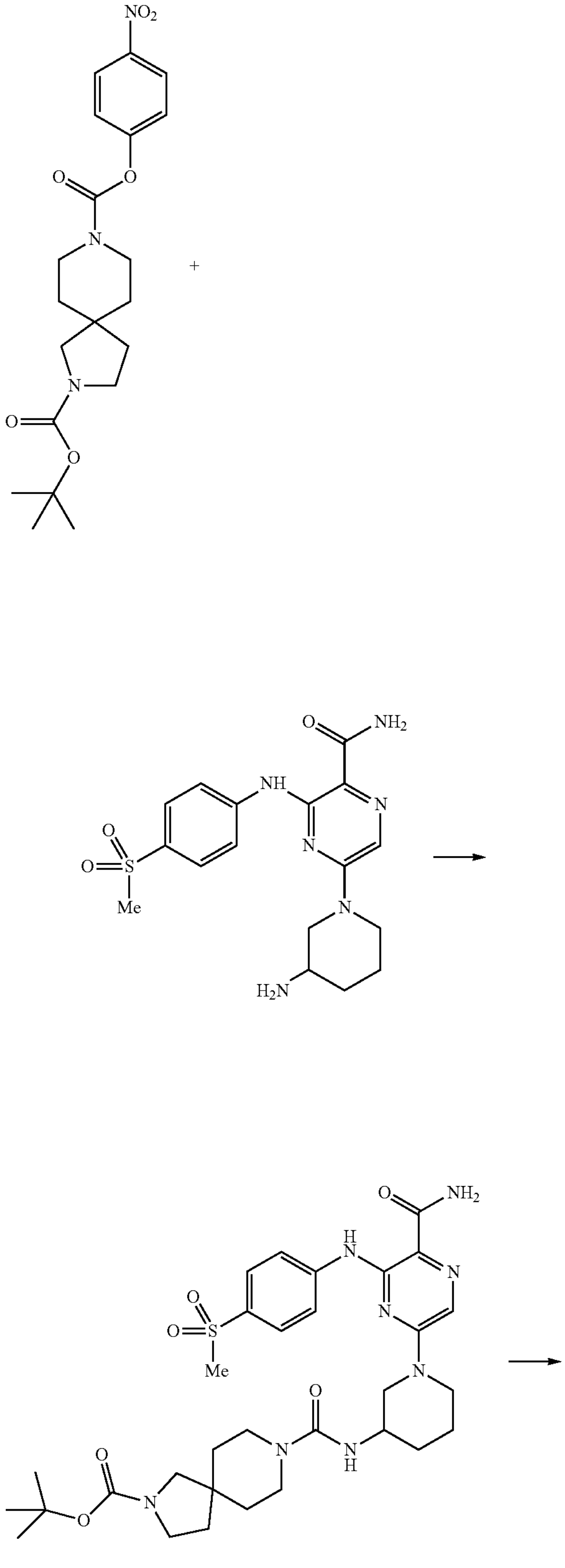

-continued

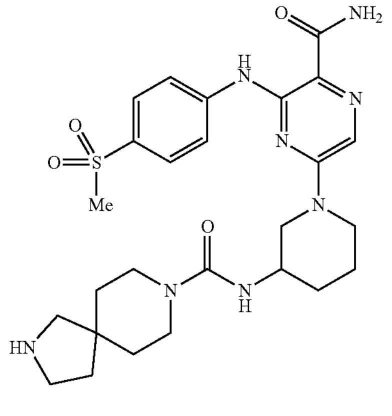

The procedures from Step 2 of Example 27 and the deprotection Step 2 of Example 20 were to afford N-[(1R)-3-{5-carbamoyl-6-[(4-methanesulfonylphenyl)amino]pyrazin-2-yl}cyclohexyl]-2,8-diazaspiro[4.5]decane-8-carboxamide (10 mg). LCMS: C27H37N704S requires 555, found, m/z=556 $[M+H]^+$.

Step 3: N-[(3R)-1-{5-carbamoyl-6-[(4-methanesulfonylphenyl)amino]pyrazin-2-yl}piperidin-3-yl]-2-{[2-(2,6-dioxopiperidin-3-yl)-1,3-dioxoisoindol-5-yl]methyl}-2,8-diazaspiro[4.5]decane-8-carboxamide

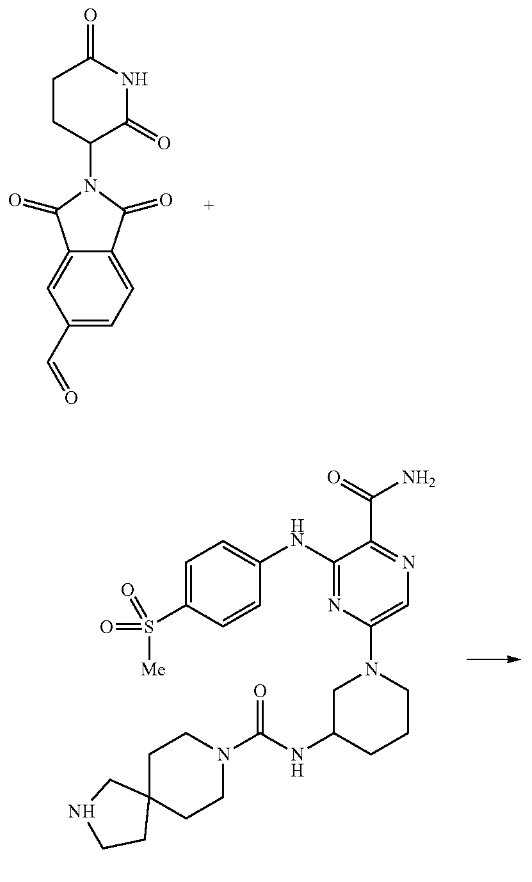

-continued

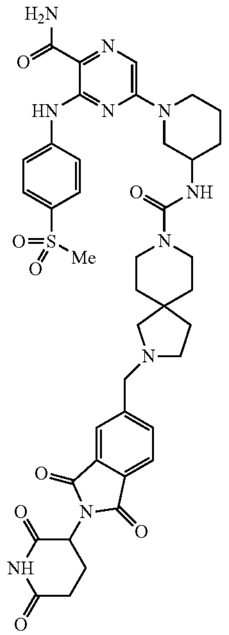

The procedure from Example 30 was followed to afford N-[(3R)-1-{5-carbamoyl-6-[(4-methanesulfonylphenyl)amino]pyrazin-2-yl}piperidin-3-yl]-2-{[2-(2,6-dioxopiperidin-3-yl)-1,3-dioxoisoindol-5-yl]methyl}-2,8-diazaspiro[4.5]decane-8-carboxamide (5 mg). H NMR (500 MHz, Methanol-d4) δ 8.15-8.09 (m, 1H), 8.09-8.01 (m, 2H), 7.88 (d, J=24.6 Hz, 2H), 7.84-7.73 (m, 2H), 7.46 (s, 1H), 5.21 (dd, J=13.4, 5.2 Hz, 1H), 4.99-4.88 (m, 2H), 4.62 (d, J=47.1 Hz, 3H), 4.03-3.82 (m, 2H), 3.67 (s, 1H), 3.47 (d, J=12.4 Hz, 1H), 3.41-3.34 (m, 2H), 3.17 (d, J=21.1 Hz, 3H), 3.09 (s, 3H), 2.97-2.85 (m, 3H), 2.85-2.72 (m, 3H), 2.28-2.16 (m, 1H), 2.12 (d, J=12.4 Hz, 2H), 2.02-1.80 (m, 2H), 1.80-1.63 (m, 2H), 1.63-1.34 (m, 3H). LCMS: $C_{40}H_{46}N_{10}O_8S$ requires: 826, found: m/z=827 $[M+H]^+$.

Example 33: Synthesis of N-[(3R)-1-{5-carbamoyl-6-[(4-methanesulfonylphenyl)amino]pyrazin-2-yl}piperidin-3-yl]-6-{[2-(2,6-dioxopiperidin-3-yl)-1,3-dioxoisoindol-5-yl]methyl}-2,6-diazaspiro[3.3]heptane-2-carboxamide (Compound 25)

Step 1: 2-tert-butyl 6-(4-nitrophenyl) 2,6-diazaspiro[3.3]heptane-2,6-dicarboxylate

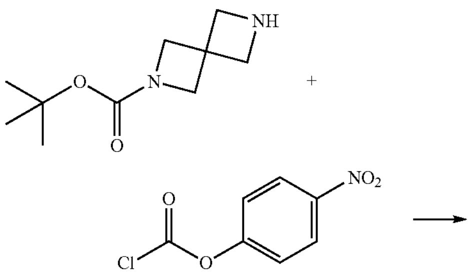

-continued

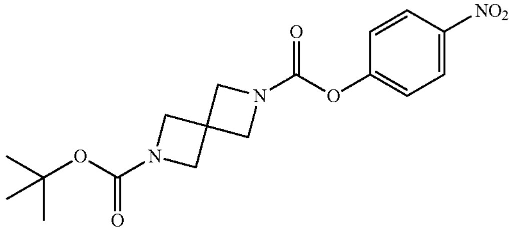

The procedure from Step 1 of Example 27 was followed to afford 2-tert-butyl 6-(4-nitrophenyl) 2,6-diazaspiro[3.3]heptane-2,6-dicarboxylate (168 mg). LCMS: $C_{17}H_{21}N_3O_6$ requires: 363, found: m/z=364 $[M+H]^+$.

Step 2: N-[(3R)-1-{5-carbamoyl-6-[(4-methanesulfonylphenyl)amino]pyrazin-2-yl}piperidin-3-yl]-2,6-diazaspiro[3.3]heptane-2-carboxamide

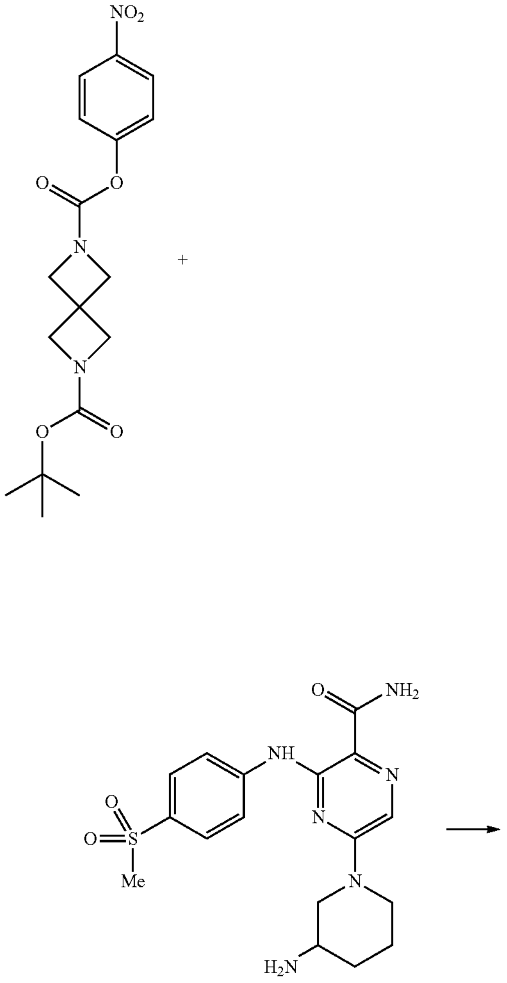

-continued

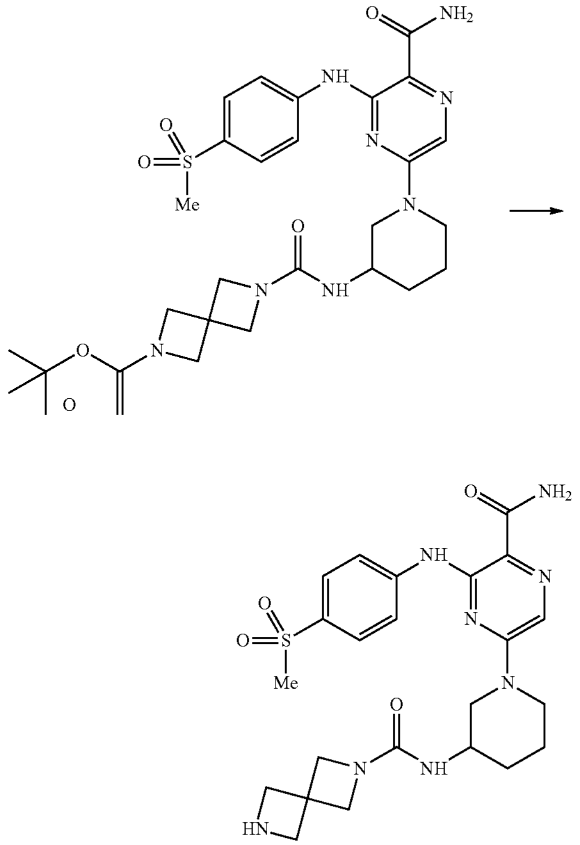

The procedures from Step 2 of Example 27 and the deprotection Step 2 of Example 20 were followed to afford N-[(3R)-1-{5-carbamoyl-6-[(4-methanesulfonylphenyl)amino]pyrazin-2-yl}piperidin-3-yl]-2,6-diazaspiro[3.3]heptane-2-carboxamide (12 mg). LCMS: $C_{23}H_{30}N_8O_4S$ requires 514, found, m/z=515 $[M+H]^+$.

Step 3: N-[(3R)-1-{5-carbamoyl-6-[(4-methanesulfonylphenyl)amino]pyrazin-2-yl}piperidin-3-yl]-6-{[2-(2,6-dioxopiperidin-3-yl)-1,3-dioxoisoindol-5-yl]methyl}-2,6-diazaspiro[3.3]heptane-2-carboxamide

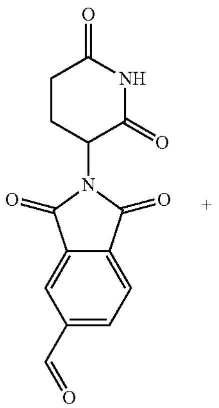

-continued

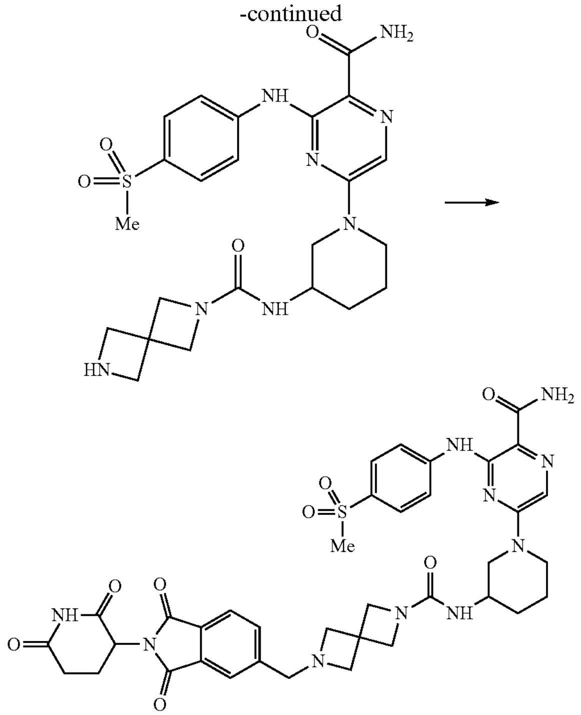

The procedure from Example 30 was followed to afford N-[(3R)-1-{5-carbamoyl-6-[(4-methanesulfonylphenyl)amino]pyrazin-2-yl}piperidin-3-yl]-6-{[2-(2,6-dioxopiperidin-3-yl)-1,3-dioxoisoindol-5-yl]methyl}-2,6-diazaspiro[3.3]heptane-2-carboxamide (3.5 mg). $^1$H NMR (500 MHz, Methanol-$d_4$) δ 8.02 (d, J=7.7 Hz, 1H), 7.98 (dd, J=8.9, 2.1 Hz, 2H), 7.94 (s, 1H), 7.86 (dd, J=7.7, 1.6 Hz, 1H), 7.83 (dd, J=9.0, 2.5 Hz, 2H), 7.45 (s, 1H), 5.20 (dd, J=12.7, 5.5 Hz, 1H), 4.48 (s, 2H), 4.19 (s, 6H), 4.09 (d, J=9.2 Hz, 4H), 3.99-3.81 (m, 3H), 3.13 (d, J=3.2 Hz, 3H), 2.98-2.82 (m, 2H), 2.82-2.69 (m, 2H), 2.28-2.05 (m, 0H), 1.87 (d, J=11.0 Hz, 1H), 1.75-1.53 (m, 3H). LCMS: $C_{37}H_{40}N_{10}O_8S$ requires: 784, found: m/z=785 $[M+H]^+$.

Example 34: Synthesis of N-[(3R)-1-{5-carbamoyl-6-[(4-methanesulfonylphenyl)amino]pyrazin-2-yl}piperidin-3-yl]-2-{[2-(2,6-dioxopiperidin-3-yl)-1,3-dioxoisoindol-5-yl]methyl}-2,7-diazaspiro[3.5]nonane-7-carboxamide (Compound 29)

Step 1: 2-tert-butyl 7-(4-nitrophenyl) 2,7-diazaspiro[3.5]nonane-2,7-dicarboxylate

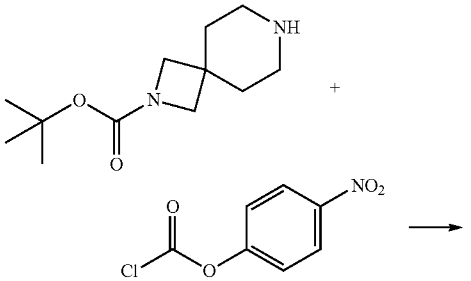

-continued

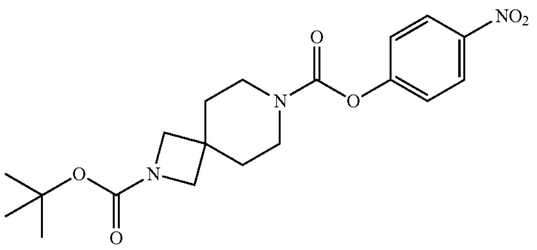

The procedure from Step 1 of Example 27 was followed to afford 2-tert-butyl 7-(4-nitrophenyl) 2,7-diazaspiro[3.5]nonane-2,7-dicarboxylate (192 mg). LCMS: $C_{19}H_{25}N_3O_6$ requires: 391, found: m/z=392 $[M+H]^+$.

Step 2: N-[(3R)-1-{5-carbamoyl-6-[(4-methanesulfonylphenyl)amino]pyrazin-2-yl}piperidin-3-yl]-2,7-diazaspiro[3.5]nonane-7-carboxamide

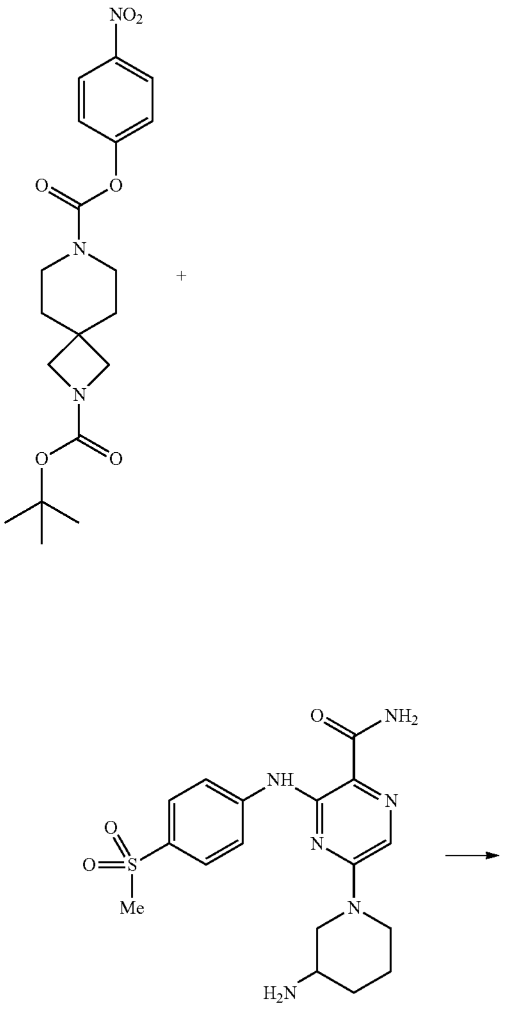

-continued

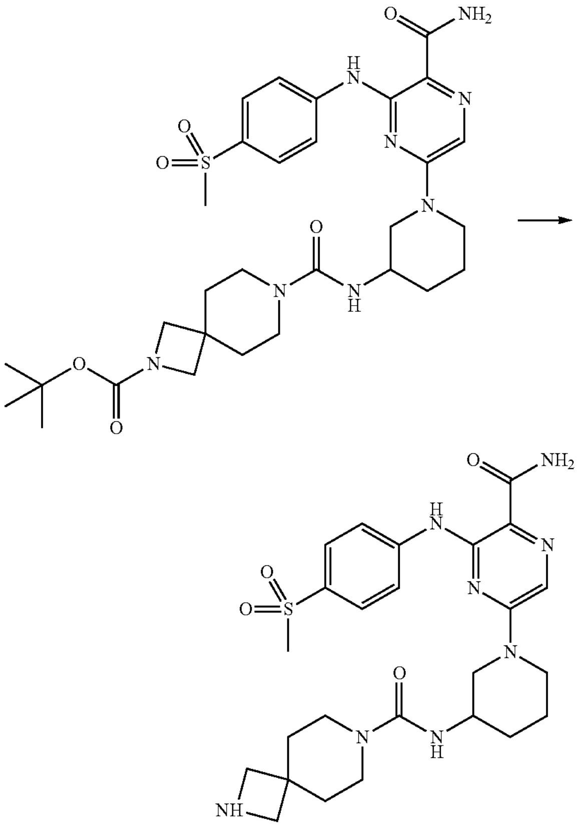

The procedures from Step 2 of Example 27 and the deprotection Step 2 of Example 20 were followed to afford N-[(3R)-1-{5-carbamoyl-6-[(4-methanesulfonylphenyl)amino]pyrazin-2-yl}piperidin-3-yl]-2,7-diazaspiro[3.5]nonane-7-carboxamide (25 mg). LCMS: $C_{25}H_{34}N_8O_4S$ requires 542, found, m/z=543 $[M+H]^+$.

Step 3: N-[(3R)-1-{5-carbamoyl-6-[(4-methanesulfonylphenyl)amino]pyrazin-2-yl}piperidin-3-yl]-2-{[2-(2,6-dioxopiperidin-3-yl)-1,3-dioxoisoindol-5-yl]methyl}-2,7-diazaspiro[3.5]nonane-7-carboxamide

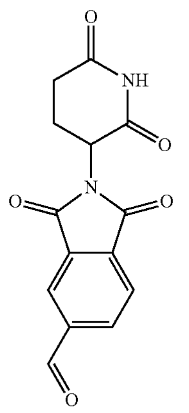

+

-continued

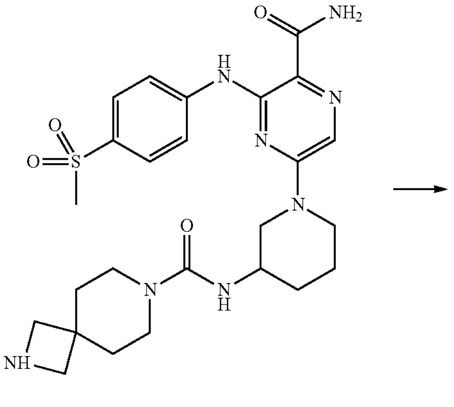

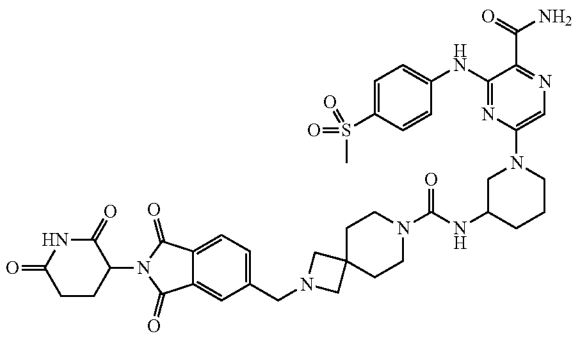

The procedure from Example 30 was followed to afford N-[(3R)-1-{5-carbamoyl-6-[(4-methanesulfonylphenyl)amino]pyrazin-2-yl}piperidin-3-yl]-2-{[2-(2,6-dioxopiperidin-3-yl)-1,3-dioxoisoindol-5-yl]methyl}-2,7-diazaspiro[3.5]nonane-7-carboxamide (6 mg). $^1H$ NMR (500 MHz, DMSO-$d_6$) δ 11.96 (s, 1H), 11.15 (s, 1H), 10.28 (s, 1H), 8.09 (s, 1H), 8.04 (d, J=7.6 Hz, 1H), 7.96 (d, J=7.8 Hz, 1H), 7.90 (d, J=8.6 Hz, 2H), 7.84 (d, J=2.7 Hz, 1H), 7.79 (d, J=8.8 Hz, 2H), 7.58-7.34 (m, 2H), 6.54 (s, 1H), 5.18 (dd, J=12.9, 5.4 Hz, 1H), 4.59 (d, J=5.9 Hz, 2H), 3.95 (s, 2H), 3.90-3.62 (m, 4H), 3.15 (s, 3H), 3.11-2.74 (m, 8H), 2.70-2.51 (m, 2H), 2.18-2.04 (m, 1H), 2.04-1.94 (m, 1H), 1.91-1.76 (m, 1H), 1.74-1.45 (m, 5H). LCMS: $C_{39}H_{44}N_{10}O_8S$ requires: 813, found: m/z=814 $[M+H]^+$.

Example 35: Synthesis of afford 5-[(3R)-3-[4-({1-[2-(2,6-dioxopiperidin-3-yl)-1,3-dioxoisoindol-5-yl]piperidin-4-yl]methyl)piperazine-1-carbonylamino}piperidin-1-yl]-3-[(3-methyl-1,2-thiazol-5-yl)amino]pyrazine-2-carboxamide (Compound 23)

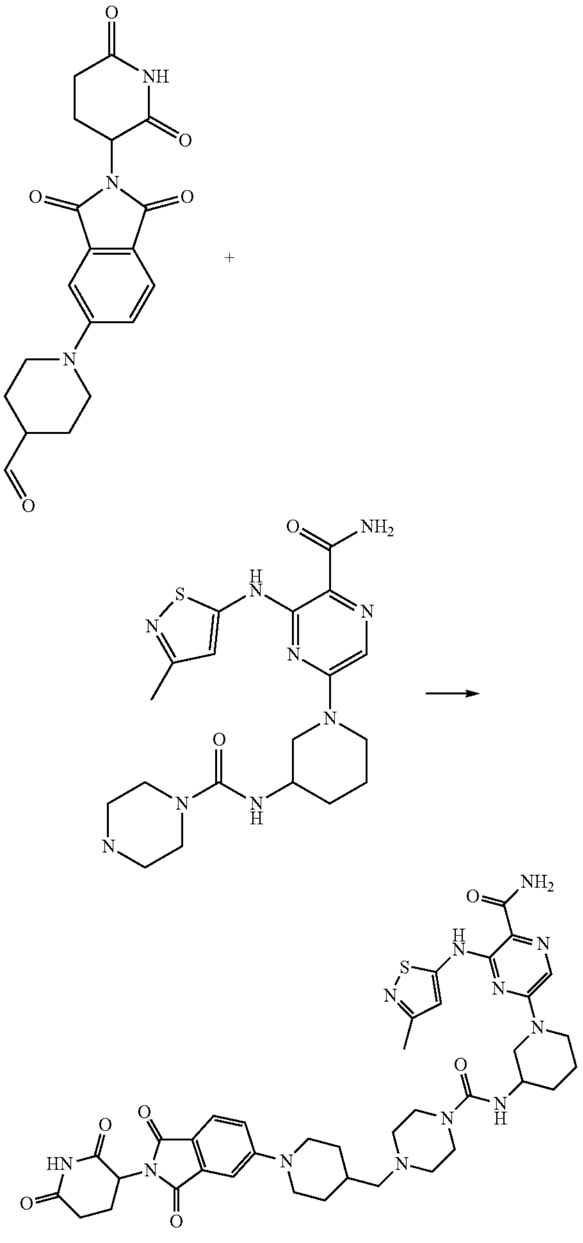

The procedure from Example 30 was followed to afford 5-[(3R)-3-[4-({1-[2-(2,6-dioxopiperidin-3-yl)-1,3-dioxoisoindol-5-yl]piperidin-4-yl}methyl)piperazine-1-carbonylamino]piperidin-1-yl]-3-[(3-methyl-1,2-thiazol-5-yl)amino]pyrazine-2-carboxamide (5 mg). $^1H$ NMR (500 MHz, DMSO-$d_6$) δ 12.28 (s, 1H), 11.08 (s, 1H), 9.31 (s, 1H), 8.13-7.95 (m, 1H), 7.84 (s, 1H), 7.68 (d, J=8.5 Hz, 1H), 7.50 (d, J=3.7 Hz, 2H), 7.36 (d, J=2.2 Hz, 1H), 7.27 (dd, J=8.7, 2.3 Hz, 1H), 6.87 (s, 1H), 5.07 (dd, J=12.7, 5.5 Hz, 1H), 4.10 (d, J=13.5 Hz, 4H), 3.86 (d, J=12.3 Hz, 1H), 3.64 (dd, J=29.6, 14.1 Hz, 2H), 3.53-3.39 (m, 4H), 3.22 (t, J=13.0 Hz, 1H), 3.17-3.02 (m, 1H), 2.97 (d, J=12.7 Hz, 3H), 2.94-2.76 (m, 2H), 2.66-2.53 (m, 2H), 2.29 (s, 3H), 2.16-2.05 (m, 2H), 2.05-1.96 (m, 1H), 1.90-1.74 (m, 4H), 1.72-1.48 (m, 2H), 1.37-1.21 (m, 2H). LCMS: $C_{38}H_{46}N_{12}O_6S$ requires: 799, found: m/z=800 $[M+H]^+$.

Example 36: Synthesis of 5-[(3R)-3-[1-({1-[2-(2,6-dioxopiperidin-3-yl)-1,3-dioxoisoindol-5-yl]piperidin-4-yl}methyl)piperidine-4-amido]piperidin-1-yl]-3-[(3-methyl-1,2-thiazol-5-yl)amino]pyrazine-2-carboxamide (Compound 22)

Step 1: tert-butyl 4-{[(3R)-1-{5-carbamoyl-6-[(3-methyl-1,2-thiazol-5-yl)amino]pyrazin-2-yl}piperidin-3-yl]carbamoyl}piperidine-1-carboxylate

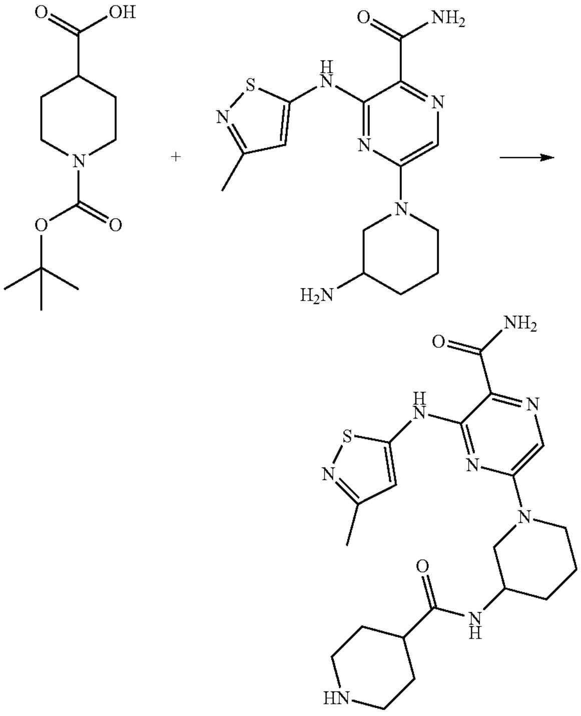

A mixture of 1-(tert-butoxycarbonyl)piperidine-4-carboxylic acid (22.35 mg, 100 μmol) and (1,2,3-benzotriazol-1-yloxy)tris(dimethylamino)phosphonium; hexafluorolambda5-phosphamide (50 mg, 110 μmol) before and i-$Pr_2NEt$ (65 μL, 370 μmol) was added at rt. After 5 min 5-[(3R)-3-aminopiperidin-1-yl]-3-[(3-methyl-1,2-thiazol-5-yl)amino]pyrazine-2-carboxamide (25.00 mg, 70 μmol) was added and the mixture was stirred for 20 min. The reaction mixture was diluted with $H_2O$ and extracted (3×5 mL $CH_2Cl_2$). The combined organic extracts were dried ($Na_2SO_4$), filtered, and concentrated. The crude residue was purified ($SiO_2$, 0→10% MeOH/$CH_2Cl_2$) to afford tert-butyl 4-{[(3R)-1-{5-carbamoyl-6-[(3-methyl-1,2-thiazol-5-yl)amino]pyrazin-2-yl}piperidin-3-yl]carbamoyl}piperidine-1-carboxylate (25 mg). The product was dissolved in a mixture of $CH_2Cl_2$ (1 mL) and TFA (1 mL) and stirred for 30 min before being concentrated to dryness. LCMS: $C_{25}H_{36}N_8O_4S$ requires: 544, found: m/z=546.

Step 2: 5-[(3R)-3-[1-({1-[2-(2,6-dioxopiperidin-3-yl)-1,3-dioxoisoindol-5-yl]piperidin-4-yl}methyl)piperidine-4-amido]piperidin-1-yl]-3-[(3-methyl-1,2-thiazol-5-yl)amino]pyrazine-2-carboxamide

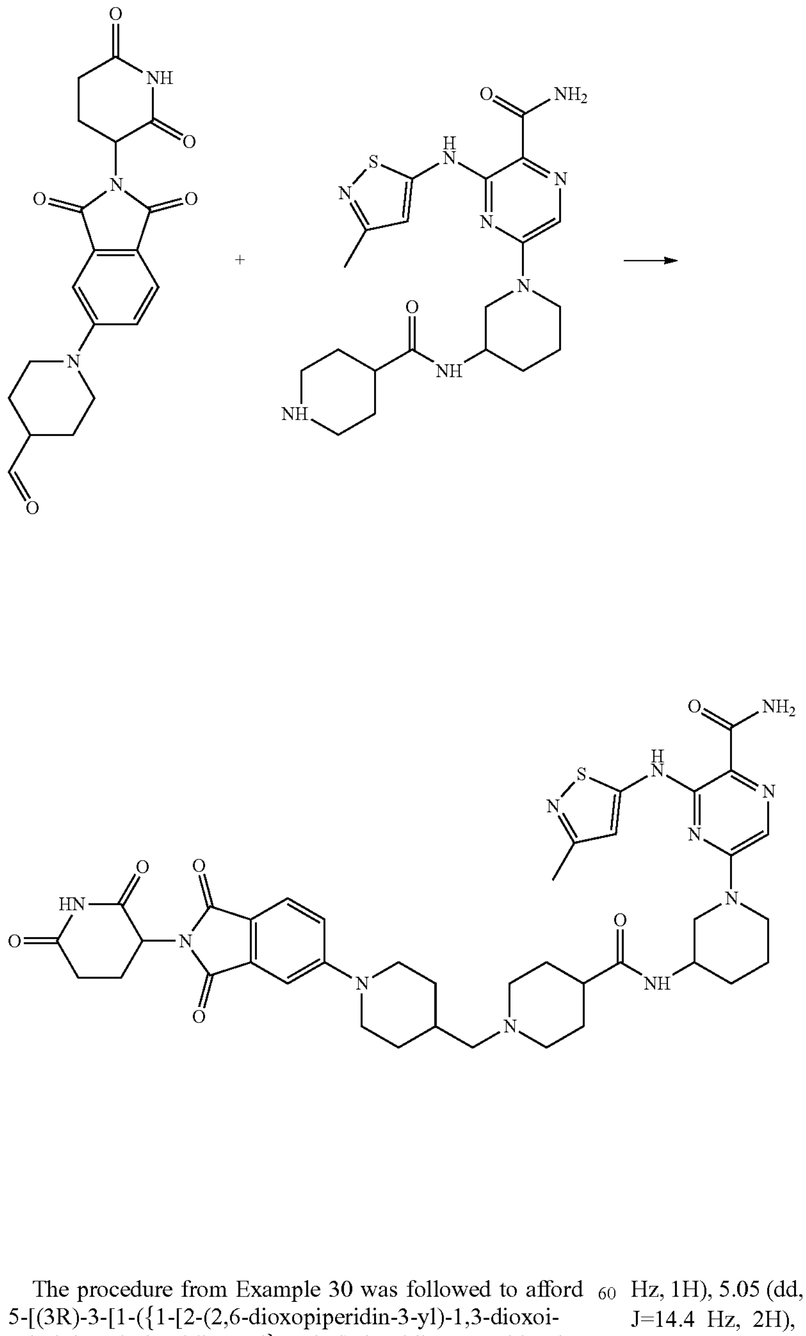

The procedure from Example 30 was followed to afford 5-[(3R)-3-[1-({1-[2-(2,6-dioxopiperidin-3-yl)-1,3-dioxoisoindol-5-yl]piperidin-4-yl}methyl)piperidine-4-amido]piperidin-1-yl]-3-[(3-methyl-1,2-thiazol-5-yl)amino]pyrazine-2-carboxamide (18 mg). $^1$H NMR (500 MHz, DMSO-$d_6$) δ 12.27 (d, J=32.4 Hz, 1H), 11.06 (s, 1H), 8.01 (s, 1H), 7.84 (d, J=18.1 Hz, 1H), 7.63 (d, J=8.4 Hz, 1H), 7.58-7.43 (m, 2H), 7.28 (s, 1H), 7.20 (d, J=9.1 Hz, 1H), 6.85 (d, J=22.5 Hz, 1H), 5.05 (dd, J=12.9, 5.4 Hz, 1H), 4.17 (s, 1H), 4.00 (d, J=14.4 Hz, 2H), 3.74 (d, J=14.2 Hz, 1H), 3.57 (s, 1H), 3.48-3.35 (m, 3H), 3.09-2.77 (m, 3H), 2.72-2.54 (m, 2H), 2.28 (s, 3H), 2.22-2.05 (m, 2H), 2.05-1.90 (m, 3H), 1.80 (s, 3H), 1.70 (d, J=11.6 Hz, 3H), 1.64-1.28 (m, 5H), 1.23 (s, 1H), 1.20-0.96 (m, 3H). LCMS: $C_{38}H_{46}N_{12}O_6S$ requires: 798, found: m/z=799 $[M+H]^+$.

Example 37: Synthesis of 5-[(3R)-3-[1-({1-[2-(2,6-dioxopiperidin-3-yl)-1,3-dioxoisoindol-5-yl]azetidin-3-yl}methyl)piperidine-4-amido]piperidin-1-yl]-3-[(3-methyl-1,2-thiazol-5-yl)amino]pyrazine-2-carboxamide (Compound 17)

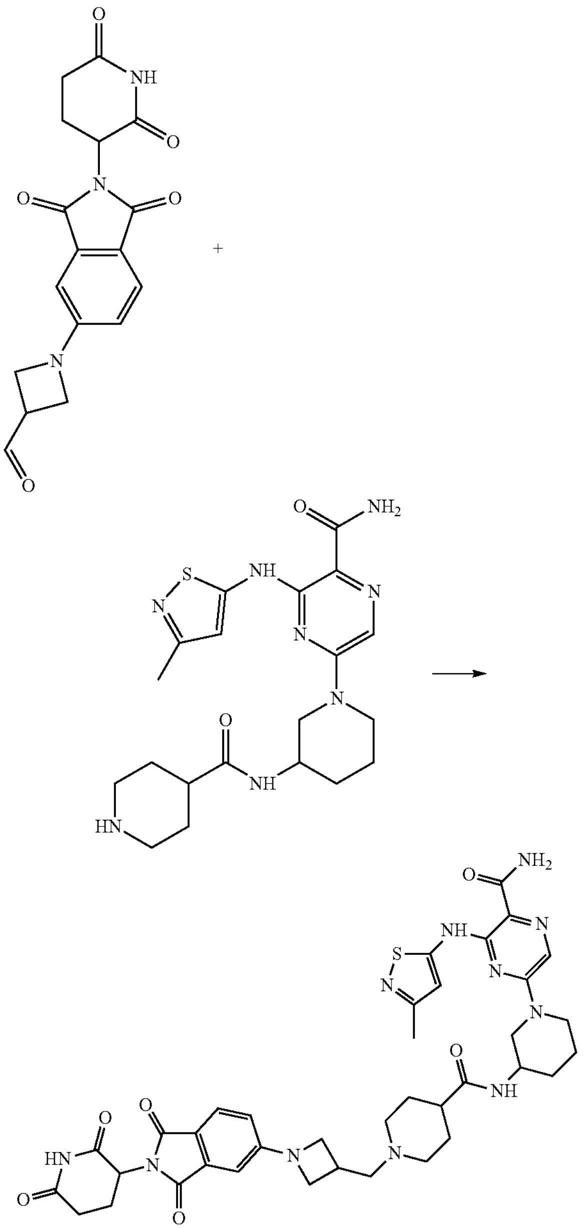

The procedure from Example 30 was followed to afford 5-[(3R)-3-[1-({1-[2-(2,6-dioxopiperidin-3-yl)-1,3-dioxoisoindol-5-yl]azetidin-3-yl}methyl)piperidine-4-amido]piperidin-1-yl]-3-[(3-methyl-1,2-thiazol-5-yl)amino]pyrazine-2-carboxamide (4 mg). $^1$H NMR (500 MHz, Methanol-$d_4$) δ 7.66 (dd, J=8.2, 6.1 Hz, 1H), 7.50 (d, J=21.9 Hz, 1H), 6.90-6.74 (m, 2H), 6.71-6.61 (m, 1H), 5.06 (dd, J=12.6, 5.4 Hz, 1H), 4.61-4.35 (m, 1H), 4.37-4.19 (m, 3H), 4.20-3.95 (m, 1H), 3.93-3.83 (m, 2H), 3.78 (s, 1H), 3.71-3.57 (m, 2H), 3.54 (t, J=8.4 Hz, 1H), 3.50-3.37 (m, 1H), 3.14 (d, J=10.7 Hz, 2H), 2.96 (t, J=11.0 Hz, 1H), 2.86 (ddd, J=18.4, 13.8, 5.2 Hz, 1H), 2.80-2.61 (m, 3H), 2.39 (d, J=3.3 Hz, 3H), 2.28 (d, J=20.4 Hz, 1H), 2.19-1.82 (m, 7H), 1.72 (dt, J=32.9, 11.9 Hz, 2H), 1.27 (q, J=6.5, 6.0 Hz, 1H). LCMS: $C_{37}H_{43}N_1O_6S$ requires: 770, found: m/z=771 $[M+H]^+$.

Example 38: Synthesis of 5-[(3R)-3-[1-({1-[2-(2,6-dioxopiperidin-3-yl)-1,3-dioxoisoindol-5-yl]piperidin-4-yl}methyl)pyrrolidine-3-amido]piperidin-1-yl]-3-[(4-methanesulfonylphenyl)amino]pyrazine-2-carboxamide (Compound 14 and Compound 46)

Step 1: 3-((4-(methylsulfonyl)phenyl)amino)-5-((3R)-3-(pyrrolidine-3-carboxamido)piperidin-1-yl)pyrazine-2-carboxamide

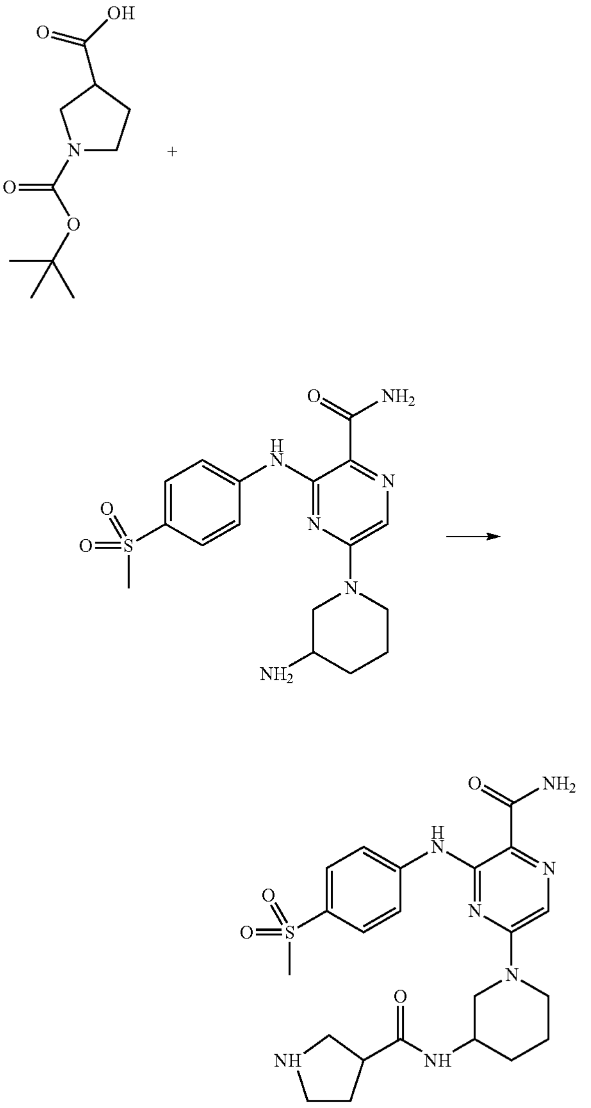

The procedure from Step 1 of Example 36 was followed to afford 3-((4-(methylsulfonyl)phenyl)amino)-5-((3R)-3-(pyrrolidine-3-carboxamido)piperidin-1-yl)pyrazine-2-carboxamide (45 mg). LCMS: $C_{22}H_{29}N_7O_4S$ requires: 487, found: m/z=488 $[M+H]^+$.

Step 2: 5-[(3R)-3-[1-({1-[2-(2,6-dioxopiperidin-3-yl)-1,3-dioxoisoindol-5-yl]piperidin-4-yl}methyl) pyrrolidine-3-amido]piperidin-1-yl]-3-[(4-methanesulfonylphenyl)amino]pyrazine-2-carboxamide

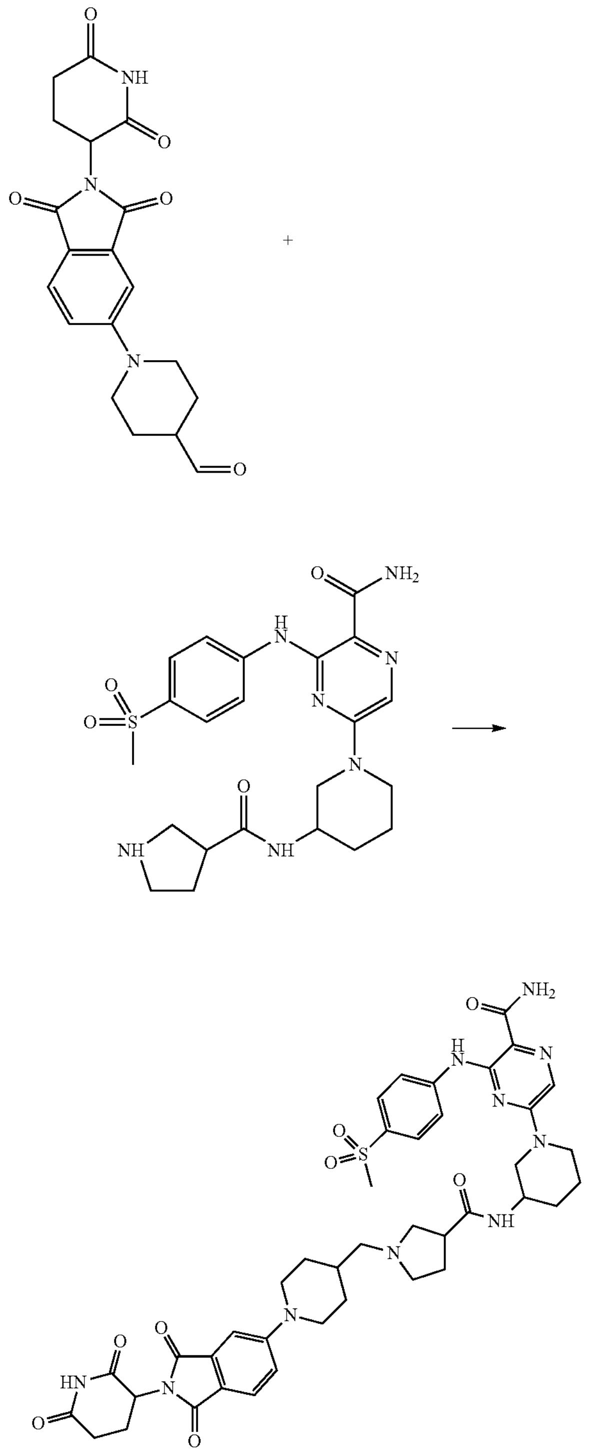

The procedure from Example 30 was followed to afford 5-[(3R)-3-[1-({1-[2-(2,6-dioxopiperidin-3-yl)-1,3-dioxoisoindol-5-yl]piperidin-4-yl}methyl)pyrrolidine-3-amido]piperidin-1-yl]-3-[(4-methanesulfonylphenyl)amino]pyrazine-2-carboxamide (80 mg). $^1H$ NMR (500 MHz, DMSO-$d_6$) δ 12.12-11.85 (m, 1H), 11.07 (s, 1H), 8.02-7.75 (m, 5H), 7.66 (d, J=8.4 Hz, 1H), 7.58-7.14 (m, 4H), 5.06 (dd, J=12.8, 5.4 Hz, 1H), 4.17-3.93 (m, 3H), 3.89-3.69 (m, 3H), 3.16 (d, J=6.4 Hz, 3H), 3.09 (d, J=7.2 Hz, 3H), 3.04-2.95 (m, 2H), 2.94-2.78 (m, 2H), 2.69-2.53 (m, 4H), 2.03 (t, J=19.0 Hz, 4H), 1.84 (s, 3H), 1.58 (s, 4H), 1.17 (t, J=7.3 Hz, 4H). LCMS: $C_{41}H_{48}N_{10}O_8S$ requires: 841, found: m/z=842 $[M+H]^+$.

Example 39: Synthesis of 5-[(3R)-3-[1-({1-[2-(2,6-dioxopiperidin-3-yl)-1,3-dioxoisoindol-5-yl]piperidin-4-yl}methyl)pyrrolidine-3-amido]piperidin-1-yl]-3-[(3-methyl-1,2-thiazol-5-yl)amino]pyrazine-2-carboxamide (Compound 15)

Step 1: 3-((3-methylisothiazol-5-yl)amino)-5-((3R)-3-(pyrrolidine-3-carboxamido)piperidin-1-yl)pyrazine-2-carboxamide

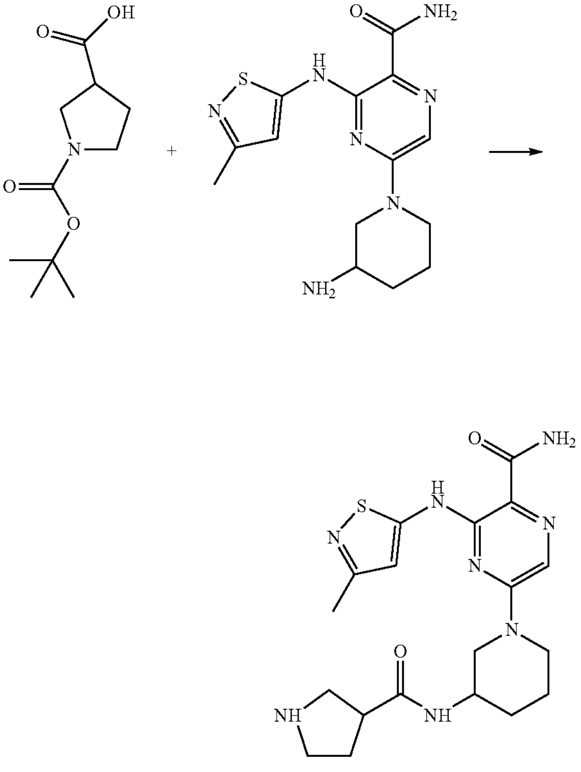

The procedure from Step 1 of Example 36 was followed to afford 3-((3-methylisothiazol-5-yl)amino)-5-((3R)-3-(pyrrolidine-3-carboxamido)piperidin-1-yl)pyrazine-2-carboxamide (10 mg). LCMS: C19H26N802S requires: 430, found: m/z=431 $[M+H]^+$.

Step 2: 5-[(3R)-3-[1-({1-[2-(2,6-dioxopiperidin-3-yl)-1,3-dioxoisoindol-5-yl]piperidin-4-yl}methyl)pyrrolidine-3-amido]piperidin-1-yl]-3-[(3-methyl-1,2-thiazol-5-yl)amino]pyrazine-2-carboxamide

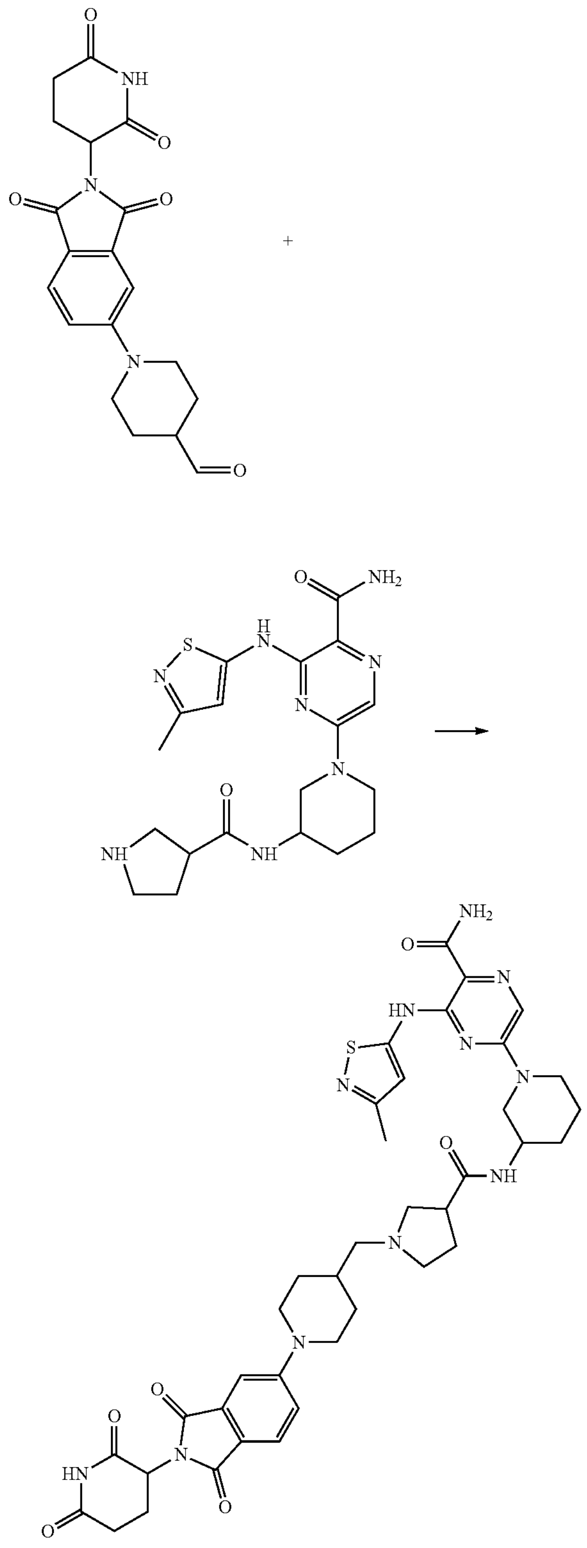

The procedure from Example 30 was followed to afford 5-[(3R)-3-[1-({1-[2-(2,6-dioxopiperidin-3-yl)-1,3-dioxoisoindol-5-yl]piperidin-4-yl}methyl)pyrrolidine-3-amido]piperidin-1-yl]-3-[(3-methyl-1,2-thiazol-5-yl)amino]pyrazine-2-carboxamide (4 mg). $^1$H NMR (500 MHz, DMSO-$d_6$) δ 12.38-12.16 (m, 1H), 11.07 (s, 1H), 9.64-9.16 (m, 1H), 8.08 (d, J=37.5 Hz, 1H), 7.84 (d, J=10.0 Hz, 1H), 7.67 (dd, J=8.5, 3.2 Hz, 1H), 7.60-7.42 (m, 2H), 7.35 (d, J=5.3 Hz, 1H), 7.26 (s, 1H), 7.00-6.77 (m, 1H), 5.07 (dd, J=12.7, 5.5 Hz, 1H), 4.31 (s, 1H), 4.23-3.92 (m, 6H), 3.83 (dd, J=30.4, 12.8 Hz, 1H), 3.73-3.40 (m, 3H), 3.34-3.19 (m, 1H), 3.13 (d, J=22.8 Hz, 2H), 3.04-2.81 (m, 3H), 2.68-2.55 (m, 2H), 2.28 (dd, J=6.4, 1.7 Hz, 3H), 2.23-1.97 (m, 2H), 1.96-1.72 (m, 3H), 1.62 (d, J=7.8 Hz, 2H), 1.35-1.09 (m, 4H). LCMS: $C_{38}H_{45}N_1O_6S$ requires: 784, found: m/z=785 $[M+H]^+$.

Example 40: Synthesis of 5-[(3R)-3-[1-({1-[2-(2,6-dioxopiperidin-3-yl)-1,3-dioxoisoindol-5-yl]azetidin-3-yl}methyl)pyrrolidine-3-amido]piperidin-1-yl]-3-[(3-methyl-1,2-thiazol-5-yl)amino]pyrazine-2-carboxamide (Compound 16)

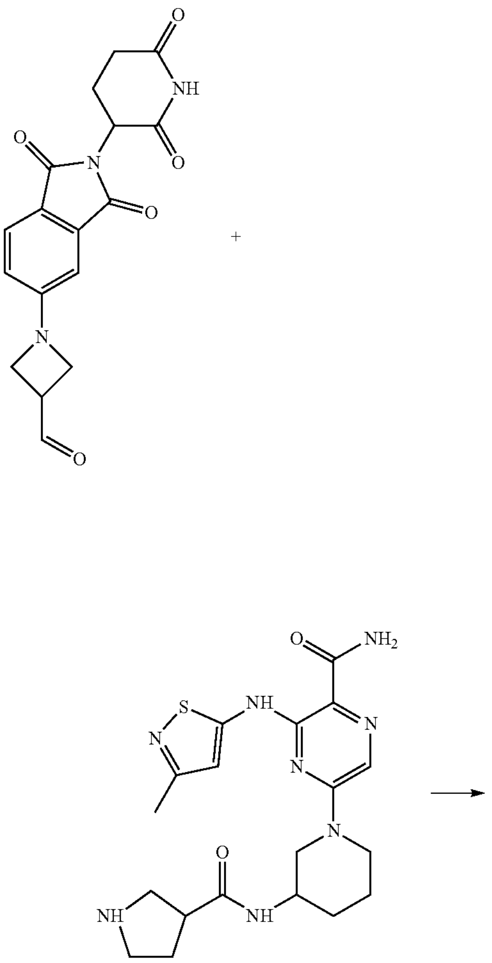

-continued

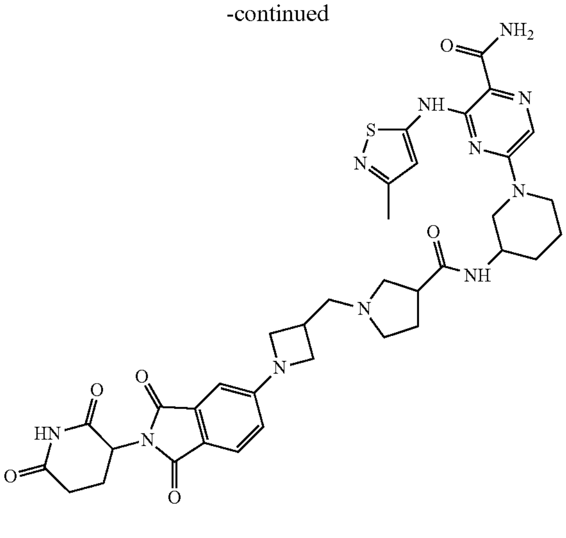

The procedure from Example 30 was followed to afford 5-[(3R)-3-[1-({1-[2-(2,6-dioxopiperidin-3-yl)-1,3-dioxoisoindol-5-yl]azetidin-3-yl}methyl)pyrrolidine-3-amido]piperidin-1-yl]-3-[(3-methyl-1,2-thiazol-5-yl)amino]pyrazine-2-carboxamide (3.1 mg). $^{1}$H NMR (500 MHz, Methanol-$d_4$) δ 7.65 (q, J=6.9 Hz, 2H), 7.53 (d, J=10.5 Hz, 1H), 7.47 (d, J=1.7 Hz, 1H), 6.86-6.71 (m, 4H), 6.65 (d, J=8.6 Hz, 2H), 5.06 (dd, J=12.0, 5.2 Hz, 2H), 4.24 (dd, J=18.3, 10.8 Hz, 5H), 4.00-3.48 (m, 12H), 2.93-2.79 (m, 2H), 2.79-2.61 (m, 3H), 2.40-2.33 (m, 3H), 2.25 (s, 0H), 2.18-2.05 (m, 2H), 2.05-1.87 (m, 1H), 1.85-1.54 (m, 2H). LCMS: $C_{36}H_{41}N_{11}O_6S$ requires: 755, found: m/z=756 $[M+H]^+$.

Example 41: Synthesis of 5-[(3R)-3-[1-({1-[2-(2,6-dioxopiperidin-3-yl)-1,3-dioxoisoindol-5-yl]azetidin-3-yl}methyl)piperidine-4-amido]piperidin-1-yl]-3-[(1-methylpyrazol-4-yl)amino]pyrazine-2-carboxamide (Compound 19)

Step 1: (R)-3-((1-methyl-1H-pyrazol-4-yl)amino)-5-(3-(piperidine-4-carboxamido)piperidin-1-yl)pyrazine-2-carboxamide

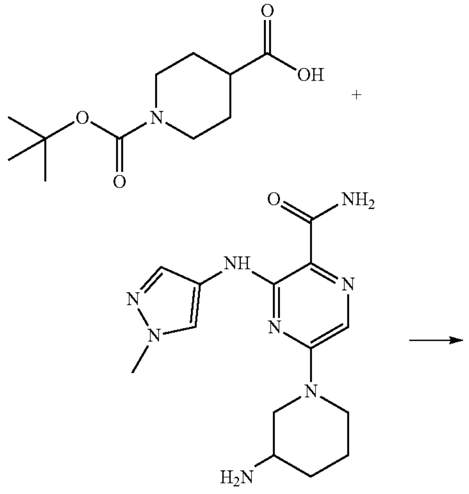

-continued

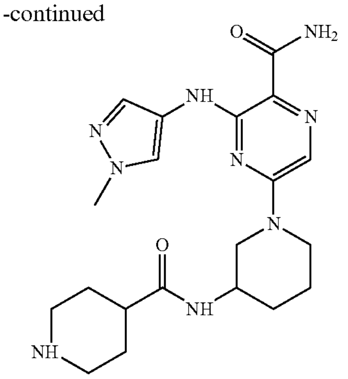

The procedure from Step 1 of Example 36 was followed to afford (R)-3-((1-methyl-1H-pyrazol-4-yl)amino)-5-(3-(piperidine-4-carboxamido)piperidin-1-yl)pyrazine-2-carboxamide (199 mg). LCMS: $C_{20}H_{29}N_9O_2$ requires: 427, found: m/z=428 $[M+H]^+$.

Step 2: 5-[(3R)-3-[1-({1-[2-(2,6-dioxopiperidin-3-yl)-1,3-dioxoisoindol-5-yl]azetidin-3-yl}methyl)piperidine-4-amido]piperidin-1-yl]-3-[(1-methylpyrazol-4-yl)amino]pyrazine-2-carboxamide

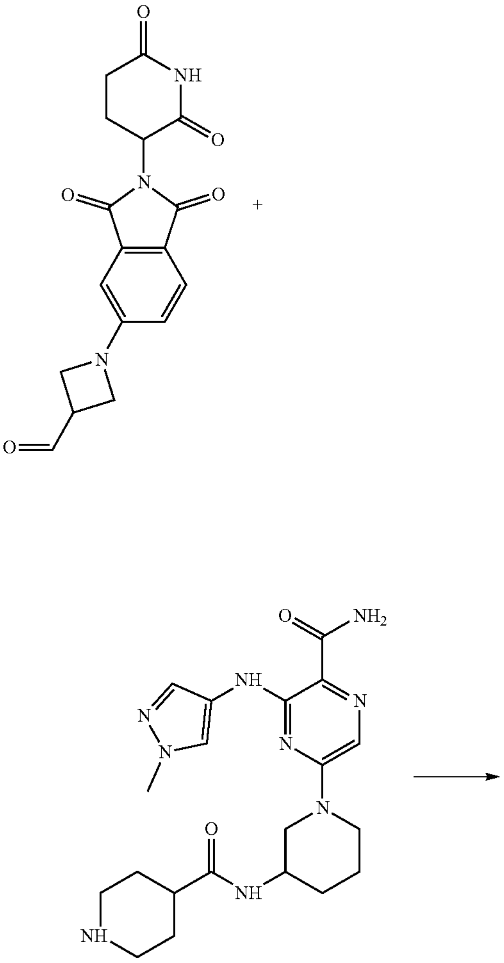

-continued

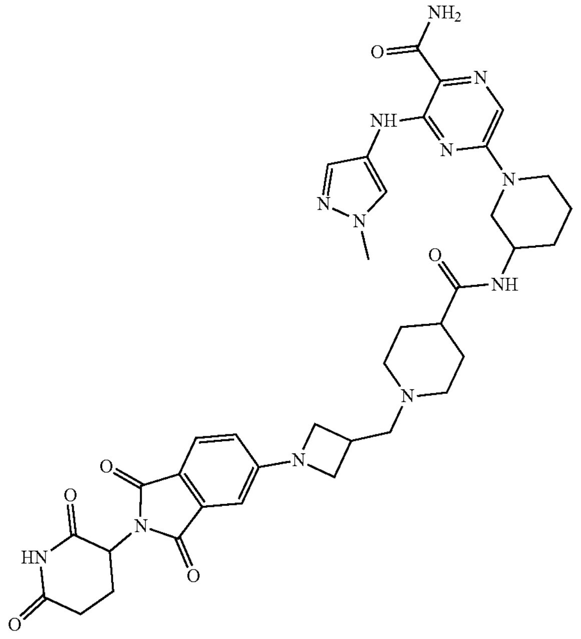

The procedure from Example 30 was followed to afford 5-[(3R)-3-[1-({1-[2-(2,6-dioxopiperidin-3-yl)-1,3-dioxoisoindol-5-yl]azetidin-3-yl}methyl)piperidine-4-amido]piperidin-1-yl]-3-[(1-methylpyrazol-4-yl)amino]pyrazine-2-carboxamide (8.4 mg). $^1$H NMR (500 MHz, Acetonitrile-$d_3$) δ 10.74 (s, 1H), 8.87 (s, 1H), 7.92 (s, 1H), 7.59 (d, J=8.3 Hz, 1H), 7.45 (d, J=7.4 Hz, 2H), 7.38-7.22 (m, 1H), 6.76 (d, J=2.1 Hz, 1H), 6.59 (dd, J=8.3, 2.2 Hz, 1H), 6.34 (d, J=7.2 Hz, 1H), 5.72 (s, 1H), 4.92 (dd, J=12.3, 5.3 Hz, 1H), 4.24-4.16 (m, 1H), 4.11 (t, J=8.1 Hz, 2H), 3.87 (s, 3H), 3.85-3.78 (m, 2H), 3.68 (dd, J=8.2, 5.4 Hz, 2H), 3.45 (td, J=9.0, 8.5, 4.4 Hz, 1H), 3.35 (dd, J=13.1, 7.8 Hz, 1H), 3.28 (s, 1H), 2.97 (ddt, J=10.1, 7.8, 4.2 Hz, 1H), 2.90-2.79 (m, 2H), 2.70 (dddt, J=21.8, 13.4, 7.8, 4.3 Hz, 3H), 2.57 (d, J=7.4 Hz, 2H), 2.11-2.01 (m, 3H), 1.87-1.77 (m, 2H), 1.71-1.49 (m, 6H). LCMS: $C_{37}H_{44}N_{12}O_6$ requires: 752, found: m/z=753.

Example 42: Synthesis of 5-((3R)-3-(1-(1-(2-(2,6-dioxopiperidin-3-yl)-1,3-dioxoisoindolin-5-yl)azetidin-3-yl)piperidine-4-carboxamido)piperidin-1-yl)-3-((3-methylisothiazol-5-yl)amino)pyrazine-2-carboxamide (Compound 38)

Step 1: (R)-5-(3-(1-(azetidin-3-yl)piperidine-4-carboxamido)piperidin-1-yl)-3-((3-methylisothiazol-5-yl)amino)pyrazine-2-carboxamide

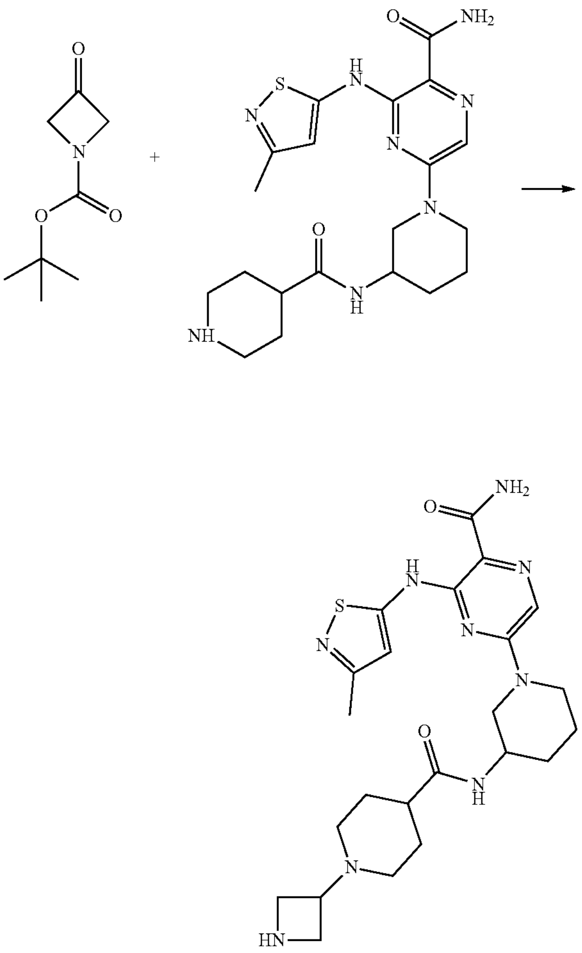

The procedures from Example 30 and the deprotection Step 2 of Example 20 were followed using tert-butyl 3-oxoazetidine-1-carboxylate and tert-butyl 4-{[(3R)-1-{5-carbamoyl-6-[(3-methyl-1,2-thiazol-5-yl)amino]pyrazin-2-yl}piperidin-3-yl]carbamoyl}piperidine-1-carboxylate to afford (R)-5-(3-(1-(azetidin-3-yl)piperidine-4-carboxamido)piperidin-1-yl)-3-((3-methylisothiazol-5-yl)amino)pyrazine-2-carboxamide (17 mg). LCMS: $C_{23}H_{33}N_9O_2S$ requires: 499, found: m/z=500 [M+H]$^+$.

Step 2: 5-((3R)-3-(1-(1-(2-(2,6-dioxopiperidin-3-yl)-1,3-dioxoisoindolin-5-yl)azetidin-3-yl)piperidine-4-carboxamido)piperidin-1-yl)-3-((3-methylisothiazol-5-yl)amino)pyrazine-2-carboxamide

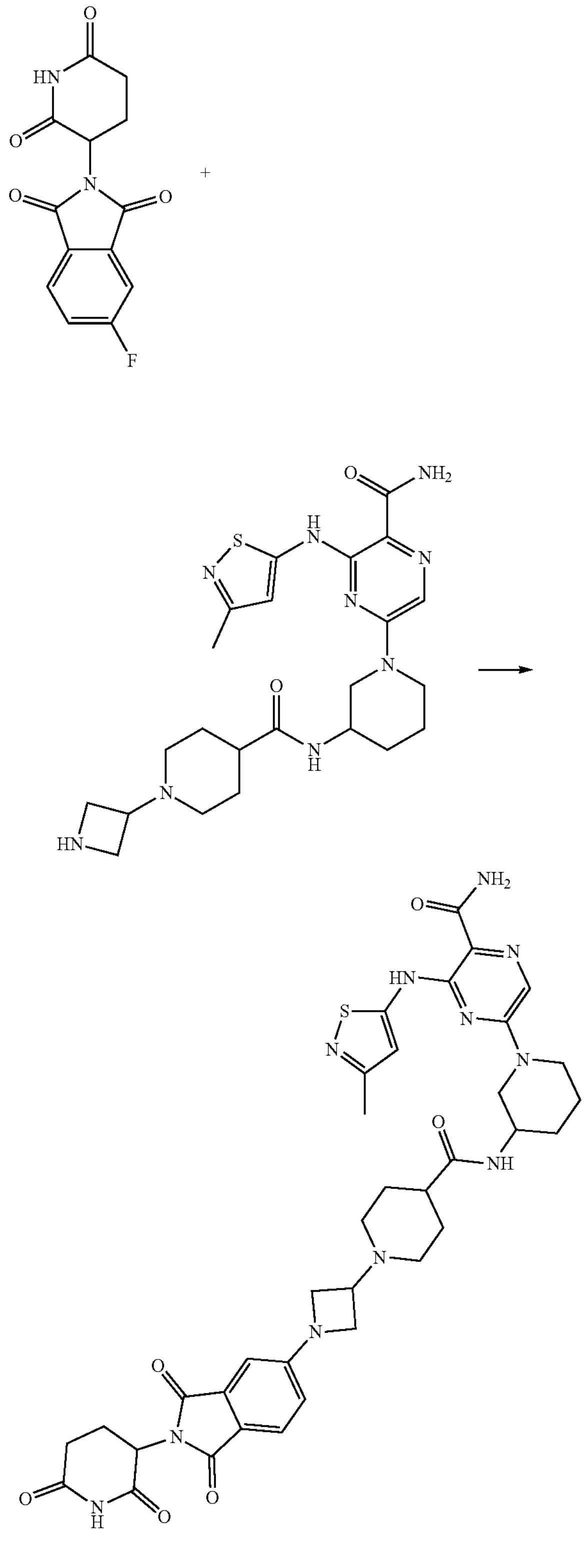

The procedure from Step 4 of Example 27 was followed to afford 5-((3R)-3-(1-(1-(2-(2,6-dioxopiperidin-3-yl)-1,3-dioxoisoindolin-5-yl)azetidin-3-yl)piperidine-4-carboxamido)piperidin-1-yl)-3-((3-methylisothiazol-5-yl)amino) pyrazine-2-carboxamide (5.0 mg). $^1$H NMR (500 MHz, Methanol-$d_4$) δ 7.70 (dd, J=10.6, 6.2 Hz, 1H), 7.61-7.39 (m, 1H), 6.94 (d, J=20.3 Hz, 1H), 6.80 (ddt, J=14.9, 10.7, 5.0 Hz, 2H), 5.14-5.01 (m, 1H), 4.30 (dd, J=83.0, 48.3 Hz, 7H), 3.99 (s, 1H), 3.88-3.63 (m, 1H), 3.50 (d, J=52.5 Hz, 1H), 3.32 (s, 3H), 3.23-2.93 (m, 3H), 2.83 (s, 2H), 2.78-2.58 (m, 2H), 2.38 (tt, J=9.9, 4.3 Hz, 3H), 2.33-1.51 (m, 7H). LCMS: $C_{36}H_{41}N_1O_6S$ requires: 755, found: m/z=756 [M+H]$^+$.

Example 43: Synthesis of N—((R)-1-(5-carbamoyl-6-((3-methylisothiazol-5-yl)amino)pyrazin-2-yl) piperidin-3-yl)-1'-(2-(2,6-dioxopiperidin-3-yl)-1,3-dioxoisoindolin-5-yl)-[1,4'-bipiperidine]-4-carboxamide (Compound 39)

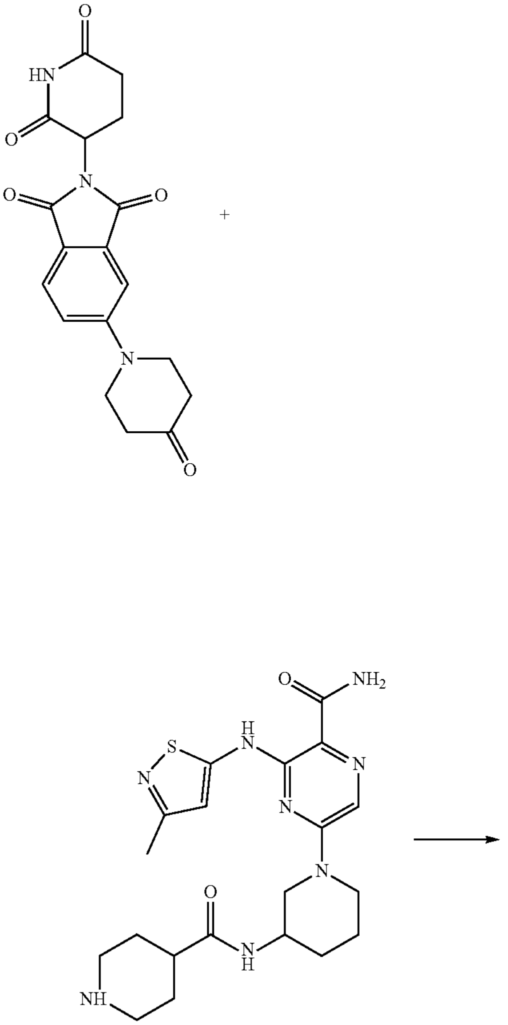

-continued

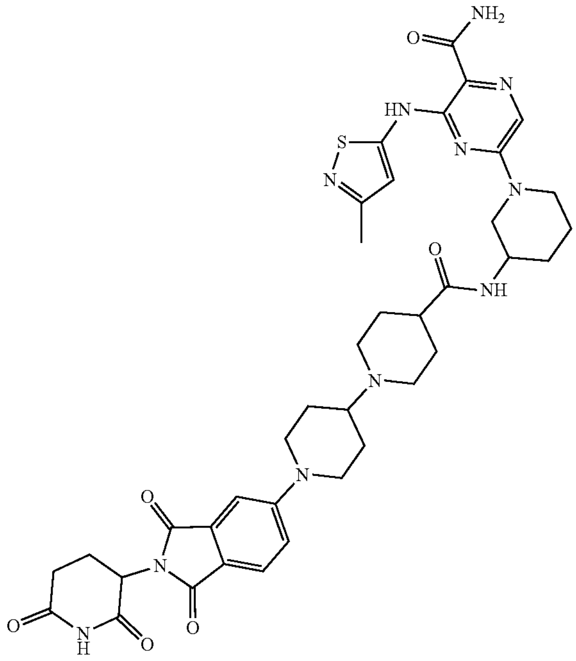

The procedure from Example 30 was followed to afford N—((R)-1-(5-carbamoyl-6-((3-methylisothiazol-5-yl)amino)pyrazin-2-yl)piperidin-3-yl)-1'-(2-(2,6-dioxopiperidin-3-yl)-1,3-dioxoisoindolin-5-yl)-[1,4'-bipiperidine]-4-carboxamide (1.9 mg). LCMS: $C_{35}H_{45}N_{11}O_6S$ requires: 783, found: m/z=784. $^1H$ NMR (500 MHz, Methanol-d4) δ 7.77-7.64 (m, 1H), 7.58-7.44 (m, 1H), 7.41 (d, J=13.2 Hz, 1H), 7.29 (t, J=11.0 Hz, 1H), 6.77 (d, J=21.6 Hz, 1H), 5.08 (dd, J=12.4, 5.5 Hz, 1H), 4.61-4.36 (m, 1H), 4.23 (dd, J=25.9, 13.6 Hz, 3H), 4.05 (dd, J=40.7, 14.3 Hz, 1H), 3.67 (t, J=14.8 Hz, 1H), 3.58-3.39 (m, 3H), 3.15 (q, J=18.1, 15.8 Hz, 2H), 3.03 (dd, J=30.5, 13.3 Hz, 2H), 2.96-2.81 (m, 2H), 2.81-2.68 (m, 4H), 2.57 (d, J=12.7 Hz, 1H), 2.35 (d, J=16.3 Hz, 3H), 2.31-1.56 (m, 11H). LCMS: $C_{35}H_{45}N_{11}O_6S$ requires: 783, found: m/z=784 $[M+H]^+$.

Example 44: Synthesis of 5-[(3R)-3-[1-({1-[2-(2,6-dioxopiperidin-3-yl)-1,3-dioxoisoindol-5-yl]piperidin-4-yl}methyl)piperidine-4-amido]piperidin-1-yl]-3-[(4-methanesulfonylphenyl)amino]pyrazine-2-carboxamide (Compound 20)

Step 1: (R)-3-((4-(methylsulfonyl)phenyl)amino)-5-(3-(piperidine-4-carboxamido)piperidin-1-yl)pyrazine-2-carboxamide

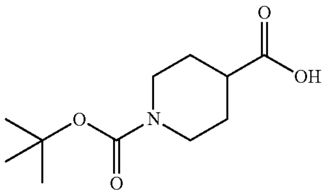

+

-continued

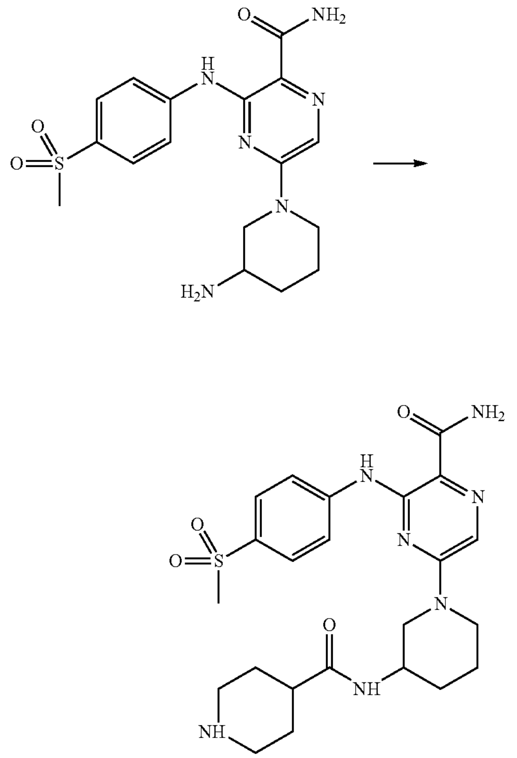

The procedure from Step 1 of Example 36 was followed to afford (R)-3-((4-(methylsulfonyl)phenyl)amino)-5-(3-(piperidine-4-carboxamido)piperidin-1-yl)pyrazine-2-carboxamide (16 mg). LCMS: $C_{23}H_{31}N_7O_4S$ requires: 501, found: m/z=502 $[M+H]^+$.

Step 2: 5-[(3R)-3-[1-({1-[2-(2,6-dioxopiperidin-3-yl)-1,3-dioxoisoindol-5-yl]piperidin-4-yl}methyl)piperidine-4-amido]piperidin-1-yl]-3-[(4-methanesulfonylphenyl)amino]pyrazine-2-carboxamide

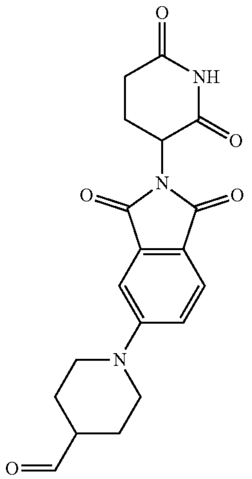

+

-continued

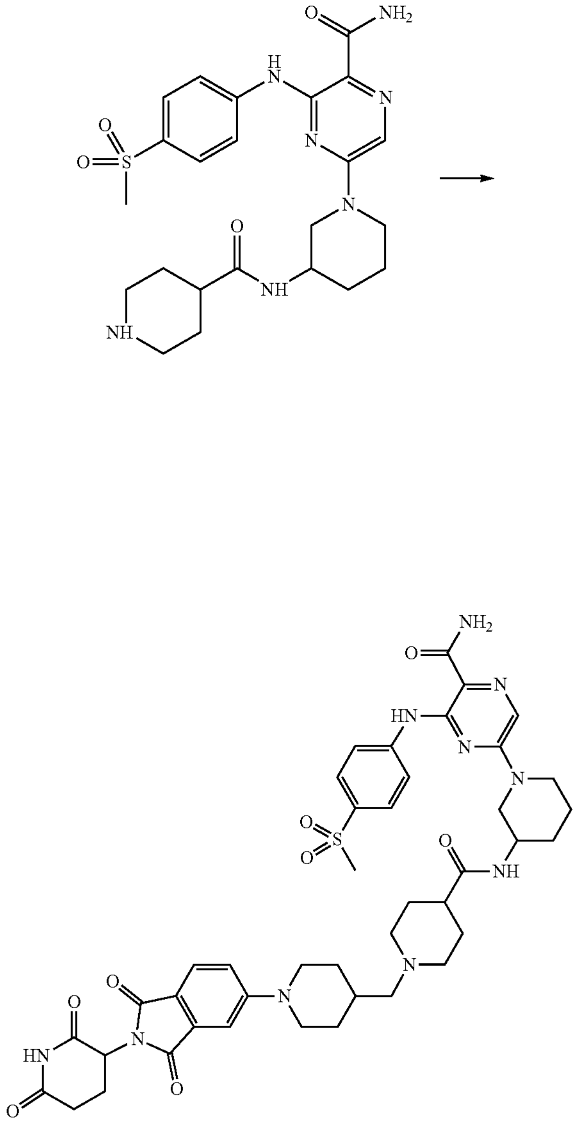

The procedure from Example 30 was followed to afford 5-[(3R)-3-[1-({1-[2-(2,6-dioxopiperidin-3-yl)-1,3-dioxoisoindol-5-yl]piperidin-4-yl}methyl)piperidine-4-amido]piperidin-1-yl]-3-[(4-methanesulfonylphenyl)amino]pyrazine-2-carboxamide (6 mg). LCMS: C42H50N1008S requires: 854, found: m/z=855. $^1$H NMR (500 MHz, Methanol-$d_4$) δ 8.06-7.81 (m, 4H), 7.74-7.62 (m, 1H), 7.47 (d, J=35.1 Hz, 1H), 7.37 (t, J=6.5 Hz, 1H), 7.24 (q, J=8.1 Hz, 1H), 5.07 (dd, J=12.4, 5.3 Hz, 1H), 4.21 (d, J=13.6 Hz, 1H), 4.09 (t, J=17.7 Hz, 4H), 4.00-3.90 (m, 2H), 3.74 (dd, J=50.5, 12.4 Hz, 1H), 3.22-2.97 (m, 10H), 2.87 (ddd, J=19.1, 14.1, 5.6 Hz, 2H), 2.79-2.52 (m, 3H), 2.31-2.07 (m, 3H), 2.05 (s, 1H), 2.01-1.86 (m, 3H), 1.81 (d, J=11.5 Hz, 2H), 1.68 (s, 2H), 1.50-1.25 (m, 2H). LCMS: $C_{42}H_{50}N_{10}O_8S$ requires: 854, found: m/z=855 [M+H]$^+$.

Example 45: Synthesis of N—((R)-1-(5-carbamoyl-6-((4-(methylsulfonyl)phenyl)amino)pyrazin-2-yl)piperidin-3-yl)-1'-(2-(2,6-dioxopiperidin-3-yl)-1,3-dioxoisoindolin-5-yl)-[1,4'-bipiperidine]-4-carboxamide (Compound 40)

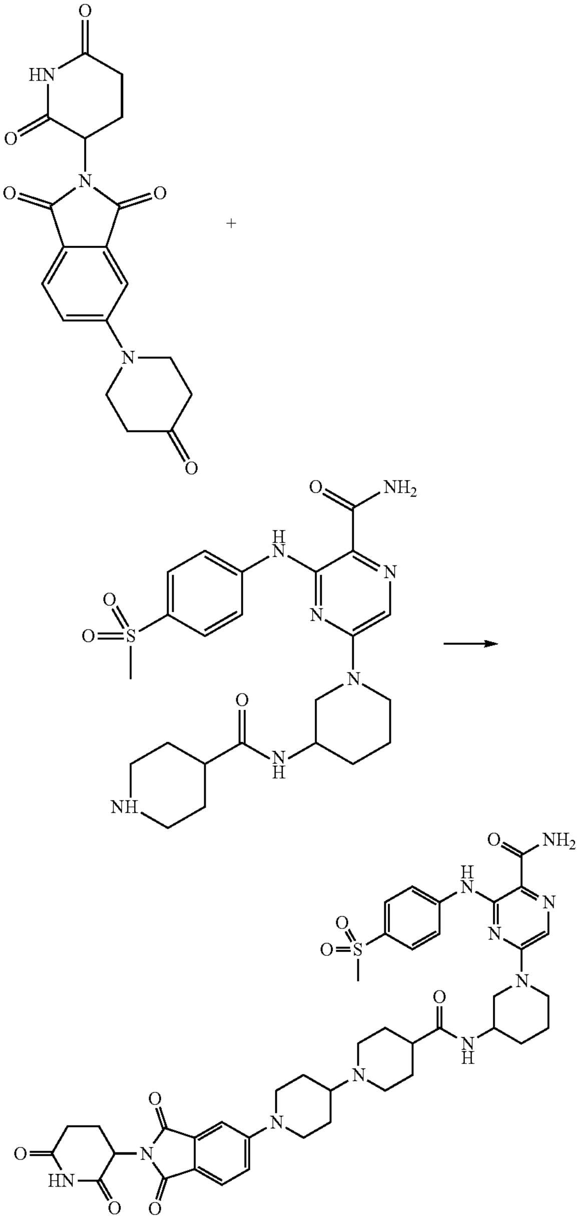

The procedure from Example 30 was followed to afford N—((R)-1-(5-carbamoyl-6-((4-(methylsulfonyl)phenyl)amino)pyrazin-2-yl)piperidin-3-yl)-1'-(2-(2,6-dioxopiperidin-3-yl)-1,3-dioxoisoindolin-5-yl)-[1,4'-bipiperidine]-4-carboxamide (1.4 mg). $^1$H NMR (500 MHz, Methanol-$d_4$) δ 8.03-7.89 (m, 2H), 7.85 (d, J=8.6 Hz, 2H), 7.74 (dd, J=13.5, 8.5 Hz, 1H), 7.47 (d, J=35.0 Hz, 2H), 7.31 (d, J=8.7 Hz, 1H), 5.16-5.05 (m, 1H), 4.26 (d, J=14.5 Hz, 2H), 4.16-3.86 (m, 3H), 3.73 (d, J=11.7 Hz, 1H), 3.66 (d, J=11.7 Hz, 1H), 3.60-3.48 (m, 1H), 3.46-3.39 (m, 2H), 3.25-3.16 (m, 2H), 3.12 (d, J=5.4 Hz, 3H), 2.90-2.80 (m, 2H), 2.74 (t, J=13.9

Hz, 3H), 2.65-2.51 (m, 2H), 2.40-2.03 (m, 6H), 2.01-1.47 (m, 6H). LCMS: $C_{41}H_{48}N_{10}O_8S$ requires: 840, found: m/z=841 $[M+H]^+$.

Example 46: Synthesis of 5-((3R)-3-(1-((1-(2-(2,6-dioxopiperidin-3-yl)-1,3-dioxoisoindolin-5-yl)piperidin-4-yl)methyl)piperidine-4-carboxamido)piperidin-1-yl)-3-((1-methyl-1H-pyrazol-4-yl)amino)pyrazine-2-carboxamide (Compound 21)

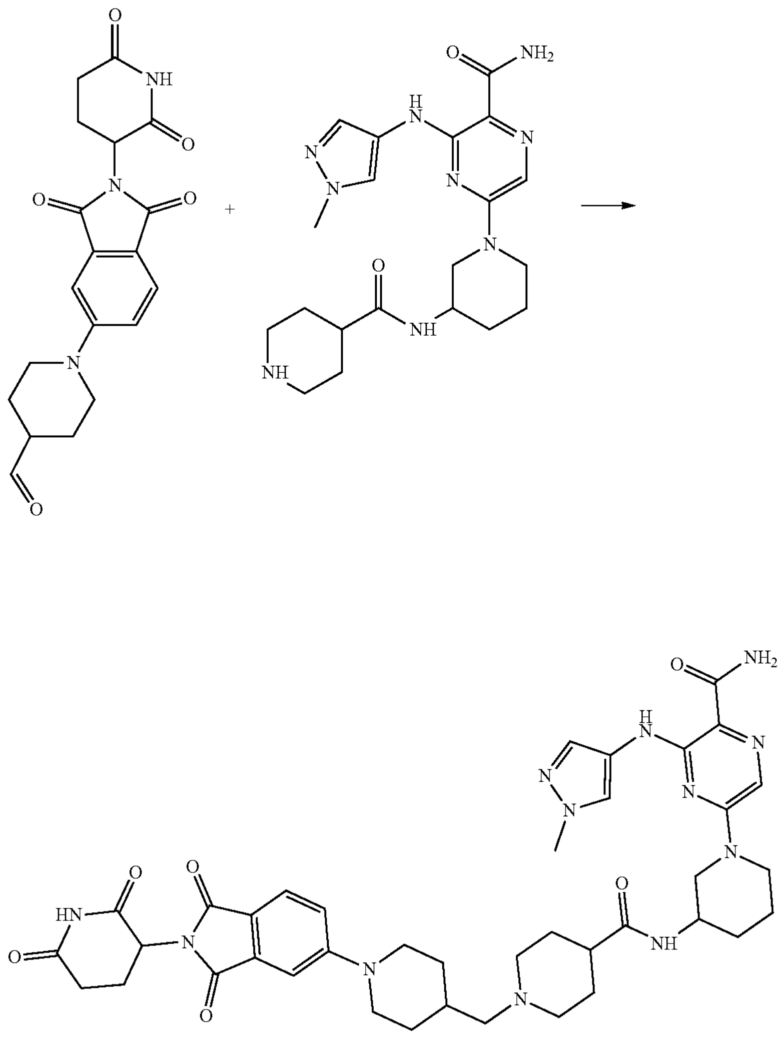 [SMILES: O=CC1CCN(c2ccc3c(c2)C(=O)N(C2CCC(=O)NC2=O)C3=O)CC1 ; Cn1cc(Nc2nc(N3CCCC(NC(=O)C4CCNCC4)C3)cnc2C(N)=O)cn1 ; Cn1cc(Nc2nc(N3CCCC(NC(=O)C4CCN(CC5CCN(c6ccc7c(c6)C(=O)N(C6CCC(=O)NC6=O)C7=O)CC5)CC4)C3)cnc2C(N)=O)cn1]

The procedure from Example 30 was followed to afford 5-((3R)-3-(1-((1-(2-(2,6-dioxopiperidin-3-yl)-1,3-dioxoisoindolin-5-yl)piperidin-4-yl)methyl)piperidine-4-carboxamido)piperidin-1-yl)-3-((1-methyl-1H-pyrazol-4-yl)amino)pyrazine-2-carboxamide (9.7 mg). $^1H$ NMR (500 MHz, DMSO-$d_6$) δ 11.07 (s, 1H), 10.87 (s, 1H), 7.98 (s, 1H), 7.81 (d, J=6.9 Hz, 1H), 7.66 (s, 1H), 7.64 (d, J=8.5 Hz, 1H), 7.55 (s, 1H), 7.48 (s, 1H), 7.30 (d, J=2.1 Hz, 1H), 7.28-7.19 (m, 2H), 5.06 (dd, J=12.8, 5.4 Hz, 1H), 4.29 (s, 1H), 4.04 (d, J=13.0 Hz, 2H), 3.94 (d, J=13.0 Hz, 1H), 3.86 (s, 3H), 3.70 (s, 1H), 3.08 (t, J=10.9 Hz, 1H), 3.01-2.92 (m, 2H), 2.90-2.78 (m, 3H), 2.09 (h, J=6.3 Hz, 3H), 2.00 (dd, J=11.8, 6.0 Hz, 1H), 1.92-1.71 (m, 8H), 1.59 (d, J=24.4 Hz, 7H), 1.12 (d, J=12.5 Hz, 3H). LCMS: $C_{39}H_{48}N_{12}O_6$ requires: 780, found: m/z=781 $[M+H]^+$.

Example 47: Synthesis of 5-((3R)-3-(1-((1-(2-(2,6-dioxopiperidin-3-yl)-1,3-dioxoisoindolin-5-yl)piperidin-4-yl)methyl)azetidine-3-carboxamido)piperidin-1-yl)-3-((4-(methylsulfonyl)phenyl)amino)pyrazine-2-carboxamide (Compound 30)

Step 1: (R)-5-(3-(azetidine-3-carboxamido)piperidin-1-yl)-3-((4-(methylsulfonyl)phenyl)amino)pyrazine-2-carboxamide

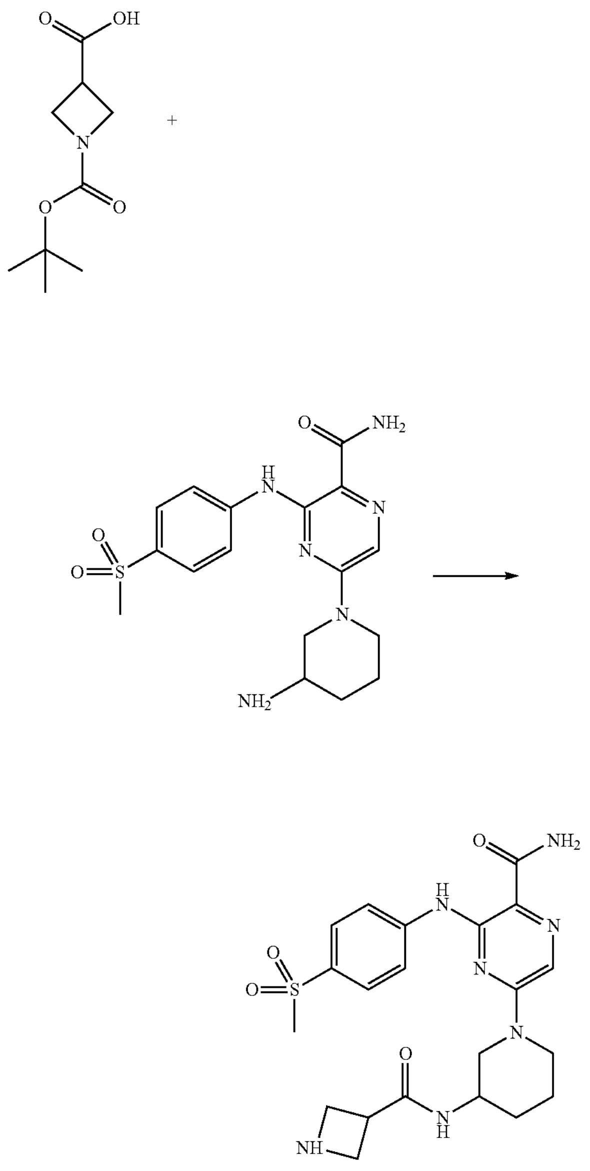

The procedure of Step 1 of Example 36 was followed to afford (R)-5-(3-(azetidine-3-carboxamido)piperidin-1-yl)-3-((4-(methylsulfonyl)phenyl)amino)pyrazine-2-carboxamide (45 mg). LCMS: C21H27N704S requires: 473, found: m/z=474 [M+H]$^+$.

Step 2: 5-((3R)-3-(1-((1-(2-(2,6-dioxopiperidin-3-yl)-1,3-dioxoisoindolin-5-yl)piperidin-4-yl)methyl) azetidine-3-carboxamido)piperidin-1-yl)-3-((4-(methylsulfonyl) phenyl)amino)pyrazine-2-carboxamide

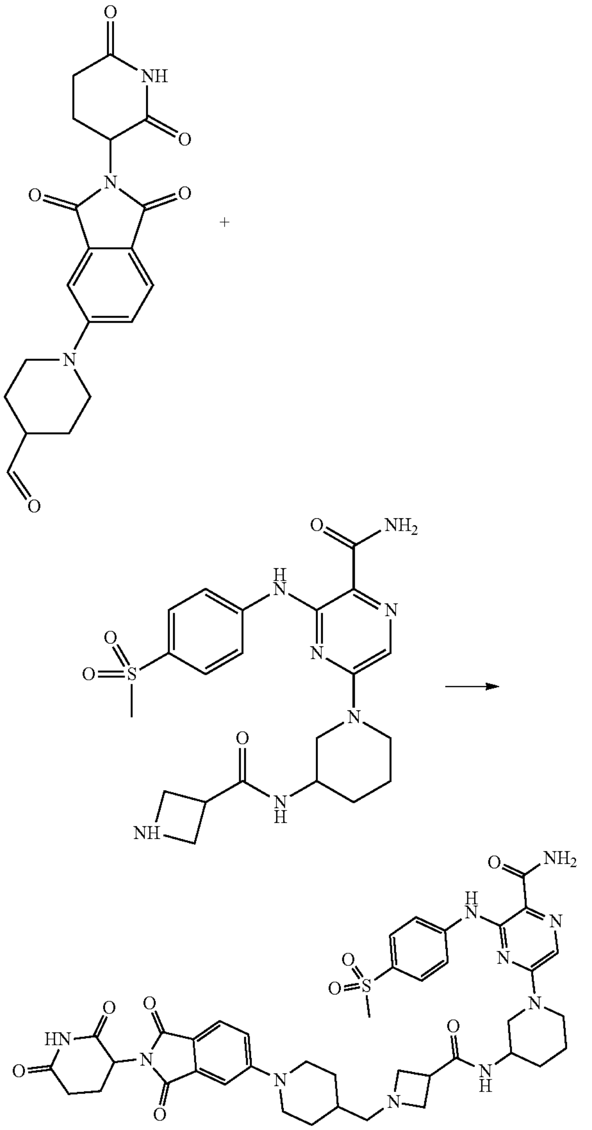

The procedure from Example 42 was followed to afford 5-((3R)-3-(1-((1-(2-(2,6-dioxopiperidin-3-yl)-1,3-dioxoisoindolin-5-yl)piperidin-4-yl)methyl)azetidine-3-carboxamido)piperidin-1-yl)-3-((4-(methylsulfonyl)phenyl)amino) pyrazine-2-carboxamide (4.0 mg). $^1$H NMR (500 MHz, DMSO-$d_6$) δ 12.00 (d, J=18.5 Hz, 1H), 11.07 (s, 1H), 8.06-7.72 (m, 4H), 7.66 (dd, J=8.6, 4.5 Hz, 1H), 7.58-7.39 (m, 1H), 7.38-7.28 (m, 1H), 7.28-7.12 (m, 1H), 6.53 (s, 1H), 5.06 (dd, J=12.7, 5.4 Hz, 1H), 4.57-4.15 (m, 3H), 4.15-3.98 (m, 2H), 3.99-3.89 (m, 1H), 3.72 (d, J=104.0 Hz, 1H), 3.46 (d, J=14.3 Hz, 1H), 3.22-3.06 (m, 4H), 3.06-2.79 (m, 4H), 2.68-2.53 (m, 4H), 2.01 (ddd, J=11.0, 5.9, 3.6 Hz, 2H), 1.92 (dd, J=13.1, 4.3 Hz, 1H), 1.77 (d, J=28.4 Hz, 3H), 1.66-1.43 (m, 4H), 1.36-1.01 (m, 4H). LCMS: $C_{40}H_{46}N_{10}O_8S$ requires: 826, found: m/z=[M+H]$^+$.

Example 48: Synthesis of N—((R)-1-(5-carbamoyl-6-((4-(methylsulfonyl)phenyl) amino)pyrazin-2-yl) piperidin-3-yl)-3-((2-(2,6-dioxopiperidin-3-yl)-1,3-dioxoisoindolin-5-yl)methyl)-3-azaspiro[5.5] undecane-9-carboxamide (Compound 31)

Step 1: Synthesis of (R)—N-(1-(5-carbamoyl-6-((4-(methylsulfonyl)phenyl) amino)pyrazin-2-yl)piperidin-3-yl)-3-azaspiro[5.5]undecane-9-carboxamide

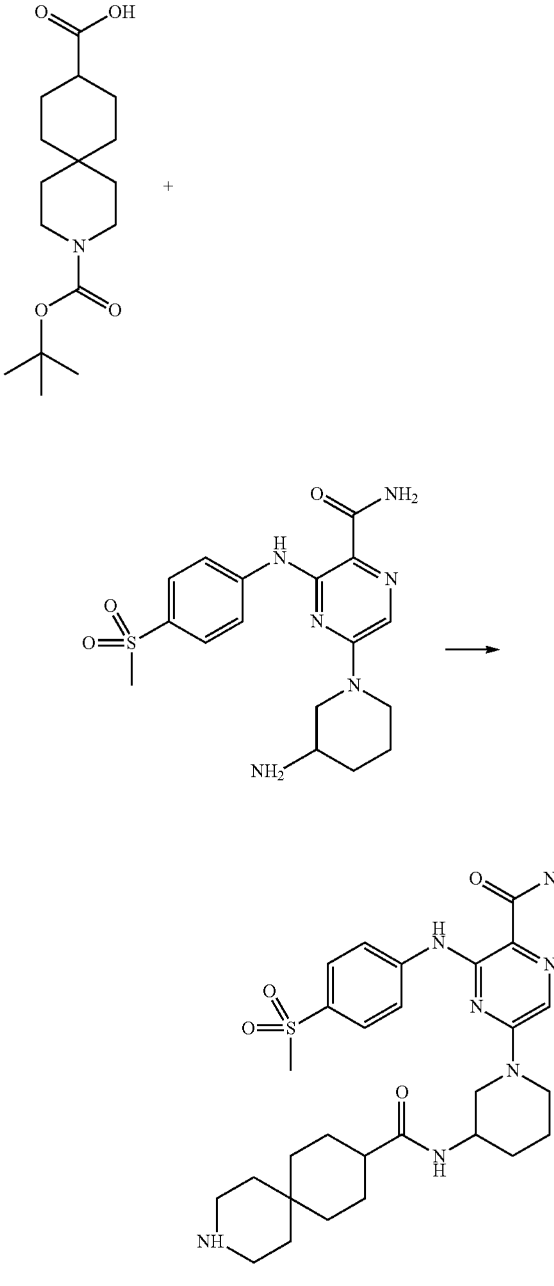

The procedure from Step 1 of Example 36 was followed to afford (R)—N-(1-(5-carbamoyl-6-((4-(methylsulfonyl) phenyl)amino)pyrazin-2-yl)piperidin-3-yl)-3-azaspiro[5.5] undecane-9-carboxamide (17 mg). LCMS: $C_{28}H_{39}N_7O_4S$ requires: 569, found: m/z=570 $[M+H]^+$.

Step 2: N—((R)-1-(5-carbamoyl-6-((4-(methylsulfonyl)phenyl)amino)pyrazin-2-yl)piperidin-3-yl)-3-((2-(2,6-dioxopiperidin-3-yl)-1,3-dioxoisoindolin-5-yl) methyl)-3-azaspiro[5.5]undecane-9-carboxamide

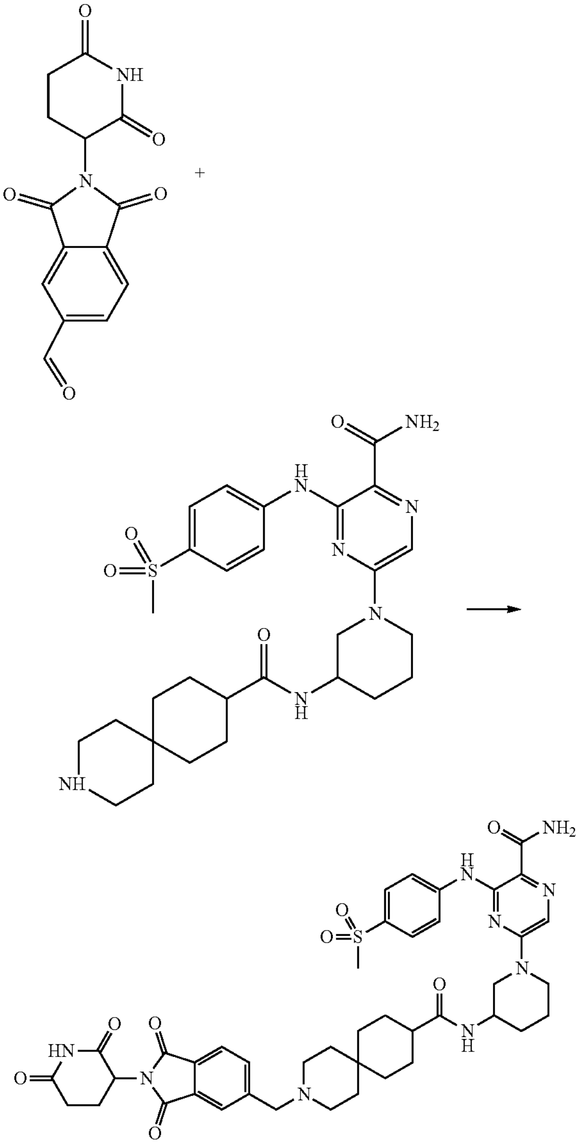

The procedure from Example 30 was followed to afford N—((R)-1-(5-carbamoyl-6-((4-(methylsulfonyl)phenyl) amino)pyrazin-2-yl)piperidin-3-yl)-3-((2-(2,6-dioxopiperidin-3-yl)-1,3-dioxoisoindolin-5-yl)methyl)-3-azaspiro[5.5] undecane-9-carboxamide (3.5 mg). $^1$H NMR (500 MHz, Acetonitrile-$d_3$) δ 11.80 (d, J=37.0 Hz, 1H), 11.23 (s, 1H), 8.93 (s, 1H), 8.04 (s, 1H), 8.00-7.86 (m, 4H), 7.82 (d, J=8.6 Hz, 2H), 7.39 (d, J=28.5 Hz, 2H), 6.14 (d, J=28.1 Hz, 1H), 5.90 (d, J=24.5 Hz, 1H), 5.03 (dd, J=12.4, 5.4 Hz, 1H), 4.64 (s, 1H), 4.35 (d, J=30.1 Hz, 3H), 4.04 (s, 1H), 3.85 (s, 3H), 3.44-3.10 (m, 6H), 3.03 (d, J=30.3 Hz, 4H), 2.87-2.54 (m, 4H), 2.16-1.99 (m, 2H), 1.90-1.72 (m, 2H), 1.64 (d, J=47.1 Hz, 4H), 1.44-1.05 (m, 4H), 0.89 (s, 0H), 0.61 (s, 0H). LCMS: $C_{42}H_{49}N_9O_8S$, requires: 839, found: m/z=840.

Example 49: Synthesis of N—((R)-1-(5-carbamoyl-6-((4-(methylsulfonyl)phenyl) amino)pyrazin-2-yl) piperidin-3-yl)-2-((2-(2,6-dioxopiperidin-3-yl)-1,3-dioxoisoindolin-5-yl)methyl)-2-azaspiro[3.3] heptane-6-carboxamide (Compound 32)

Step 1: (R)—N-(1-(5-carbamoyl-6-((4-(methylsulfonyl)phenyl)amino)pyrazin-2-yl)piperidin-3-yl)-2-azaspiro[3.3]heptane-6-carboxamide

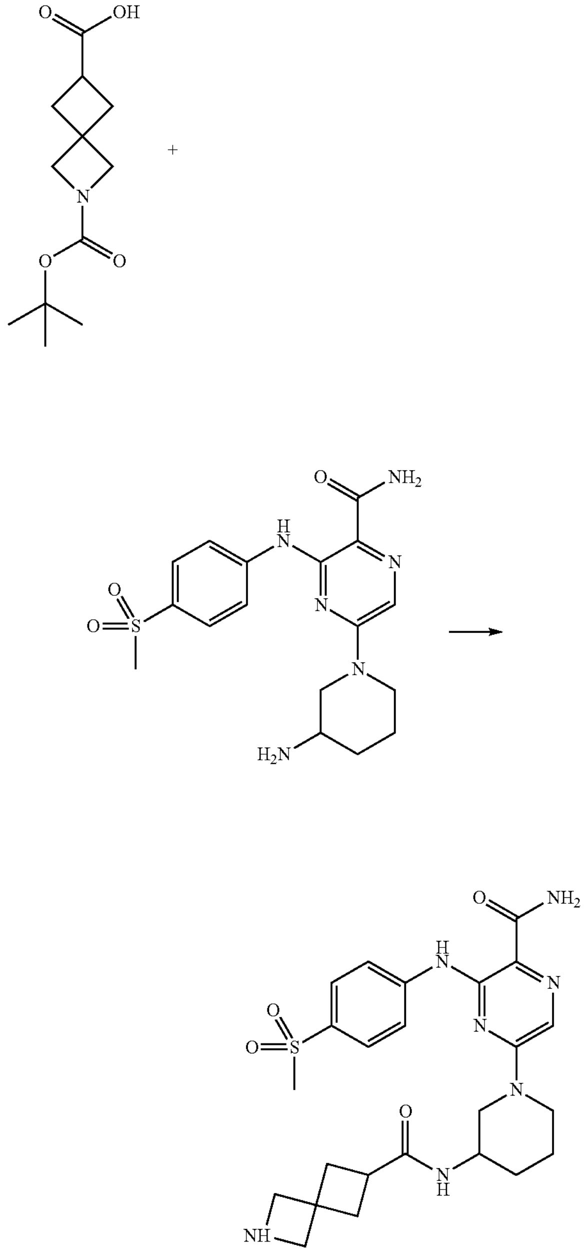

The procedure from Step 1 of Example 36 was followed to afford (R)—N-(1-(5-carbamoyl-6-((4-(methylsulfonyl) phenyl)amino)pyrazin-2-yl)piperidin-3-yl)-2-azaspiro[3.3] heptane-6-carboxamide (16 mg). LCMS: $C_{24}H_{31}N_7O_4S$ requires: 513, found: m/z=514 $[M+H]^+$.

Step 2: N—((R)-1-(5-carbamoyl-6-((4-(methylsulfonyl)phenyl)amino)pyrazin-2-yl)piperidin-3-yl)-2-((2-(2,6-dioxopiperidin-3-yl)-1,3-dioxoisoindolin-5-yl) methyl)-2-azaspiro[3.3]heptane-6-carboxamide

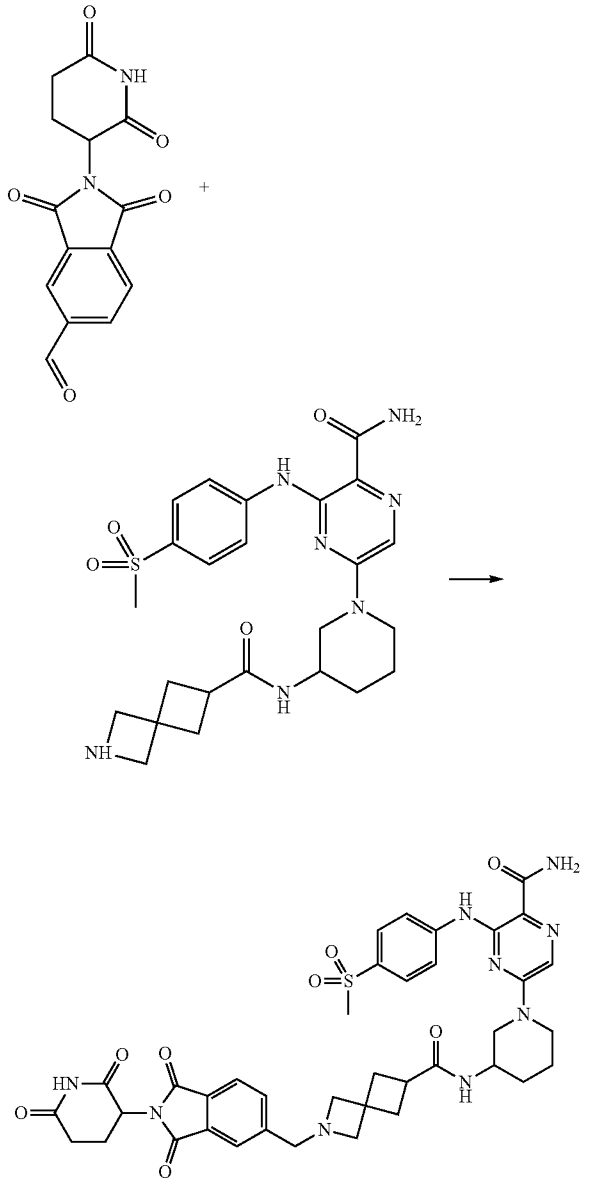

The procedure from Example 30 was followed to afford N—((R)-1-(5-carbamoyl-6-((4-(methylsulfonyl)phenyl) amino)pyrazin-2-yl)piperidin-3-yl)-2-((2-(2,6-dioxopiperidin-3-yl)-1,3-dioxoisoindolin-5-yl)methyl)-2-azaspiro[3.3] heptane-6-carboxamide (2.6 mg). $^1H$ NMR (500 MHz, Acetonitrile-$d_3$) δ 11.77 (s, 1H), 8.93 (s, 1H), 8.12-7.69 (m, 7H), 7.37 (dd, J=47.1, 28.8 Hz, 2H), 6.43-6.04 (m, 1H), 5.90 (d, J=17.5 Hz, 1H), 5.03 (dd, J=12.7, 5.4 Hz, 1H), 4.35 (d, J=54.9 Hz, 2H), 4.17 (d, J=34.8 Hz, 1H), 4.09-3.73 (m, 3H), 3.64 (s, 2H), 3.23 (s, 1H), 3.04 (d, J=18.3 Hz, 4H), 2.83-2.62 (m, 3H), 2.50 (s, 1H), 2.08 (q, J=2.4 Hz, 2H), 1.96 (s, 3H), 1.87-1.70 (m, 1H), 1.58 (d, J=43.4 Hz, 4H). LCMS: $C_{35}H_{41}N_9O_8S$ requires: 783, found: m/z=784 $[M+H]^+$.

Example 50: Synthesis of 1R,5S,6r)-N—((R)-1-(5-carbamoyl-6-((4-(methylsulfonyl)phenyl)amino) pyrazin-2-yl)piperidin-3-yl)-3-((1-(2-(2,6-dioxopiperidin-3-yl)-1,3-dioxoisoindolin-5-yl)piperidin-4-yl) methyl)-3-azabicyclo[3.1.0]hexane-6-carboxamide (Compound 33)

Step 1: (1R,5S,6R)—N-[(3R)-1-{5-carbamoyl-6-[(4-methanesulfonylphenyl) amino]pyrazin-2-yl}piperidin-3-yl]-3-azabicyclo[3.1.0]hexane-6-carboxamide

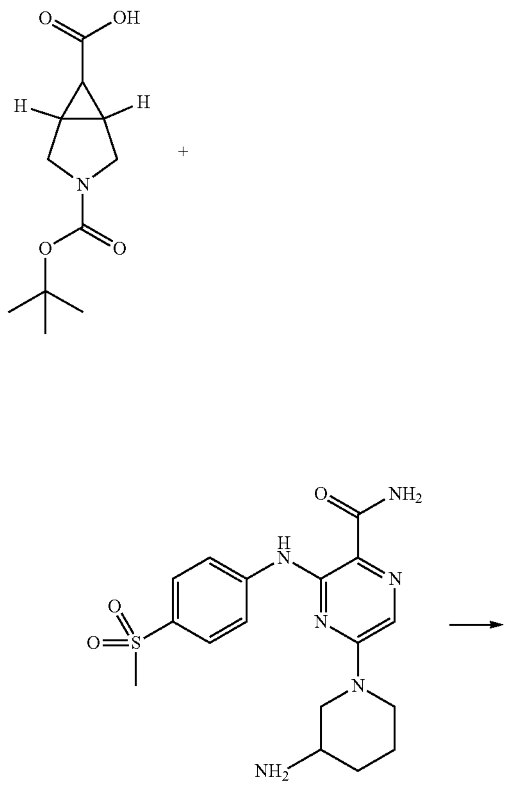

-continued

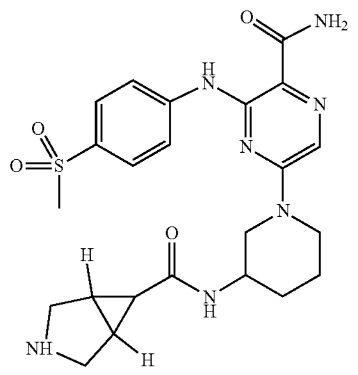

The procedure from Step 1 of Example 36 was followed to afford (1R,5S,6R)—N-[(3R)-1-{5-carbamoyl-6-[(4-methanesulfonylphenyl)amino]pyrazin-2-yl}piperidin-3-yl]-3-azabicyclo[3.1.0]hexane-6-carboxamide (17 mg). LCMS: $C_{23}H_{29}N_7O_4S$ requires: 499, found: m/z=500 $[M+H]^+$.

Step 2: 1R,5S,6r)-N—((R)-1-(5-carbamoyl-6-((4-(methylsulfonyl)phenyl)amino)pyrazin-2-yl)piperidin-3-yl)-3-((1-(2-(2,6-dioxopiperidin-3-yl)-1,3-dioxoisoindolin-5-yl)piperidin-4-yl)methyl)-3-azabicyclo[3.1.0]hexane-6-carboxamide

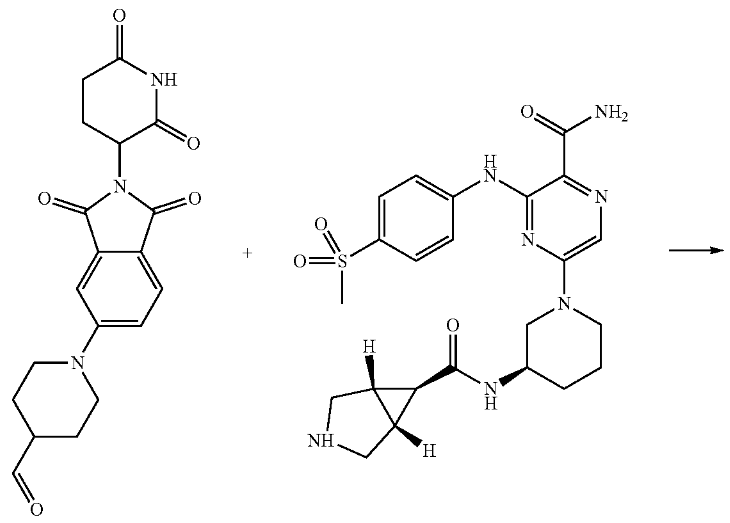

-continued

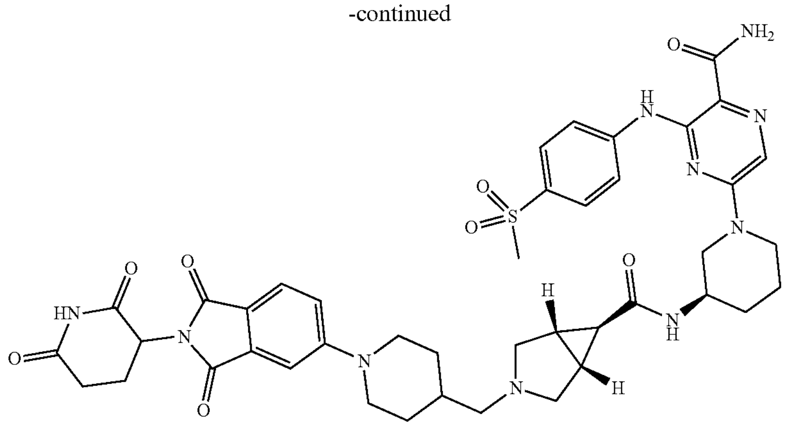

The procedure from Example 30 was followed to afford (1R,5S,6r)-N—((R)-1-(5-carbamoyl-6-((4-(methylsulfonyl)phenyl)amino)pyrazin-2-yl)piperidin-3-yl)-3-((1-(2-(2,6-dioxopiperidin-3-yl)-1,3-dioxoisoindolin-5-yl)piperidin-4-yl)methyl)-3-azabicyclo[3.1.0]hexane-6-carboxamide (2.3 mg). $^1$H NMR (500 MHz, Acetonitrile-$d_3$) δ 11.82 (d, J=89.8 Hz, 1H), 8.87 (s, 1H), 8.02 (d, J=8.5 Hz, 1H), 7.89 (d, J=8.6 Hz, 1H), 7.81 (dd, J=17.9, 8.4 Hz, 2H), 7.65 (t, J=8.7 Hz, 1H), 7.52-7.32 (m, 1H), 7.16 (d, J=8.6 Hz, 1H), 6.39-6.06 (m, 1H), 4.94 (dt, J=12.0, 6.1 Hz, 1H), 4.47 (d, J=14.2 Hz, 1H), 4.14 (s, 1H), 3.95 (dd, J=35.9, 14.0 Hz, 6H), 3.31 (d, J=31.9 Hz, 4H), 3.05 (d, J=10.3 Hz, 3H), 3.02-2.83 (m, 4H), 2.83-2.62 (m, 5H), 2.37 (d, J=52.6 Hz, 2H), 2.08 (q, J=2.5 Hz, 2H), 1.87-1.75 (m, 2H), 1.59 (d, J=57.1 Hz, 3H), 1.43-1.07 (m, 4H). LCMS: $C_{42}H_{48}N_{10}O_8S$ requires: 852, found: m/z=853 $[M+H]^+$.

Example 51: Synthesis of (1R,3s,5S)—N—((R)-1-(5-carbamoyl-6-((4-(methylsulfonyl)phenyl)amino)pyrazin-2-yl)piperidin-3-yl)-8-((1-(2-(2,6-dioxopiperidin-3-yl)-1,3-dioxoisoindolin-5-yl)piperidin-4-yl)methyl)-8-azabicyclo[3.2.1]octane-3-carboxamide (Compound 34)

Step 1: (1R,3s,5S)—N—((R)-1-(5-carbamoyl-6-((4-(methylsulfonyl)phenyl)amino) pyrazin-2-yl)piperidin-3-yl)-8-azabicyclo[3.2.1]octane-3-carboxamide

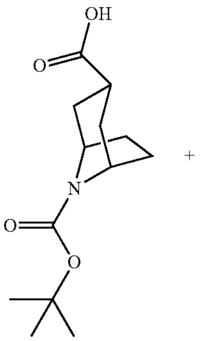

-continued

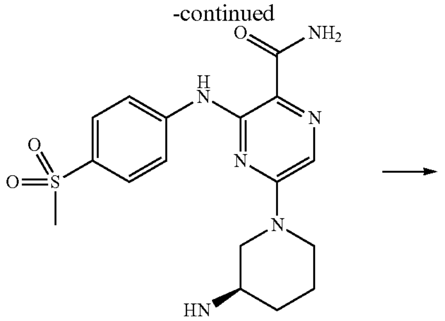

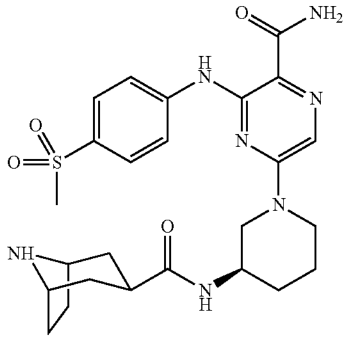

The procedure from Step 1 of Example 36 was followed to afford (1R,3s,5S)—N—((R)-1-(5-carbamoyl-6-((4-(methylsulfonyl)phenyl)amino)pyrazin-2-yl)piperidin-3-yl)-8-azabicyclo[3.2.1]octane-3-carboxamide (16 mg). LCMS: $C_{25}H_{33}N_7O_4S$ requires: 527, found: m/z=528 $[M+H]^+$.

Step 2: (1R,3s,5S)—N—((R)-1-(5-carbamoyl-6-((4-(methylsulfonyl)phenyl)amino) pyrazin-2-yl)piperidin-3-yl)-8-((1-(2-(2,6-dioxopiperidin-3-yl)-1,3-dioxoisoindolin-5-yl)piperidin-4-yl)methyl)-8-azabicyclo[3.2.1]octane-3-carboxamide

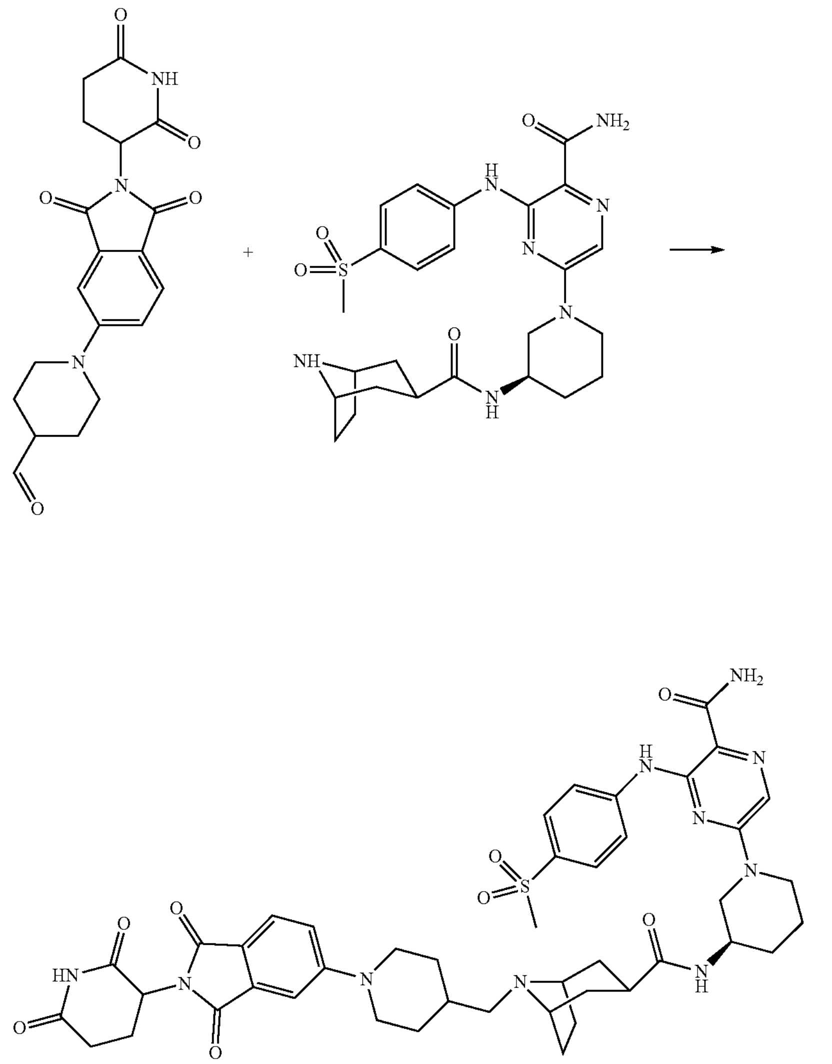

The procedure from Example 30 was followed to afford (1R,3s,5S)—N—((R)-1-(5-carbamoyl-6-((4-(methylsulfonyl)phenyl)amino)pyrazin-2-yl)piperidin-3-yl)-8-((1-(2-(2,6-dioxopiperidin-3-yl)-1,3-dioxoisoindolin-5-yl)piperidin-4-yl)methyl)-8-azabicyclo[3.2.1]octane-3-carboxamide (3.3 mg). $^1$H NMR (500 MHz, Acetonitrile-$d_3$) δ 11.98-11.46 (m, 1H), 8.87 (s, 1H), 7.98-7.77 (m, 4H), 7.66 (d, J=8.8 Hz, 1H), 7.52-7.35 (m, 2H), 7.30 (d, J=16.4 Hz, 1H), 7.17 (dd, J=17.6, 8.4 Hz, 1H), 6.35-6.06 (m, 1H), 5.93 (d, J=35.7 Hz, 1H), 5.02-4.84 (m, 1H), 4.04 (s, 5H), 3.92-3.61 (m, 2H), 3.68-3.41 (m, 2H), 3.28-2.86 (m, 6H), 2.72 (td, J=19.3, 18.5, 10.8 Hz, 4H), 2.55 (d, J=44.1 Hz, 4H), 2.16-2.01 (m, 4H), 1.87-1.68 (m, 4H), 1.68-1.10 (m, 7H). LCMS: $C_{44}H_{52}N_{10}O_8S$ requires: 880, found: m/z=881 $[M+H]^+$.

Example 52: Synthesis of (1R,5S,6r)-N—((R)-1-(5-carbamoyl-6-((4-(methylsulfonyl)phenyl)amino)pyrazin-2-yl)piperidin-3-yl)-3-(1-(2-(2,6-dioxopiperidin-3-yl)-1,3-dioxoisoindolin-5-yl)piperidin-4-yl)-3-azabicyclo[3.1.0]hexane-6-carboxamide (Compound 35)

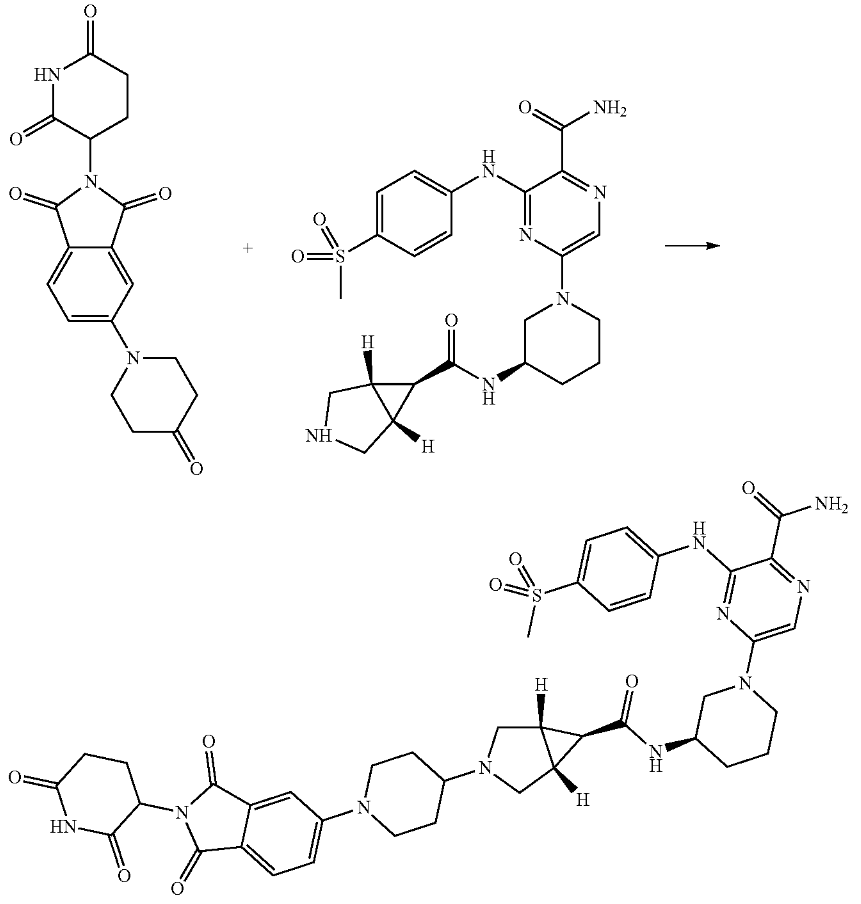

The procedure from Example 30 was followed to afford (1R,5S,6r)-N—((R)-1-(5-carbamoyl-6-((4-(methylsulfonyl)phenyl)amino)pyrazin-2-yl)piperidin-3-yl)-3-(1-(2-(2,6-dioxopiperidin-3-yl)-1,3-dioxoisoindolin-5-yl)piperidin-4-yl)-3-azabicyclo[3.1.0]hexane-6-carboxamide (1.6 mg). $^1$H NMR (500 MHz, Acetonitrile-$d_3$) δ 11.99-11.68 (m, 1H), 11.51 (s, 1H), 8.89 (s, 1H), 7.97 (d, J=8.5 Hz, 1H), 7.92 (d, J=8.6 Hz, 1H), 7.82 (d, J=8.7 Hz, 1H), 7.70 (t, J=9.1 Hz, 1H), 7.45 (s, 1H), 7.42-7.32 (m, 2H), 7.22 (t, J=8.4 Hz, 1H), 6.32-6.07 (m, 1H), 5.94 (d, J=42.1 Hz, 1H), 4.97 (dd, J=12.3, 5.3 Hz, 1H), 4.48 (d, J=12.1 Hz, 1H), 4.25-3.80 (m, 8H), 3.44 (s, 4H), 3.34-3.11 (m, 2H), 3.07 (s, 3H), 2.98 (t, J=13.8 Hz, 2H), 2.76 (ddd, J=35.0, 19.8, 10.9 Hz, 4H), 2.53 (d, J=7.3 Hz, 1H), 2.22-2.03 (m, 2H), 1.99 (s, 1H), 1.85-1.76 (m, 2H), 1.72-1.51 (m, 2H). LCMS: $C_{41}H_{46}N_{10}O_8S$ requires: 838, found: m/z=839 $[M+H]^+$.

Example 53: Synthesis of N-[(3R)-1-{5-carbamoyl-6-[(4-methanesulfonylphenyl)amino]pyrazin-2-yl}piperidin-3-yl]-3-[2-(2,6-dioxopiperidin-3-yl)-1,3-dioxoisoindol-5-yl]-3-azaspiro[5.5]undecane-9-carboxamide (Compound 36)

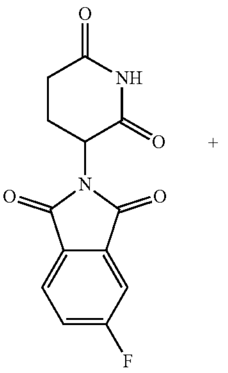

-continued

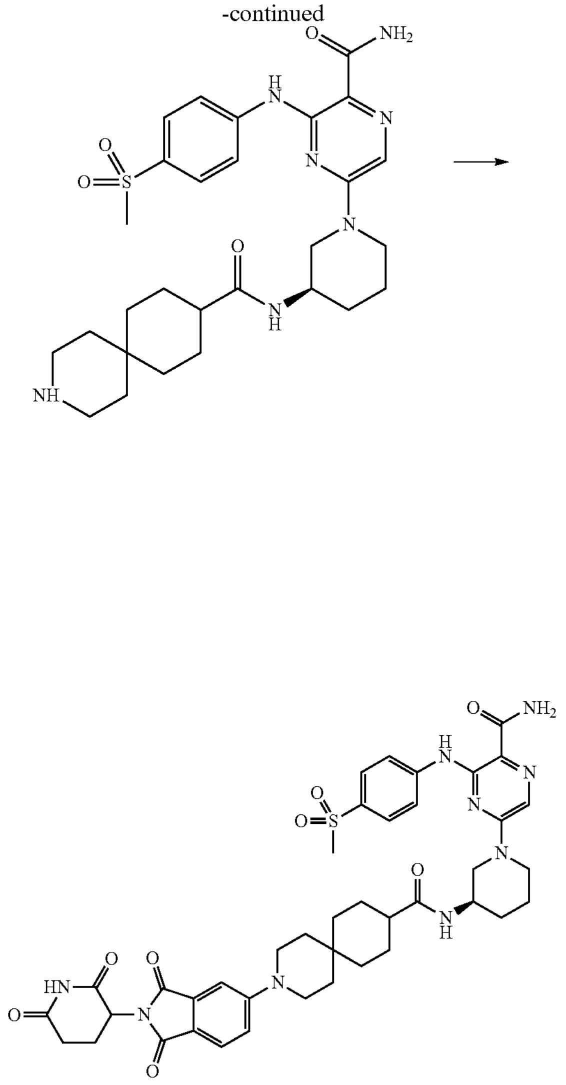

The procedure from Step 4 of Example 27 was followed to afford N-[(3R)-1-{5-carbamoyl-6-[(4-methanesulfonylphenyl)amino]pyrazin-2-yl}piperidin-3-yl]-3-[2-(2,6-dioxopiperidin-3-yl)-1,3-dioxoisoindol-5-yl]-3-azaspiro[5.5]undecane-9-carboxamide (3.2 mg). $^1$H NMR (500 MHz, Methanol-$d_4$) δ 7.95 (dd, J=8.8, 3.6 Hz, 2H), 7.87 (d, J=8.6 Hz, 2H), 7.65 (dd, J=13.5, 8.5 Hz, 1H), 7.47 (d, J=45.2 Hz, 1H), 7.31 (d, J=30.6 Hz, 1H), 7.18 (dd, J=30.3, 8.4 Hz, 1H), 5.14-5.00 (m, 1H), 4.04 (d, J=19.5 Hz, 1H), 3.94 (s, 1H), 3.78 (d, J=11.8 Hz, 1H), 3.72-3.63 (m, 1H), 3.59-3.42 (m, 4H), 3.13-3.06 (m, 4H), 2.86 (t, J=15.2 Hz, 1H), 2.79-2.54 (m, 3H), 2.17 (d, J=50.9 Hz, 3H), 2.05-1.87 (m, 2H), 1.86-1.70 (m, 2H), 1.61 (d, J=50.4 Hz, 3H), 1.35 (dt, J=36.6, 10.2 Hz, 5H), 0.78-0.61 (m, 1H), 0.48 (s, 1H). LCMS: $C_{41}H_{47}N_9O_8S$ requires: 825, found: m/z=826 $[M+H]^+$.

Example 54: Synthesis of 5-[(3R)-3-[1-(1-{[2-(2,6-dioxopiperidin-3-yl)-1,3-dioxoisoindol-5-yl]methyl}azetidin-3-yl)piperidine-4-amido]piperidin-1-yl]-3-[(3-methyl-1,2-thiazol-5-yl)amino]pyrazine-2-carboxamide (Compound 37)

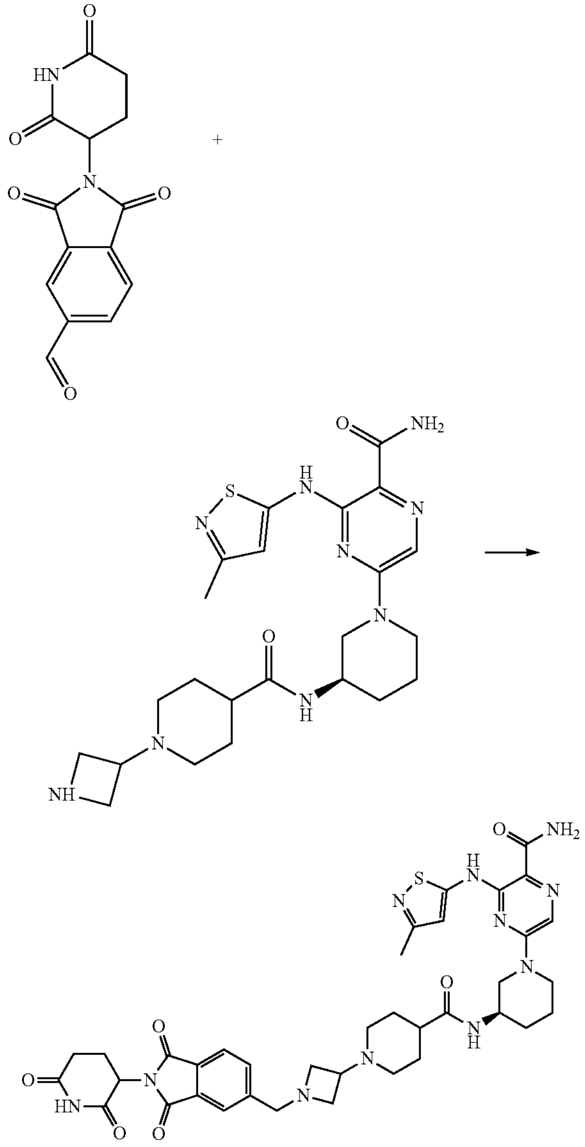

The procedure from Example 30 was followed to afford 5-[(3R)-3-[1-(1-{[2-(2,6-dioxopiperidin-3-yl)-1,3-dioxoisoindol-5-yl]methyl}azetidin-3-yl)piperidine-4-amido]piperidin-1-yl]-3-[(3-methyl-1,2-thiazol-5-yl)amino]pyrazine-2-carboxamide (5.8 mg). $^1$H NMR (500 MHz, Methanol-$d_4$) δ 8.06-7.77 (m, 4H), 7.53 (s, 1H), 6.82 (d, J=17.3 Hz, 1H), 5.23-5.09 (m, 1H), 4.57-4.32 (m, 3H), 4.25 (d, J=7.0 Hz, 2H), 4.20-3.90 (m, 2H), 3.77 (s, 1H), 3.42 (d, J=12.0 Hz, 2H), 3.32 (s, 2H), 3.18 (d, J=12.3 Hz, 1H), 3.07 (s, 1H), 3.02-2.95 (m, 1H), 2.95-2.81 (m, 2H), 2.81-2.67 (m, 2H), 2.43 (s, 1H), 2.37 (s, 1H), 2.25 (s, 2H), 2.18-2.11 (m, 1H), 2.11-1.56 (m, 5H). LCMS: $C_{37}H_{43}N_{11}O_6S$ requires: 769, found: m/z=770 $[M+H]^+$.

Example 55: Synthesis of N-[(3R)-1-{5-carbamoyl-6-[(4-methanesulfonylphenyl)amino]pyrazin-2-yl}piperidin-3-yl]-8-{1-[2-(2,6-dioxopiperidin-3-yl)-1,3-dioxoisoindol-5-yl]piperidin-4-yl}-8-azabicyclo[3.2.1]octane-3-carboxamide (Compound 41)

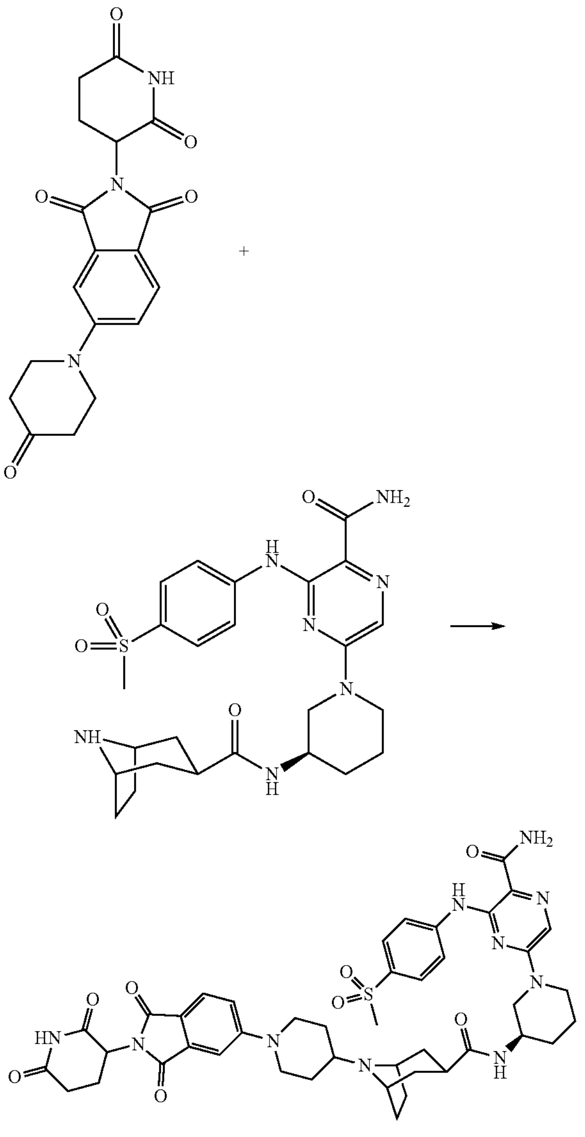

The procedure from Example 30 was followed to afford N-[(3R)-1-{5-carbamoyl-6-[(4-methanesulfonylphenyl)amino]pyrazin-2-yl}piperidin-3-yl]-8-{1-[2-(2,6-dioxopiperidin-3-yl)-1,3-dioxoisoindol-5-yl]piperidin-4-yl}-8-azabicyclo[3.2.1]octane-3-carboxamide (0.5 mg). $^1$H NM/R (500 MHz, Methanol-$d_4$) δ 7.96 (d, J=16.9 Hz, 2H), 7.86 (d, J=16.0 Hz, 1H), 7.71 (d, J=9.9 Hz, 1H), 7.55 (s, 1H), 7.43 (d, J=16.3 Hz, 2H), 7.32 (d, J=25.4 Hz, 1H), 5.08 (d, J=9.1 Hz, 2H), 4.48-4.35 (m, 1H), 4.33-3.83 (m, 7H), 3.55-3.39 (m, 3H), 3.15 (t, J=9.3 Hz, 4H), 3.00 (d, J=15.9 Hz, 2H), 2.85 (d, J=18.6 Hz, 1H), 2.75 (d, J=17.2 Hz, 3H), 2.66 (s, 1H), 2.43-2.05 (m, 5H), 1.96 (d, J=27.0 Hz, 3H), 1.85-1.50 (m, 4H), 1.29 (s, 2H). LCMS: $C_{43}H_{50}N_{10}O_8S$ requires: 866, found: m/z=867 $[M+H]^+$.

Example 56: Synthesis of 5-((3R)-3-(2-((1-(2-(2,6-dioxopiperidin-3-yl)-1,3-dioxoisoindolin-5-yl)azetidin-3-yl)methyl)-6-oxo-5-oxa-2,7-diazaspiro[3.4]octan-7-yl)piperidin-1-yl)-3-((1-methyl-1H-pyrazol-4-yl)amino)pyrazine-2-carboxamide (Compound 42)

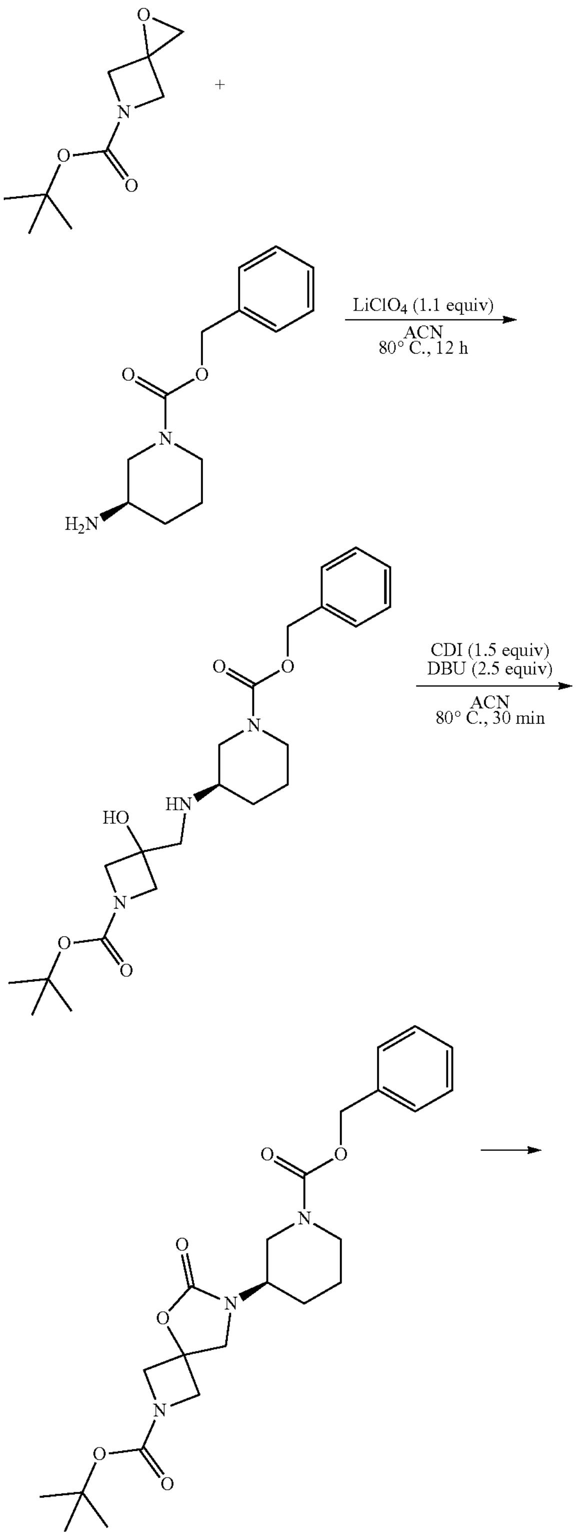

-continued

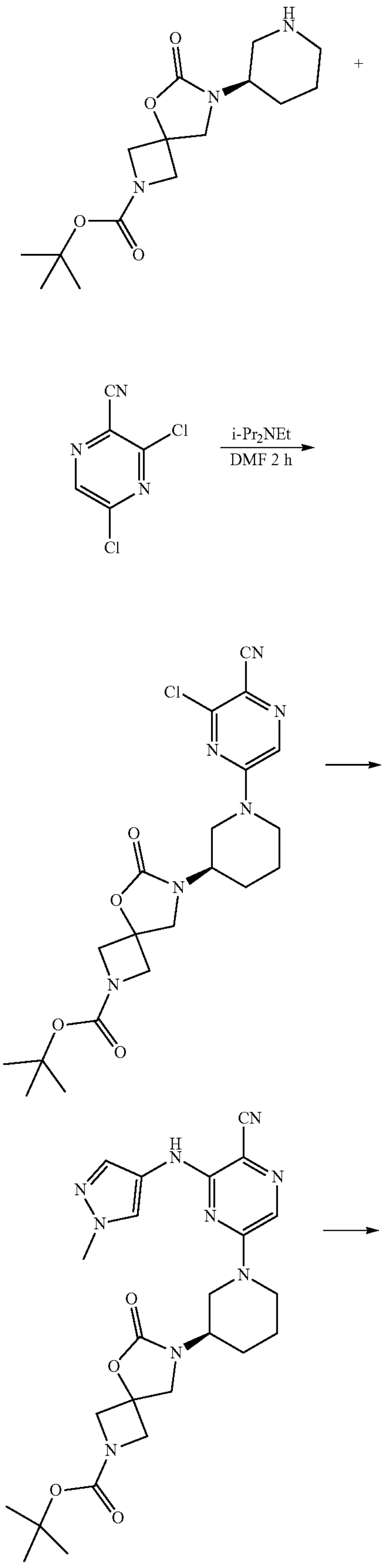

-continued

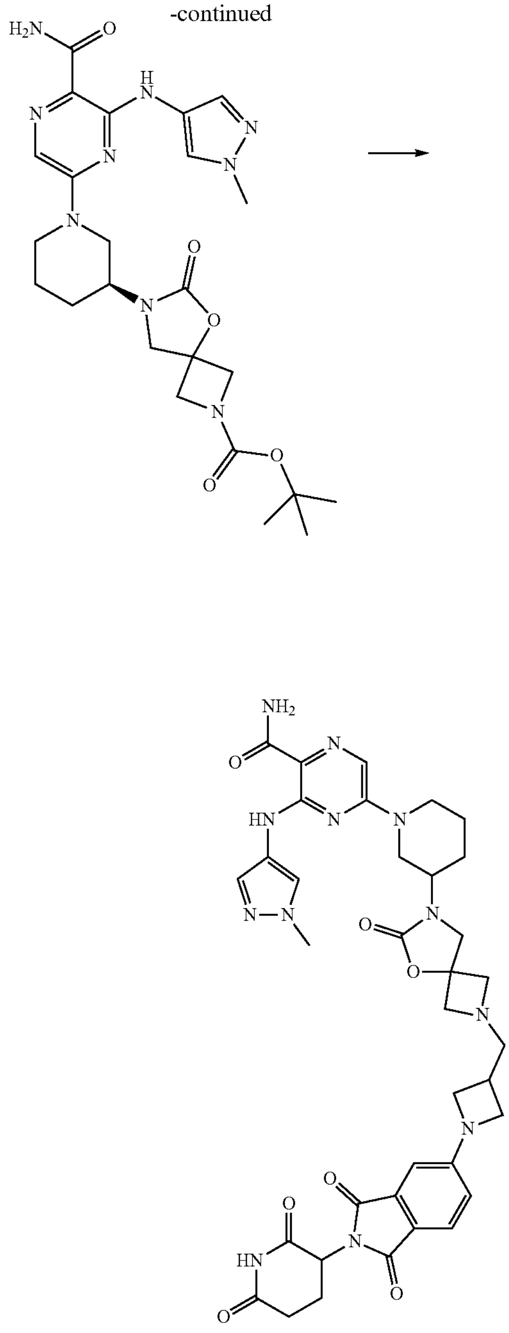

Step 1: Benzyl-(R)-3-(((1-(tert-butoxycarbonyl)-3-hydroxyazetidin-3-yl)methyl)amino)piperidine-1-carboxylate (R)-3-amino-1-N-Cbz-piperidine (253 mg, 1.08 mmol) and $LiClO_4$ (126 mg, 1.19 mmol) were added sequentially to a solution of tert-butyl-1-oxa-5-azaspiro[2.3]hexane-5-carboxylate (200 mg, 1.08 mmol) in ACN (10 mL). After stirring at 80° C. for 16 h the reaction mixture was concentrated under reduced pressure. Purification ($SiO_2$, 0-5% $MeOH/CH_2Cl_2$) afforded the desired product (441 mg). LCMS: $C_{22}H_{33}N_3O_5$ requires: 419, found: m/z=420 $[M+H]^+$.

Step 2: tert-butyl (R)-7-(1-((benzyloxy)carbonyl)piperidin-3-yl)-6-oxo-5-oxa-2,7-diazaspiro[3.4]octane-2-carboxylate CDI (255 mg, 1.57 mmol) and DBU (392 μL, 2.62 mmol) were added sequentially to a solution of benzyl (3R)-3-({[1-(tert-butoxycarbonyl)-3-hydroxyazetidin-3-yl]methyl}amino)piperidine-1-carboxylate (440 mg, 1.05 mmol) in ACN (2.6 mL). After stirring at 80° C. for 30 min, the reaction mixture was concentrated under reduced pressure. Purification ($SiO_2$, 0→5% $MeOH/CH_2Cl_2$) afforded the desired product (363 mg). LCMS: $C_{23}H_{31}N_3O_6$ requires: 445, found: m/z=446 $[M+H]^+$.

Step 3: tert-butyl (R)-6-oxo-7-(piperidin-3-yl)-5-oxa-2,7-diazaspiro[3.4]octane-2-carboxylate A solution of tert-butyl 7-[(3R)-1-[(benzyloxy)carbonyl]piperidin-3-yl]-6-oxo-5-oxa-2,7-diazaspiro[3.4]octane-2-carboxylate (363 mg, 0.81 mmol, 1 eq.) in MeOH (8.1 mL) was stirred with Pd/C (36.3 mg, 10 wt %) under a balloon of $H_2$. After stirring for 2 h, the reaction mixture was filtered through Celite and concentrated under reduced pressure to afford tert-butyl (R)-6-oxo-7-(piperidin-3-yl)-5-oxa-2,7-diazaspiro[3.4]octane-2-carboxylate. LCMS: $C_{15}H_{25}N_3O_4$ requires: 311, found: m/z=312 $[M+H]^+$.

Step 4: tert-butyl 7-[(3R)-1-(6-chloro-5-cyanopyrazin-2-yl)piperidin-3-yl]-6-oxo-5-oxa-2,7-diazaspiro[3.4]octane-2-carboxylate The procedure from Step 1 of Example 1 was followed to afford tert-butyl 7-[(3R)-1-(6-chloro-5-cyanopyrazin-2-yl)piperidin-3-yl]-6-oxo-5-oxa-2,7-diazaspiro[3.4]octane-2-carboxylate (364 mg, 2 steps). LCMS: $C_{20}H_{25}ClN_6O_4$ requires: 448, found: m/z=449 $[M+H]^+$.

Step 5: tert-butyl (R)-7-(1-(5-cyano-6-((1-methyl-1H-pyrazol-4-yl)amino)pyrazin-2-yl)piperidin-3-yl)-6-oxo-5-oxa-2,7-diazaspiro[3.4]octane-2-carboxylate The procedure from Step 2 of Example 1 was followed to afford tert-butyl (R)-7-(1-(5-cyano-6-((1-methyl-1H-pyrazol-4-yl)amino)pyrazin-2-yl)piperidin-3-yl)-6-oxo-5-oxa-2,7-diazaspiro[3.4]octane-2-carboxylate (131 mg). LCMS: $C_{24}H_{31}N_9O_4$ requires: 509, found: m/z=510 $[M+H]^+$.

Step 6: tert-butyl (R)-7-(1-(5-carbamoyl-6-((1-methyl-1H-pyrazol-4-yl)amino)pyrazin-2-yl)piperidin-3-yl)-6-oxo-5-oxa-2,7-diazaspiro[3.4]octane-2-carboxylate The procedure from Step 3 of Example 1 was followed to afford tert-butyl (R)-7-(1-(5-carbamoyl-6-((1-methyl-1H-pyrazol-4-yl)amino)pyrazin-2-yl)piperidin-3-yl)-6-oxo-5-oxa-2,7-diazaspiro[3.4]octane-2-carboxylate (121 mg). LCMS: $C_{24}H_{33}N_9O_5$ requires: 527, found: m/z=528 $[M+H]^+$.

Step 7: 5-((3R)-3-(2-((1-(2-(2,6-dioxopiperidin-3-yl)-1,3-dioxoisoindolin-5-yl)azetidin-3-yl)methyl)-6-oxo-5-oxa-2,7-diazaspiro[3.4]octan-7-yl)piperidin-1-yl)-3-((1-methyl-1H-pyrazol-4-yl)amino)pyrazine-2-carboxamide The procedure from Step 4 of Example 1 was followed to afford a crude amine that was subject to the procedure from Example 30 to afford 5-((3R)-3-(2-((1-(2-(2,6-dioxopiperidin-3-yl)-1,3-dioxoisoindolin-5-yl)azetidin-3-yl)methyl)-6-oxo-5-oxa-2,7-diazaspiro[3.4]octan-7-yl)piperidin-1-yl)-3-((1-methyl-1H-pyrazol-4-yl)amino)pyrazine-2-carboxamide (8.4 mg, 2 steps). $^1H$ NMR (500 MHz, $CD_3CN$) δ 10.72 (s, 1H), 8.91-8.84 (m, 1H), 7.84 (s, 1H), 7.60 (d, J=8.3 Hz, 1H), 7.46 (d, J=17.7 Hz, 2H), 7.34 (s, 1H), 6.76 (s, 1H), 6.59 (d, J=8.5 Hz, 1H), 5.75 (s, 1H), 4.92 (dd, J=12.2, 5.3 Hz, 1H), 4.49 (dd, J=12.6, 4.2 Hz, 1H), 4.18 (d, J=13.7 Hz, 1H), 4.08 (t, J=7.7 Hz, 2H), 3.83-3.66 (m, 6H), 3.47-3.33 (m, 4H), 3.16-3.03 (m, 2H), 2.81-2.62 (m, 5H), 2.08 (d, J=17.1 Hz, 2H), 2.01-1.96 (m, 1H), 1.92-1.75 (m, 1H), 1.66 (qt, J=11.5, 4.0 Hz, 1H). LCMS: $C_{36}H_{40}N_{12}O_7$ requires: 752, found: m/z=753 $[M+H]^+$.

Example 57: Synthesis of 5-[(3R)-3-[2-({1-[2-(2,6-dioxopiperidin-3-yl)-1,3-dioxoisoindol-5-yl]piperidin-4-yl}methyl)-6-oxo-5-oxa-2,7-diazaspiro[3.4]octan-7-yl]piperidin-1-yl]-3-[(1-methylpyrazol-4-yl)amino]pyrazine-2-carboxamide (Compound 43)

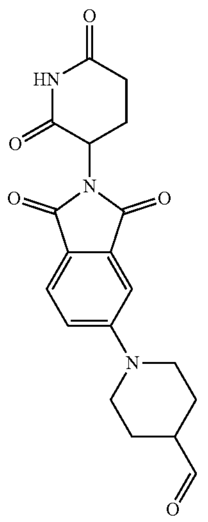

+

-continued

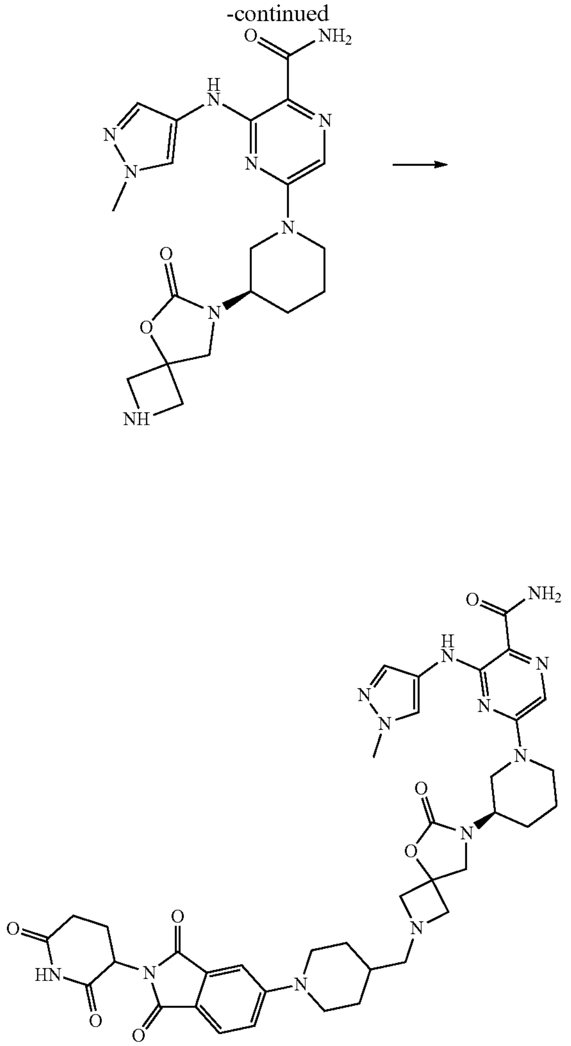

The procedure from Example 56 was followed to afford a crude amine that was subject to the procedure from Example 30 to afford 5-[(3R)-3-[2-({1-[2-(2,6-dioxopiperidin-3-yl)-1,3-dioxoisoindol-5-yl]piperidin-4-yl}methyl)-6-oxo-5-oxa-2,7-diazaspiro[3.4]octan-7-yl]piperidin-1-yl]-3-[(1-methylpyrazol-4-yl)amino]pyrazine-2-carboxamide (13.8 mg, 2 steps). $^{1}$H NMR (500 MHz, Acetonitrile-$d_3$) δ 10.74 (s, 1H), 8.94 (s, 1H), 7.87 (s, 1H), 7.65 (d, J=8.6 Hz, 1H), 7.50 (s, 1H), 7.47 (d, J=0.8 Hz, 1H), 7.37 (s, 1H), 7.31 (d, J=2.4 Hz, 1H), 7.17 (dd, J=8.7, 2.4 Hz, 1H), 5.79 (s, 1H), 5.07-4.88 (m, 1H), 4.50 (d, J=12.8 Hz, 1H), 4.19 (d, J=13.6 Hz, 1H), 4.00 (d, J=13.1 Hz, 2H), 3.84 (s, 3H), 3.78 (dd, J=19.2, 10.2 Hz, 2H), 3.45 (d, J=8.1 Hz, 1H), 3.39 (d, J=8.1 Hz, 1H), 3.34 (d, J=8.1 Hz, 1H), 3.31-3.25 (m, 1H), 3.17 (dd, J=12.9, 10.4 Hz, 1H), 3.14-3.07 (m, 1H), 2.97 (td, J=12.8, 2.7 Hz, 2H), 2.87-2.63 (m, 3H), 2.39 (d, J=6.9 Hz, 2H), 2.31-2.26 (m, 1H), 2.15-2.08 (m, 1H), 1.91 (dt, J=13.3, 3.5 Hz, 1H), 1.88-1.84 (m, 0H), 1.81 (dd, J=12.1, 3.6 Hz, 3H), 1.70 (tt, J=11.1, 3.9 Hz, 1H), 1.61 (dtd, J=11.6, 7.4, 4.0 Hz, 1H), 0.90 (dq, J=7.8, 6.0, 5.5 Hz, 3H). LCMS: $C_{38}H_{44}N_{12}O_7$ requires: 780, found: m/z=781 $[M+H]^+$.

Example 58: Synthesis of 5-[(3R)-3-(2-{1-[2-(2,6-dioxopiperidin-3-yl)-1,3-dioxoisoindol-5-yl]piperidin-4-yl}-6-oxo-5-oxa-2,7-diazaspiro[3.4]octan-7-yl)piperidin-1-yl]-3-[(1-methylpyrazol-4-yl)amino]pyrazine-2-carboxamide (Compound 44)

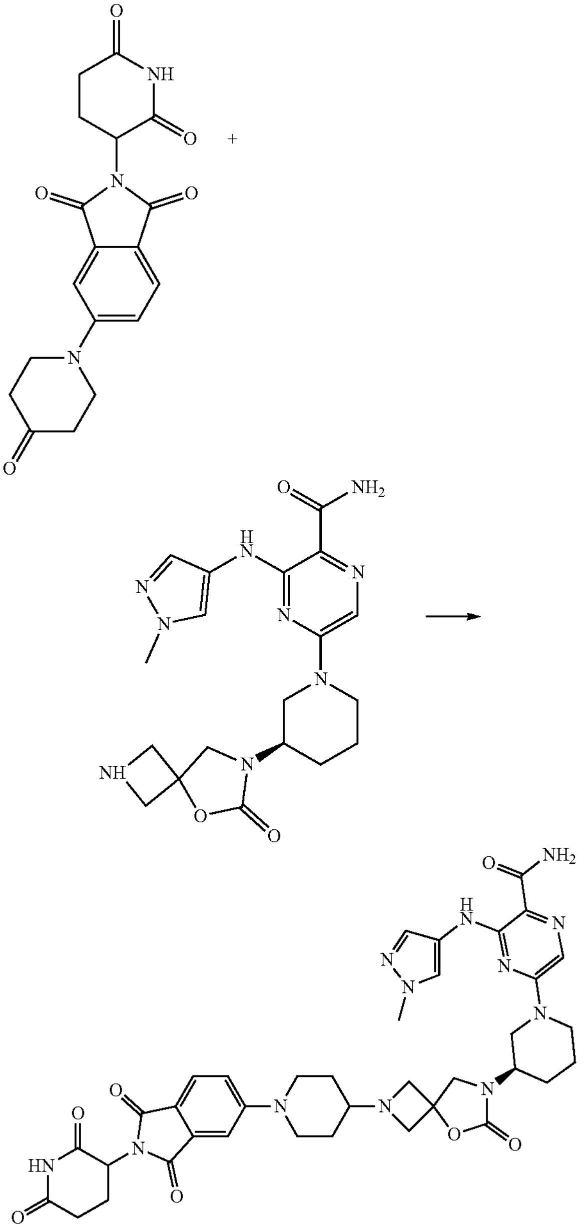

The procedure from Example 56 was followed to afford a crude amine that was subject to the procedure from Example 30 to afford 5-[(3R)-3-(2-{1-[2-(2,6-dioxopiperidin-3-yl)-1,3-dioxoisoindol-5-yl]piperidin-4-yl}-6-oxo-5-oxa-2,7-diazaspiro[3.4]octan-7-yl)piperidin-1-yl]-3-[(1-methylpyrazol-4-yl)amino]pyrazine-2-carboxamide (9.5 mg, 2 steps). $^{1}$H NMR (500 MHz, Acetonitrile-$d_3$) δ 10.71 (s, 1H), 8.90 (s, 1H), 7.84 (s, 1H), 7.63 (d, J=8.5 Hz, 1H), 7.47 (s, 1H), 7.44 (s, 1H), 7.34 (s, 1H), 7.28 (d, J=2.4 Hz, 1H), 7.15 (dd, J=8.6, 2.4 Hz, 1H), 5.75 (s, 1H), 4.93 (dd, J=12.3, 5.4 Hz, 1H), 4.50 (dd, J=13.1, 4.1 Hz, 1H), 4.18 (d, J=13.6 Hz, 1H), 3.81 (s, 3H), 3.81-3.66 (m, 3H), 3.44 (d, J=8.0 Hz, 1H), 3.40 (d, J=8.0 Hz, 1H), 3.34 (d, J=7.9 Hz, 1H), 3.31 (d, J=7.8 Hz, 1H), 3.17-3.00 (m, 4H), 2.83-2.60 (m, 3H), 2.36 (tt, J=8.3, 3.7 Hz, 1H), 2.12-2.05 (m, 2H), 1.96 (s, 1H), 1.87 (dq, J=13.4, 3.3 Hz, 1H), 1.79 (ddd, J=16.5, 10.2, 4.2 Hz, 3H), 1.70-1.59 (m, 1H), 1.33 (qd, J=9.6, 5.0 Hz, 1H), 0.87 (dt, J=11.1, 5.7 Hz, 2H). LCMS: $C_{37}H_{42}N_{12}O_7$ requires: 766, found: m/z=767 $[M+H]^+$.
Example 59: Synthesis of 5-[(3R)-3-[8-({1-[2-(2,6-dioxopiperidin-3-yl)-1,3-dioxoisoindol-5-yl]piperidin-4-yl}methyl)-1-oxo-2,8-diazaspiro[4.5]decan-2-yl]piperidin-1-yl]-3-[(1-methylpyrazol-4-yl)amino]pyrazine-2-carboxamide (Compound 48)
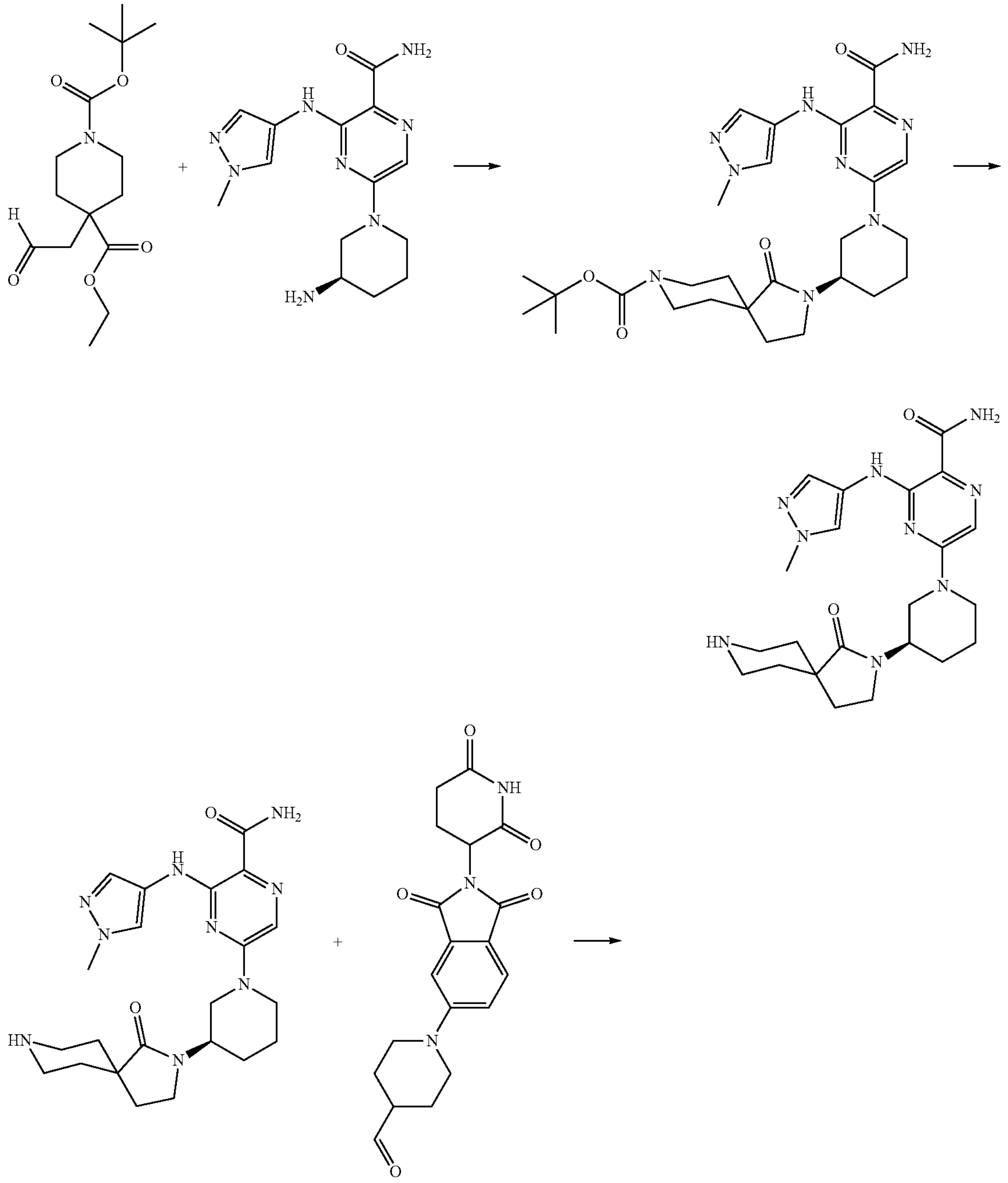

-continued

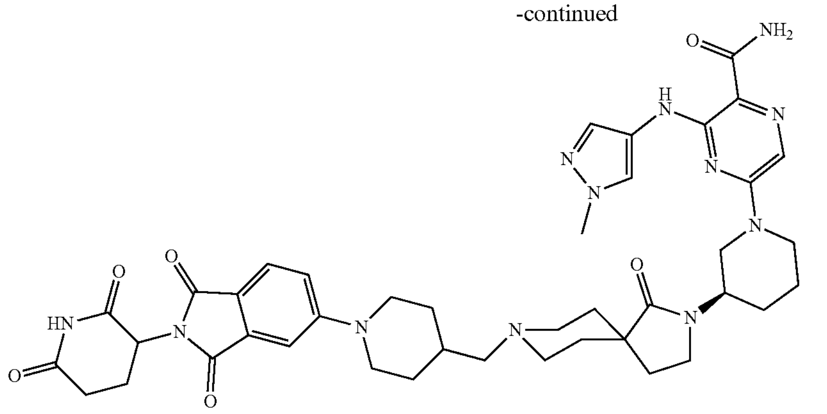

Step 1

A mixture of 1-(tert-butyl) 4-ethyl 4-(2-oxoethyl)piperidine-1,4-dicarboxylate (23.7 mg, 79 μmol) and (R)-5-(3-aminopiperidin-1-yl)-3-((1-methyl-1H-pyrazol-4-yl)amino)pyrazine-2-carboxamide (41 mg, 103 μmol, TFA salt) was dissolved in DCE (1 mL) and stirred at rt for 5 min before $NaBH(OAc)_3$ (33 mg, 160 μmol) was added in one portion. After 16 h the mixture was diluted with $CH_2Cl_2$ and $NaHCO_3$ (sat. aq.) and the aqueous phase was extracted (3×5 mL $CH_2Cl_2$). The combined organic extracts were dried ($Na_2SO_4$), filtered, and concentrated. The crude residue was purified (RP-HPLC) to afford tert-butyl (R)-2-(1-(5-carbamoyl-6-((1-methyl-1H-pyrazol-4-yl)amino)pyrazin-2-yl)piperidin-3-yl)-1-oxo-2,8-diazaspiro[4.5]decane-8-carboxylate (44 mg).

Step 2

The procedure from Step 4 of Example 1 was followed to afford a crude amine that was then subjected to the procedure from Example 30 to afford 5-[(3R)-3-[8-({1-[2-(2,6-dioxopiperidin-3-yl)-1,3-dioxoisoindol-5-yl]piperidin-4-yl}methyl)-1-oxo-2,8-diazaspiro[4.5]decan-2-yl]piperidin-1-yl]-3-[(1-methylpyrazol-4-yl)amino]pyrazine-2-carboxamide (10 mg, 2 steps). $^1H$ NMR (500 MHz, Acetonitrile-$d_3$) δ 10.73 (s, 1H), 8.86 (s, 1H), 7.84 (s, 1H), 7.63 (d, J=8.5 Hz, 1H), 7.48 (s, 1H), 7.44 (s, 1H), 7.34 (s, 1H), 7.29 (d, J=2.3 Hz, 1H), 7.15 (dd, J=8.6, 2.4 Hz, 1H), 5.72 (s, 1H), 4.93 (dd, J=12.1, 5.4 Hz, 1H), 4.44 (d, J=13.1 Hz, 1H), 4.24 (d, J=13.2 Hz, 1H), 4.00 (d, J=13.0 Hz, 2H), 3.96-3.87 (m, 1H), 3.84 (s, 3H), 3.44-3.27 (m, 2H), 3.10-2.90 (m, 4H), 2.87-2.75 (m, 1H), 2.75-2.60 (m, 3H), 2.18 (d, J=6.9 Hz, 2H), 2.11-1.98 (m, 8H), 1.91-1.72 (m, 5H), 1.65 (d, J=12.9 Hz, 2H), 1.39 (d, J=13.0 Hz, 2H), 1.21 (d, J=12.4 Hz, 2H). LCMS: C41H50N12O6 requires: 806, found: m/z=807 [M+H]$^+$.

Example 60: Synthesis of 5-[(3R)-3-(8-{1-[2-(2,6-dioxopiperidin-3-yl)-1,3-dioxoisoindol-5-yl]piperidin-4-yl}-1-oxo-2,8-diazaspiro[4.5]decan-2-yl)piperidin-1-yl]-3-[(1-methylpyrazol-4-yl)amino]pyrazine-2-carboxamide (Compound 49)

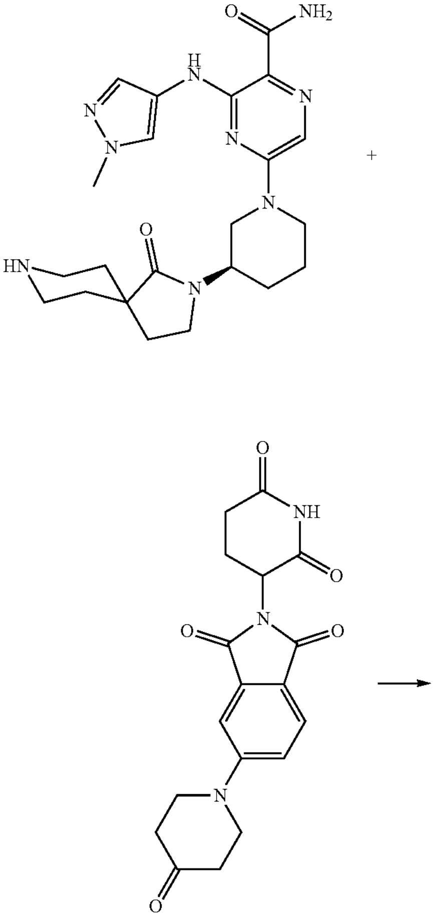

-continued

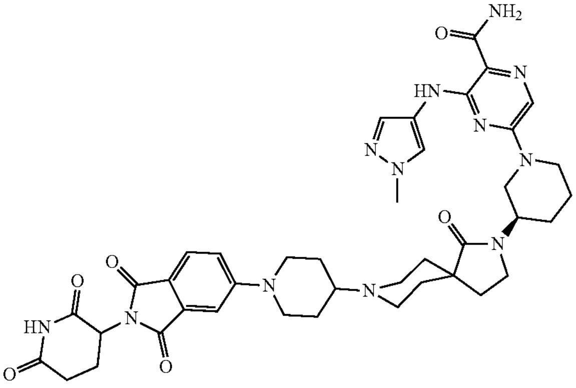

The procedure from Example 59 was followed to afford a crude amine that was subject to the procedure from Example 30 to afford 5-[(3R)-3-(8-{1-[2-(2,6-dioxopiperidin-3-yl)-1,3-dioxoisoindol-5-yl]piperidin-4-yl}-1-oxo-2,8-diazaspiro[4.5]decan-2-yl)piperidin-1-yl]-3-[(1-methylpyrazol-4-yl)amino]pyrazine-2-carboxamide (8 mg, 2 steps). $^1$H NMR (500 MHz, Acetonitrile-$d_3$) δ 10.72 (s, 1H), 8.86 (s, 1H), 7.83 (s, 1H), 7.63 (d, J=8.6 Hz, 1H), 7.47 (s, 1H), 7.45 (s, 1H), 7.34 (s, 1H), 7.29 (d, J=2.4 Hz, 1H), 7.16 (dd, J=8.6, 2.4 Hz, 1H), 5.72 (s, 1H), 4.93 (dd, J=12.2, 5.4 Hz, 1H), 4.43 (d, J=16.5 Hz, 1H), 4.24 (d, J=13.4 Hz, 1H), 4.03 (d, J=13.1 Hz, 2H), 3.97-3.87 (m, 1H), 3.82 (d, J=1.7 Hz, 3H), 3.42-3.27 (m, 2H), 3.01 (p, J=12.0 Hz, 4H), 2.90 (s, 2H), 2.81-2.64 (m, 5H), 2.60 (s, 2H), 2.33 (s, 2H), 2.11-2.04 (m, 1H), 1.90-1.70 (m, 5H), 1.62 (dd, J=24.9, 11.7 Hz, 4H), 1.43 (s, 2H). LCMS: $C_{40}H_{48}N_{12}O_6$ requires: 792, found: m/z=792 [M+H]$^+$.

Example 61: Synthesis of 5-[(3R)-3-[8-({1-[2-(2,6-dioxopiperidin-3-yl)-1,3-dioxoisoindol-5-yl]azetidin-3-yl}methyl)-1-oxo-2,8-diazaspiro[4.5]decan-2-yl]piperidin-1-yl]-3-[(1-methylpyrazol-4-yl)amino]pyrazine-2-carboxamide (Compound 50)

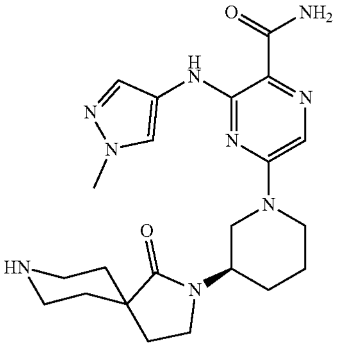

+

-continued

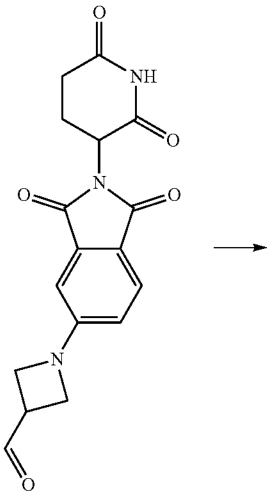

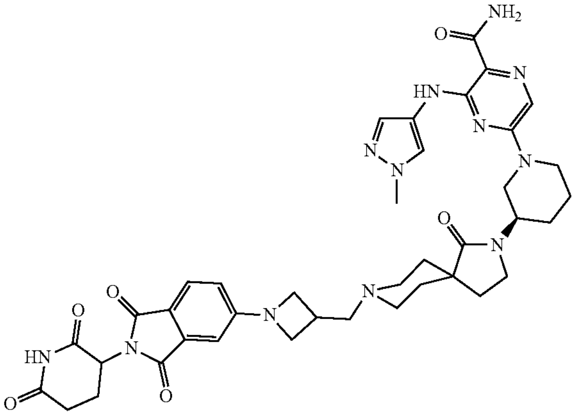

The procedure from Example 59 was followed to afford a crude amine that was subject to the procedure from Example 30 to afford 5-[(3R)-3-[8-({1-[2-(2,6-dioxopiperidin-3-yl)-1,3-dioxoisoindol-5-yl]azetidin-3-yl}methyl)-1-oxo-2,8-diazaspiro[4.5]decan-2-yl]piperidin-1-yl]-3-[(1-methylpyrazol-4-yl)amino]pyrazine-2-carboxamide (10.3 mg). $^1$H NMR (500 MHz, Acetonitrile-$d_3$) δ 10.73 (s, 1H), 8.86 (s, 1H), 7.82 (s, 1H), 7.60 (d, J=8.2 Hz, 1H), 7.47 (d, J=6.8 Hz, 2H), 7.34 (s, 1H), 6.76 (d, J=2.2 Hz, 1H), 6.60 (dd, J=8.4, 2.2 Hz, 1H), 5.73 (s, 1H), 4.92 (dd, J=12.2, 5.3 Hz, 1H), 4.44 (d, J=13.0 Hz, 1H), 4.24 (d, J=13.0 Hz, 1H), 4.15 (t, J=8.1 Hz, 2H), 3.92 (ddt, J=10.8, 8.3, 4.1 Hz, 1H), 3.84 (s, 3H), 3.74 (s, 2H), 3.45-3.31 (m, 2H), 3.28 (s, 3H), 3.12-2.97 (m, 3H), 2.84 (d, J=38.6 Hz, 1H), 2.79-2.62 (m, 4H), 1.92-1.76 (m, 7H), 1.65 (d, J=12.6 Hz, 1H), 1.39 (d, J=49.0 Hz, 1H), 0.88 (d, J=6.5 Hz, 3H). LCMS: $C_{39}H_{46}N_{12}O_6$ requires: 778, found: m/z=779 [M+H]$^+$.

Example 62: Synthesis of 5-[(3R)-3-(3-{3-[2-(2,6-dioxopiperidin-3-yl)-1-oxo-3H-isoindol-4-yl]propoxy}propanamido)piperidin-1-yl]-3-[(3-methyl-1,2-thiazol-5-yl)amino]pyrazine-2-carboxamide (Compound 45)

Step 1: Methyl 3-bromo-2-(bromomethyl)benzoate

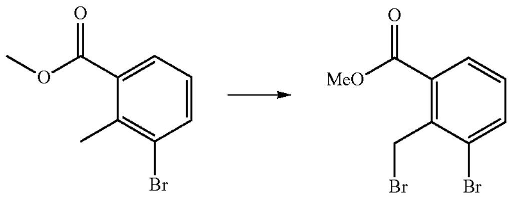

To a solution of methyl 3-bromo-2-methyl-benzoate (50 g, 218 mmol), NBS (46.6 g, 262 mmol) in $CHCl_3$ (400 mL) was added AIBN (3.58 g, 21.8 mmol). The mixture was stirred at 70° C. for 12 h. The reaction mixture was concentrated in vacuum, diluted with DCM (400 mL), washed with $H_2O$ (100 mL) and brine (100 mL), extracted with DCM (100 mL), and washed with brine (50 mL) again. The organic phase was combined, dried over $Na_2SO_4$, and concentrated in vacuum. The residue was purified ($SiO_2$, 0→100% EtOAc/Hexanes) to yield 3-bromo-2-(bromomethyl)benzoate (63 g) as a light yellow solid.

Step 2: 3-(4-bromo-1-oxo-isoindolin-2-yl)piperidine-2,6-dione

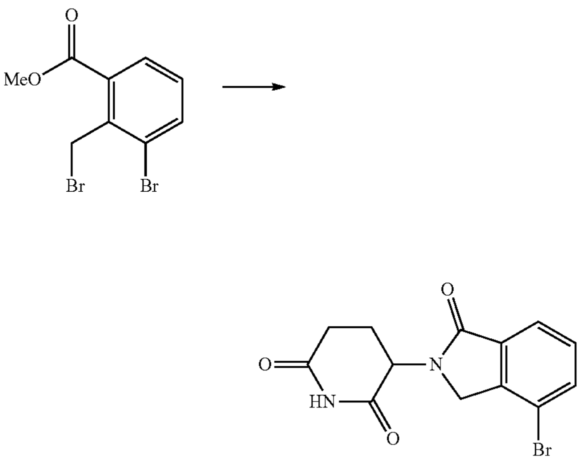

To a solution of methyl 3-bromo-2-(bromomethyl)benzoate (88.2 g, 287 mmol) in ACN (600 mL) was added $i\text{-}Pr_2NEt$ (66.4 mL, 381 mmol) and 3-aminopiperidine-2,6-dione hydrochloride (51 g, 310 mmol). The mixture was stirred at 80° C. for 16 hr. The reaction mixture was filtered and the filter cake was triturated by with $EtOAc/H_2O$ (300 mL, 1:2 $EtOAc/H_2O$) to yield 3-(4-bromo-1-oxo-isoindolin-2-yl)piperidine-2,6-dione (56.5 g) as a purple powder. LCMS: $C_{13}H_{11}BrN_2O_3$ requires: 322, found: m/z=323 $[M+H]^+$.

Step 3: tert-butyl 3-(prop-2-yn-1-yloxy)propanoate

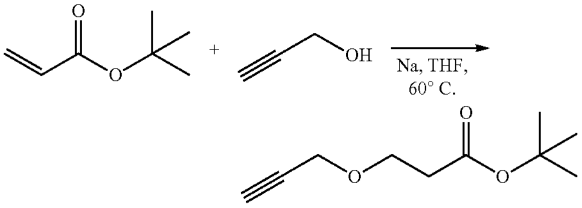

A mixture of Na (108 mg, 4.68 mmol) and prop-2-yn-1-ol (6.6 g, 117 mmol) in anhydrous THF (60 mL) was stirred at 60° C. for 15 min under nitrogen atmosphere. The mixture was then cooled to room temperature and was added tert-butyl acrylate (10.0 g, 78.0 mmol). The resulting solution was stirred at room temperature for 16 h. The reaction was quenched by the addition of water, and then extracted with ethyl acetate. The combined organic layer was washed with brine, dried over anhydrous $Na_2SO_4$, filtered and concentrated under vacuum. The residue was purified ($SiO_2$, 0→10% EtOAc/Hexanes) to afford tert-butyl 3-(prop-2-yn-1-yloxy)propanoate (7.8 g) as a colorless oil. $^1H$ NMR (400 MHz, DMSO-$d_6$) δ 4.12 (d, J=2.4 Hz, 2H), 3.63 (t, J=6.2 Hz, 2H), 3.43 (t, J=2.4 Hz, 1H), 2.45 (t, J=6.2 Hz, 2H), 1.41 (s, 9H). LCMS: $C_{10}H_{16}O_3$ requires: 184, found: m/z=185 $[M+H]^+$.

Step 4: tert-butyl 3-((3-(2-(2,6-dioxopiperidin-3-yl)-1-oxoisoindolin-4-yl)prop-2-yn-1-yl)oxy)propanoate

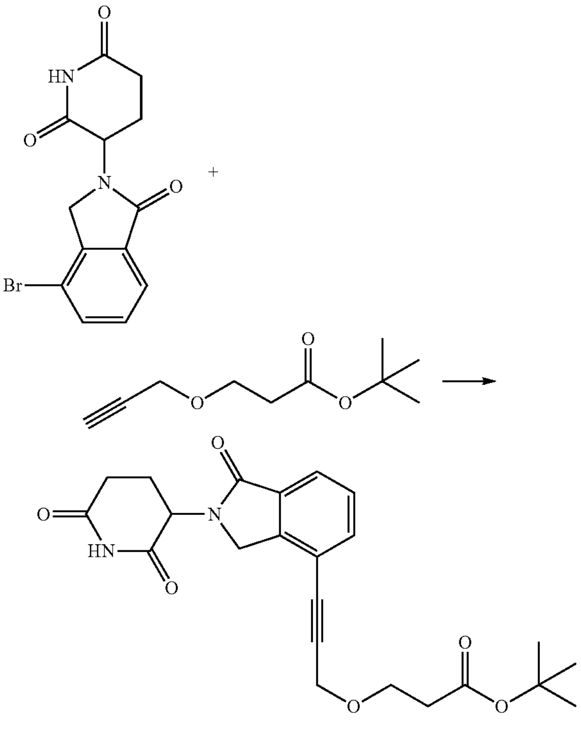

A mixture of 3-(4-bromo-1-oxo-2,3-dihydro-1H-isoindol-2-yl)piperidine-2,6-dione (1.22 g, 3.80 mmol), $(PPh_3)_2PdCl_2$ (160 mg, 228 μmol), CuI (72.2 mg, 380 μmol), tert-butyl-3-(prop-2-yn-1-yloxy)propanoate (1.41 g, 7.60 mmol) were added to a vial. The vial was evacuated and backfilled with $N_2$ 5 times. DMF (20 mL) and triethylamine (6.35 mL, 45.6 mmol) were added and the mixture was allowed to stir at 90° C. overnight. The mixture was filtered through celite and the filter cake was washed with MeOH and EtOAc. The filtrate was diluted with EtOAc and brine and the organic layer was removed. The organic phase was dried ($MgSO_4$), filtered, concentrated and purified by reverse phase MPLC (5→100% MeCN in $H_2O$) to afford tert-butyl 3-((3-(2-(2,6-dioxopiperidin-3-yl)-1-oxoisoindolin-4-yl)prop-2-yn-1-yl)oxy)propanoate (347 mg). LCMS: $C_{23}H_{26}N_2O_6$ requires: 426, found: m/z=427 $[M+H]^+$.

Step 5: tert-butyl 3-(3-(2-(2,6-dioxopiperidin-3-yl)-1-oxoisoindolin-4-yl)propoxy)propanoate

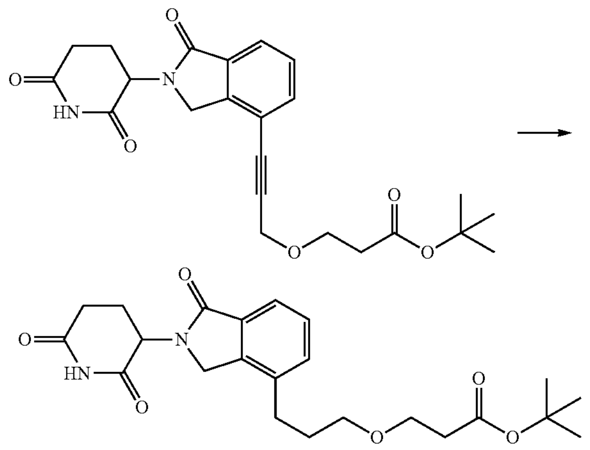

A mixture of tert-butyl 3-((3-(2-(2,6-dioxopiperidin-3-yl)-1-oxoisoindolin-4-yl)prop-2-yn-1-yl)oxy)propanoate (350 mg, 0.81 mmol), Pd/C 10 wt % (81 μmmol) and EtOH were mixed in a flask. The flask was evacuated and backfilled with $H_2$ 5 times and allowed to stir at rt for 2 h. The mixture was filtered through celite and concentrated to afford tert-butyl 3-(3-(2-(2,6-dioxopiperidin-3-yl)-1-oxoisoindolin-4-yl)propoxy)propanoate (350 mg). LCMS: $C_{23}H_{30}N_2O_6$ requires: 430, found: m/z=431 $[M+H]^+$.

Step 6: 3-(3-(2-(2,6-dioxopiperidin-3-yl)-1-oxoisoindolin-4-yl)propoxy)propanoic acid

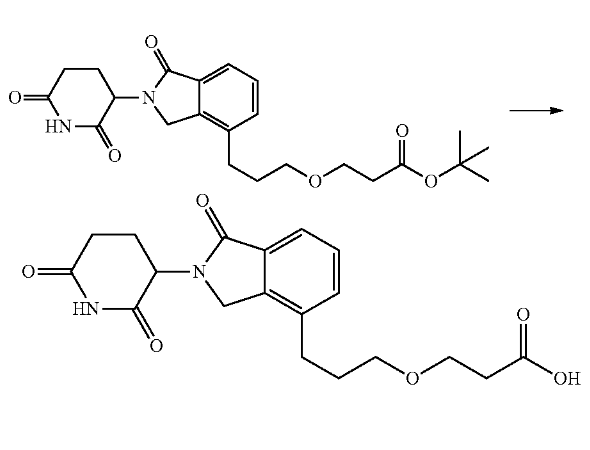

A mixture of tert-butyl 3-(3-(2-(2,6-dioxopiperidin-3-yl)-1-oxoisoindolin-4-yl)propoxy)propanoate (350 mg, 99%), $CH_2Cl_2$ (2 mL), and TFA (2 mL) was allowed to stir at rt for 2 h. The mixture was concentrated to afford 3-(3-(2-(2,6-dioxopiperidin-3-yl)-1-oxoisoindolin-4-yl)propoxy)propanoic acid (304 mg). LCMS: $C_{19}H_{22}N_2O_6$ requires: 374, found: m/z=375 $[M+H]^+$.

Step 7: 5-[(3R)-3-(3-{3-[2-(2,6-dioxopiperidin-3-yl)-1-oxo-3H-isoindol-4-yl]propoxy}propanamido)piperidin-1-yl]-3-[(3-methyl-1,2-thiazol-5-yl)amino]pyrazine-2-carboxamide

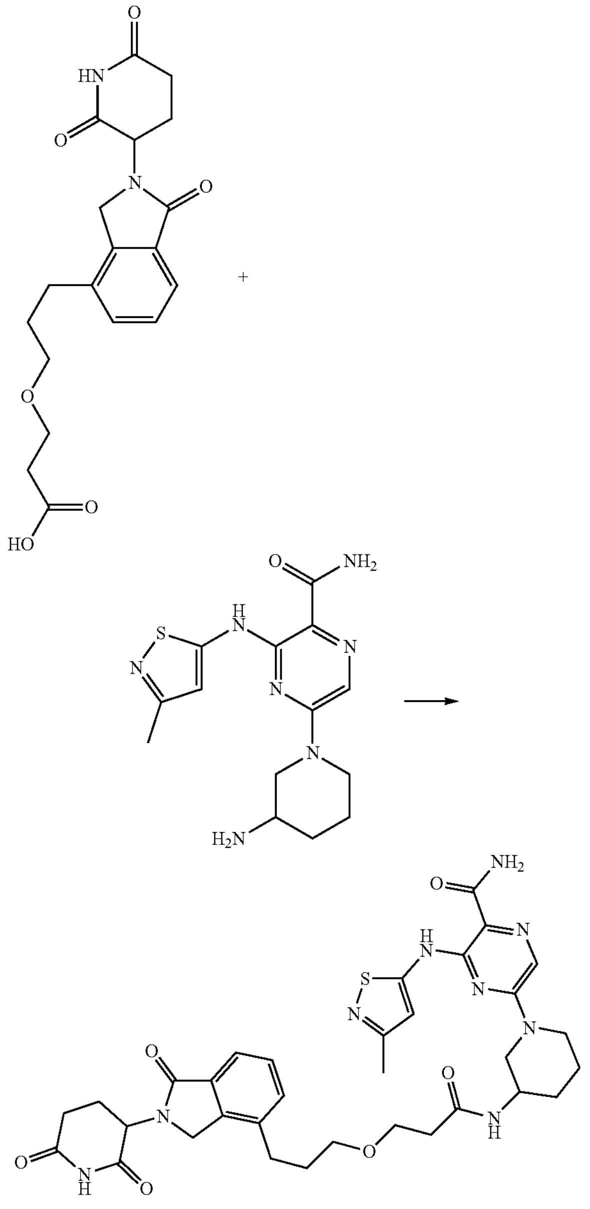 [SMILES: O=C(O)CCOCCCc1cccc2c1CN(C1CCC(=O)NC1=O)C2=O ; Cc1cc(Nc2nc(N3CCCC(N)C3)cnc2C(N)=O)sn1 ; Cc1cc(Nc2nc(N3CCCC(NC(=O)CCOCCCc4cccc5c4CN(C4CCC(=O)NC4=O)C5=O)C3)cnc2C(N)=O)sn1]

The general procedure from step 5 of Example 65 was followed starting with 3-(3-(2-(2,6-dioxopiperidin-3-yl)-1-oxoisoindolin-4-yl)propoxy)propanoic acid to afford 5-[(3R)-3-(3-{3-[2-(2,6-dioxopiperidin-3-yl)-1-oxo-3H-isoindol-4-yl]propoxy}propanamido)piperidin-1-yl]-3-[(3- methyl-1,2-thiazol-5-yl)amino]pyrazine-2-carboxamide (20 mg). $^1$H NMR (500 MHz, Methanol-$d_4$) δ 7.60 (dt, J=12.7, 5.3 Hz, 4H), 7.44 (d, J=6.9 Hz, 2H), 7.39 (t, J=7.6 Hz, 1H), 7.36-7.26 (m, 1H), 6.91 (d, J=7.2 Hz, 1H), 6.85 (d, J=12.7 Hz, 1H), 5.27-5.03 (m, 2H), 4.58-4.24 (m, 6H), 4.22-3.91 (m, 3H), 3.85 (t, J=17.9 Hz, 0H), 3.74 (dt, J=12.4, 6.1 Hz, 1H), 3.61 (t, J=6.2 Hz, 1H), 3.53-3.39 (m, 1H), 2.95-2.60 (m, 3H), 2.59-2.30 (m, 4H), 2.30-2.09 (m, 1H), 1.93 (d, J=9.5 Hz, 2H), 1.86-1.52 (m, 2H). LCMS: $C_{33}H_{39}N_9O_6S$ requires 689, found: m/z=690 [M+H]$^+$.

Example 63: Synthesis of 5-[(3R)-3-(3-{3-[2-(2,6-dioxopiperidin-3-yl)-1-oxo-3H-isoindol-4-yl] propoxy}propanamido)piperidin-1-yl]-3-[(4-methanesulfonylphenyl)amino] pyrazine-2-carboxamide (Compound 47)

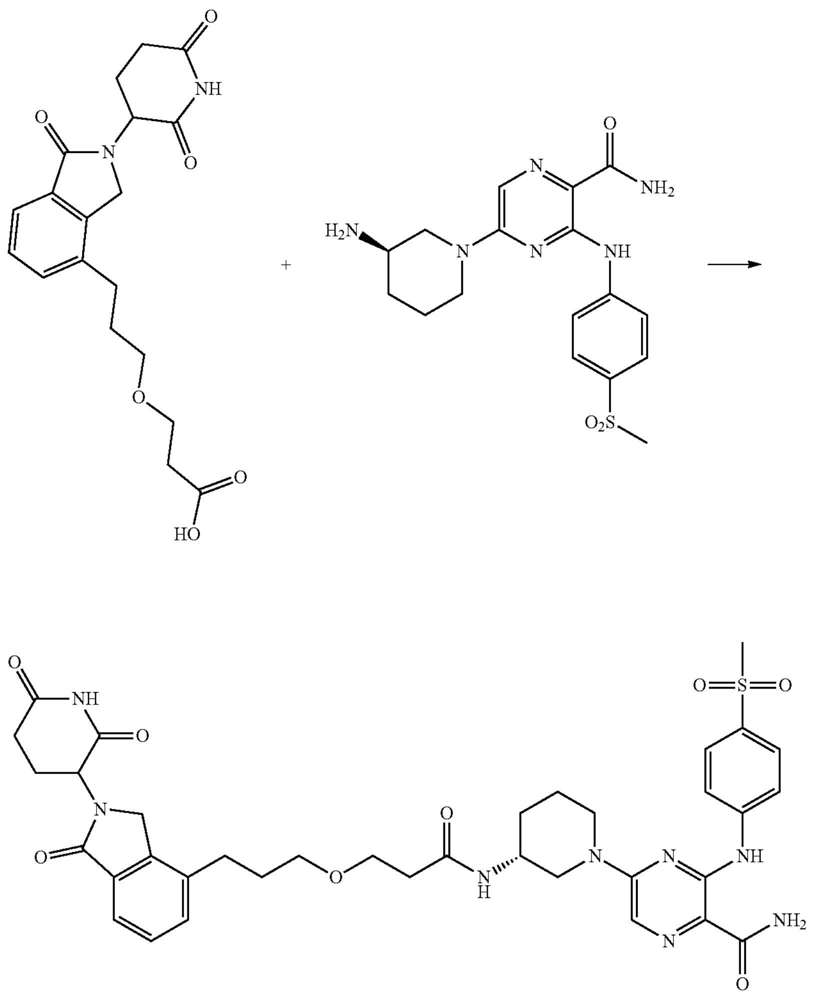

3-{3-[2-(2,6-dioxopiperidin-3-yl)-1-oxo-3H-isoindol-4-yl]propoxy}propanoic acid (24.7 mg, 0.07 mmol) was dissolved in DMF (0.5 mL) and (1,2,3-benzotriazol-1-yloxy) tris(dimethylamino)phosphonium; hexafluoro-lambda5-phosphamide (34.5 mg, 0.08 mmol) was added before adding N,N-diisopropylethylamine (0.05 mL, 0.30 mmol) at rt. After 5 min, crude (R)-5-(3-aminopiperidin-1-yl)-3-((4-(methylsulfonyl)phenyl)amino)pyrazine-2-carboxamide (20 mg, 0.06 mmol) was added as a solution in DMF (0.5 mL). The mixture was stirred for 30 min before being filtered and purified (RP-HPLC, 10-90% MeCN in H2O with 0.1% TFA) to afford 5-((R)-3-(3-(3-(2-((RS)-2,6-dioxopiperidin-3-yl)-1-oxoisoindolin-4-yl)propoxy)propanamido)piperidin-1-yl)-3-((4-(methylsulfonyl)phenyl)amino)pyrazine-2-carboxamide (20 mg). $^1$H NMR (500 MHz, Methanol-$d_4$) δ 7.60 (dt, J=12.7, 5.3 Hz, 4H), 7.44 (d, J=6.9 Hz, 2H), 7.39 (t, J=7.6 Hz, 1H), 7.36-7.26 (m, 1H), 6.91 (d, J=7.2 Hz, 1H), 6.85 (d, J=12.7 Hz, 1H), 5.27-5.03 (m, 2H), 4.58-4.24 (m, 6H), 4.22-3.91 (m, 3H), 3.85 (t, J=17.9 Hz, 0H), 3.74 (dt, J=12.4, 6.1 Hz, 1H), 3.61 (t, J=6.2 Hz, 1H), 3.53-3.39 (m, 1H), 2.95-2.60 (m, 3H), 2.59-2.30 (m, 4H), 2.30-2.09 (m, 1H), 1.93 (d, J=9.5 Hz, 2H), 1.86-1.52 (m, 2H). LCMS: $C_{33}H_{39}N_9O_6S$ requires 689, found: m/z=690 [M+H]$^+$.

Example 64: Synthesis of 5-[(3R)-3-{7-[2-(2,6-dioxopiperidin-3-yl)-1-oxo-3H-isoindol-4-yl]heptanamido}piperidin-1-yl]-3-[(4-methanesulfonylphenyl)amino]pyrazine-2-carboxamide (Compound 5)

Step 1: benzyl 6-[2-(2,6-dioxopiperidin-3-yl)-1-oxo-3H-isoindol-4-yl]hex-5-ynoate

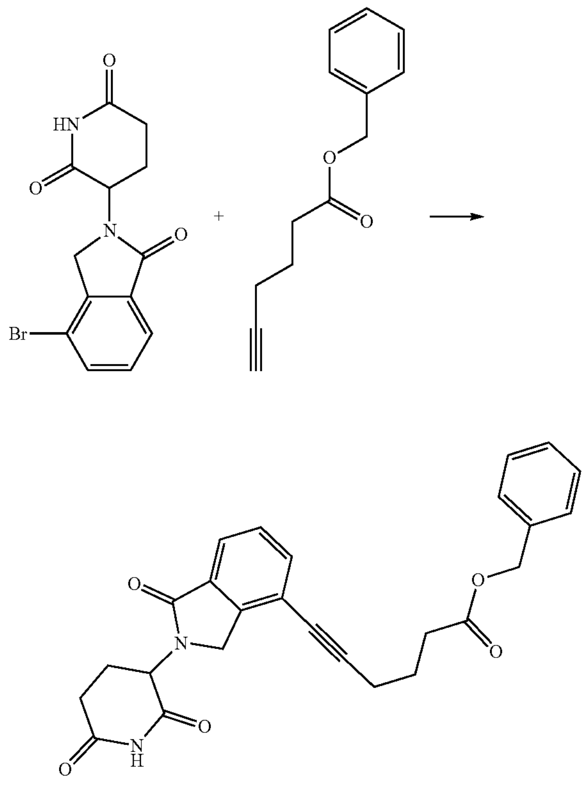

The general procedure from Step 4 of Example 62 was followed starting with benzyl hex-5-ynoate to afford benzyl 6-[2-(2,6-dioxopiperidin-3-yl)-1-oxo-3H-isoindol-4-yl]hex-5-ynoate (55 mg). LCMS: $C_{26}H_{24}N_2O_5$ requires: 444, found: m/z=445 $[M+H]^+$.

Step 2: 7-[2-(2,6-dioxopiperidin-3-yl)-1-oxo-3H-isoindol-4-yl]heptanoic acid

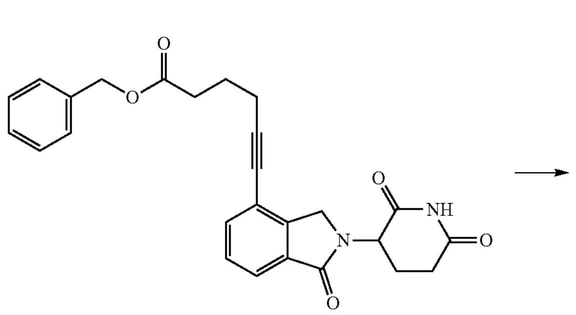

-continued

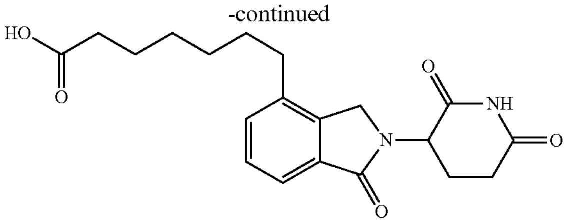

The general procedure from Step 5 of Example 62 was followed to afford 7-[2-(2,6-dioxopiperidin-3-yl)-1-oxo-3H-isoindol-4-yl]heptanoic acid (51 mg). LCMS: $C_{20}H_{24}N_2O_5$ requires: 372, found: m/z=373 $[M+H]^+$.

Step 3. 5-[(3R)-3-{7-[2-(2,6-dioxopiperidin-3-yl)-1-oxo-3H-isoindol-4-yl]heptanamido}piperidin-1-yl]-3-[(4-methanesulfonylphenyl)amino]pyrazine-2-carboxamide

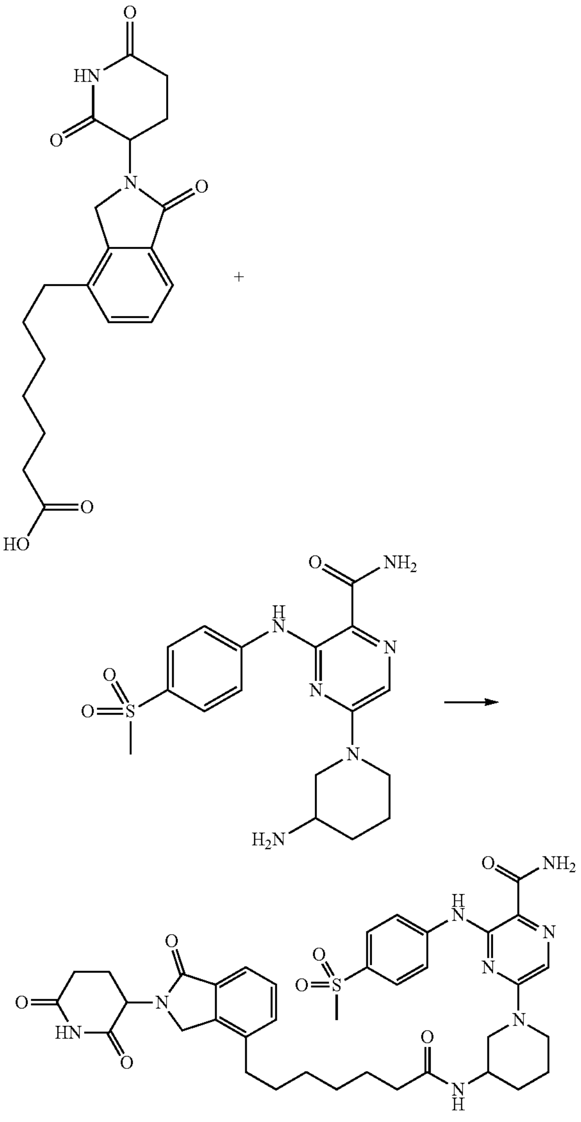

The general procedure from Step 5 of Example 65 was followed starting with 7-[2-(2,6-dioxopiperidin-3-yl)-1- oxo-3H-isoindol-4-yl]heptanoic acid to afford 5-[(3R)-3-{7-[2-(2,6-dioxopiperidin-3-yl)-1-oxo-3H-isoindol-4-yl]heptanamido}piperidin-1-yl]-3-[(4-methanesulfonylphenyl)amino]pyrazine-2-carboxamide (3.0 mg). $^1H$ NMR (500 MHz, Methanol-$d_4$) δ 7.98-7.87 (m, 2H), 7.87-7.77 (m, 2H), 7.63 (dd, J=7.0, 4.8 Hz, 1H), 7.51-7.35 (m, 3H), 5.25-5.07 (m, 1H), 4.46 (dt, J=12.4, 6.3 Hz, 2H), 3.94-3.75 (m, 2H), 3.12-3.01 (m, 3H), 2.71 (t, J=7.7 Hz, 1H), 2.61-2.51 (m, 2H), 2.25-1.82 (m, 6H), 1.66 (dt, J=43.4, 7.1 Hz, 1H), 1.51-1.37 (m, 3H), 0.94-0.69 (m, 12H). LCMS: $C_{37}H_{44}N_8O_7S$ requires: 744, found: m/z=745 $[M+H]^+$.

Example 65: Synthesis of 5-[(3R)-3-{5-[2-(2,6-dioxopiperidin-3-yl)-3-oxo-1H-isoindol-5-yl]pentanamido}piperidin-1-yl]-3-[(4-methanesulfonylphenyl)amino]pyrazine-2-carboxamide (Compound 4)

Step 1: Methyl 5-bromo-2-(bromomethyl)benzoate

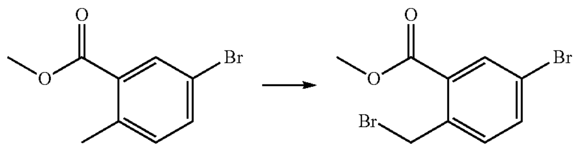

The general procedure from Step 1 of Example 62 was followed starting with methyl 5-bromo-2-methylbenzoate to afford methyl 5-bromo-2-(bromomethyl)benzoate (23.5 g) as yellow oil. 1H NMR (300 MHz, DMSO-$d_6$) δ 7.98 (d, J=2.1 Hz, 1H), 7.81 (dd, J=8.4, 2.1 Hz, 1H), 7.56 (d, J=8.4 Hz, 1H), 4.98 (s, 2H), 3.88 (s, 3H).

Step 2: 3-(6-bromo-1-oxoisoindolin-2-yl)piperidine-2,6-dione

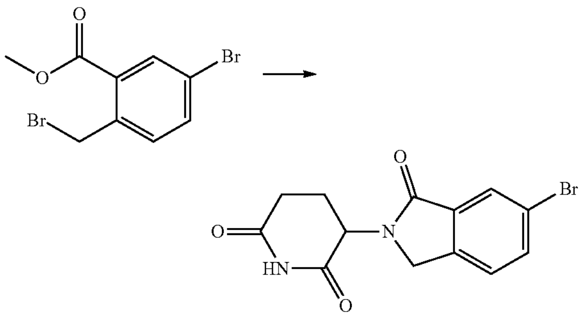

The general procedure from Step 2 of Example 62 was followed to afford 3-(6-bromo-1-oxoisoindolin-2-yl)piperidine-2,6-dione (5.8 g) as a dark blue solid. $^1H$ NMR (300 MHz, DMSO-$d_6$) δ 11.01 (s, 1H), 7.91-7.78 (m, 2H), 7.61 (d, J=8.1 Hz, 1H), 5.13 (dd, J=13.2, 5.1 Hz, 1H), 4.46 (d, J=17.7 Hz, 1H), 4.32 (d, J=17.7 Hz, 1H), 2.98-2.86 (m, 1H), 2.67-2.54 (m, 1H), 2.47-2.33 (m, 1H), 2.08-1.99 (m, 1H). LCMS: $C_{13}H_{11}BrN_2O_3$ requires: 322, found: m/z=323 $[M+H]^+$.

Step 3: Benzyl 5-[2-(2,6-dioxopiperidin-3-yl)-3-oxo-1H-isoindol-5-yl]pent-4-ynoate

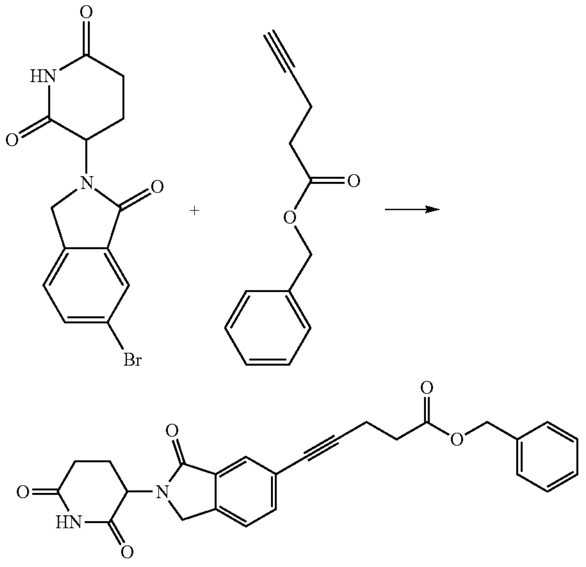 [SMILES: O=C1CCC(N2Cc3ccc(Br)cc3C2=O)C(=O)N1 ; C#CCCC(=O)OCc1ccccc1 ; O=C1CCC(N2Cc3ccc(C#CCCC(=O)OCc4ccccc4)cc3C2=O)C(=O)N1]

The general procedure from Step 4 of Example 62 was followed starting with 3-(6-bromo-1-oxoisoindolin-2-yl)piperidine-2,6-dione and benzyl pent-4-ynoate to afford benzyl 5-[2-(2,6-dioxopiperidin-3-yl)-3-oxo-1H-isoindol-5-yl]pent-4-ynoate (76 mg). $^1H$ NMR (500 MHz, Chloroform-d) δ 7.97-7.85 (m, 2H), 7.57 (dd, J=7.8, 1.5 Hz, 1H), 7.44-7.34 (m, 5H), 5.24 (dd, J=13.3, 5.1 Hz, 1H), 4.52 (d, J=16.2 Hz, 1H), 4.36 (d, J=16.2 Hz, 1H), 2.99-2.92 (m, 1H), 2.90-2.83 (m, 1H), 2.82-2.70 (m, 4H), 2.38 (qd, J=13.2, 4.7 Hz, 1H), 2.25 (dtd, J=12.9, 5.3, 2.5 Hz, 1H). LCMS: $C_{25}H_{22}N_2O_5$ requires: 430, found: m/z=430 $[M+H]^+$.

Step 4: Synthesis of 5-[2-(2,6-dioxopiperidin-3-yl)-3-oxo-1H-isoindol-5-yl]pentanoic acid

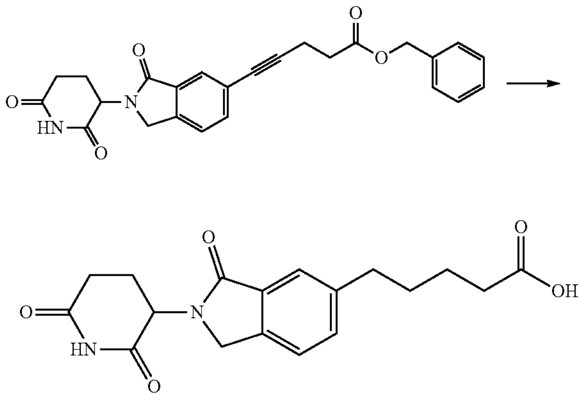

The general procedure from Step 5 of Example 62 was followed starting with to afford 5-[2-(2,6-dioxopiperidin-3-yl)-3-oxo-1H-isoindol-5-yl]pentanoic acid (58 mg). LCMS: $C_{18}H_{20}N_2O_5$ requires: 344, found: m/z=345 $[M+H]^+$.

Step 5: 5-[(3R)-3-f{5-[2-(2,6-dioxopiperidin-3-yl)-3-oxo-1H-isoindol-5-yl]pentanamido}piperidin-1-yl]-3-[(4-methanesulfonylphenyl)amino]pyrazine-2-carboxamide

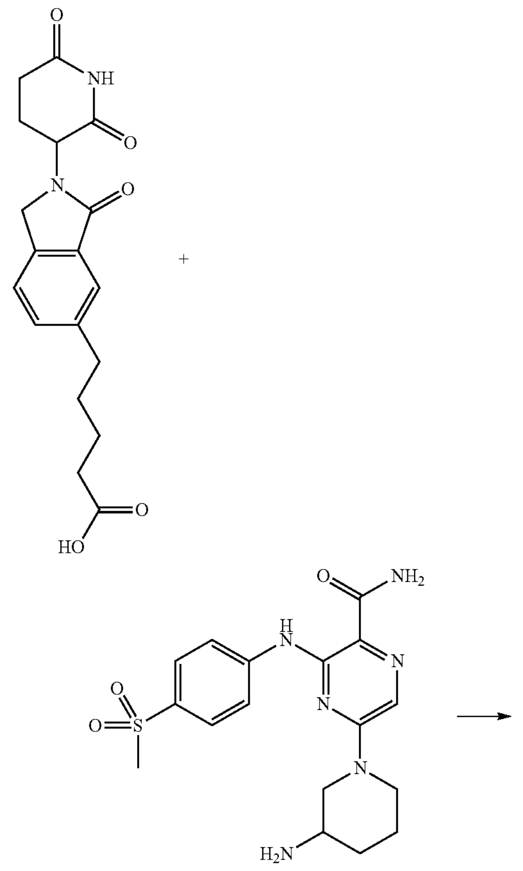

-continued

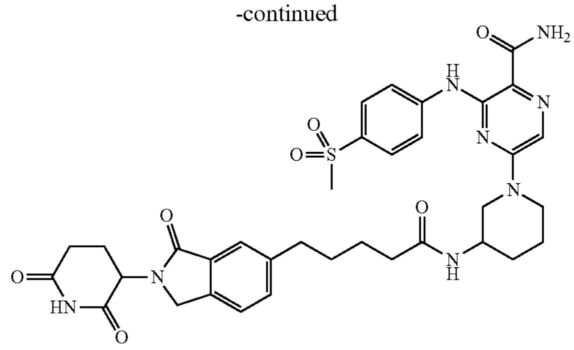

5-[2-(2,6-dioxopiperidin-3-yl)-3-oxo-1H-isoindol-5-yl] pentanoic acid (3.2 mg, 10.3 μmol) was dissolved in DMF (500 μL) and (1,2,3-benzotriazol-1-yloxy)tris(dimethylamino)phosphonium; hexafluoro-lambda5-phosphamide (5.3 mg, 13.3 μmol) was added before adding i-$Pr_2NEt$ (8.0 μL, 50 μmol) at rt. After 5 min 5-[(3R)-3-aminopiperidin-1-yl]-3-[(4-methanesulfonylphenyl)amino]pyrazine-2-carboxamide (4.0 mg, 10.3 μmol) was added as a solution in DMF (500 μL). The mixture was stirred for 30 min before being filtered and purified (RP-HPLC). The product containing fractions were concentrated to remove ACN and the aqueous phase was basified ($NaHCO_3$ solid) to pH=10. The aqueous phase was extracted (3×5 mL $CH_2Cl_2$) and the combined organic phases were dried ($Na_2SO_4$), filtered, and concentrated to afford 5-[(3R)-3-{5-[2-(2,6-dioxopiperidin-3-yl)-3-oxo-1H-isoindol-5-yl]pentanamido}piperidin-1-yl]-3-[(4-methanesulfonylphenyl)amino]pyrazine-2-carboxamide (3.3 mg). $^1$H NMR (500 MHz, Methanol-$d_4$) δ 7.96-7.87 (m, 2H), 7.83 (dd, J=9.0, 2.2 Hz, 2H), 7.54-7.44 (m, 2H), 7.43-7.36 (m, 1H), 7.35-7.26 (m, 1H), 5.14 (dd, J=13.4, 5.2 Hz, 1H), 4.51-4.32 (m, 2H), 3.79 (d, J=15.8 Hz, 2H), 3.12-3.05 (m, 3H), 2.98-2.72 (m, 3H), 2.63-2.40 (m, 4H), 2.25-2.08 (m, 2H), 1.75 (dq, J=15.0, 7.5 Hz, 1H), 1.70-1.48 (m, 3H), 1.49-1.35 (m, 2H), 1.07-0.98 (m, 2H), 0.82-0.69 (m, 4H). LCMS: $C_{35}H_{40}N_8O_7S$ requires: 716, found: m/z=717 $[M+H]^+$.

Physical data for representative compounds of the present invention are provided in Table 2.

TABLE 2

Physical data for representative compound of Formula (I).

| Compound No. | $^1$H NMR | Mass Spec (LCMS) |
|---|---|---|
| 1 | $^1$H NMR (500 MHz, DMSO-$d_6$) δ 11.89 (s, 1H), 11.11 (s, 1H), 7.84 (s, 6H), 7.56-6.96 (m, 4H), 5.10 (dd, J = 12.8, 5.5 Hz, 1H), 4.38-4.03 (m, 3H), 3.87 (s, 6H), 3.14 (s, 3H), 2.89 (ddd, J = 18.1, 13.6, 5.4 Hz, 1H), 2.71-2.55 (m, 2H), 2.28-1.94 (m, 3H), 1.90-1.65 (m, 3H), 1.54 (s, 3H). | LCMS: C35H37N7O10S requires: 747, found: m/z = 748 $[M + H]^+$. |
| 2 | $^1$H NMR (500 MHz, DMSO-$d_6$) δ 11.97 (s, 1H), 11.10 (s, 1H), 8.09-7.62 (m, 8H), 7.62-7.07 (m, 5H), 5.11 (dd, J = 12.8, 5.4 Hz, 1H), 4.43-3.77 (m, 6H), 3.14 (s, 3H), 2.89 (ddd, J = 16.8, 13.8, 5.5 Hz, 1H), 2.74-2.55 (m, 3H), 2.16-1.91 (m, 1H), 1.91-0.97 (m, 11H). | LCMS: $C_{37}H_{41}N_7O_{10}S$ requires: 775, found: m/z = 776 $[M + H]^+$. |
| 3 | $^1$H NMR (500 MHz, DMSO-$d_6$) δ 12.01 (s, 1H), 11.12 (s, 1H), 8.02-7.71 (m, 6H), 7.64-7.10 (m, 4H), 5.12 (dd, J = 12.8, 5.4 Hz, 1H), 4.08 (s, 7H), 3.15 (s, 3H), 2.90 (ddd, J = 16.9, 13.8, 5.4 Hz, 1H), 2.75-2.57 (m, 2H), 2.22-1.92 (m, 2H), 1.92-0.79 (m, 17H). | LCMS: $C_{39}H_{45}N_7O_{10}S$ requires: 803, found: m/z = 804 $[M + H]^+$. |
| 4 | $^1$H NMR (500 MHz, Methanol-$d_4$) δ 7.96-7.87 (m, 2H), 7.83 (dd, J = 9.0, 2.2 Hz, 2H), 7.54-7.44 (m, 2H), 7.43-7.36 (m, 1H), 7.35-7.26 (m, 1H), 5.14 (dd, J = 13.4, 5.2 Hz, 1H), 4.51-4.32 (m, 2H), 3.79 (d, J = 15.8 Hz, 2H), 3.12-3.05 (m, 3H), 2.98-2.72 (m, 3H), 2.63-2.40 (m, 4H), 2.25-2.08 (m, 2H), 1.75 (dq, J = 15.0, 7.5 Hz, 1H), | LCMS: $C_{35}H_{40}N_8O_7S$ requires: 716, found: m/z = 717 $[M + H]^+$. |

TABLE 2-continued

| Physical data for representative compound of Formula (I). | | |
|---|---|---|
| Compound No. | $^1$H NMR | Mass Spec (LCMS) |
| | 1.70-1.48 (m, 3H), 1.49-1.35 (m, 2H), 1.07-0.98 (m, 2H), 0.82-0.69 (m, 4H). | |
| 5 | $^1$H NMR (500 MHz, Methanol-$d_4$) δ 7.98-7.87 (m, 2H), 7.87-7.77 (m, 2H), 7.63 (dd, J = 7.0, 4.8 Hz, 1H), 7.51-7.35 (m, 3H), 5.25-5.07 (m, 1H), 4.46 (dt, J = 12.4, 6.3 Hz, 2H), 3.94-3.75 (m, 2H), 3.12-3.01 (m, 3H), 2.71 (t, J = 7.7 Hz, 1H), 2.61-2.51 (m, 2H), 2.25-1.82 (m, 6H), 1.66 (dt, J = 43.4, 7.1 Hz, 1H), 1.51-1.37 (m, 3H), 0.94-0.69 (m, 12H). | LCMS: $C_{37}H_{44}N_8O_7S$ requires: 744, found: m/z = 745 $[M + H]^+$. |
| 6 | $^1$H NMR (500 MHz, Chloroform-d) δ 11.55 (d, J = 8.4 Hz, 1H), 8.23 (s, 1H), 7.92-7.78 (m, 3H), 7.74-7.60 (m, 1H), 7.45 (d, J = 12.2 Hz, 1H), 7.32 (d, J = 2.0 Hz, 1H), 7.06 (d, J = 12.9 Hz, 1H), 5.82-5.25 (m, 1H), 5.15 (s, 1H), 4.95 (dd, J = 12.2, 5.3 Hz, 1H), 4.36-3.11 (m, 11H), 2.82 (dddd, J = 40.8, 29.1, 16.4, 4.2 Hz, 3H), 2.14 (td, J = 7.5, 2.5 Hz, 1H), 2.09-1.96 (m, 1H), 1.95-1.29 (m, 15H). | LCMS: $C_{38}H_{43}N_9O_9S$ requires: 801, found: m/z = 802 $[M + H]^+$. |
| 7 | $^1$H NMR (500 MHz, Chloroform-d) δ 12.01 (s, 1H), 8.26 (s, 1H), 7.68-7.62 (m, 1H), 7.39 (s, 1H), 7.35 (s, 1H), 7.22 (s, 2H), 7.00 (s, 1H), 6.64 (s, 1H), 5.50 (s, 2H), 4.99-4.91 (m, 1H), 4.40 (d, J = 43.4 Hz, 1H), 4.14 (s, 2H), 4.04-3.18 (m, 8H), 2.93-2.69 (m, 3H), 2.46 (s, 3H), 2.17-2.10 (m, OH), 1.78 (d, J = 61.7 Hz, 9H), 1.25 (s, 2H). | LCMS: $C_{35}H_{40}N_{10}O_7S$ requires: 744, found: m/z = 745 $[M + H]^+$. |
| 8 | $^1$H NMR (500 MHz, Chloroform-d) δ 11.60 (s, 1H), 7.99 (d, J = 13.7 Hz, 1H), 7.94-7.75 (m, 4H), 7.55 (s, OH), 5.30 (s, 2H), 4.96 (dd, J = 12.2, 5.8 Hz, 1H), 4.39-3.12 (m, 13H), 2.89 (t, J = 19.6 Hz, 1H), 2.84-2.65 (m, 1H), 2.20-2.10 (m, 1H), 2.10-1.98 (m, 1H), 1.59 (s, 15H). | LCMS: $C_{37}H_{41}N_9O_9S$ requires: 787, found: m/z = 788 $[M + H]^+$. |
| 9 | $^1$H NMR (500 MHz, Chloroform-d) 6 11.55 (s, 1H), 8.07 (s, 2H), 7.86 (q, J = 9.0 Hz, 5H), 7.50 (d, J = 32.5 Hz, 1H), 7.34-7.26 (m, 1H), 5.33 (s, 2H), 4.94 (dd, J = 11.9, 5.3 Hz, 1H), 4.12 (s, 2H), 4.02 (s, 1H), 3.84 (s, 4H), 3.68 (s, 2H), 3.33 (s, 4H), 3.05 (d, J = 12.0 Hz, 4H), 2.88 (s, 1H), 2.79-2.69 (m, 1H), 2.14 (d, J = 10.4 Hz, 1H), 2.06 (s, 2H), 1.67 (s, 2H), 1.25 (s, 2H). | LCMS: $C_{36}H_{39}N_9O_9S$ requires: 773, found: m/z = 774. |
| 10 | $^1$H NMR (500 MHz, Chloroform-d) δ 11.61 (d, J = 2.5 Hz, 1H), 8.37 (d, J = 9.0 Hz, 1H), 7.93 (d, J = 8.6 Hz, 2H), 7.86 (h, J = 3.2, 2.8 Hz, 2H), 7.71 (d, J = 8.5 Hz, 1H), 7.50 (s, 1H), 7.39 (s, 1H), 7.33 (d, J = 2.3 Hz, 1H), 7.10 (d, J = 8.0 Hz, 1H), 6.77 (s, 1H), 5.55-5.50 (m, 1H), 4.97 (dd, J = 12.2, 5.4 Hz, 1H), 4.09 (s, 1H), 3.79 (s, 1H), 3.58-3.48 (m, 1H), 3.40 (q, J = 6.8 Hz, 1H), 3.35 (s, 4H), 3.29 (d, J = 4.6 Hz, 2H), 3.21 (s, 1H), 3.08 (d, J = 3.0 Hz, 0H), 3.07 (s, 3H), 2.96-2.71 (m, 3H), 2.20-2.12 (m, 2H), 2.03 (s, 1H), 1.91 (d, J = 13.2 Hz, OH), 1.81 (s, 3H), 1.68 (d, J = 11.4 Hz, 2H), 1.66-1.54 (m, 4H), 1.28 (s, 1H). | LCMS: $C_{39}H_{44}N_{10}O_8S$ requires: 812, found: m/z = 813 $[M + H]^+$. |
| 11 | $^1$H NMR (500 MHz, Chloroform-d) δ 11.56 (s, 1H), 8.14 (d, J = 7.6 Hz, 1H), 7.91 (d, J = 8.9 Hz, 2H), 7.83 (d, J = 8.9 Hz, 2H), 7.70 (d, J = 8.5 Hz, 1H), 7.47 (d, J = 7.7 Hz, 1H), 7.39-7.30 (m, 2H), 7.15 (d, J = 8.2 Hz, 1H), 5.35 (s, 1H), 4.95 (dd, J = 12.3, 5.4 Hz, 1H), 4.06 (s, 1H), 3.63 (s, 1H), 3.50-3.13 (m, 9H), 3.05 (s, 4H), 2.98-2.63 (m, 4H), 2.25-2.05 (m, 3H), 1.95-1.72 (m, 1H), 1.68 (t, J = 5.9 Hz, 4H), 1.60-1.41 (m, 5H). | LCMS: $C_{40}H_{46}N_{10}O_8S$ requires: 826, found: m/z = 827 $[M + H]^+$. |
| 12 | $^1$H NMR (500 MHz, Chloroform-d) δ 11.88 (s, 1H), 8.18 (d, J = 3.5 Hz, 1H), 7.68 (d, J = 8.5 Hz, 1H), 7.37 (s, 2H), 7.03 (dd, J = 8.6, 2.4 Hz, 1H), 6.63 (s, 1H), 5.38-5.34 (m, 1H), 4.94 (dd, J = 12.3, 5.4 Hz, 1H), 4.36 (s, 1H), 3.81 (s, 1H), 3.51-3.38 (m, 5H), 3.37-3.30 (m, 3H), 3.33-3.20 (m, 4H), 3.14 (t, J = 12.0 Hz, 1H), 2.93-2.68 (m, 4H), 2.42 (s, 3H), 2.24 (d, J = 12.2 Hz, 1H), 2.13 (ddd, J = 12.2, 5.5, 2.3 Hz, 1H), 1.94 (t, J = 13.0 Hz, 1H), 1.79-1.70 (m, 1H), 1.63 (d, J = 11.9 Hz, 2H), 1.50-1.41 (m, 5H), 0.84 (s, 1H). | LCMS: $C_{37}H_{43}N_{11}O_6S$ requires: 769, found: m/z = 770 $[M + H]^+$. |
| 13 | $^1$H NMR (500 MHz, Methanol-d4) δ 8.15-8.09 (m, 1H), 8.09-8.01 (m, 2H), 7.88 (d, J = 24.6 Hz, 2H), 7.84-7.73 (m, 2H), 7.46 (s, 1H), 5.21 (dd, J = 13.4, 5.2 Hz, 1H), 4.99-4.88 (m, 2H), 4.62 (d, J = 47.1 Hz, 3H), 4.03-3.82 (m, 2H), 3.67 (s, 1H), 3.47 (d, J = 12.4 Hz, 1H), 3.41-3.34 (m, 2H), 3.17 (d, J = 21.1 Hz, 3H), 3.09 (s, 3H), 2.97-2.85 (m, 3H), 2.85-2.72 (m, 3H), 2.28-2.16 (m, 1H), 2.12 (d, J = 12.4 Hz, 2H), 2.02-1.80 (m, 2H), 1.80-1.63 (m, 2H), 1.63-1.34 (m, 3H). | LCMS: $C_{40}H_{46}N_{10}O_8S$ requires: 826, found: m/z = 827 $[M + H]^+$. |

TABLE 2-continued

Physical data for representative compound of Formula (I).

| Compound No. | $^1$H NMR | Mass Spec (LCMS) |
|---|---|---|
| 14 | $^1$H NMR (500 MHz, DMSO-$d_6$) δ 12.12-11.85 (m, 1H), 11.07 (s, 1H), 8.02-7.75 (m, 5H), 7.66 (d, J = 8.4 Hz, 1H), 7.58-7.14 (m, 4H), 5.06 (dd, J = 12.8, 5.4 Hz, 1H), 4.17-3.93 (m, 3H), 3.89-3.69 (m, 3H), 3.16 (d, J = 6.4 Hz, 3H), 3.09 (d, J = 7.2 Hz, 3H), 3.04-2.95 (m, 2H), 2.94-2.78 (m, 2H), 2.69-2.53 (m, 4H), 2.03 (t, J = 19.0 Hz, 4H), 1.84 (s, 3H), 1.58 (s, 4H), 1.17 (t, J = 7.3 Hz, 4H). | LCMS: $C_{41}H_{48}N_{10}O_8S$ requires: 841, found: m/z = 842 [M + H]$^+$. |
| 15 | $^1$H NMR (500 MHz, DMSO-$d_6$) δ 12.38-12.16 (m, 1H), 11.07 (s, 1H), 9.64-9.16 (m, 1H), 8.08 (d, J = 37.5 Hz, 1H), 7.84 (d, J = 10.0 Hz, 1H), 7.67 (dd, J = 8.5, 3.2 Hz, 1H), 7.60-7.42 (m, 2H), 7.35 (d, J = 5.3 Hz, 1H), 7.26 (s, 1H), 7.00-6.77 (m, 1H), 5.07 (dd, J = 12.7, 5.5 Hz, 1H), 4.31 (s, 1H), 4.23-3.92 (m, 6H), 3.83 (dd, J = 30.4, 12.8 Hz, 1H), 3.73-3.40 (m, 3H), 3.34-3.19 (m, 1H), 3.13 (d, J = 22.8 Hz, 2H), 3.04-2.81 (m, 3H), 2.68-2.55 (m, 2H), 2.28 (dd, J = 6.4, 1.7 Hz, 3H), 2.23-1.97 (m, 2H), 1.96-1.72 (m, 3H), 1.62 (d, J = 7.8 Hz, 2H), 1.35-1.09 (m, 4H). | LCMS: $C_{38}H_{45}N_{11}O_6S$ requires: 784, found: m/z = 785 [M + H]$^+$. |
| 16 | $^1$H NMR (500 MHz, Methanol-$d_4$) δ 7.65 (q, J = 6.9 Hz, 2H), 7.53 (d, J = 10.5 Hz, 1H), 7.47 (d, J = 1.7 Hz, 1H), 6.86-6.71 (m, 4H), 6.65 (d, J = 8.6 Hz, 2H), 5.06 (dd, J = 12.0, 5.2 Hz, 2H), 4.24 (dd, J = 18.3, 10.8 Hz, 5H), 4.00-3.48 (m, 12H), 2.93-2.79 (m, 2H), 2.79-2.61 (m, 3H), 2.40-2.33 (m, 3H), 2.25 (s, OH), 2.18-2.05 (m, 2H), 2.05-1.87 (m, 1H), 1.85-1.54 (m, 2H). | LCMS: $C_{36}H_{45}N_{11}O_6S$ requires: 755, found: m/z = 756 [M + H]$^+$. |
| 17 | 1H NMR (500 MHz, Methanol-$d_4$) δ 7.66 (dd, J = 8.2, 6.1 Hz, 1H), 7.50 (d, J = 21.9 Hz, 1H), 6.90-6.74 (m, 2H), 6.71-6.61 (m, 1H), 5.06 (dd, J = 12.6, 5.4 Hz, 1H), 4.61-4.35 (m, 1H), 4.37-4.19 (m, 3H), 4.20-3.95 (m, 1H), 3.93-3.83 (m, 2H), 3.78 (s, 1H), 3.71-3.57 (m, 2H), 3.54 (t, J = 8.4 Hz, 1H), 3.50-3.37 (m, 1H), 3.14 (d, J = 10.7 Hz, 2H), 2.96 (t, J = 11.0 Hz, 1H), 2.86 (ddd, J = 18.4, 13.8, 5.2 Hz, 1H), 2.80-2.61 (m, 3H), 2.39 (d, J = 3.3 Hz, 3H), 2.28 (d, J = 20.4 Hz, 1H), 2.19-1.82 (m, 7H), 1.72 (dt, J = 32.9, 11.9 Hz, 2H), 1.27 (q, J = 6.5, 6.0 Hz, 1H). | LCMS: $C_{37}H_{43}N_{11}O_6S$ requires: 770, found: m/z = 771 [M + H]$^+$. |
| 18 | $^1$H NMR (500 MHz, Methanol-$d_4$) δ 7.62 (dd, J = 8.3, 1.2 Hz, 1H), 7.48 (s, 1H), 6.78 (dd, J = 4.0, 2.1 Hz, 1H), 6.72 (d, J = 1.6 Hz, 1H), 6.62 (dd, J = 8.3, 2.2 Hz, 1H), 5.06 (dd, J = 12.7, 5.5 Hz, 1H), 4.25 (t, J = 8.1 Hz, 2H), 4.18 (s, 1H), 4.03 (d, J = 12.4, 3.6 Hz, 1H), 3.88-3.78 (m, 3H), 3.68-3.51 (m, 4H), 3.51-3.33 (m, 2H), 3.30-3.15 (m, 2H), 3.10 (ddd, J = 13.4, 10.3, 3.1 Hz, 1H), 2.96 (dd, J = 12.7, 9.0 Hz, 1H), 2.91-2.78 (m, 1H), 2.77-2.62 (m, 4H), 2.34 (d, J = 3.3 Hz, 4H), 2.23-2.14 (m, 1H), 2.09 (dtd, J = 13.1, 5.6, 2.8 Hz, 1H), 2.00-1.87 (m, 1H), 1.78 (dt, J = 13.8, 10.3 Hz, 1H), 1.72-1.59 (m, 1H). | LCMS: $C_{36}H_{42}N_{12}O_6S$ requires: 771, found: m/z = 772 [M + H]$^+$. |
| 19 | $^1$H NMR (500 MHz, Acetonitrile-$d_3$) δ 10.74 (s, 1H), 8.87 (s, 1H), 7.92 (s, 1H), 7.59 (d, J = 8.3 Hz, 1H), 7.45 (d, J = 7.4 Hz, 2H), 7.38-7.22 (m, 1H), 6.76 (d, J = 2.1 Hz, 1H), 6.59 (dd, J = 8.3, 2.2 Hz, 1H), 6.34 (d, J = 7.2 Hz, 1H), 5.72 (s, 1H), 4.92 (dd, J = 12.3, 5.3 Hz, 1H), 4.24-4.16 (m, 1H), 4.11 (t, J = 8.1 Hz, 2H), 3.87 (s, 3H), 3.85-3.78 (m, 2H), 3.68 (dd, J = 8.2, 5.4 Hz, 2H), 3.45 (td, J = 9.0, 8.5, 4.4 Hz, 1H), 3.35 (dd, J = 13.1, 7.8 Hz, 1H), 3.28 (s, 1H), 2.97 (ddt, J = 10.1, 7.8, 4.2 Hz, 1H), 2.90-2.79 (m, 2H), 2.70 (dddt, J = 21.8, 13.4, 7.8, 4.3 Hz, 3H), 2.57 (d, J = 7.4 Hz, 2H), 2.11-2.01 (m, 3H), 1.87-1.77 (m, 2H), 1.71-1.49 (m, 6H). | LCMS: $C_{37}H_{44}N_{12}O_6$ requires: 752, found: m/z = 753. |
| 20 | $^1$H NMR (500 MHz, Methanol-$d_4$) δ 8.06-7.81 (m, 4H), 7.74-7.62 (m, 1H), 7.47 (d, J = 35.1 Hz, 1H), 7.37 (t, J = 6.5 Hz, 1H), 7.24 (q, J = 8.1 Hz, 1H), 5.07 (dd, J = 12.4, 5.3 Hz, 1H), 4.21 (d, J = 13.6 Hz, 1H), 4.09 (t, J = 17.7 Hz, 4H), 4.00-3.90 (m, 2H), 3.74 (dd, J = 50.5, 12.4 Hz, 1H), 3.22-2.97 (m, 10H), 2.87 (ddd, J = 19.1, 14.1, 5.6 Hz, 2H), 2.79-2.52 (m, 3H), 2.31-2.07 (m, 3H), 2.05 (s, 1H), 2.01-1.86 (m, 3H), 1.81 (d, J = 11.5 Hz, 2H), 1.68 (s, 2H), 1.50-1.25 (m, 2H). | LCMS: $C_{42}H_{50}N_{10}O_8S$ requires: 854, found: m/z = 855 [M + H]$^+$. |
| 21 | $^1$H NMR (500 MHz, DMSO-$d_6$) δ 11.07 (s, 1H), 10.87 (s, 1H), 7.98 (s, 1H), 7.81 (d, J = 6.9 Hz, 1H), 7.66 (s, 1H), 7.64 (d, J = 8.5 Hz, 1H), 7.55 (s, 1H), 7.48 (s, 1H), 7.30 (d, J = 2.1 Hz, 1H), 7.28-7.19 (m, 2H), 5.06 (dd, J = 12.8, 5.4 Hz, 1H), 4.29 (s, 1H), 4.04 (d, J = 13.0 Hz, 2H), | LCMS: $C_{39}H_{48}N_{12}O_6$ requires: 780, found: m/z = 781 [M + H]$^+$. |

TABLE 2-continued

Physical data for representative compound of Formula (I).

| Compound No. | $^1$H NMR | Mass Spec (LCMS) |
|---|---|---|
| | 3.94 (d, J = 13.0 Hz, 1H), 3.86 (s, 3H), 3.70 (s, 1H), 3.08 (t, J = 10.9 Hz, 1H), 3.01-2.92 (m, 2H), 2.90-2.78 (m, 3H), 2.09 (h, J = 6.3 Hz, 3H), 2.00 (dd, J = 11.8, 6.0 Hz, 1H), 1.92-1.71 (m, 8H), 1.59 (d, J = 24.4 Hz, 7H), 1.12 (d, J = 12.5 Hz, 3H). | |
| 22 | $^1$H NMR (500 MHz, DMSO-$d_6$) δ 12.27 (d, J = 32.4 Hz, 1H), 11.06 (s, 1H), 8.01 (s, 1H), 7.84 (d, J = 18.1 Hz, 1H), 7.63 (d, J = 8.4 Hz, 1H), 7.58-7.43 (m, 2H), 7.28 (s, 1H), 7.20 (d, J = 9.1 Hz, 1H), 6.85 (d, J = 22.5 Hz, 1H), 5.05 (dd, J = 12.9, 5.4 Hz, 1H), 4.17 (s, 1H), 4.00 (d, J = 14.4 Hz, 2H), 3.74 (d, J = 14.2 Hz, 1H), 3.57 (s, 1H), 3.48-3.35 (m, 3H), 3.09-2.77 (m, 3H), 2.72-2.54 (m, 2H), 2.28 (s, 3H), 2.22-2.05 (m, 2H), 2.05-1.90 (m, 3H), 1.80 (s, 3H), 1.70 (d, J = 11.6 Hz, 3H), 1.64-1.28 (m, 5H), 1.23 (s, 1H), 1.20-0.96 (m, 3H). | LCMS: $C_{38}H_{46}N_{12}O_6S$ requires: 798, found: m/z = 799 $[M + H]^+$. |
| 23 | $^1$H NMR (500 MHz, DMSO-$d_6$) δ 12.28 (s, 1H), 11.08 (s, 1H), 9.31 (s, 1H), 8.13-7.95 (m, 1H), 7.84 (s, 1H), 7.68 (d, J = 8.5 Hz, 1H), 7.50 (d, J = 3.7 Hz, 2H), 7.36 (d, J = 2.2 Hz, 1H), 7.27 (dd, J = 8.7, 2.3 Hz, 1H), 6.87 (s, 1H), 5.07 (dd, J = 12.7, 5.5 Hz, 1H), 4.10 (d, J = 13.5 Hz, 4H), 3.86 (d, J = 12.3 Hz, 1H), 3.64 (dd, J = 29.6, 14.1 Hz, 2H), 3.53-3.39 (m, 4H), 3.22 (t, J = 13.0 Hz, 1H), 3.17-3.02 (m, 1H), 2.97 (d, J = 12.7 Hz, 3H), 2.94-2.76 (m, 2H), 2.66-2.53 (m, 2H), 2.29 (s, 3H), 2.16-2.05 (m, 2H), 2.05-1.96 (m, 1H), 1.90-1.74 (m, 4H), 1.72-1.48 (m, 2H), 1.37-1.21 (m, 2H). | LCMS: $C_{38}H_{46}N_{12}O_6S$ requires: 799, found: m/z = 800 $[M + H]^+$. |
| 24 | $^1$H NMR (500 MHz, Methanol-$d_4$) δ 7.97 (d, J = 8.8 Hz, 2H), 7.86 (d, J = 8.8 Hz, 2H), 7.63 (d, J = 8.3 Hz, 1H), 7.46 (s, 1H), 6.77 (d, J = 2.1 Hz, 1H), 6.61 (dd, J = 8.2, 2.1 Hz, 1H), 5.05 (dd, J = 12.6, 5.5 Hz, 1H), 4.17-4.02 (m, 4H), 4.02-3.93 (m, 4H), 3.77 (d, J = 13.3 Hz, 1H), 3.13 (s, 3H), 2.98 (t, J = 10.6 Hz, 1H), 2.92-2.81 (m, 2H), 2.79-2.66 (m, 2H), 2.21-2.03 (m, 2H), 1.91-1.81 (m, 2H), 1.74-1.59 (m, 2H). | LCMS: $C_{36}H_{38}N_{10}O_8S$ requires: 770, found: m/z = 771 $[M + H]^+$. |
| 25 | $^1$H NMR (500 MHz, Methanol-$d_4$) δ 8.02 (d, J = 7.7 Hz, 1H), 7.98 (dd, J = 8.9, 2.1 Hz, 2H), 7.94 (s, 1H), 7.86 (dd, J = 7.7, 1.6 Hz, 1H), 7.83 (dd, J = 9.0, 2.5 Hz, 2H), 7.45 (s, 1H), 5.20 (dd, J = 12.7, 5.5 Hz, 1H), 4.48 (s, 2H), 4.19 (s, 6H), 4.09 (d, J = 9.2 Hz, 4H), 3.99-3.81 (m, 3H), 3.13 (d, J = 3.2 Hz, 3H), 2.98-2.82 (m, 2H), 2.82-2.69 (m, 2H), 2.28-2.05 (m, OH), 1.87 (d, J = 11.0 Hz, 1H), 1.75-1.53 (m, 3H). | LCMS: $C_{37}H_{40}N_{10}O_8S$ requires: 784, found: m/z = 785 $[M + H]^+$. |
| 26 | $^1$H NMR (500 MHz, Methanol-$d_4$) δ 8.07-7.98 (m, 2H), 7.95 (d, J = 8.8 Hz, 2H), 7.90 (d, J = 7.5 Hz, 1H), 7.87-7.81 (m, 2H), 7.46 (s, 1H), 5.20 (dd, J = 12.6, 5.4 Hz, 1H), 4.39 (d, J = 14.3 Hz, 2H), 4.04 (s, 1H), 3.92 (d, J = 12.6 Hz, 1H), 3.59 (d, J = 13.9 Hz, 1H), 3.49-3.34 (m, 1H), 3.13 (d, J = 1.5 Hz, 3H), 3.07 (d, J = 26.5 Hz, 4H), 2.90 (ddd, J = 19.1, 14.5, 5.8 Hz, 3H), 2.84-2.68 (m, 3H), 2.16 (t, J = 16.0 Hz, 4H), 1.92 (d, J = 12.6 Hz, 1H), 1.77-1.58 (m, 2H). | LCMS: $C_{36}H_{40}N_{10}O_8S$ requires: 772, found: m/z = 773 $[M + H]^+$. |
| 27 | $^1$H NMR (500 MHz, Acetonitrile-$d_3$) δ 11.97 (d, J = 7.3 Hz, 1H), 8.88 (s, 1H), 7.66 (dd, J = 8.6, 1.2 Hz, 1H), 7.41 (s, 1H), 7.31 (s, 1H), 7.19 (dd, J = 5.0, 2.4 Hz, 1H), 7.07 (t, J = 6.7 Hz, 1H), 6.67 (d, J = 1.4 Hz, 1H), 6.46 (d, J = 6.5 Hz, 1H), 5.88 (s, 1H), 5.06-4.87 (m, 1H), 4.26 (s, 1H), 3.66 (s, 1H), 3.39-3.00 (m, 16H), 2.90-2.56 (m, 4H), 2.16-2.02 (m, 1H), 1.80-1.55 (m, 1H). | LCMS: $C_{32}H_{35}N_{11}O_6S$ requires: 701, found: m/z = 702 $[M + H]^+$. |
| 28 | $^1$H NMR (500 MHz, DMSO-$d_6$) δ 11.97 (s, 1H), 11.06 (s, 1H), 7.91 (d, J = 8.6 Hz, 2H), 7.88-7.81 (m, 2H), 7.79 (d, J = 8.8 Hz, 2H), 7.64 (d, J = 8.2 Hz, 1H), 7.50 (s, 1H), 7.47-7.38 (m, 1H), 6.74 (d, J = 2.0 Hz, 1H), 6.62 (dd, J = 8.4, 2.1 Hz, 1H), 5.05 (dd, J = 12.8, 5.4 Hz, 1H), 3.90 (s, 1H), 3.68 (d, J = 10.8 Hz, 5H), 3.16 (s, 3H), 3.04 (d, J = 6.7 Hz, 4H), 2.88 (ddd, J = 16.5, 13.6, 5.3 Hz, 2H), 2.57 (dd, J = 17.5, 12.7 Hz, 4H), 2.00 (d, J = 11.5 Hz, 2H), 1.85 (s, 1H), 1.67-1.42 (m, 6H). | LCMS: $C_{38}H_{42}N_{10}O_8S$ requires: 799, found: m/z = 800 $[M + H]^+$. |
| 29 | $^1$H NMR (500 MHz, DMSO-$d_6$) δ 11.96 (s, 1H), 11.15 (s, 1H), 10.28 (s, 1H), 8.09 (s, 1H), 8.04 (d, J = 7.6 Hz, 1H), 7.96 (d, J = 7.8 Hz, 1H), 7.90 (d, J = 8.6 Hz, 2H), 7.84 (d, J = 2.7 Hz, 1H), 7.79 (d, J = 8.8 Hz, 2H), 7.58-7.34 (m, 2H), 6.54 (s, 1H), 5.18 (dd, J = 12.9, 5.4 Hz, 1H), 4.59 (d, J = 5.9 Hz, 2H), 3.95 (s, 2H), 3.90-3.62 (m, 4H), 3.15 | LCMS: $C_{39}H_{42}N_{10}O_8S$ requires: 813, found: m/z = 814 $[M + H]^+$. |

TABLE 2-continued

| Compound No. | $^1$H NMR | Mass Spec (LCMS) |
|---|---|---|
| | (s, 3H), 3.11-2.74 (m, 8H), 2.70-2.51 (m, 2H), 2.18-2.04 (m, 1H), 2.04-1.94 (m, 1H), 1.91-1.76 (m, 1H), 1.74-1.45 (m, 5H). | |
| 30 | $^1$H NMR (500 MHz, DMSO-$d_6$) δ 12.00 (d, J = 18.5 Hz, 1H), 11.07 (s, 1H), 8.06-7.72 (m, 4H), 7.66 (dd, J = 8.6, 4.5 Hz, 1H), 7.58-7.39 (m, 1H), 7.38-7.28 (m, 1H), 7.28-7.12 (m, 1H), 6.53 (s, 1H), 5.06 (dd, J = 12.7, 5.4 Hz, 1H), 4.57-4.15 (m, 3H), 4.15-3.98 (m, 2H), 3.99-3.89 (m, 1H), 3.72 (d, J = 104.0 Hz, 1H), 3.46 (d, J = 14.3 Hz, 1H), 3.22-3.06 (m, 4H), 3.06-2.79 (m, 4H), 2.68-2.53 (m, 4H), 2.01 (ddd, J = 11.0, 5.9, 3.6 Hz, 2H), 1.92 (dd, J = 13.1, 4.3 Hz, 1H), 1.77 (d, J = 28.4 Hz, 3H), 1.66-1.43 (m, 4H), 1.36-1.01 (m, 4H). | LCMS: $C_{40}H_{46}N_{10}O_8S$ requires: 826, found: m/z = $[M + H]^+$. |
| 31 | $^1$H NMR (500 MHz, Acetonitrile-$d_3$) δ 11.80 (d, J = 37.0 Hz, 1H), 11.23 (s, 1H), 8.93 (s, 1H), 8.04 (s, 1H), 8.00-7.86 (m, 4H), 7.82 (d, J = 8.6 Hz, 2H), 7.39 (d, J = 28.5 Hz, 2H), 6.14 (d, J = 28.1 Hz, 1H), 5.90 (d, J = 24.5 Hz, 1H), 5.03 (dd, J = 12.4, 5.4 Hz, 1H), 4.64 (s, 1H), 4.35 (d, J = 30.1 Hz, 3H), 4.04 (s, 1H), 3.85 (s, 3H), 3.44-3.10 (m, 6H), 3.03 (d, J = 30.3 Hz, 4H), 2.87-2.54 (m, 4H), 2.16-1.99 (m, 2H), 1.90-1.72 (m, 2H), 1.64 (d, J = 47.1 Hz, 4H), 1.44-1.05 (m, 4H), 0.89 (s, OH), 0.61 (s, OH). | LCMS: $C_{38}H_{42}N_{10}O_8S$ requires: 839, found: m/z = 840. |
| 32 | $^1$H NMR (500 MHz, Acetonitrile-$d_3$) δ 11.77 (s, 1H), 8.93 (s, 1H), 8.12-7.69 (m, 7H), 7.37 (dd, J = 47.1, 28.8 Hz, 2H), 6.43-6.04 (m, 1H), 5.90 (d, J = 17.5 Hz, 1H), 5.03 (dd, J = 12.7, 5.4 Hz, 1H), 4.35 (d, J = 54.9 Hz, 2H), 4.17 (d, J = 34.8 Hz, 1H), 4.09-3.73 (m, 3H), 3.64 (s, 2H), 3.23 (s, 1H), 3.04 (d, J = 18.3 Hz, 4H), 2.83-2.62 (m, 3H), 2.50 (s, 1H), 2.08 (q, J = 2.4 Hz, 2H), 1.96 (s, 3H), 1.87-1.70 (m, 1H), 1.58 (d, J = 43.4 Hz, 4H). | LCMS: $C_{38}H_{41}N_9O_8S$ requires: 783, found: m/z = 784 $[M + H]^+$. |
| 33 | $^1$H NMR (500 MHz, Acetonitrile-$d_3$) δ 11.82 (d, J = 89.8 Hz, 1H), 8.87 (s, 1H), 8.02 (d, J = 8.5 Hz, 1H), 7.89 (d, J = 8.6 Hz, 1H), 7.81 (dd, J = 17.9, 8.4 Hz, 2H), 7.65 (t, J = 8.7 Hz, 1H), 7.52-7.32 (m, 1H), 7.16 (d, J = 8.6 Hz, 1H), 6.39-6.06 (m, 1H), 4.94 (dt, J = 12.0, 6.1 Hz, 1H), 4.47 (d, J = 14.2 Hz, 1H), 4.14 (s, 1H), 3.95 (dd, J = 35.9, 14.0 Hz, 6H), 3.31 (d, J = 31.9 Hz, 4H), 3.05 (d, J = 10.3 Hz, 3H), 3.02-2.83 (m, 4H), 2.83-2.62 (m, 5H), 2.37 (d, J = 52.6 Hz, 2H), 2.08 (q, J = 2.5 Hz, 2H), 1.87-1.75 (m, 2H), 1.59 (d, J = 57.1 Hz, 3H), 1.43-1.07 (m, 4H). | LCMS: $C_{42}H_{48}N_{10}O_8S$ requires: 852, found: m/z = 853 $[M + H]^+$. |
| 34 | $^1$H NMR (500 MHz, Acetonitrile-$d_3$) δ 11.98-11.46 (m, 1H), 8.87 (s, 1H), 7.98-7.77 (m, 4H), 7.66 (d, J = 8.8 Hz, 1H), 7.52-7.35 (m, 2H), 7.30 (d, J = 16.4 Hz, 1H), 7.17 (dd, J = 17.6, 8.4 Hz, 1H), 6.35-6.06 (m, 1H), 5.93 (d, J = 35.7 Hz, 1H), 5.02-4.84 (m, 1H), 4.04 (s, 5H), 3.92-3.61 (m, 2H), 3.68-3.41 (m, 2H), 3.28-2.86 (m, 6H), 2.72 (td, J = 19.3, 18.5, 10.8 Hz, 4H), 2.55 (d, J = 44.1 Hz, 4H), 2.16-2.01 (m, 4H), 1.87-1.68 (m, 4H), 1.68-1.10 (m, 7H). | LCMS: $C_{44}H_{52}N_{10}O_8S$ requires: 880, found: m/z = 881 $[M + H]^+$. |
| 35 | $^1$H NMR (500 MHz, Acetonitrile-$d_3$) δ 11.99-11.68 (m, 1H), 11.51 (s, 1H), 8.89 (s, 1H), 7.97 (d, J = 8.5 Hz, 1H), 7.92 (d, J = 8.6 Hz, 1H), 7.82 (d, J = 8.7 Hz, 1H), 7.70 (t, J = 9.1 Hz, 1H), 7.45 (s, 1H), 7.42-7.32 (m, 2H), 7.22 (t, J = 8.4 Hz, 1H), 6.32-6.07 (m, 1H), 5.94 (d, J = 42.1 Hz, 1H), 4.97 (dd, J = 12.3, 5.3 Hz, 1H), 4.48 (d, J = 12.1 Hz, 1H), 4.25-3.80 (m, 8H), 3.44 (s, 4H), 3.34-3.11 (m, 2H), 3.07 (s, 3H), 2.98 (t, J = 13.8 Hz, 2H), 2.76 (ddd, J = 35.0, 19.8, 10.9 Hz, 4H), 2.53 (d, J = 7.3 Hz, 1H), 2.22-2.03 (m, 2H), 1.99 (s, 1H), 1.85-1.76 (m, 2H), 1.72-1.51 (m, 2H). | LCMS: $C_{41}H_{46}N_{10}O_8S$ requires: 838, found: m/z = 839 $[M + H]^+$. |
| 36 | $^1$H NMR (500 MHz, Methanol-$d_4$) δ 7.95 (dd, J = 8.8, 3.6 Hz, 2H), 7.87 (d, J = 8.6 Hz, 2H), 7.65 (dd, J = 13.5, 8.5 Hz, 1H), 7.47 (d, J = 45.2 Hz, 1H), 7.31 (d, J = 30.6 Hz, 1H), 7.18 (dd, J = 30.3, 8.4 Hz, 1H), 5.14-5.00 (m, 1H), 4.04 (d, J = 19.5 Hz, 1H), 3.94 (s, 1H), 3.78 (d, J = 11.8 Hz, 1H), 3.72-3.63 (m, 1H), 3.59-3.42 (m, 4H), 3.13-3.06 (m, 4H), 2.86 (t, J = 15.2 Hz, 1H), 2.79-2.54 (m, 3H), 2.17 (d, J = 50.9 Hz, 3H), 2.05-1.87 (m, 2H), 1.86-1.70 (m, 2H), 1.61 (d, J = 50.4 Hz, 3H), 1.35 (dt, J = 36.6, 10.2 Hz, 5H), 0.78-0.61 (m, 1H), 0.48 (s, 1H). | LCMS: $C_{41}H_{47}N_9O_8S$ requires: 825, found: m/z = 826 $[M + H]^+$. |
| 37 | $^1$H NMR (500 MHz, Methanol-$d_4$) δ 8.06-7.77 (m, 4H), 7.53 (s, 1H), 6.82 (d, J = 17.3 Hz, 1H), 5.23-5.09 (m, 1H), 4.57-4.32 (m, 3H), 4.25 (d, J = 7.0 Hz, 2H), 4.20-3.90 (m, 2H), 3.77 (s, 1H), 3.42 (d, J = 12.0 Hz, 2H), 3.32 | LCMS: $C_{37}H_{43}N_{11}O_6S$ requires: 769, found: m/z = |

TABLE 2-continued

| Compound No. | $^1$H NMR | Mass Spec (LCMS) |
|---|---|---|
| Physical data for representative compound of Formula (I). | | |
| | (s, 2H), 3.18 (d, J = 12.3 Hz, 1H), 3.07 (s, 1H), 3.02-2.95 (m, 1H), 2.95-2.81 (m, 2H), 2.81-2.67 (m, 2H), 2.43 (s, 1H), 2.37 (s, 1H), 2.25 (s, 2H), 2.18-2.11 (m, 1H), 2.11-1.56 (m, 5H). | 770 [M + H]$^+$. |
| 38 | $^1$H NMR (500 MHz, Methanol-$d_4$) δ 7.70 (dd, J = 10.6, 6.2 Hz, 1H), 7.61-7.39 (m, 1H), 6.94 (d, J = 20.3 Hz, 1H), 6.80 (ddt, J = 14.9, 10.7, 5.0 Hz, 2H), 5.14-5.01 (m, 1H), 4.30 (dd, J = 83.0, 48.3 Hz, 7H), 3.99 (s, 1H), 3.88-3.63 (m, 1H), 3.50 (d, J = 52.5 Hz, 1H), 3.32 (s, 3H), 3.23-2.93 (m, 3H), 2.83 (s, 2H), 2.78-2.58 (m, 2H), 2.38 (tt, J = 9.9, 4.3 Hz, 3H), 2.33-1.51 (m, 7H). | LCMS: $C_{36}H_{41}N_{11}O_6S$ requires: 755, found: m/z = 756 [M + H]$^+$. |
| 39 | $^1$H NMR (500 MHz, Methanol-$d_4$) δ 7.77-7.64 (m, 1H), 7.58-7.44 (m, 1H), 7.41 (d, J = 13.2 Hz, 1H), 7.29 (t, J = 11.0 Hz, 1H), 6.77 (d, J = 21.6 Hz, 1H), 5.08 (dd, J = 12.4, 5.5 Hz, 1H), 4.61-4.36 (m, 1H), 4.23 (dd, J = 25.9, 13.6 Hz, 3H), 4.05 (dd, J = 40.7, 14.3 Hz, 1H), 3.67 (t, J = 14.8 Hz, 1H), 3.58-3.39 (m, 3H), 3.15 (q, J = 18.1, 15.8 Hz, 2H), 3.03 (dd, J = 30.5, 13.3 Hz, 2H), 2.96-2.81 (m, 2H), 2.81-2.68 (m, 4H), 2.57 (d, J = 12.7 Hz, 1H), 2.35 (d, J = 16.3 Hz, 3H), 2.31-1.56 (m, 11H). | LCMS: $C_{38}H_{45}N_{11}O_6S$ requires: 783, found: m/z = 784 [M + H]$^+$. |
| 40 | $^1$H NMR (500 MHz, Methanol-$d_4$) δ 8.03-7.89 (m, 2H), 7.85 (d, J = 8.6 Hz, 2H), 7.74 (dd, J = 13.5, 8.5 Hz, 1H), 7.47 (d, J = 35.0 Hz, 2H), 7.31 (d, J = 8.7 Hz, 1H), 5.16-5.05 (m, 1H), 4.26 (d, J = 14.5 Hz, 2H), 4.16-3.86 (m, 3H), 3.73 (d, J = 11.7 Hz, 1H), 3.66 (d, J = 11.7 Hz, 1H), 3.60-3.48 (m, 1H), 3.46-3.39 (m, 2H), 3.25-3.16 (m, 2H), 3.12 (d, J = 5.4 Hz, 3H), 2.90-2.80 (m, 2H), 2.74 (t, J = 13.9 Hz, 3H), 2.65-2.51 (m, 2H), 2.40-2.03 (m, 6H), 2.01-1.47 (m, 6H). | LCMS: $C_{41}H_{48}N_{10}O_8S$ requires: 840, found: m/z = 841 [M + H]$^+$. |
| 41 | $^1$H NMR (500 MHz, Methanol-$d_4$) δ 7.96 (d, J = 16.9 Hz, 2H), 7.86 (d, J = 16.0 Hz, 1H), 7.71 (d, J = 9.9 Hz, 1H), 7.55 (s, 1H), 7.43 (d, J = 16.3 Hz, 2H), 7.32 (d, J = 25.4 Hz, 1H), 5.08 (d, J = 9.1 Hz, 2H), 4.48-4.35 (m, 1H), 4.33-3.83 (m, 7H), 3.55-3.39 (m, 3H), 3.15 (t, J = 9.3 Hz, 4H), 3.00 (d, J = 15.9 Hz, 2H), 2.85 (d, J = 18.6 Hz, 1H), 2.75 (d, J = 17.2 Hz, 3H), 2.66 (s, 1H), 2.43-2.05 (m, 5H), 1.96 (d, J = 27.0 Hz, 3H), 1.85-1.50 (m, 4H), 1.29 (s, 2H). | LCMS: $C_{43}H_{50}N_{10}O_8S$ requires: 866, found: m/z = 867 [M + H]$^+$. |
| 42 | $^1$H NMR (500 MHz, $CD_3CN$) δ 10.72 (s, 1H), 8.91-8.84 (m, 1H), 7.84 (s, 1H), 7.60 (d, J = 8.3 Hz, 1H), 7.46 (d, J = 17.7 Hz, 2H), 7.34 (s, 1H), 6.76 (s, 1H), 6.59 (d, J = 8.5 Hz, 1H), 5.75 (s, 1H), 4.92 (dd, J = 12.2, 5.3 Hz, 1H), 4.49 (dd, J = 12.6, 4.2 Hz, 1H), 4.18 (d, J = 13.7 Hz, 1H), 4.08 (t, J = 7.7 Hz, 2H), 3.83-3.66 (m, 6H), 3.47-3.33 (m, 4H), 3.16-3.03 (m, 2H), 2.81-2.62 (m, 5H), 2.08 (d, J = 17.1 Hz, 2H), 2.01-1.96 (m, 1H), 1.92-1.75 (m, 1H), 1.66 (qt, J = 11.5, 4.0 Hz, 1H). | LCMS: $C_{36}H_{40}N_{12}O_7$ requires: 752, found: m/z = 753 [M + H]$^+$. |
| 43 | $^1$H NMR (500 MHz, Acetonitrile-$d_3$) δ 10.74 (s, 1H), 8.94 (s, 1H), 7.87 (s, 1H), 7.65 (d, J = 8.6 Hz, 1H), 7.50 (s, 1H), 7.47 (d, J = 0.8 Hz, 1H), 7.37 (s, 1H), 7.31 (d, J = 2.4 Hz, 1H), 7.17 (dd, J = 8.7, 2.4 Hz, 1H), 5.79 (s, 1H), 5.07-4.88 (m, 1H), 4.50 (d, J = 12.8 Hz, 1H), 4.19 (d, J = 13.6 Hz, 1H), 4.00 (d, J = 13.1 Hz, 2H), 3.84 (s, 3H), 3.78 (dd, J = 19.2, 10.2 Hz, 2H), 3.45 (d, J = 8.1 Hz, 1H), 3.39 (d, J = 8.1 Hz, 1H), 3.34 (d, J = 8.1 Hz, 1H), 3.31-3.25 (m, 1H), 3.17 (dd, J = 12.9, 10.4 Hz, 1H), 3.14-3.07 (m, 1H), 2.97 (td, J = 12.8, 2.7 Hz, 2H), 2.87-2.63 (m, 3H), 2.39 (d, J = 6.9 Hz, 2H), 2.31-2.26 (m, 1H), 2.15-2.08 (m, 1H), 1.91 (dt, J = 13.3, 3.5 Hz, 1H), 1.88-1.84 (m, OH), 1.81 (dd, J = 12.1, 3.6 Hz, 3H), 1.70 (tt, J = 11.1, 3.9 Hz, 1H), 1.61 (dtd, J = 11.6, 7.4, 4.0 Hz, 1H), 0.90 (dq, J = 7.8, 6.0, 5.5 Hz, 3H). | LCMS: $C_{38}H_{44}N_{12}O_7$ requires: 780, found: m/z = 781 [M + H]$^+$. |
| 44 | $^1$H NMR (500 MHz, Acetonitrile-$d_3$) δ 10.71 (s, 1H), 8.90 (s, 1H), 7.84 (s, 1H), 7.63 (d, J = 8.5 Hz, 1H), 7.47 (s, 1H), 7.44 (s, 1H), 7.34 (s, 1H), 7.28 (d, J = 2.4 Hz, 1H), 7.15 (dd, J = 8.6, 2.4 Hz, 1H), 5.75 (s, 1H), 4.93 (dd, J = 12.3, 5.4 Hz, 1H), 4.50 (dd, J = 13.1, 4.1 Hz, 1H), 4.18 (d, J = 13.6 Hz, 1H), 3.81 (s, 3H), 3.81-3.66 (m, 3H), 3.44 (d, J = 8.0 Hz, 1H), 3.40 (d, J = 8.0 Hz, 1H), 3.34 (d, J = 7.9 Hz, 1H), 3.31 (d, J = 7.8 Hz, 1H), 3.17-3.00 (m, 4H), 2.83-2.60 (m, 3H), 2.36 (tt, J = 8.3, 3.7 Hz, 1H), 2.12-2.05 (m, 2H), 1.96 (s, 1H), 1.87 (dq,J = 13.4, 3.3 Hz, 1H), 1.79 (ddd, J = 16.5, 10.2, 4.2 Hz, 3H), 1.70-1.59 (m, 1H), 1.33 (qd, J = 9.6, 5.0 Hz, 1H), 0.87 (dt, J = 11.1, 5.7 Hz, 2H). | LCMS: $C_{37}H_{42}NN_{12}O_7$ requires: 766, found: m/z = 767 [M + H]$^+$. |

TABLE 2-continued

| Physical data for representative compound of Formula (I). | | |
|---|---|---|
| Compound No. | $^1$H NMR | Mass Spec (LCMS) |
| 45 | $^1$H NMR (500 MHz, Methanol-$d_4$) δ 7.60 (dt, J = 12.7, 5.3 Hz, 4H), 7.44 (d, J = 6.9 Hz, 2H), 7.39 (t, J = 7.6 Hz, 1H), 7.36-7.26 (m, 1H), 6.91 (d, J = 7.2 Hz, 1H), 6.85 (d, J = 12.7 Hz, 1H), 5.27-5.03 (m, 2H), 4.58-4.24 (m, 6H), 4.22-3.91 (m, 3H), 3.85 (t, J = 17.9 Hz, 0H), 3.74 (dt, J = 12.4, 6.1 Hz, 1H), 3.61 (t, J = 6.2 Hz, 1H), 3.53-3.39 (m, 1H), 2.95-2.60 (m, 3H), 2.59-2.30 (m, 4H), 2.30-2.09 (m, 1H), 1.93 (d, J = 9.5 Hz, 2H), 1.86-1.52 (m, 2H). | LCMS: $C_{33}H_{39}N_9O_6S$ requires 689, found: m/z = 690 [M + H]$^+$. |
| 46 | $^1$H NMR (500 MHz, DMSO-$d_6$) δ 12.12-11.85 (m, 1H), 11.07 (s, 1H), 8.02-7.75 (m, 5H), 7.66 (d, J = 8.4 Hz, 1H), 7.58-7.14 (m, 4H), 5.06 (dd, J = 12.8, 5.4 Hz, 1H), 4.17-3.93 (m, 3H), 3.89-3.69 (m, 3H), 3.16 (d, J = 6.4 Hz, 3H), 3.09 (d, J = 7.2 Hz, 3H), 3.04-2.95 (m, 2H), 2.94-2.78 (m, 2H), 2.69-2.53 (m, 4H), 2.03 (t, J = 19.0 Hz, 4H), 1.84 (s, 3H), 1.58 (s, 4H), 1.17 (t, J = 7.3 Hz, 4H). | LCMS: $C_{41}H_{48}N_{10}O_8S$ requires: 841, found: m/z = 842 [M + H]$^+$. |
| 47 | $^1$H NMR (500 MHz, Methanol-$d_4$) δ 8.00-7.76 (m, 5H), 7.59 (dd, J = 7.8, 5.7 Hz, 1H), 7.51-7.28 (m, 4H), 5.11 (dtd, J = 28.0, 13.7, 5.0 Hz, 1H), 4.50-4.27 (m, 2H), 4.11-3.72 (m, 5H), 3.61-3.40 (m, 3H), 3.26-3.16 (m, 1H), 3.07 (dd, J = 3.9, 2.6 Hz, 4H), 2.98-2.66 (m, 4H), 2.66-2.30 (m, 3H), 2.26-2.02 (m, 3H), 1.99-1.82 (m, 1H), 1.69 (ddd, J = 40.7, 16.2, 8.9 Hz, 3H). | LCMS: $C_{36}H_{42}N_8O_8S$ requires 746, found: m/z = 747 [M + H]$^+$. |
| 48 | $^1$H NMR (500 MHz, Acetonitrile-$d_3$) δ 10.73 (s, 1H), 8.86 (s, 1H), 7.84 (s, 1H), 7.63 (d, J = 8.5 Hz, 1H), 7.48 (s, 1H), 7.44 (s, 1H), 7.34 (s, 1H), 7.29 (d, J = 2.3 Hz, 1H), 7.15 (dd, J = 8.6, 2.4 Hz, 1H), 5.72 (s, 1H), 4.93 (dd, J = 12.1, 5.4 Hz, 1H), 4.44 (d, J = 13.1 Hz, 1H), 4.24 (d, J = 13.2 Hz, 1H), 4.00 (d, J = 13.0 Hz, 2H), 3.96-3.87 (m, 1H), 3.84 (s, 3H), 3.44-3.27 (m, 2H), 3.10-2.90 (m, 4H), 2.87-2.75 (m, 1H), 2.75-2.60 (m, 3H), 2.18 (d, J = 6.9 Hz, 2H), 2.11-1.98 (m, 8H), 1.91-1.72 (m, 5H), 1.65 (d, J = 12.9 Hz, 2H), 1.39 (d, J = 13.0 Hz, 2H), 1.21 (d, J = 12.4 Hz, 2H). | LCMS: C41H50N12O6 requires: 806, found: m/z = 807 [M + H]$^+$. |
| 49 | $^1$H NMR (500 MHz, Acetonitrile-$d_3$) δ 10.72 (s, 1H), 8.86 (s, 1H), 7.83 (s, 1H), 7.63 (d, J = 8.6 Hz, 1H), 7.47 (s, 1H), 7.45 (s, 1H), 7.34 (s, 1H), 7.29 (d, J = 2.4 Hz, 1H), 7.16 (dd, J = 8.6, 2.4 Hz, 1H), 5.72 (s, 1H), 4.93 (dd, J = 12.2, 5.4 Hz, 1H), 4.43 (d, J = 16.5 Hz, 1H), 4.24 (d, J = 13.4 Hz, 1H), 4.03 (d, J = 13.1 Hz, 2H), 3.97-3.87 (m, 1H), 3.82 (d, J = 1.7 Hz, 3H), 3.42-3.27 (m, 2H), 3.01 (p, J = 12.0 Hz, 4H), 2.90 (s, 2H), 2.81-2.64 (m, 5H), 2.60 (s, 2H), 2.33 (s, 2H), 2.11-2.04 (m, 1H), 1.90-1.70 (m, 5H), 1.62 (dd, J = 24.9, 11.7 Hz, 4H), 1.43 (s, 2H). | LCMS: $C_{40}H_{48}N_{12}O_6$ requires: 792, found: m/z = 792 [M + H]$^+$. |
| 50 | $^1$H NMR (500 MHz, Acetonitrile-$d_3$) δ 10.73 (s, 1H), 8.86 (s, 1H), 7.82 (s, 1H), 7.60 (d, J = 8.2 Hz, 1H), 7.47 (d, J = 6.8 Hz, 2H), 7.34 (s, 1H), 6.76 (d, J = 2.2 Hz, 1H), 6.60 (dd, J = 8.4, 2.2 Hz, 1H), 5.73 (s, 1H), 4.92 (dd, J = 12.2, 5.3 Hz, 1H), 4.44 (d, J = 13.0 Hz, 1H), 4.24 (d, J = 13.0 Hz, 1H), 4.15 (t, J = 8.1 Hz, 2H), 3.92 (ddt, J = 10.8, 8.3, 4.1 Hz, 1H), 3.84 (s, 3H), 3.74 (s, 2H), 3.45-3.31 (m, 2H), 3.28 (s, 3H), 3.12-2.97 (m, 3H), 2.84 (d, J = 38.6 Hz, 1H), 2.79-2.62 (m, 4H), 1.92-1.76 (m, 7H), 1.65 (d, J = 12.6 Hz, 1H), 1.39 (d, J = 49.0 Hz, 1H), 0.88 (d, J = 6.5 Hz, 3H). | LCMS: $C_{39}H_{46}N_{12}O_6$ requires: 778, found: m/z = 779 [M + H]$^+$. |

Example 66: Assays

Cell Culture

Ramos (CRL-1596) cells were obtained from American Type Culture Collection and were grown in RPMI-1640 media (ATCC, 30-2001) supplemented with 10% heat-inactivated FBS (Corning Premium Fetal Bovine Serum from Fisher, MT35015CV).

Cellular BTK HTRF Assay

Compounds of the present invention were added to 50,000 Ramos cells in round-bottom 96 well plates with a final DMSO concentration of >0.2% and were incubated at 37° C., 5% $CO_2$ for four hours. BTK levels were determined using Cisbio Total-BTK HTRF (Homologous Time-Resolved Fluorescence) kit (63ADK064PEG) according to manufacturer's protocol. Briefly, cells were incubated in 1× supplied lysis buffer for 30 minutes. In an opaque white low volume 96 well plate (Cisbio, 66PL96005), cell lysate was combined with two different specific BTK antibodies, one conjugated with $Eu^{3+}$-Cryptate FRET donor and one conjugated with d2 FRET acceptor. Assay controls include wells containing cell lysate with only the $Eu^{3+}$-Cryptate FRET donor antibody and wells containing both HTRF antibodies and lysis buffer without cells or control lysate provided by Cisbio. HTRF ratio was calculated as (acceptor signal at 665 nm/donor signal at 620 nm)×$10^4$. Background HTRF levels were determined from the control well containing the donor, but no acceptor, antibody. Background HTRF levels were subtracted from all samples. Readouts were reported as HTRF levels relative to HTRF levels of DMSO-treated cells. Four-parameter non-linear regressions were performed in GraphPad Prism 7.02 to obtain $DC_{50}$ values. $DC_{50}$ values are provided in Table 3, wherein A<7.5 nM, 7.5 nM≤B≤50 nM, and 50 nM<C<500 nM.

TABLE 3

Activity of bifunctional compound of the present invention.

| Compound No. | Cellular BTK HTRF Ramos: $DC_{50}$ (uM) |
|---|---|
| 1 | C |
| 2 | B |
| 3 | B |
| 4 | C |
| 5 | C |
| 6 | B |
| 7 | C |
| 8 | B |
| 9 | C |
| 10 | B |
| 11 | A |
| 12 | B |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | B |
| 25 | B |
| 26 | C |
| 27 | C |
| 28 | B |
| 29 | A |
| 30 | B |
| 31 | A |
| 32 | B |
| 33 | A |
| 34 | B |
| 35 | B |
| 36 | A |
| 37 | A |
| 38 | B |
| 39 | A |
| 40 | C |
| 41 | C |
| 42 | A |
| 43 | A |
| 44 | A |
| 45 | C |
| 46 | B |
| 47 | C |
| 48 | A |
| 49 | A |
| 50 | A |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I)

(I)

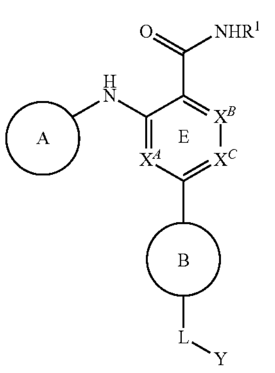

or a pharmaceutically acceptable salt thereof, wherein $R^1$ is —H or —$C_{1-4}$ alkyl;

$X^A$ is N;

$X^B$ is N;

$X^C$ is $CR^2$;

$R^2$ is —H, or $R^1$ and $R^2$ taken together with the atoms to which they are attached form a monocyclic heterocycle fused to ring E;

ring A is phenyl, a 4-6 membered monocyclic heteroaryl group having 1-3 heteroatoms independently selected from N, O, and S, or a 9-10 membered bicyclic heteroaryl having 1-3 heteroatoms independently selected from N, O, and S, wherein ring A is optionally substituted with —$Z^A$—$R^A$;

$Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, —$CO_2$—, —OCO—, —O—, —S—, —S(O)—, —$S(O)_2$, —$S(O)_2N(R)$—, or —$N(R)S(O)_2$—;

$R^A$ is hydrogen, halo, —OH, —$NH_2$, —$NO_2$, —CN, —$CF_3$, —$CH_3$, or —$OCH_3$;

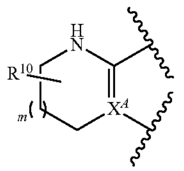

or

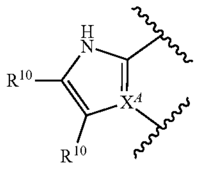

ring B is

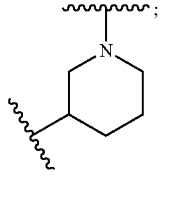 [SMILES: *C1CCCN(*)C1]

L is —$X^1$—$X^2$—$X^3$—$X^4$—;

$X^1$ is —N(R)—C(O)—O—, —N(R)—C(O)—, —C(O)—N(R)—, or 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo;

$X^2$ is a bond, $-(CH_2)_n-O-$, $-O-(CH_2)_n-$, $-C_{1-8}$ alkyl-, a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, a 6-10 membered fused bicyclic heterocycloalkyl having 1-3 heteroatoms independently selected from N, O, or S, or a 6-9 membered bridged bicyclic heterocycloalkyl having 1-3 heteroatoms independently selected from N, O, or S, wherein the spiro bicyclic heterocycloalkyl ring system is optionally substituted with —OH or oxo;

$X^3$ is a bond, —O—, $-(CH_2)_n-O-$, $-C_{1-4}$ alkyl-, or a 4-6 membered heterocycloalkyl ring having 1-2 heteroatoms independently selected from N, O, or S;

$X^4$ is a bond, $-C_{1-4}$ alkyl-, or a 4-6 membered heterocycloalkyl ring having 1-2 heteroatoms independently selected from N, O, or S;

each R is independently —H or $-C_{1-3}$ alkyl;

Y is

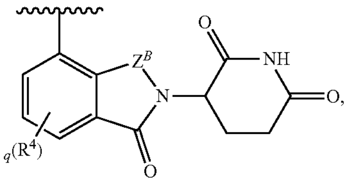

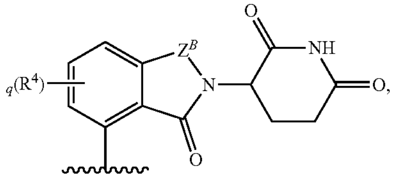

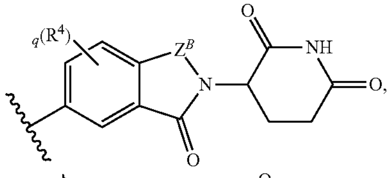

or

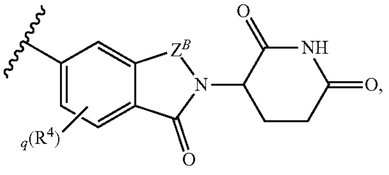

wherein:

each $R^4$ is independently halo or $C_{1-4}$ alkyl;

each $Z^B$ is $-C(R^B)_2-$ or —C(O)—;

each $R^B$ is —H or $-C_{1-4}$ alkyl;

each n is independently 1, 2, or 3; and q is 0, 1, or 2.

2. The compound or pharmaceutically acceptable salt of claim 1, wherein the compound of Formula (I) is a compound of Formula (IA)

(IA)

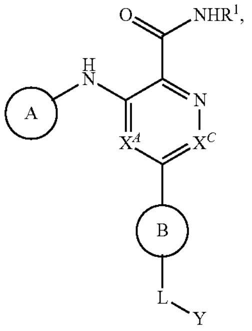

or a pharmaceutically acceptable salt thereof.

3. The compound or pharmaceutically acceptable salt of claim 1, wherein the compound of Formula (I) is a compound of Formula (II)

(II)

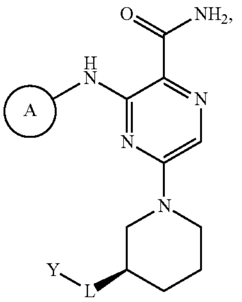

or a pharmaceutically acceptable salt thereof.

4. The compound or pharmaceutically acceptable salt of claim 3, wherein the compound of Formula (II) is a compound of Formula (II-A), (II-B), (II-C), (II-B1), (II-B2), (II-B3), or (II-B4)

(II-A)

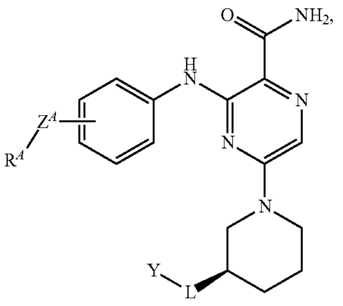

(II-B)

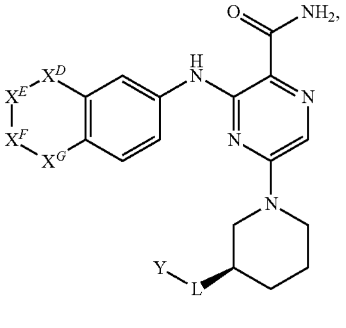

-continued (II-C)

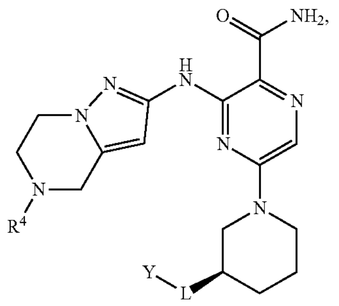

(II-B1)

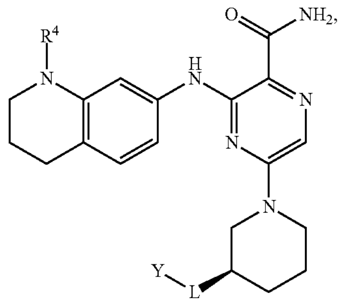

(II-B2)

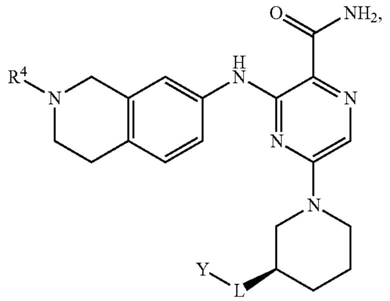

(II-B3)

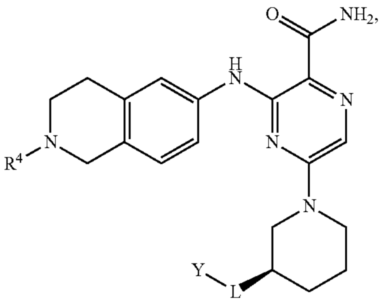

or (II-B4)

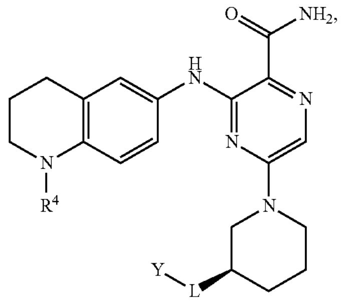

wherein one of $X^D$, $X^E$, $X^F$, and $X^G$ is optionally a bond, one of $X^D$, $X^E$, $X^F$, and $X^G$ is —$CH_2$— or —$CH_2$—$CH_2$—, one of $X^D$, $X^E$, $X^F$, and $X^G$ is —$NR^5$—, and the remainder are —$CH_2$—; and each $R^5$ is independently —H or —$C_{1-4}$ alkyl optionally substituted with halo;

or a pharmaceutically acceptable salt thereof.

5. The compound or pharmaceutically acceptable salt of claim 3, wherein ring A is a 9-10 membered bicyclic heteroaryl having 1-3 heteroatoms independently selected from N, O, and S, wherein ring A is optionally substituted with —$Z^A$—$R^A$, $Z^A$ is a bond, or an optionally substituted branched or straight $C_{1-3}$ aliphatic chain wherein up to two carbon units of $Z^A$ are optionally and independently replaced by —C(O)—, —C(S)—, —N(R)—, —C(O)N(R)—, —N(R)C(O)—, —$CO_2$—, —OCO—, —O—, —S—, —S(O)—, —$S(O)_2$—, —$S(O)_2N(R)$—, or —$N(R)S(O)_2$— and $R^A$ is hydrogen, halo, —OH, —$NH_2$, —$NO_2$, —CN, —$CF_3$, —$CH_3$, or —$OCH_3$.

6. The compound or pharmaceutically acceptable salt of claim 1, wherein q is 0; and Y is

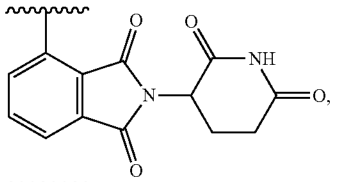

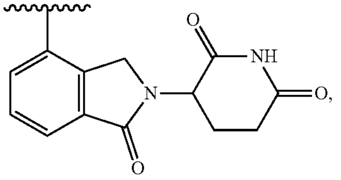

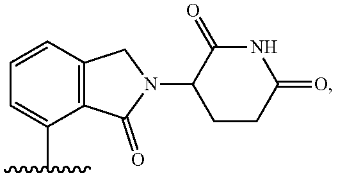

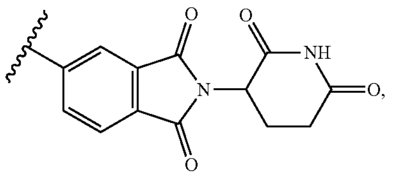

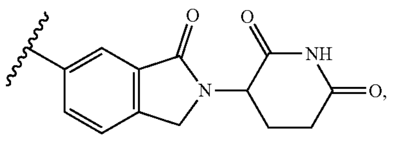

or

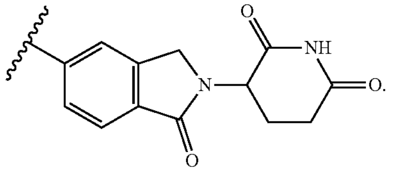

7. The compound or pharmaceutically acceptable salt of claim 1, wherein ring A is

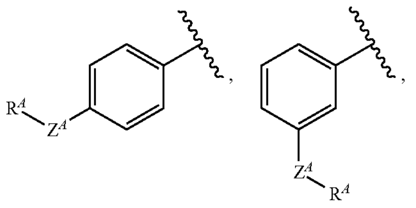

or

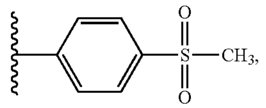

wherein $Z^A$ is a bond, —C(O)—, —$CO_2$—, —OCO—, —S—, —O—, —S(O)—, or —$S(O)_2$—, and $R^A$ is hydrogen, halo, —OH, —$CF_3$, or —$CH_3$.

8. The compound or pharmaceutically acceptable salt of claim 1, wherein ring A is

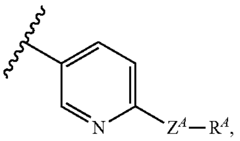

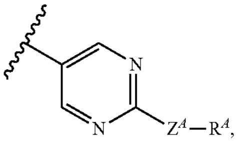

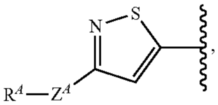

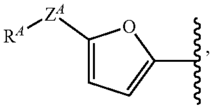

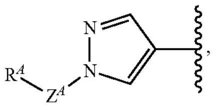

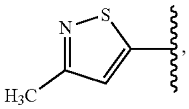

or

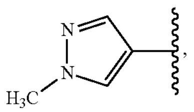

wherein $Z^A$ is an optionally substituted branched or straight $C_{1-3}$ aliphatic chain, and $R^A$ is hydrogen, halo, —OH, —$NH_2$, —$NO_2$, —CN, —$CF_3$, or —$OCH_3$.

9. The compound or pharmaceutically acceptable salt of claim 1, wherein $X^1$ is —NH—C(O)— or —N($CH_3$)—C(O)—.

10. The compound or pharmaceutically acceptable salt of claim 1, wherein $X^2$ is —$CH_2$—O—, —$(CH_2)_2$—O—, —$(CH_2)_3$—O—, —$CH_2$—, -n-butyl-, or -n-hexyl-, an 7-12 membered spiro bicyclic heterocycloalkyl ring system having 1-3 heteroatoms independently selected from N, O, or S, wherein the spiro bicyclic heterocycloalkyl ring system is optionally substituted with —OH or oxo.

11. The compound or pharmaceutically acceptable salt of claim 10, wherein $X^2$ is

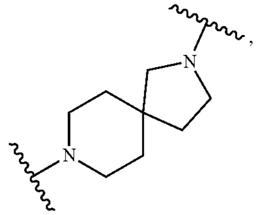

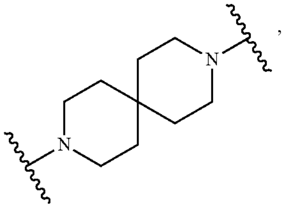

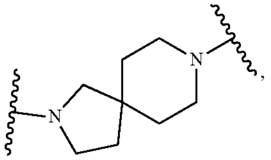

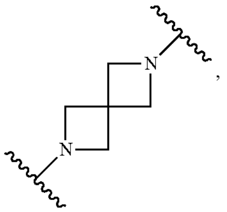

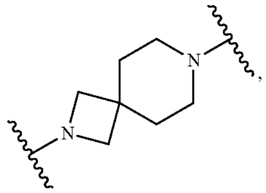

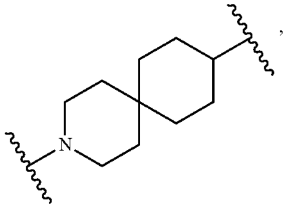

, or

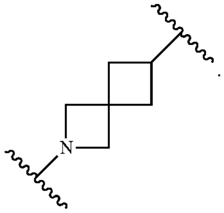

12. The compound or pharmaceutically acceptable salt of claim 1, wherein $X^2$ is a 4-6 membered monocyclic heterocycloalkyl having 1-2 heteroatoms independently selected from N, O, or S, 6-10 membered fused bicyclic heterocycloalkyl having 1-3 heteroatoms independently selected from N, O, or S, or a 6-9 membered bridged bicyclic heterocycloalkyl having 1-3 heteroatoms independently selected from N, O, or S.

13. The compound or pharmaceutically acceptable salt of claim 12, wherein $X^2$ wherein $X^2$ is

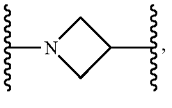

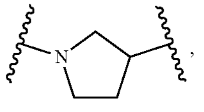

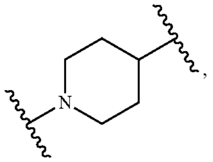

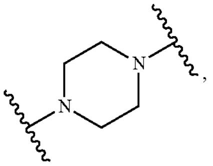

-continued
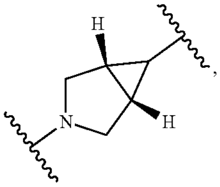
or
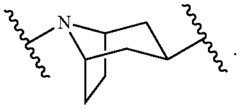
14. The compound or pharmaceutically acceptable salt of claim 1,
wherein $X^3$ is a bond, —$CH_2$—O—, —$C_{1-4}$ alkyl,
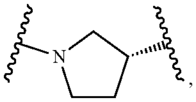
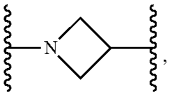
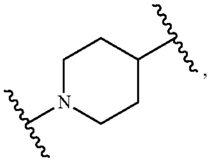
or
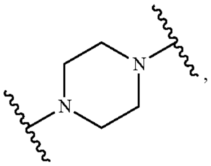
$X^4$ is a bond, —$C_{1-4}$ alkyl-,
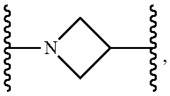
or
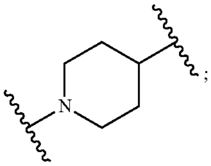
and
L is selected from
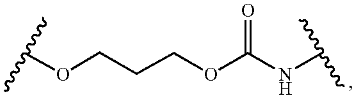
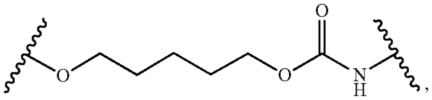
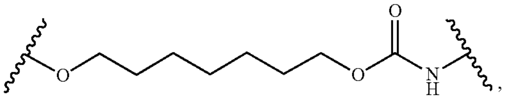
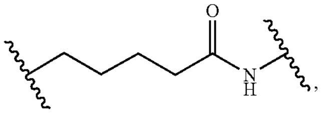
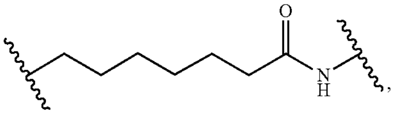
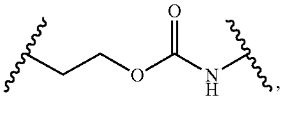
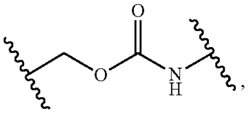
-continued
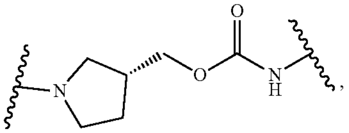
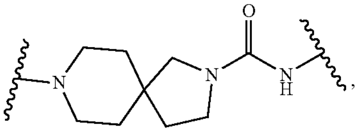
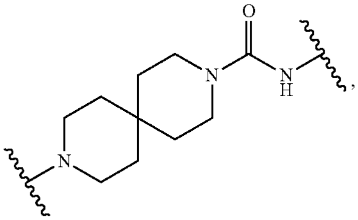
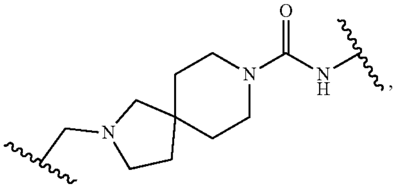
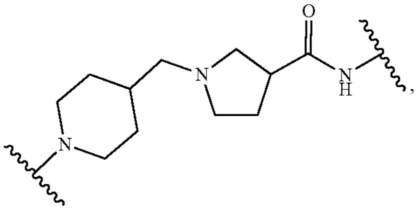
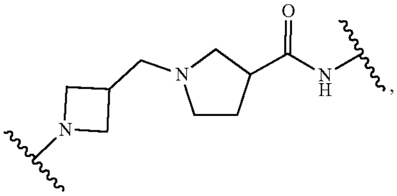
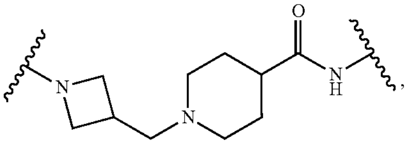
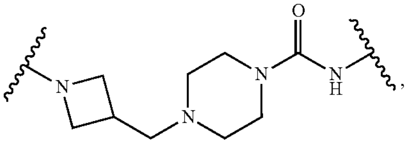
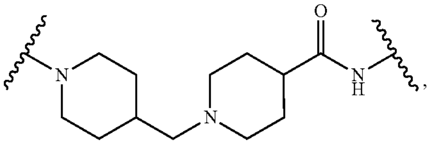
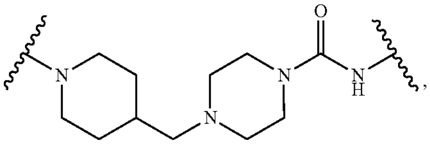

-continued
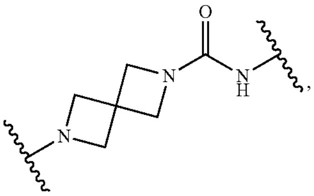
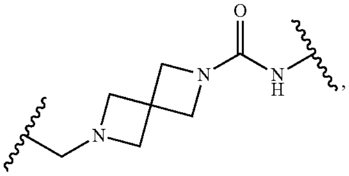
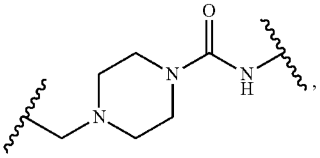
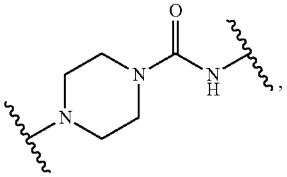
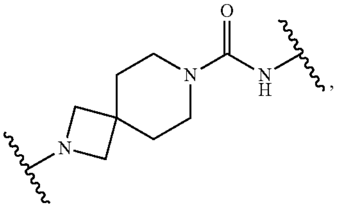
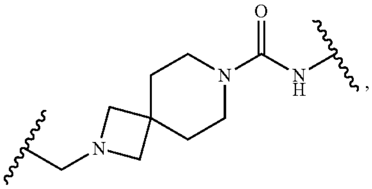
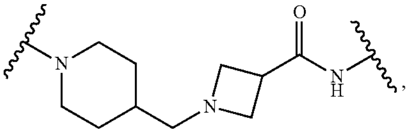
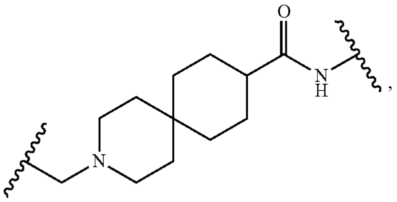
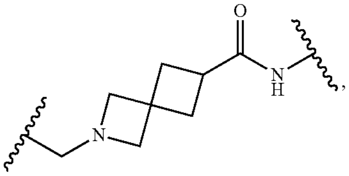
-continued
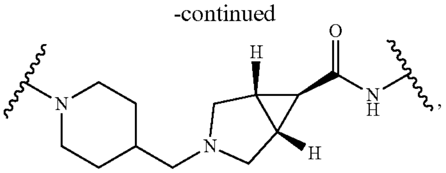
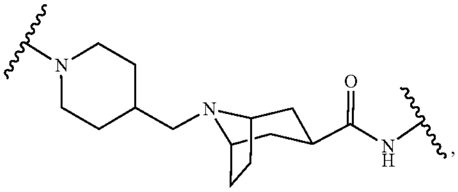
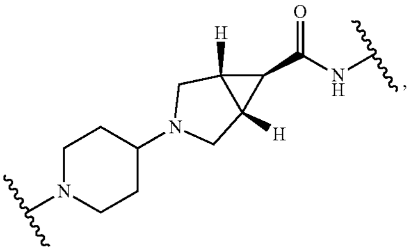
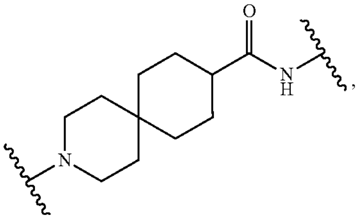
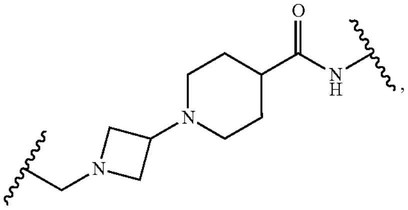
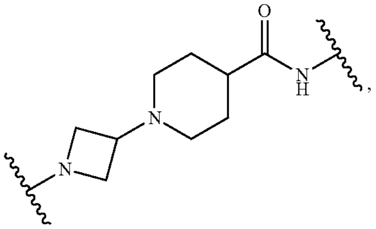
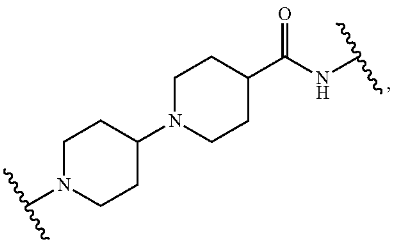
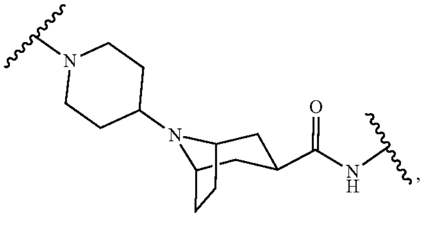

-continued

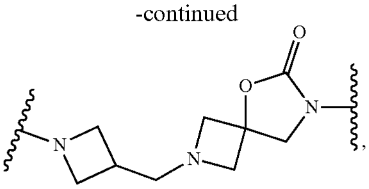

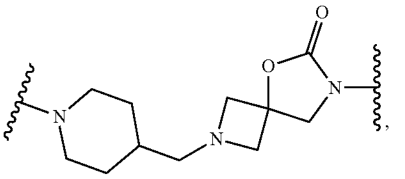

or

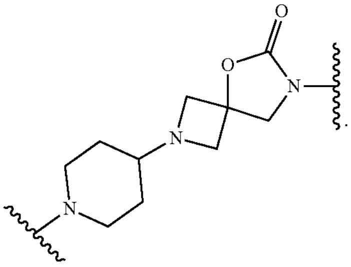

15. The compound or pharmaceutically acceptable salt of claim 1, wherein (i) ring A is

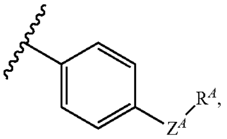

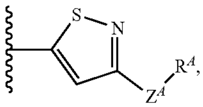

or

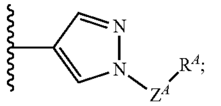

(ii) L is $—X^1—X^2—X^3—X^4—$;

(iii) $X^1$ is —NH—C(O)—;

(iv) $X^2$ is a 7-12 membered spiro bicyclic heterocycloalkyl ring system having 1-3 heteroatoms independently selected from N, O, or S, a 4-6 membered monocyclic heterocycloalkyl having 1-2 heteroatoms independently selected from N, O, or S, or a 6-10 membered fused bicyclic heterocycloalkyl having 1-3 heteroatoms independently selected from N, O, or S, wherein the spiro bicyclic heterocycloalkyl ring system is optionally substituted with —OH or oxo;

(v) $X^3$ is a bond, a 4-6 membered monocyclic heterocycloalkyl having 1-2 heteroatoms independently selected from N, O, or S, or a $—C_{1-4}$ alkyl-;

(vi) $X^4$ is a bond, a 4-6 membered heterocycloalkyl having 1-2 heteroatoms independently selected from N, O, or S, or a $—C_{1-4}$ alkyl-; and (vii) Y is

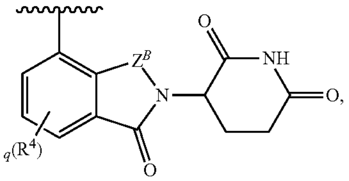

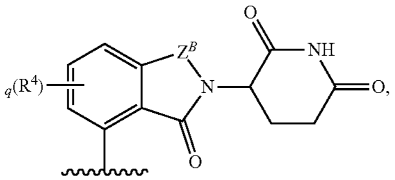

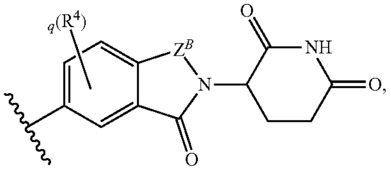

or

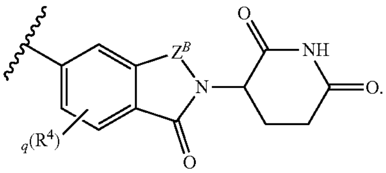

16. The compound or pharmaceutically acceptable salt of claim 15, wherein q is 0;

Y is

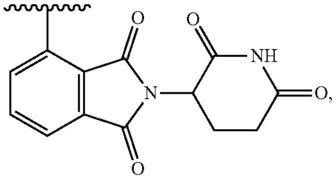

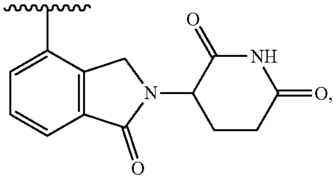

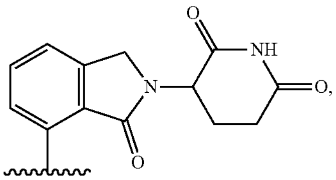

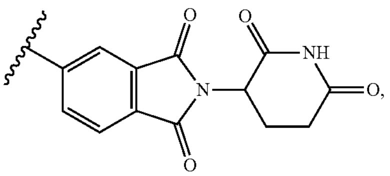

-continued
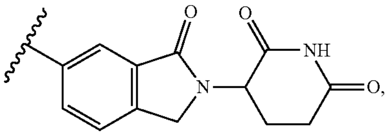
or
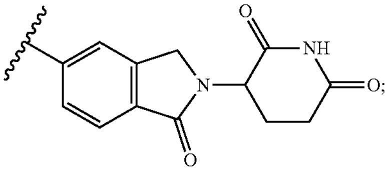
ring A is
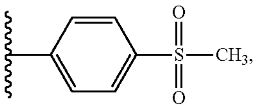
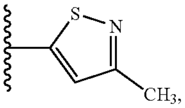
or
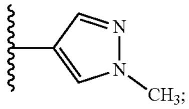
$X^2$ is
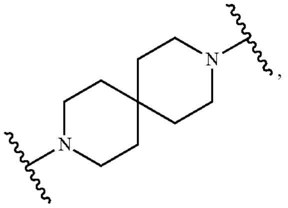
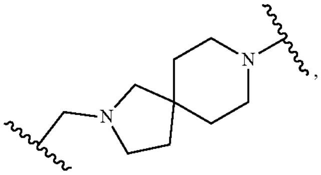
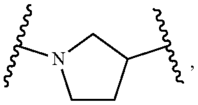
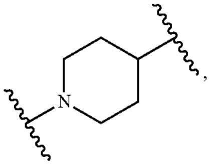
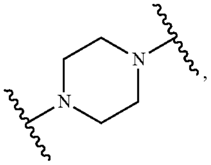
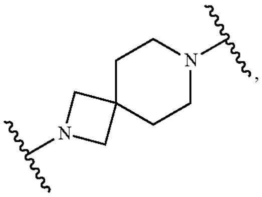
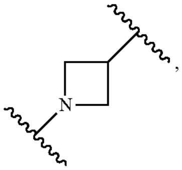
-continued
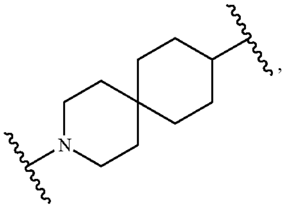
or
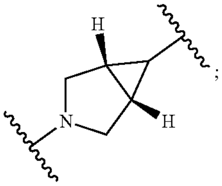
$X^3$ is bond, —$C_{1-4}$ alkyl-, or
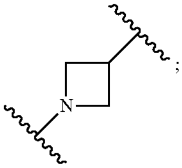 [SMILES: *C1CN(*)C1]
$X^4$ is bond, —$C_{1-4}$ alkyl
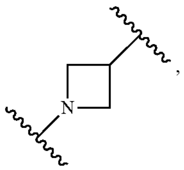
or
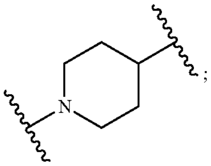
and
L is selected from
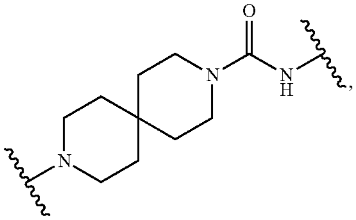
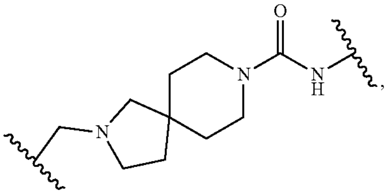
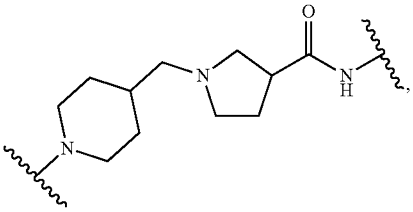

-continued
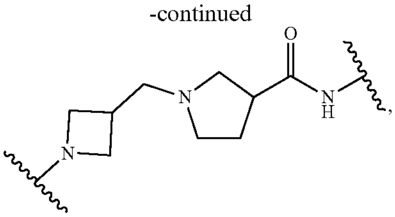,
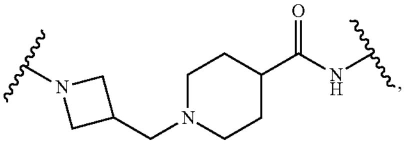,
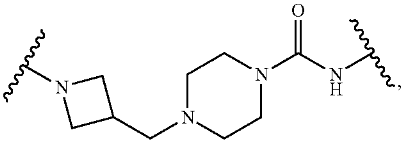,
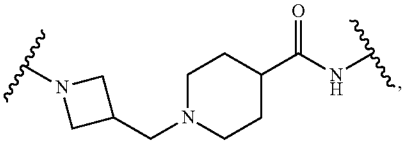,
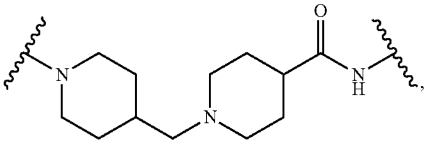,
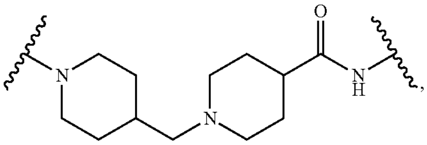,
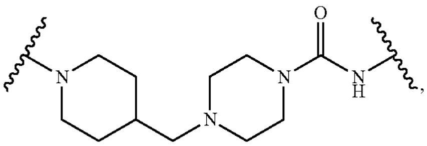,
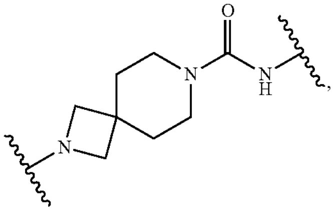,
-continued
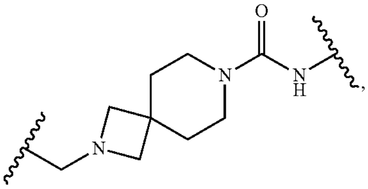,
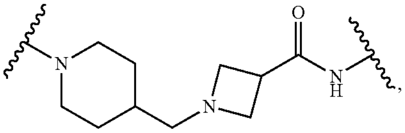,
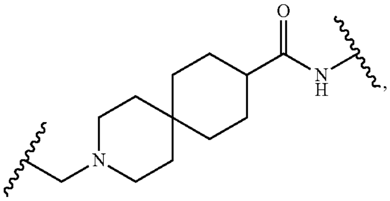,
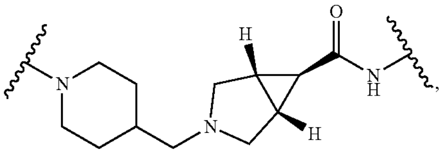,
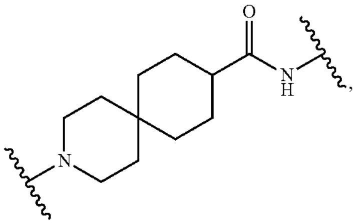,
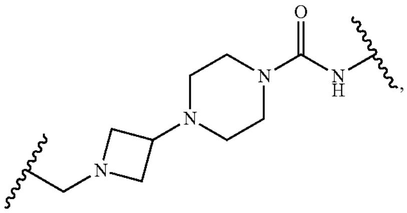, and
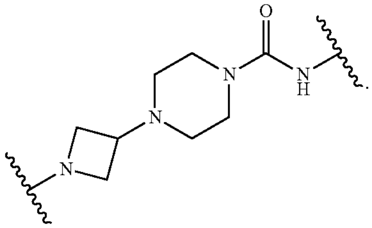.

17. A compound selected from the group consisting of:
(1)
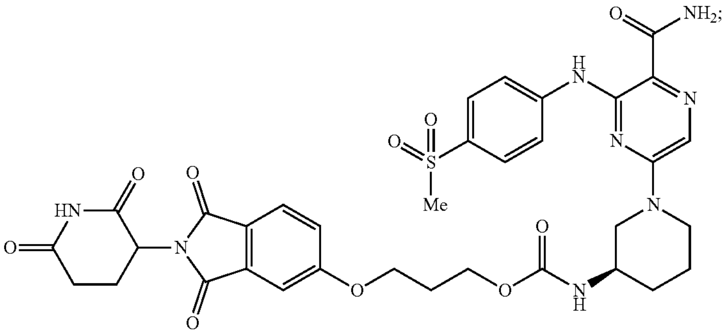
(2)
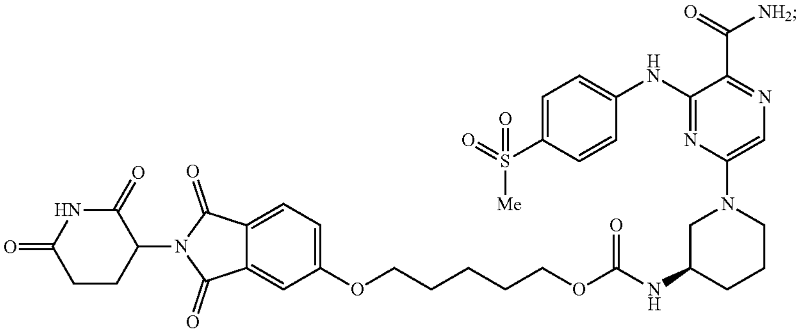
(3)
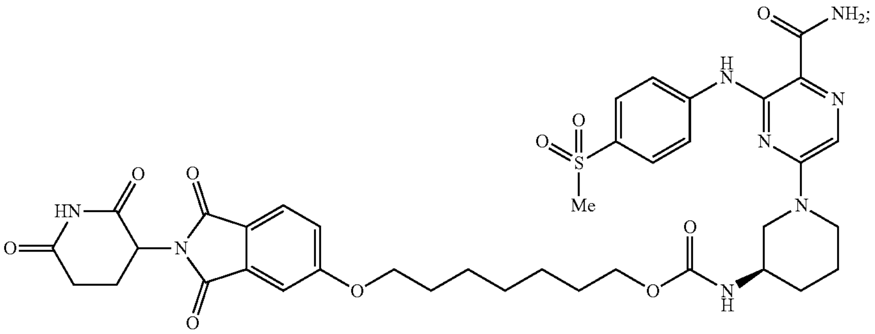
(4)
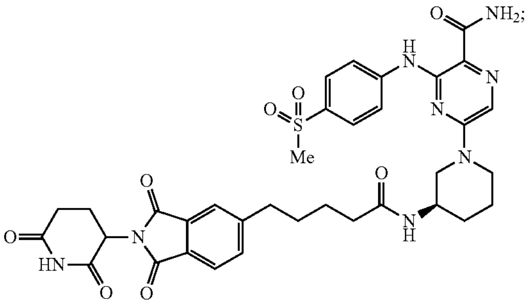
(5)
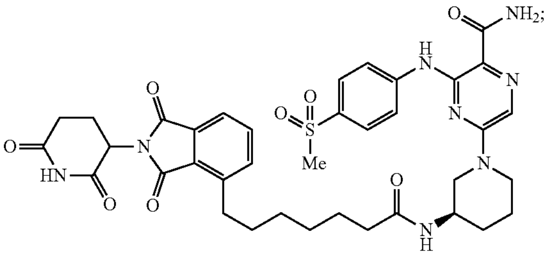
(6)
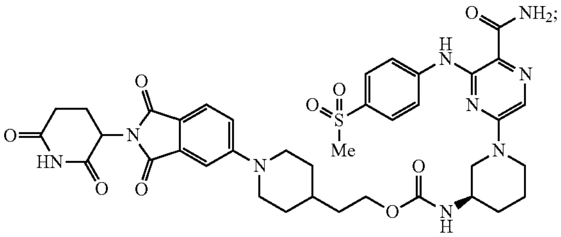
(7)
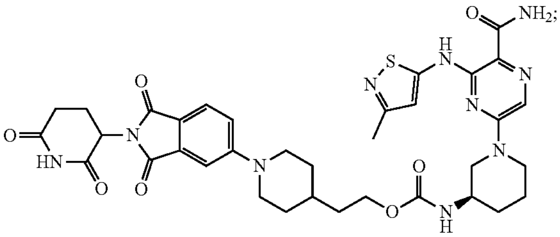

-continued
(8)
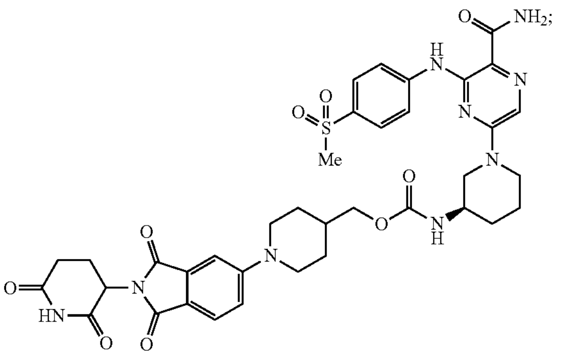
(9)
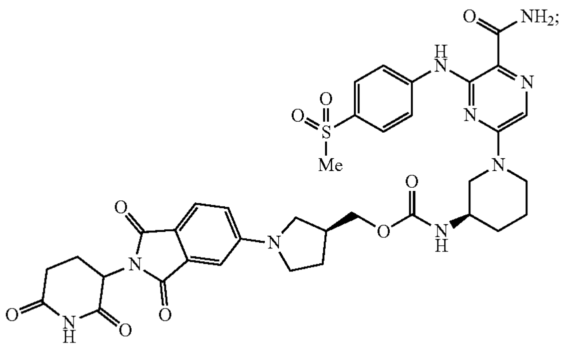
(10)
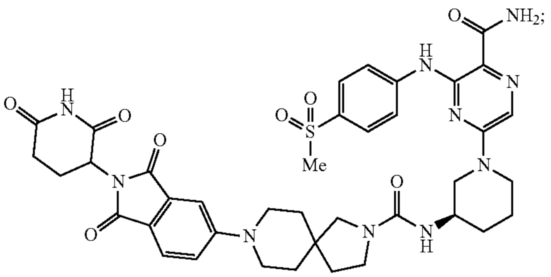
(11)
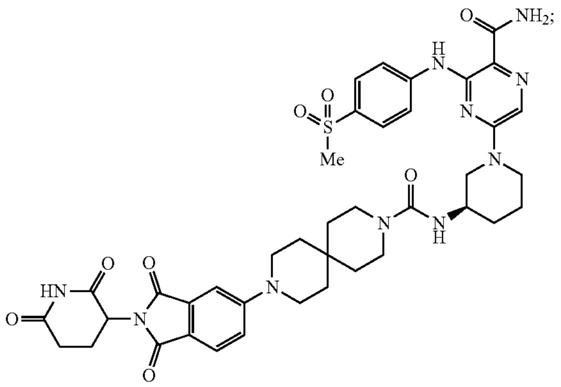
(12)
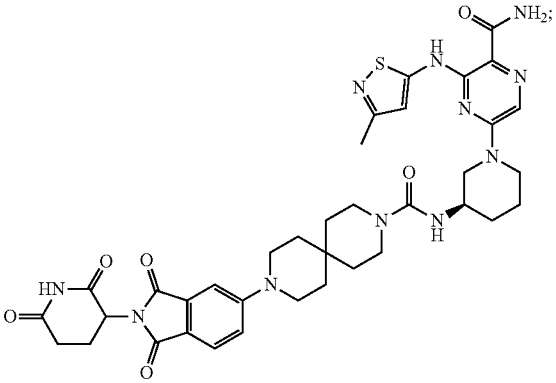
(13)
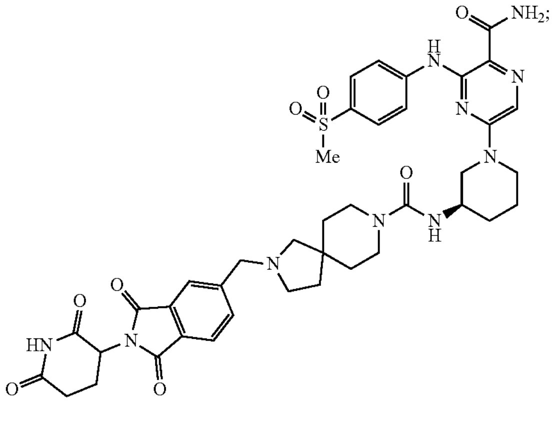

-continued
(14)
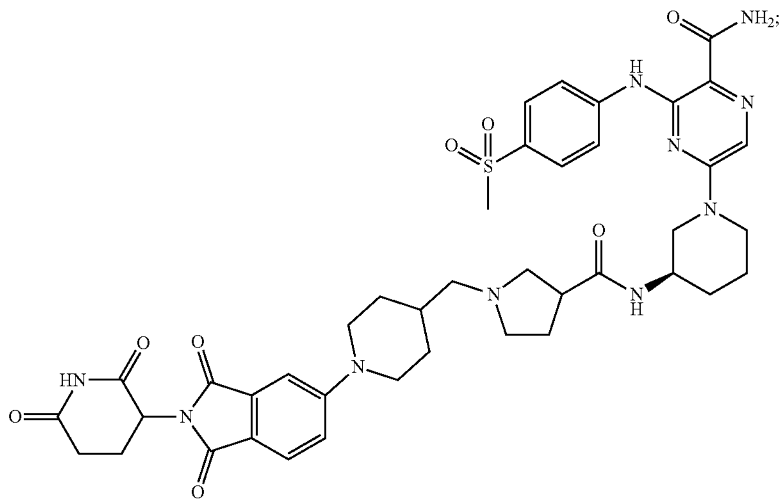
(15)
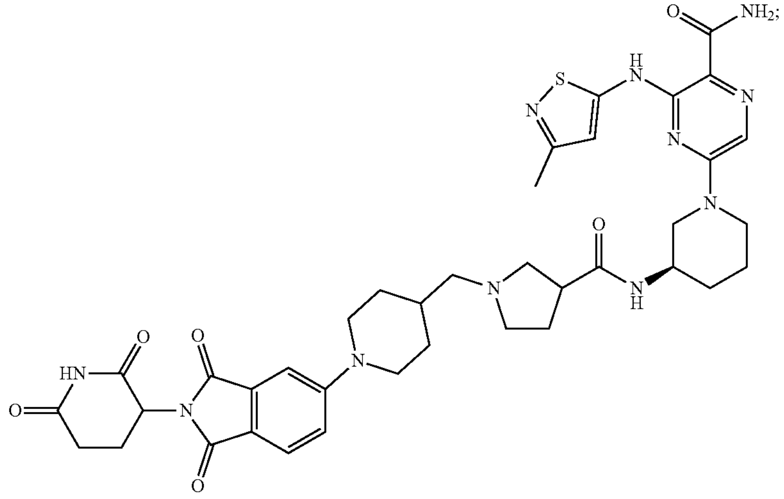
(16)
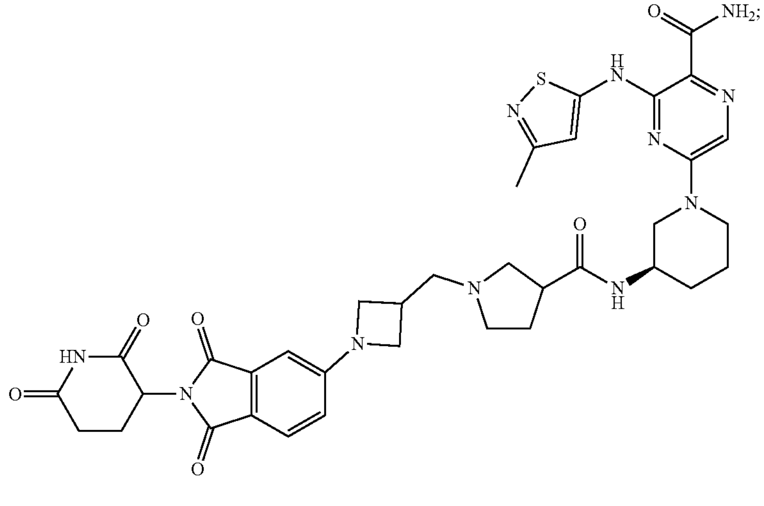

-continued
(17)
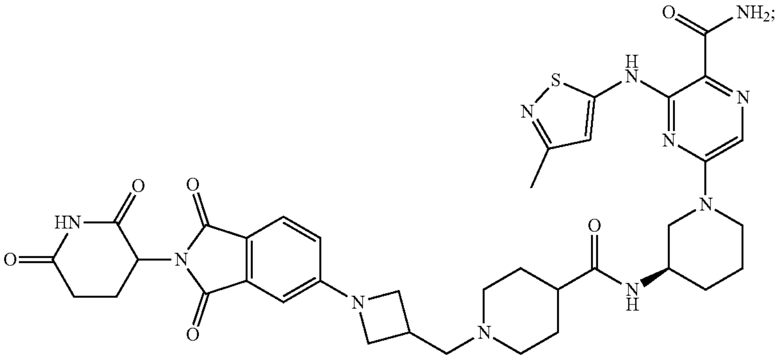
(18)
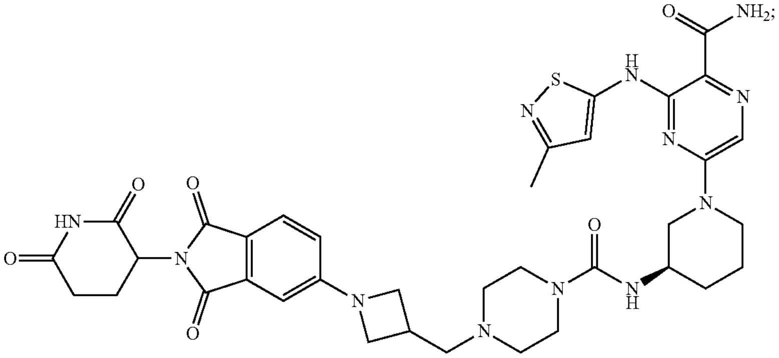
(19)
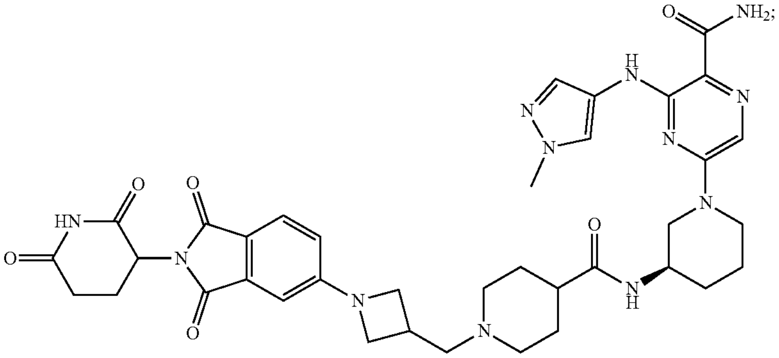
(20)
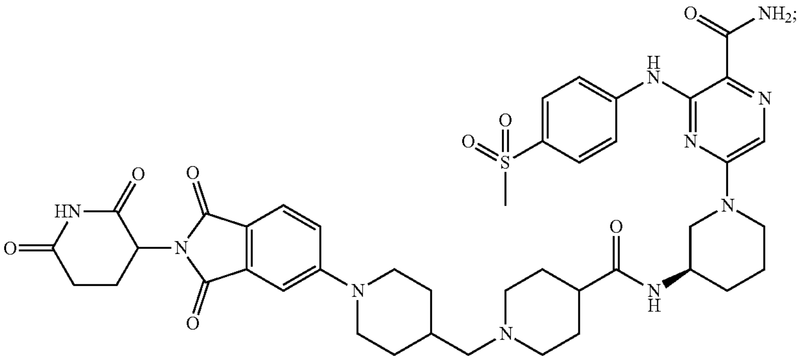

-continued
(21)
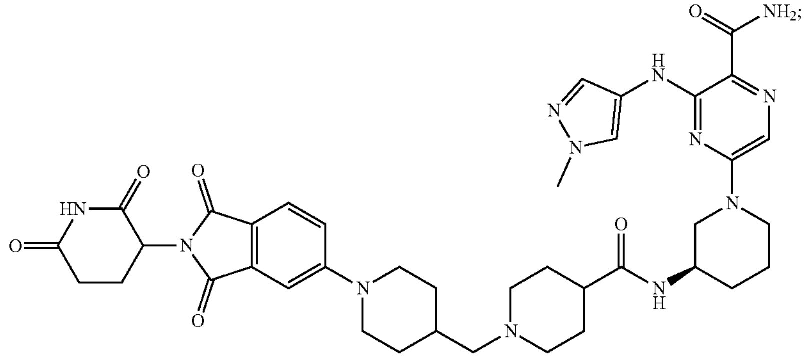
(22)
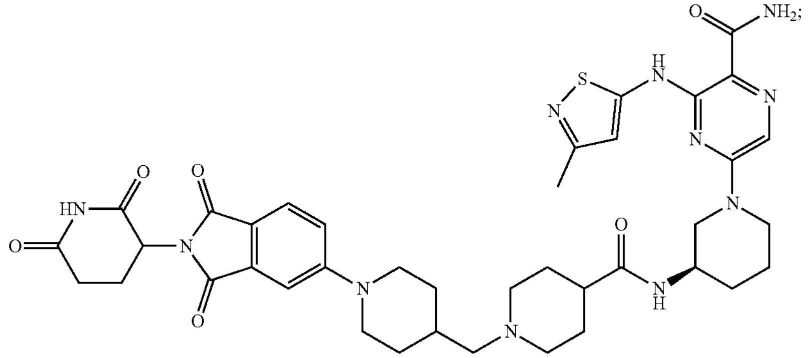
(23)
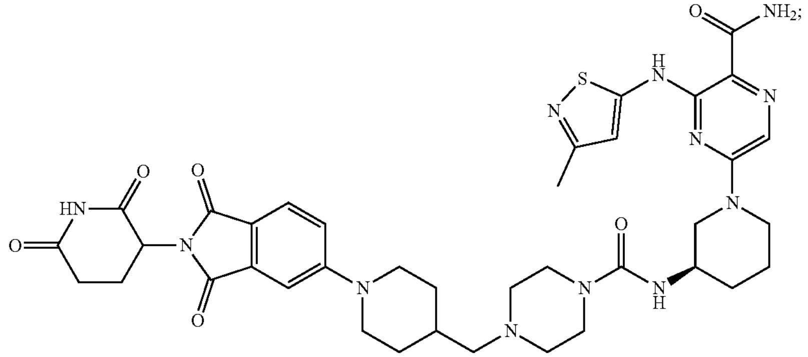
(24)
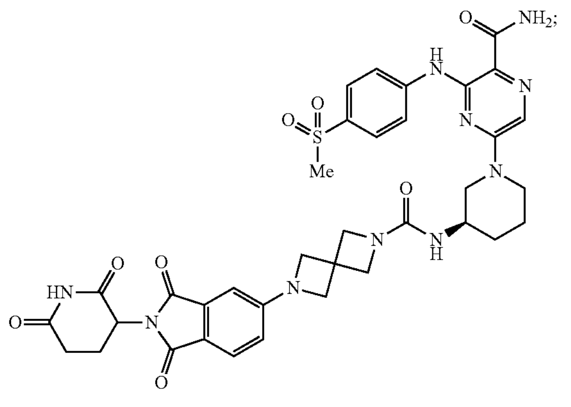
(25)
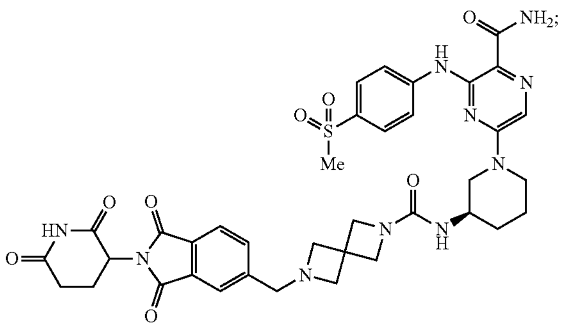

-continued
(26)
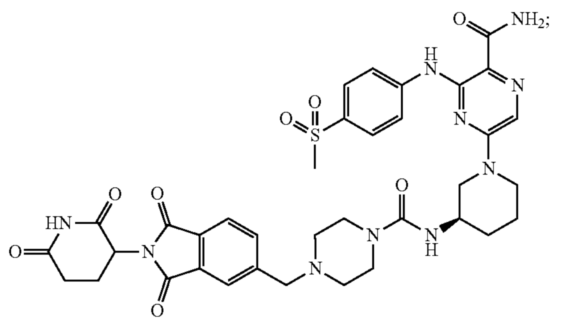
(27)
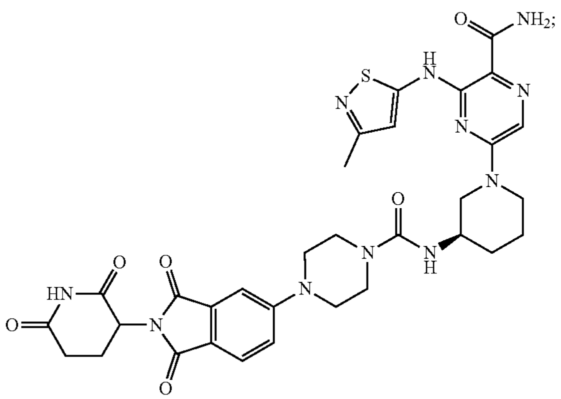
(28)
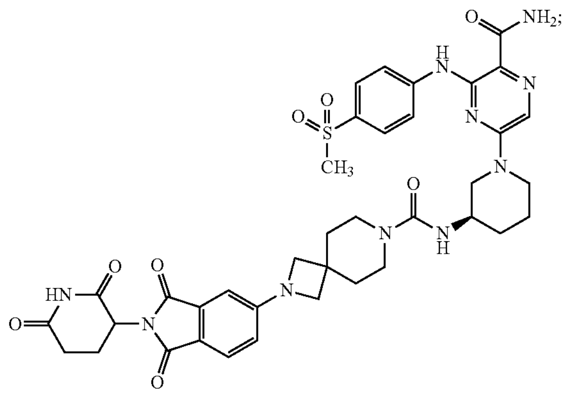
(29)
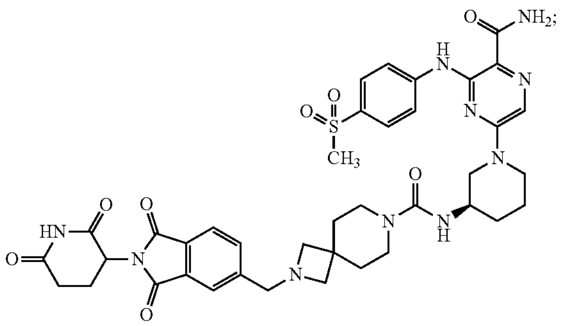
(30)
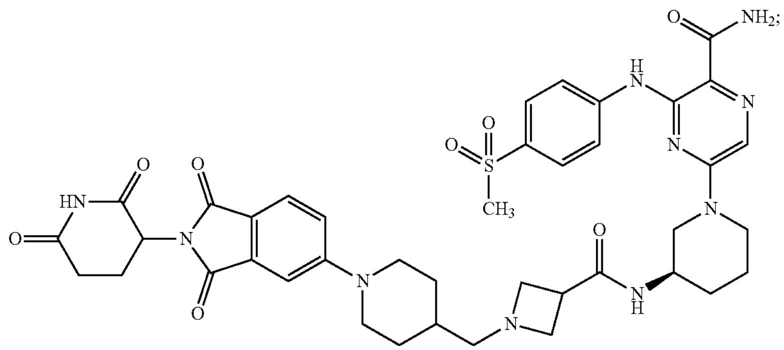
(31)
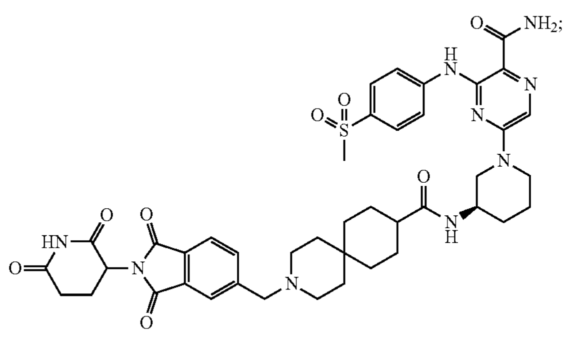
(32)
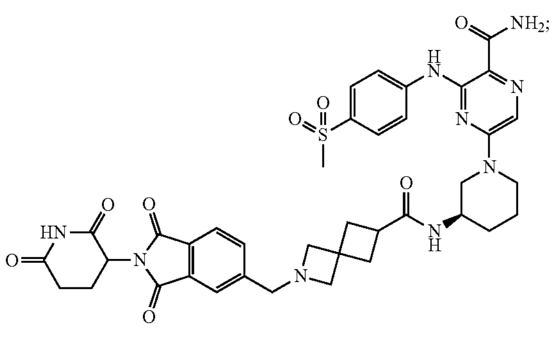

-continued
(33)
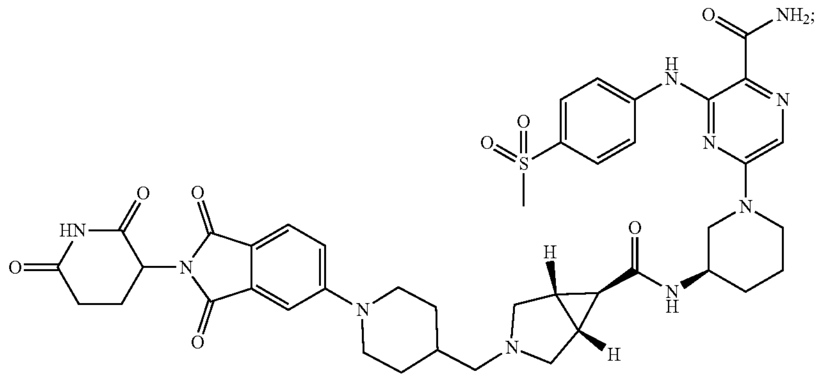
(34)
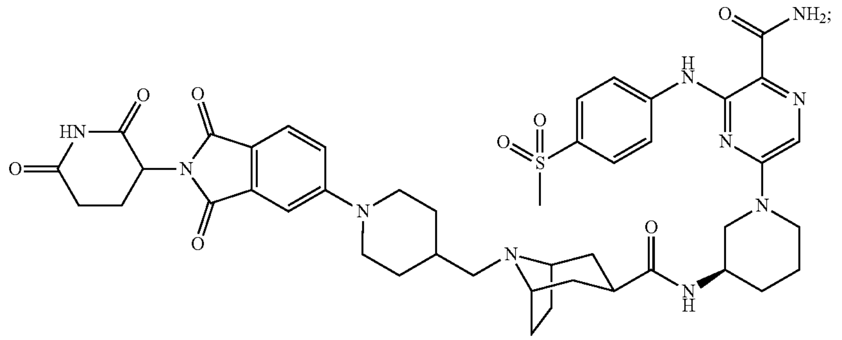
(35)
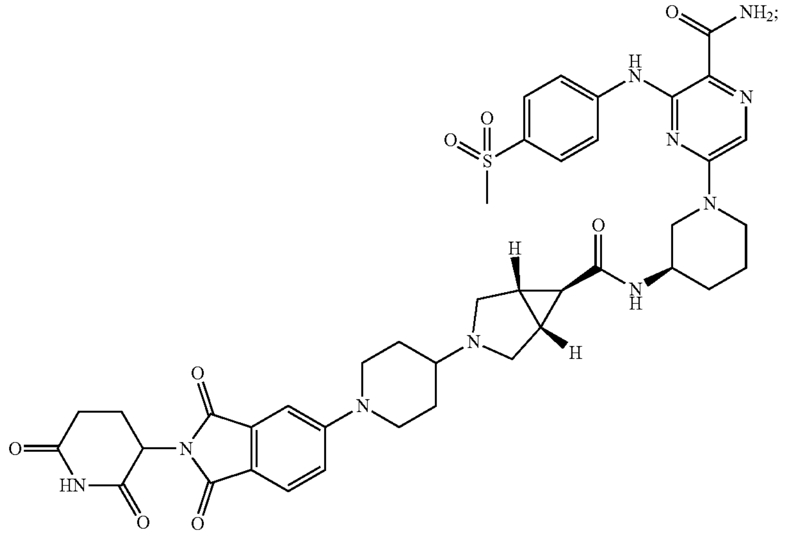

-continued
(36)
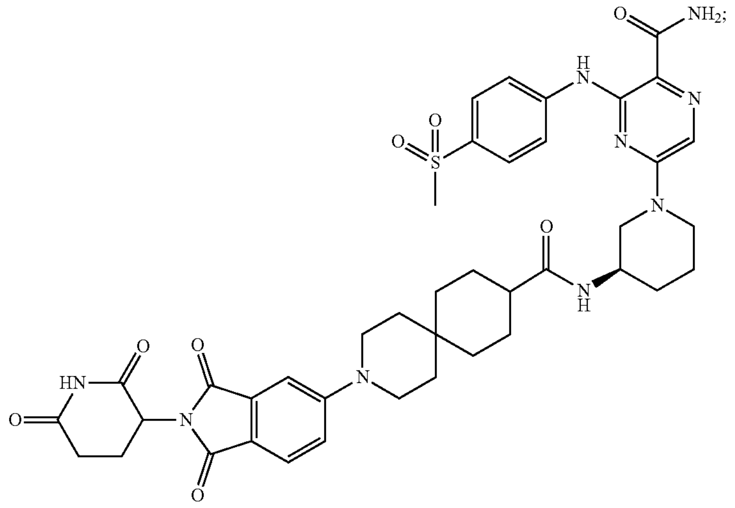
(37)
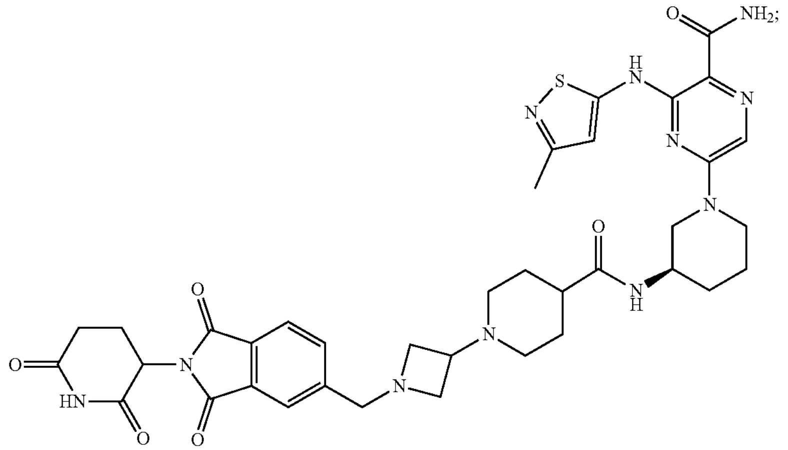
(38)
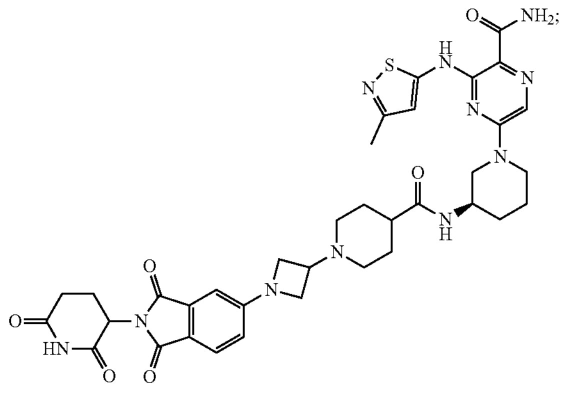
(39)
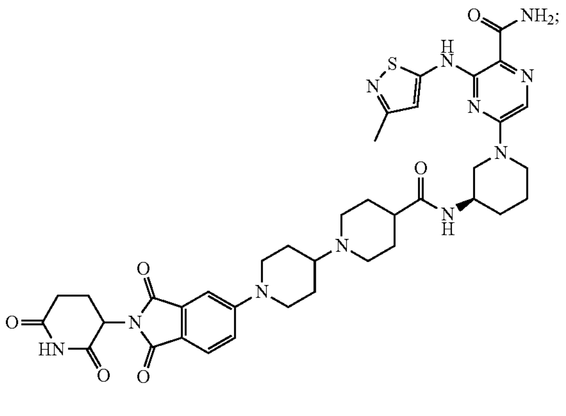

(40)
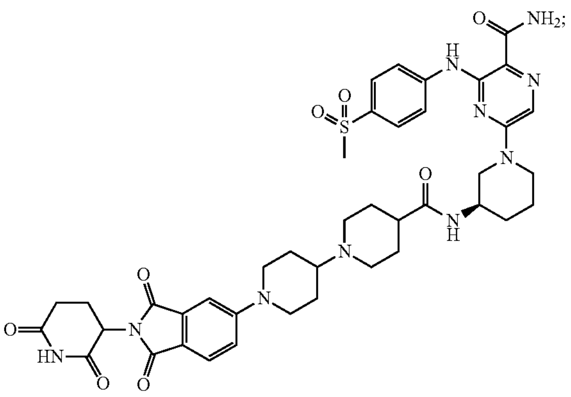
(41)
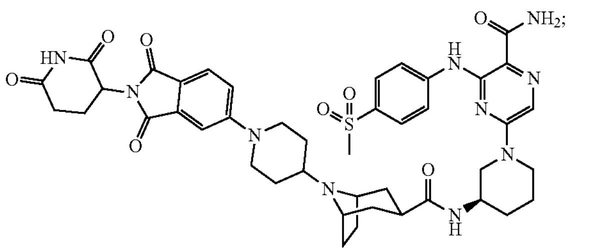
(42)
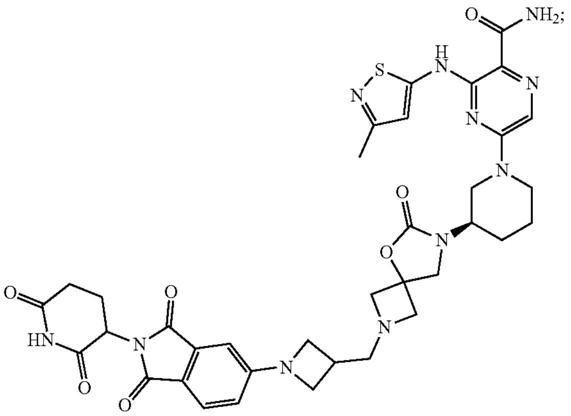
(43)
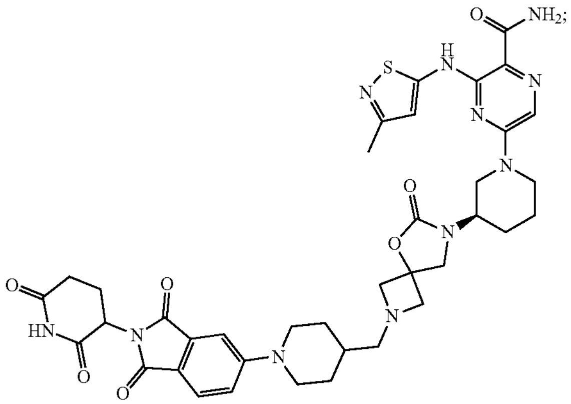
(44)
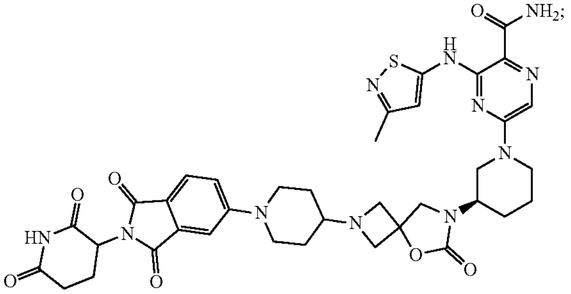
(45)
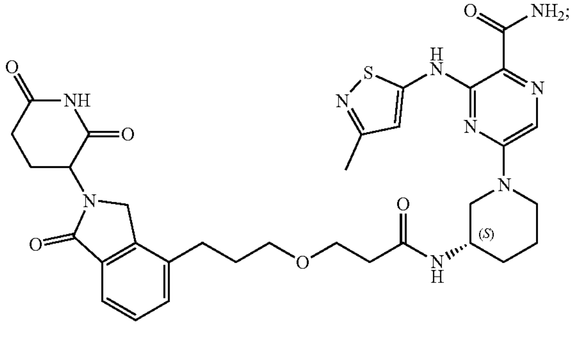

-continued
(46)
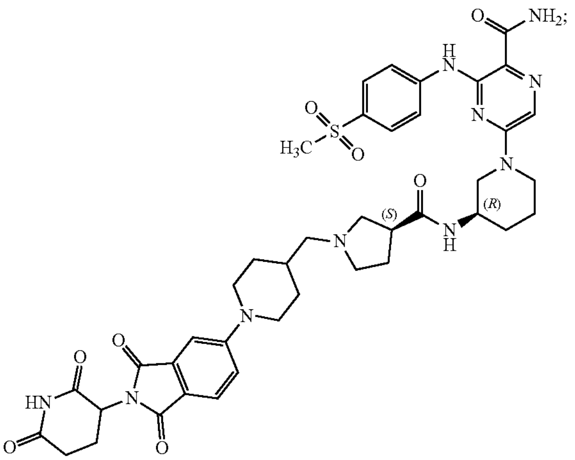
(47)
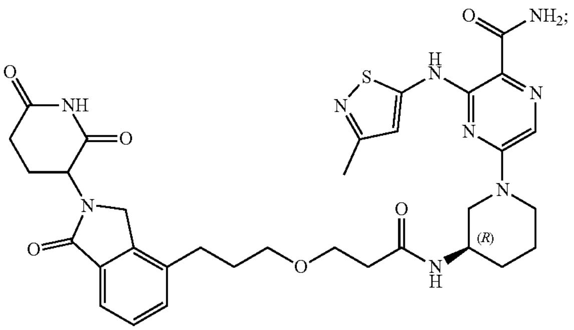
(48)
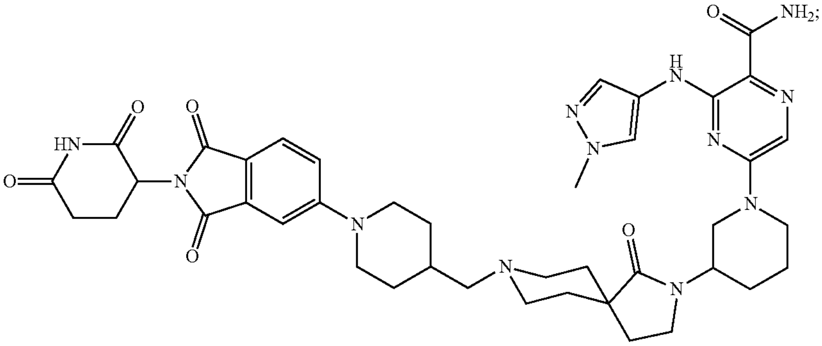
(49)
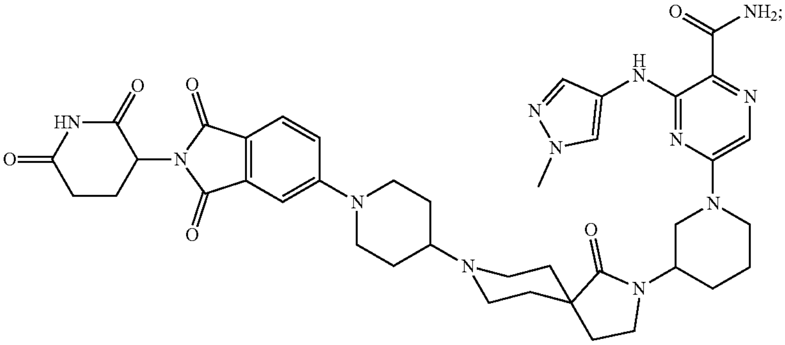
or
(50)
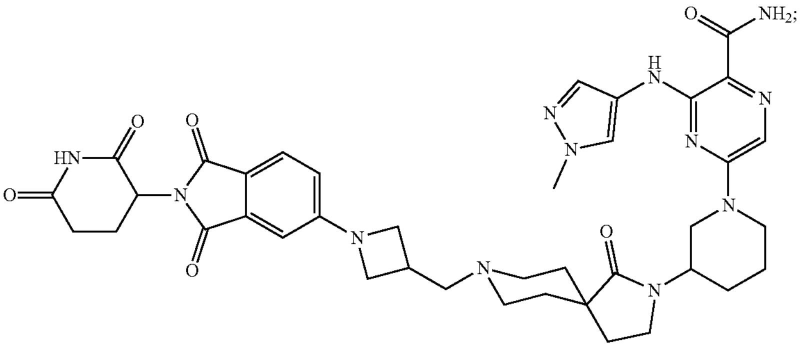
or a pharmaceutically acceptable salt thereof.

18. A pharmaceutical composition comprising a compound or pharmaceutically acceptable salt of a compound of claim 1 or 17 and a pharmaceutically acceptable carrier, vehicle, or adjuvant.

19. A method of treating a disease or disorder mediated by degrading Bruton's tyrosine kinase, comprising administering to a patient or biological sample a compound or pharmaceutically acceptable salt of a compound of claim 1 or 17, wherein the disease or disorder is cancer or an autoimmune disease.

20. The method of claim 19, wherein the cancer is a hematological cancer selected from myeloid leukemia (acute and chronic), acute lymphoblastic leukemia, chronic lymphocytic leukemia, myeloproliferative diseases, multiple myeloma, myelodysplastic syndrome, Hodgkin's disease, non-Hodgkin's lymphoma (malignant lymphoma) hairy cell, mantle cell lymphoma, Waldenstrom's macroglobulinemia, marginal zone lymphoma, and follicular lymphoma.

21. The method of claim 19, wherein the autoimmune disease is selected from urticarial, graft-versus-host disease, pemphigus vulgaris, achalasia, Addison's disease, Adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, axonal and neuronal neuropathy (AMAN), Balo disease, Behcet's disease, benign mucosal pemphigoid, bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss Syndrome (CSS) or Eosinophilic Granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, evans syndrome, fibromyalgia, fibrosing alveolitis, giant cell arteritis (temporal arteritis), giant cell myocarditis, glomerulonephritis, goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (Acne Inversa), hypogammalglobulinemia, IgA nephropathy, IgG4-related sclerosing disease, immune thrombocytopeniaurpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, Multifocal Motor Neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Tumer syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRC A), pyoderma gangrenosum, Raynaud's phenomenon, reactive Arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome (SPS), subacute bacterial endocarditis (SBE), Susac's syndrome, sympathetic ophthalmia (SO), Takayasu's arteritis, temporal arteritis (giant cell arteritis), thrombocytopenia purpura (TTP), Tolosa-Hunt syndrome (THS), transverse myelitis, Type 1 diabetes, ulcerative colitis (UC), undifferentiated connective tissue disease (UCTD), uveitis, vasculitis, vitiligo, Vogt-Koyanagi-Harada Disease, and Wegener's granulomatosis (or Granulomatosis with Polyangiitis (GPA)).

* * * * *